(12) United States Patent
Attie et al.

(10) Patent No.: US 11,471,510 B2
(45) Date of Patent: Oct. 18, 2022

(54) ACTIVIN-ACTRII ANTAGONISTS AND USES FOR TREATING ANEMIA

(71) Applicants: CELGENE CORPORATION, Summit, NJ (US); Acceleron Pharma Inc., Cambridge, MA (US)

(72) Inventors: Kenneth M. Attie, Boston, MA (US); Christopher Rovaldi, Swampscott, MA (US); Abderrahmane Laadem, Belle Mead, NJ (US)

(73) Assignees: CELGENE CORPORATION, Summit, NJ (US); ACCELERON PHARMA INC., Cambridge, MA (US)

( * ) Notice: Subject to any disclaimer, the term of this patent is extended or adjusted under 35 U.S.C. 154(b) by 571 days.

(21) Appl. No.: 15/532,329

(22) PCT Filed: Dec. 3, 2015

(86) PCT No.: PCT/US2015/063595
§ 371 (c)(1),
(2) Date: Jun. 1, 2017

(87) PCT Pub. No.: WO2016/090077
PCT Pub. Date: Jun. 9, 2016

(65) Prior Publication Data
US 2017/0360887 A1 Dec. 21, 2017

Related U.S. Application Data

(60) Provisional application No. 62/086,977, filed on Dec. 3, 2014, provisional application No. 62/088,478, filed on Dec. 5, 2014, provisional application No. 62/153,872, filed on Apr. 28, 2015, provisional application No. 62/173,782, filed on Jun. 10, 2015, provisional application No. 62/218,728, filed on Sep. 15, 2015.

(51) Int. Cl.
| | | |
|---|---|---|
| A61K 38/00 | (2006.01) |
| A61K 39/00 | (2006.01) |
| C07K 14/00 | (2006.01) |
| C07K 16/00 | (2006.01) |
| G01N 33/50 | (2006.01) |
| A61K 38/17 | (2006.01) |
| C07K 14/71 | (2006.01) |
| G01N 33/49 | (2006.01) |

(52) U.S. Cl.
CPC ............ A61K 38/179 (2013.01); C07K 14/71 (2013.01); G01N 33/49 (2013.01); *C07K 2319/30* (2013.01)

(58) Field of Classification Search
None
See application file for complete search history.

(56) References Cited

U.S. PATENT DOCUMENTS

| | | |
|---|---|---|
| 4,973,577 A | 11/1990 | Vale, Jr. et al. |
| 5,096,815 A | 3/1992 | Ladner et al. |
| 5,118,667 A | 6/1992 | Adams et al. |
| 5,198,346 A | 3/1993 | Ladner et al. |
| 5,223,409 A | 6/1993 | Ladner et al. |
| 5,283,317 A | 2/1994 | Saifer et al. |
| 5,525,490 A | 6/1996 | Erickson et al. |
| 5,658,876 A | 8/1997 | Crowley et al. |
| 5,677,196 A | 10/1997 | Herron et al. |
| 5,703,043 A | 12/1997 | Celeste et al. |
| 5,760,010 A | 6/1998 | Klein |
| 5,808,007 A | 9/1998 | Lee et al. |
| 5,824,637 A | 10/1998 | Crowley et al. |
| 5,847,078 A | 12/1998 | Eto et al. |
| 5,885,794 A | 3/1999 | Mathews et al. |
| 5,955,280 A | 9/1999 | Vidal et al. |
| 5,965,368 A | 10/1999 | Vidal et al. |
| 6,004,780 A | 12/1999 | Soppet et al. |
| 6,093,547 A | 7/2000 | Jin et al. |
| 6,132,988 A | 10/2000 | Sugino et al. |
| 6,162,896 A | 12/2000 | Mathews et al. |
| 6,287,816 B1 | 9/2001 | Rosen et al. |
| 6,319,499 B1 | 11/2001 | Elliot |
| 6,440,930 B1 | 8/2002 | Rinella, Jr. |
| 6,451,334 B2 | 9/2002 | Perrine |
| 6,521,750 B2 | 2/2003 | Hair et al. |
| 6,537,966 B1 | 3/2003 | Duan et al. |

(Continued)

FOREIGN PATENT DOCUMENTS

| | | |
|---|---|---|
| AU | 2013221910 | 9/2013 |
| EP | 1 416 273 A1 | 11/1992 |

(Continued)

OTHER PUBLICATIONS

Bhattacharya et al. Impact of genetic variation on three dimensional structure and function of proteins; PLOS One 12(3): e0171355, pp. 1-22 (Mar. 2017). (Year: 2017).*

(Continued)

*Primary Examiner* — Elizabeth C. Kemmerer
*Assistant Examiner* — Regina M DeBerry
(74) *Attorney, Agent, or Firm* — Jones Day

(57) ABSTRACT

Provided herein are methods for the treatment in a subject of anemia, anemia requiring RBC transfusion, low or intermediate-1-risk myelodysplastic syndromes (MDS), and/or non-proliferative chronic myelomonocytic leukemia (CMML) in any mammals wherein the methods comprise administration of Activin-ActRII signaling inhibitors to a subject in need of the treatment.

20 Claims, 19 Drawing Sheets

Specification includes a Sequence Listing.

(56) References Cited

U.S. PATENT DOCUMENTS

| | | |
|---|---|---|
| 6,548,634 B1 | 4/2003 | Ballinger et al. |
| 6,599,876 B2 | 7/2003 | Kojima |
| 6,605,699 B1 | 8/2003 | Ni et al. |
| 6,632,180 B1 | 10/2003 | Laragh |
| 6,656,475 B1 | 12/2003 | Lee et al. |
| 6,656,708 B1 | 12/2003 | Yu et al. |
| 6,692,925 B1 | 2/2004 | Miyazono et al. |
| 6,696,260 B1 | 2/2004 | Lee et al. |
| 6,777,205 B1 | 8/2004 | Carcagno et al. |
| 6,835,544 B2 | 12/2004 | Mathews et al. |
| 6,891,082 B2 | 5/2005 | Lee et al. |
| 7,192,717 B2 | 3/2007 | Hill et al. |
| 7,202,210 B2 | 4/2007 | Wolfman et al. |
| 7,261,893 B2 | 8/2007 | Veldman et al. |
| 7,320,789 B2 | 1/2008 | Dunham et al. |
| 7,560,441 B2 | 7/2009 | Wolfman et al. |
| 7,612,041 B2 | 11/2009 | Knopf et al. |
| 7,709,605 B2 | 5/2010 | Knopf et al. |
| 7,842,663 B2 | 11/2010 | Knopf et al. |
| 7,893,213 B2 | 2/2011 | Mathews et al. |
| 7,919,296 B2 | 4/2011 | Wang |
| 7,951,771 B2 | 5/2011 | Knopf et al. |
| 7,960,343 B2 | 6/2011 | Knopf et al. |
| 7,988,973 B2 | 8/2011 | Sherman |
| 8,007,809 B2 | 8/2011 | Sherman |
| 8,058,229 B2 | 11/2011 | Seehra et al. |
| 8,067,360 B2 | 11/2011 | Knopf et al. |
| 8,128,933 B2 | 3/2012 | Knopf et al. |
| 8,138,142 B2 | 3/2012 | Seehra et al. |
| 8,173,601 B2 | 5/2012 | Knopf |
| 8,178,488 B2 | 5/2012 | Knopf et al. |
| 8,216,997 B2 | 7/2012 | Seehra et al. |
| 8,252,900 B2 | 8/2012 | Knopf et al. |
| 8,293,881 B2 | 10/2012 | Seehra et al. |
| 8,343,933 B2 | 1/2013 | Knopf et al. |
| 8,361,957 B2 | 1/2013 | Seehra et al. |
| 8,367,611 B2 | 2/2013 | Knopf et al. |
| 8,388,968 B2 | 3/2013 | Berger et al. |
| 8,629,109 B2 | 1/2014 | Knopf et al. |
| 8,637,611 B2 | 1/2014 | Dershem |
| 8,703,694 B2 | 4/2014 | Knopf et al. |
| 8,703,927 B2 | 4/2014 | Seehra et al. |
| 8,710,016 B2 | 4/2014 | Seehra et al. |
| 8,765,663 B2 | 7/2014 | Seehra et al. |
| 8,895,016 B2 | 11/2014 | Sherman et al. |
| 9,138,459 B2 | 9/2015 | Knopf et al. |
| 9,163,075 B2 | 10/2015 | Knopf et al. |
| 9,181,533 B2 | 11/2015 | Seerah et al. |
| 9,353,356 B2 | 5/2016 | Knopf et al. |
| 9,399,669 B2 | 7/2016 | Knopf et al. |
| 9,505,813 B2 | 11/2016 | Seerah et al. |
| 9,526,759 B2 | 12/2016 | Knopf et al. |
| 9,572,865 B2 | 2/2017 | Knopf et al. |
| 9,617,319 B2 | 4/2017 | Seehra et al. |
| 9,745,559 B2 | 8/2017 | Seerah et al. |
| 9,790,284 B2 | 10/2017 | Knopf et al. |
| 9,850,298 B2 | 12/2017 | Attie |
| 9,919,030 B2 | 3/2018 | Sherman et al. |
| 9,932,379 B2 | 4/2018 | Seehra et al. |
| 10,071,135 B2 | 9/2018 | Knopf et al. |
| 10,093,707 B2 | 10/2018 | Sherman et al. |
| 10,131,700 B2 | 11/2018 | Seehra et al. |
| 10,189,882 B2 | 1/2019 | Attie et al. |
| 10,195,249 B2 | 2/2019 | Sung et al. |
| 10,259,861 B2 | 4/2019 | Knopf et al. |
| 10,358,633 B2 | 7/2019 | Seehra et al. |
| 10,377,996 B2 | 8/2019 | Seehra et al. |
| 10,487,144 B2 | 11/2019 | Attie et al. |
| 10,548,976 B2 | 2/2020 | Cappellini et al. |
| 10,550,170 B2 | 2/2020 | Sherman et al. |
| 10,689,427 B2 | 6/2020 | Seehra et al. |
| 10,695,405 B2 | 6/2020 | Kumar et al. |
| 10,722,558 B2 | 7/2020 | Kumar et al. |
| 10,889,626 B2 | 1/2021 | Seehra et al. |
| 2001/0039036 A1 | 11/2001 | Mathews et al. |
| 2003/0082233 A1 | 5/2003 | Lyons et al. |
| 2003/0083251 A1 | 5/2003 | Westenfelder |
| 2003/0118556 A1 | 6/2003 | Kaspar et al. |
| 2003/0133939 A1 | 7/2003 | Ledbetter et al. |
| 2003/0144203 A1 | 7/2003 | Bowen |
| 2003/0215913 A1 | 11/2003 | Alvarez et al. |
| 2003/0224397 A1 | 12/2003 | Lowman et al. |
| 2004/0033511 A1 | 2/2004 | Pfizenmaier et al. |
| 2004/0121008 A1 | 6/2004 | Shiraishi et al. |
| 2004/0132675 A1 | 7/2004 | Kuo et al. |
| 2004/0138129 A1 | 7/2004 | MacLeod |
| 2004/0197828 A1 | 10/2004 | Gaddy |
| 2004/0209805 A1 | 10/2004 | Phillips et al. |
| 2004/0223966 A1 | 11/2004 | Wolfman et al. |
| 2005/0106148 A1 | 5/2005 | Kay et al. |
| 2005/0197292 A1 | 9/2005 | Smithson et al. |
| 2005/0238646 A1 | 10/2005 | Ledbetter et al. |
| 2005/0239070 A1 | 10/2005 | Von Knebel-Doeberitz et al. |
| 2005/0244867 A1 | 11/2005 | Soppet et al. |
| 2005/0257278 A1 | 11/2005 | Lee et al. |
| 2006/0068468 A1 | 3/2006 | Knopf et al. |
| 2006/0172347 A1 | 8/2006 | Mellor et al. |
| 2006/0208106 A1 | 9/2006 | Boehland et al. |
| 2006/0210657 A1 | 9/2006 | Chou |
| 2007/0048830 A1 | 3/2007 | Gilbert et al. |
| 2007/0149455 A1 | 6/2007 | Wolfman et al. |
| 2007/0172956 A1 | 7/2007 | Magari et al. |
| 2007/0184052 A1 | 8/2007 | Lin et al. |
| 2007/0249022 A1 | 10/2007 | Knopf et al. |
| 2007/0275895 A1 | 11/2007 | Duan et al. |
| 2007/0292885 A1 | 12/2007 | Bejanin et al. |
| 2008/0021104 A1 | 1/2008 | Tarallo |
| 2008/0026406 A1 | 1/2008 | Moore et al. |
| 2008/0075692 A1 | 3/2008 | Perrine |
| 2008/0089897 A1 | 4/2008 | Wolfman |
| 2008/0102065 A1 | 5/2008 | Borges et al. |
| 2008/0139590 A1 | 6/2008 | Qian et al. |
| 2009/0005308 A1 | 1/2009 | Knopf et al. |
| 2009/0017019 A1 | 1/2009 | Shields et al. |
| 2009/0047281 A1 | 2/2009 | Sherman |
| 2009/0074768 A1 | 3/2009 | Knopf et al. |
| 2009/0087433 A1 | 4/2009 | Wolfman et al. |
| 2009/0098113 A1 | 4/2009 | Knopf et al. |
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0148436 A1 | 6/2009 | LaVallie et al. |
| 2009/0163417 A1 | 6/2009 | Sherman |
| 2010/0008918 A1 | 1/2010 | Sherman et al. |
| 2010/0015144 A1 | 1/2010 | Sherman et al. |
| 2010/0028331 A1 | 2/2010 | Sherman et al. |
| 2010/0028332 A1 | 2/2010 | Sherman et al. |
| 2010/0068215 A1 | 3/2010 | Seehra et al. |
| 2010/0111852 A1 | 5/2010 | Yoshida |
| 2010/0113932 A1 | 5/2010 | Antich et al. |
| 2010/0160220 A1 | 6/2010 | Cao |
| 2010/0183624 A1 | 7/2010 | Seehra et al. |
| 2010/0204092 A1 | 8/2010 | Sherman |
| 2010/0272734 A1 | 10/2010 | Berger et al. |
| 2010/0316644 A1 | 12/2010 | Seehra et al. |
| 2011/0038831 A1 | 2/2011 | Seehra et al. |
| 2011/0053930 A1 | 3/2011 | Yu et al. |
| 2011/0070233 A1 | 3/2011 | Seehra et al. |
| 2011/0092670 A1 | 4/2011 | Knopf et al. |
| 2011/0129469 A1 | 6/2011 | Koncarevic et al. |
| 2011/0135638 A1 | 6/2011 | Seehra et al. |
| 2011/0218147 A1 | 9/2011 | Knopf et al. |
| 2011/0294734 A1 | 12/2011 | Garreta et al. |
| 2012/0003218 A1 | 1/2012 | Sherman et al. |
| 2012/0015877 A1 | 1/2012 | Seehra et al. |
| 2012/0028276 A1 | 2/2012 | Moore et al. |
| 2012/0052067 A1 | 3/2012 | Sherman |
| 2012/0148588 A1 | 6/2012 | Knopf et al. |
| 2012/0156204 A1 | 6/2012 | Seehra et al. |
| 2012/0237521 A1 | 9/2012 | Berger et al. |
| 2013/0004489 A1 | 1/2013 | Knopf et al. |
| 2013/0065299 A1 | 3/2013 | Knopf et al. |
| 2013/0071393 A1 | 3/2013 | Seehra et al. |
| 2013/0177559 A1 | 7/2013 | Seehra et al. |

(56) References Cited

U.S. PATENT DOCUMENTS

| | | |
|---|---|---|
| 2013/0184210 A1 | 7/2013 | Knopf et al. |
| 2013/0195862 A1 | 8/2013 | Knopf et al. |
| 2013/0243743 A1 | 9/2013 | Seehra et al. |
| 2013/0244324 A1 | 9/2013 | Seehra et al. |
| 2014/0056902 A1 | 2/2014 | Shimizu et al. |
| 2014/0079700 A1 | 3/2014 | Knopf et al. |
| 2014/0314759 A1 | 10/2014 | Seehra et al. |
| 2015/0183845 A1 | 7/2015 | Sherman et al. |
| 2015/0266950 A1 | 9/2015 | Sung et al. |
| 2015/0276766 A1* | 10/2015 | Sung .................. G01N 33/6893 424/134.1 |
| 2015/0283209 A1 | 10/2015 | Sung et al. |
| 2015/0361163 A1 | 12/2015 | Kumar et al. |
| 2016/0039922 A1 | 2/2016 | Attie |
| 2016/0046690 A1 | 2/2016 | Kumar et al. |
| 2016/0108379 A1 | 4/2016 | Knopf et al. |
| 2016/0120939 A1 | 5/2016 | Knopf et al. |
| 2016/0279197 A1 | 9/2016 | Sherman et al. |
| 2016/0279203 A1 | 9/2016 | Sherman et al. |
| 2016/0289286 A1 | 10/2016 | Attie et al. |
| 2016/0318983 A1 | 11/2016 | Koncarevic et al. |
| 2016/0319254 A1 | 11/2016 | Knopf et al. |
| 2016/0326228 A1 | 11/2016 | Seerah et al. |
| 2017/0037100 A1 | 2/2017 | Kumar |
| 2017/0058016 A1 | 3/2017 | Knopf et al. |
| 2017/0137791 A1 | 5/2017 | Seerah et al. |
| 2017/0145074 A1 | 5/2017 | Knopf et al. |
| 2017/0190784 A1 | 7/2017 | Knopf et al. |
| 2017/0204382 A1 | 7/2017 | Seerah et al. |
| 2017/0274077 A1 | 9/2017 | Kumar et al. |
| 2017/0291935 A1 | 10/2017 | Sherman et al. |
| 2017/0304397 A1 | 10/2017 | Hruska et al. |
| 2017/0320925 A1 | 11/2017 | Seehra et al. |
| 2017/0327800 A1 | 11/2017 | Seerah et al. |
| 2017/0360887 A1 | 12/2017 | Attie et al. |
| 2018/0009872 A1 | 1/2018 | Sherman et al. |
| 2018/0037622 A1 | 2/2018 | Seerah et al. |
| 2018/0050085 A1 | 2/2018 | Kumar et al. |
| 2018/0050089 A1 | 2/2018 | Kumar et al. |
| 2018/0125928 A1 | 5/2018 | Attie et al. |
| 2018/0162954 A1 | 6/2018 | Knopf et al. |
| 2018/0194828 A1 | 7/2018 | Seehra et al. |
| 2019/0049469 A1 | 2/2019 | Sung et al. |
| 2019/0062392 A1 | 2/2019 | Koncarevic et al. |
| 2019/0192625 A1 | 6/2019 | Knopf et al. |
| 2019/0225664 A1 | 7/2019 | Sherman et al. |
| 2019/0233486 A1 | 8/2019 | Attie et al. |
| 2019/0262423 A1 | 8/2019 | Sung et al. |
| 2019/0263876 A1 | 8/2019 | Seehra et al. |
| 2019/0352619 A1 | 11/2019 | Kumar et al. |
| 2020/0031903 A1 | 1/2020 | Sherman |
| 2020/0071381 A1 | 3/2020 | Knopf et al. |
| 2020/0071383 A1 | 3/2020 | Sherman et al. |
| 2020/0101134 A1 | 4/2020 | Gale et al. |
| 2020/0101157 A1 | 4/2020 | Cappellini et al. |
| 2020/0109193 A1 | 4/2020 | Attie et al. |
| 2020/0148788 A1 | 5/2020 | Knopf et al. |
| 2020/0165583 A1 | 5/2020 | Seehra et al. |
| 2020/0181217 A1 | 6/2020 | Seehra et al. |
| 2020/0181218 A1 | 6/2020 | Seehra et al. |
| 2020/0199186 A1 | 6/2020 | Seehra et al. |
| 2020/0199546 A1 | 6/2020 | Seehra et al. |
| 2020/0199547 A1 | 6/2020 | Seehra et al. |
| 2020/0199548 A1 | 6/2020 | Seehra et al. |
| 2020/0208124 A1 | 7/2020 | Seehra et al. |
| 2020/0255495 A1 | 8/2020 | Sherman et al. |
| 2020/0360475 A1 | 11/2020 | Sherman et al. |
| 2020/0384080 A1 | 12/2020 | Kumar et al. |
| 2020/0390860 A1 | 12/2020 | Kumar et al. |
| 2020/0397865 A1 | 12/2020 | Kumar et al. |
| 2020/0405814 A1 | 12/2020 | Kumar et al. |
| 2021/0023174 A1 | 1/2021 | Kumar et al. |
| 2021/0038689 A1 | 2/2021 | Sherman et al. |
| 2021/0115105 A1 | 4/2021 | Seehra et al. |
| 2021/0188955 A1 | 6/2021 | Kumar et al. |
| 2021/0207107 A1 | 7/2021 | Seehra et al. |
| 2021/0230239 A1 | 7/2021 | Attie et al. |
| 2021/0253658 A1 | 8/2021 | Seehra et al. |
| 2021/0261682 A1 | 8/2021 | Knopf et al. |
| 2021/0269494 A1 | 9/2021 | Koncarevic et al. |
| 2021/0299216 A1 | 9/2021 | Kumar et al. |
| 2021/0299220 A1 | 9/2021 | Kumar et al. |
| 2021/0322514 A1 | 10/2021 | Kumar et al. |
| 2021/0346464 A1 | 11/2021 | Laadem et al. |
| 2021/0355181 A1 | 11/2021 | Sherman et al. |
| 2021/0355191 A1 | 11/2021 | Sherman |
| 2022/0017639 A1 | 1/2022 | Knopf et al. |

FOREIGN PATENT DOCUMENTS

| | | |
|---|---|---|
| EP | 1174149 A1 | 1/2002 |
| EP | 1 362 062 | 5/2005 |
| EP | 1 884 235 | 2/2008 |
| JP | 2007/99764 | 4/2007 |
| WO | WO 1987/05330 | 9/1987 |
| WO | WO 1992/004913 A1 | 4/1992 |
| WO | WO 1992/020793 A1 | 11/1992 |
| WO | WO 1993/000432 A1 | 1/1993 |
| WO | WO 1994/015965 A1 | 7/1994 |
| WO | WO 1994/026893 A1 | 11/1994 |
| WO | WO 1995/010611 A1 | 4/1995 |
| WO | WO 1995/029685 A1 | 11/1995 |
| WO | WO 1996/26432 | 8/1996 |
| WO | WO 1997/023613 A2 | 7/1997 |
| WO | WO 1998/018926 A1 | 5/1998 |
| WO | WO 1999/006559 A1 | 2/1999 |
| WO | WO 2000/018932 A2 | 4/2000 |
| WO | WO 2000/043781 A2 | 7/2000 |
| WO | WO 2000/062809 | 10/2000 |
| WO | WO 2001/036001 | 5/2001 |
| WO | WO 2001/043763 A1 | 6/2001 |
| WO | WO 2002/010214 A2 | 2/2002 |
| WO | WO 2002/022680 A2 | 3/2002 |
| WO | WO 2002/032925 | 4/2002 |
| WO | WO 2002/036152 A1 | 5/2002 |
| WO | WO 2002/040501 A2 | 5/2002 |
| WO | WO 2002/043759 A2 | 6/2002 |
| WO | WO 2002/074340 A1 | 9/2002 |
| WO | WO 2002/085306 A2 | 10/2002 |
| WO | WO 2002/088171 | 11/2002 |
| WO | WO 2002/094852 A2 | 11/2002 |
| WO | WO 2003/006057 A1 | 1/2003 |
| WO | WO 2003/053219 A2 | 7/2003 |
| WO | WO 2003/072808 A1 | 9/2003 |
| WO | WO 2003/087162 A2 | 10/2003 |
| WO | WO 2004/016639 A1 | 2/2004 |
| WO | WO 2004/034962 | 4/2004 |
| WO | WO 2004/039948 | 5/2004 |
| WO | WO 2004/069237 A1 | 8/2004 |
| WO | WO 2004/086953 A2 | 10/2004 |
| WO | WO 2004/092199 | 10/2004 |
| WO | WO 2004/108157 A2 | 12/2004 |
| WO | WO 2005/003158 A2 | 1/2005 |
| WO | WO 2005/009460 A2 | 2/2005 |
| WO | WO 2005/014650 A2 | 2/2005 |
| WO | WO 2005/025601 | 3/2005 |
| WO | WO 2005/028517 A2 | 3/2005 |
| WO | WO 2005/037989 | 4/2005 |
| WO | WO 2005/053795 A2 | 6/2005 |
| WO | WO 2005/070967 A2 | 8/2005 |
| WO | WO 2005/094871 A2 | 10/2005 |
| WO | WO 2005/097825 A2 | 10/2005 |
| WO | WO 2005/113590 A2 | 12/2005 |
| WO | WO 2006/002387 A2 | 1/2006 |
| WO | WO 2006/012627 A2 | 2/2006 |
| WO | WO 2006/020884 | 2/2006 |
| WO | WO 2006/039400 A2 | 4/2006 |
| WO | WO 2006/055689 | 5/2006 |
| WO | WO 2006/083183 A1 | 8/2006 |
| WO | WO 2006/088972 | 8/2006 |
| WO | WO 2006/115274 A1 | 11/2006 |
| WO | WO 2007/038703 A2 | 4/2007 |
| WO | WO 2007/053775 A1 | 5/2007 |
| WO | WO 2007/062188 | 5/2007 |

(56) References Cited

FOREIGN PATENT DOCUMENTS

| | | |
|---|---|---|
| WO | WO 2007/067616 A2 | 6/2007 |
| WO | WO 2007/071023 | 6/2007 |
| WO | WO 2007/075702 | 7/2007 |
| WO | WO 2007/076127 A2 | 7/2007 |
| WO | WO 2007/087505 | 8/2007 |
| WO | WO 2007/101060 | 9/2007 |
| WO | WO 2008/015383 A2 | 2/2008 |
| WO | WO 2008/031061 | 3/2008 |
| WO | WO 2008/060139 | 5/2008 |
| WO | WO 2008/072723 A1 | 6/2008 |
| WO | WO 2008/073292 A2 | 6/2008 |
| WO | WO 2008/076437 A2 | 6/2008 |
| WO | WO 2008/094708 A2 | 8/2008 |
| WO | WO 2008/097541 A2 | 8/2008 |
| WO | WO 2008/100384 A2 | 8/2008 |
| WO | WO 2008/109167 A2 | 9/2008 |
| WO | WO 2008/151078 A1 | 12/2008 |
| WO | WO 2009/009059 A1 | 1/2009 |
| WO | WO 2009/019504 A1 | 2/2009 |
| WO | WO 2009/019505 A2 | 2/2009 |
| WO | WO 2009/021747 | 2/2009 |
| WO | WO 2009/025651 A1 | 2/2009 |
| WO | WO 2009/058346 | 5/2009 |
| WO | WO 2009/070243 | 6/2009 |
| WO | WO 2009/137075 A1 | 11/2009 |
| WO | WO 2009/137613 A2 | 11/2009 |
| WO | WO 2009/158015 A2 | 12/2009 |
| WO | WO 2009/158025 A2 | 12/2009 |
| WO | WO 2009/158033 A2 | 12/2009 |
| WO | WO 2009/158035 | 12/2009 |
| WO | WO 2010/019261 A1 | 2/2010 |
| WO | WO 2010/083034 A1 | 7/2010 |
| WO | WO 2010/144452 | 12/2010 |
| WO | WO 2010/151426 | 12/2010 |
| WO | WO 2011/020045 | 2/2011 |
| WO | WO 2011/031901 A1 | 3/2011 |
| WO | WO 2012/027065 | 3/2012 |
| WO | WO 2013/006437 | 1/2013 |
| WO | WO 2013/059347 | 4/2013 |
| WO | WO 2014/066487 | 1/2014 |
| WO | WO 2014/066486 | 5/2014 |
| WO | WO 2014/071158 | 8/2014 |
| WO | WO 2015/161220 | 10/2015 |
| WO | WO 2015/192111 | 12/2015 |
| WO | WO 2016/069234 | 5/2016 |
| WO | WO 2016/090077 | 6/2016 |
| WO | WO 2016/090188 | 6/2016 |
| WO | WO 2016/183280 | 11/2016 |
| WO | WO 2016/187378 | 11/2016 |
| WO | WO 2017/079591 | 5/2017 |
| WO | WO 2017/091706 | 6/2017 |
| WO | WO 2018/022762 | 2/2018 |
| WO | WO 2018/067874 | 4/2018 |
| WO | WO 2018/231905 | 12/2018 |
| WO | WO 2020/092523 | 5/2020 |

OTHER PUBLICATIONS

Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin", Journal of Protein Chemistry, 11(5):433-444 (1992).
Abbiotec: ACTR-IIA Antibody: Catalog No. 251303 (http://www.abbiotec.com) Jun. 3, 2010.
Acceleron Pharma Presents Positive Phase 1 Results Demonstrating ACE-011 Increases Markers of Bone Formation, Acceleron Pharma, pp. 1-2, retrieved from the Internet, www.acceleronpharma.com/contents/news/press-releases/detail.jsp/q/news-id/47> (2007).
Acta Cryst., "The CCP4 suite: programs for protein crystallography: Collaborative Computational Project, No. 4," D50: 760-763 (1994). (Abstract only).

Akel et al., "Neutralization of Autocrine Transforming Growth Factor—☐ ☐ in Human Cord Blood $CD34^+CD38^-Lin^-$ Cells Promotes Stem-Cell-Factor-Mediated Erythropoietin-Independent Early Erythroid Progenitor Development and Reduces Terminal Differentiation." Stem Cells, 21:557-567 (2003).
Akpan et al., "The effects of a soluble activin type IIB receptor on obesity and insulin sensitivity," International Journal of Obesity, 33(11):1265-1273 (2009).
"Anti-human Activin RIIA Antibody," R&D Systems, Catalog No. AF340 (Feb. 14, 2006).
Allendorph, G.P., et al., "Structure of the ternary signaling complex of a TGF-β superfamily member," PNAS, 103(20):7643-7648 (2006).
Anonymous "Iron and Thalassemia," Accessed on the Internet Apr. 3, 2014 at <sickle.bwh.harvard.edu/thaliron.html>. Published Apr. 25, 1997.
Anonymous "Learning about Thalassemia" <http://www.genome.gov/10001221> Accessed on Internet Jul. 9, 2013. Published Jun. 28, 2010.
Anti-ActRIIA Antibodies: Commercial Monoclonal Antibodies Against Human ActRIIA (2010).
Antibodies for ACVR2A: http://www.genecards.org/cgi-bin/carddisp.pl?gene=Acvr2a (Jun. 8, 2010).
Attie et al., "A Single Ascending-Dose Study of Muscle Regulator Ace-031 in Healthy volunteers," Muscle & Nerve, pp. 1-8 (2012).
Banks et al., "The Value of Mammalian Models for Duchenne Muscular Dystrophy in Developing Therapeutic Strategies," Current Topics in Developmental Biology, 84:431-453 (2008).
Benny Klimek et al., "Acute inhibition of myostatin-family proteins preserves skeletal muscle in mouse models of cancer cachexia," Biochemical and Biophysical Research Communications, 391:1548-1554 (2010).
Berenson, "Multiple Myeloma," Multiple Myeloma: Plasma Cell Disorders: Merck Manual Professional, pp. 1-5, Jul. 2008.
Bhatia et al., "Protein Glycosylation: Implications for In Vivo Functions and Therapeutic Applications". Advances in Biochemical Engineering/Biotechnology, vol. 64: 155-201 (1998).
Binkert et al., "Cloning, sequence analysis and expression of a cDNA encoding a novel insulin-like growth factor binding protein (IGFBP-2)," The EMBO Journal, 8(9):2497-2502 (1989).
Bodey et al., "Failure of Cancer Vaccines: The Significant Limitations of this Approach to Immunotherapy," Anticancer Research, 20:2665-2676 (2000).
Bogdanovich et al., "Functional improvement of dystrophic muscle by myostatin blockade," Nature, 420:418-421 (2002).
Bork, "Powers and Pitfalls in Sequence Analysis: The 70% Hurdle," Genome Research, 10:398-400 (2000).
Bowie et al., "Deciphering the Message in Protein Sequences: Tolerance to Amino Acid Substitutions," Science, 247:1306-1310 (1990).
Broxmeyer et al., "Selective and indirect modulation of human multipotential and erythroid hematopoietic progenitor cell proliferation by recombinant human activin and inhibin," Proc. Natl. Acad. Sci. USA, 85:9052-9056 (1988).
Burdette et al., "Activin A mediates growth inhibition and cell cycle arrest through Smads in human breast cancer cells." Cancer Research, 65(17):7968-7975; (2005).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-2138 (1990).
Cadena et al., "Administration of a Soluble Activin Type IIB Receptor Promotes Skeletal Muscle Growth Independent of Fiber Type," Journal of Applied Physiology, 109:635-642 (2010).
Caricasole et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).
Cannon and Nedergaard, "Neither fat nor flesh," Nature, vol. 454(7207): 947-948 (2008).

(56) References Cited

OTHER PUBLICATIONS

Carrancio et al. "An activin receptor IIA ligand trap promotes erythropoiesis resulting in a rapid induction of red blood cells and haemoglobin," British Journal of Haematology, vol. 165: 870-882 (2014).
Casset et al., "A Peptide mimetic of an anti-CD4 monoclonal antibody by rational design," Biochemical and Biophysical Research Communications, vol. 307:198-205 (2003).
CDR Definitions from Handbook of Therapeutic Antibodies, (2007).
Centrella et al., "Activin-A Binding and Biochemical Effects in Osteoblast-Enriched Cultures from Fetal-Rat Parietal Bone," Molecular and Cellular Biology, 11(1):250-58 (1991).
Chamberlain et al., "Innovations and strategies for the development of anticancer vaccines," Expert Opinion on Pharmacotherapy, 1(4):603-614 (2000).
Chamow and Ashkenazi, "Immunoadhesins: Principles and Applications," TIBTECH, 14: 52-60 (1996).
Chang, "Exploring the Effects of Luteinizing Hormone-Releasing Hormone Agonist Therapy on Bone Health: Implications in the Management of Prostate Cancer," Urology, vol. 52: 29-35 (2003).
Chapman et al., "Effect of intron A from human cytomegalovirus (Towne) immediate-early gene on heterologous expression in mammalian cells," Nucleic Acids Research, 19(14):3979-3986 (1991).
Chantry et al., "Inhibiting Activin-A Signaling Stimulates Bone Formation and Prevents Cancer-Induced Bone Destruction in Vivo," Journal of Bone and Mineral Research, vol. 25(12): 2357-2370 (2010).
Chardès et al., "Efficient amplification and direct sequencing of mouse variable regions from any immunoglobulin gene family," FEBS Lett. vol. 452(3): 386-394 (1999).
Chavez-Tapia et al., "Insulin sensitizers in treatment of nonalcoholic fatty liver disease: Systematic review," World Journal of Gastroenterology, vol. 12(48): 7826-7831 (2006).
Chen et al., "Selection and Analysis of an Optimized Anti-VEGF Antibody: Crystal Structure of an Affinity-matured Fab in Complex with Antigen," J. Mol. Biol., vol. 293: 865-881 (1999).
Chen et al. "Regulation of Cell Proliferation, Apoptosis, and Carcinogenesis by Activin," Exp. Biol. Med., 227(2):75-87 (2002).
Cirillo et al., "Hematocrit, blood pressure, and hypertension. The Gubbio Population Study," Hypertension, 20(3):319-326 (1992).
Coerver et al., "Activin Signaling through Activin Receptor Type II Causes the Cachexia-Like Symptoms in Inhibin-Deficent Mice," Molecular Endocrinology, 10(5):534-543 (1996).
Collins, "Multidisciplinary Symposium: Haematological Malignancies," Cancer Imaging 5:S119-S126 (2005).
Colman, "Effects of amino acid sequence changes on antibody-antigen interactions," Research of Immunology, 145(1):33-36 (1994).
Crisan et al., "A Reservoir of Brown Adipocyte Progenitors in Human Skeletal Muscle," Stem Cells, vol. 26(9): 2425-2433 (2008).
Daluiski et al., "Bone Morphogenetic Protein-3 is a Negative Regulator of Bone Density," Nature Genetics, 27:84-88 (2001).
Database Geneseq [Online], "Variable heavy chain of anti-human Fas ligand antibody NOK-4," retrieved from EBI accession No. GSP:AAW00829; Database accession No. AAW00829; abstract, sequence (1997).
Database Geneseq [Online]; "Monoclonal antibody 10D4 HMGB1 Vkappa domain," retrieved from EBI accession No. GSP:ADY85028, Database accession No. GSP:ADY85028; abstract, sequence (2005).
Deal, "Potential New Drug Targets for Osteoporosis," Nature Clinical Practice, 5(1):20-27 (2009).
Deconinck et al., "Pathophysiology of Duchenne Muscular Dystrophy: Current Hypotheses," Pediatr. Neurol., 36:1-7 (2007).
Del Re et al., "Reconstitution and Analysis of Soluble Inhibin and Activin Receptor Complexes in a Cell-free System," The Journal of Biological Chemistry, 279(51):53126-53135 (2004).
Delogu et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).

Depaolo et al., "Passive Immunoneutralization with a Monoclonal Antibody Reveals a Role For Endogenous Activin-B in Mediating FSH Hypersecretion during Estrus and Following Ovariectomy of Hypophysectomized, Pituitary-Grafted Rats," Endocrinology, 130(3):1741-1743 (1992).
Donald et al., "SDR: a database of predicted specificity-determining residues in proteins," Nucleic Acids Research, vol. 37: D191-D194 (2009).
Donaldson et al., GenBank: BAA06548.1: activin typeII A receptor precursor [*Homo sapiens*] (1992).
Donaldson et al., "Activin and inhibin binding to the soluble extracellular domain of activin receptor II", Endocrinology 140(4):1760-1766 (1999).
Donaldson et al., "Molecular Cloning and Binding Properties of the Human Type II Activin Receptor", Biochemical and Biophysical Research Communications, 184(1):310-316 (1992).
Dussiot et al., "An activin receptor IIA ligand trap corrects ineffective erythropoiesis in B-thalassemia," Nature Medicine, vol. 20: 398-407 (2014).
Ear et al., "RAP-011 Efficiently Rescues Erthropoiesis in Zebrafish Models of Diamond Blackfan Anemia," 55 ASH Annual Meeting and Exposition, Abstract #3702 (2013).
Eijken, "The Activin A-Follistatin System: Potent Regulator of Human Extracellular Matrix Mineralization," The FASEB Journal, 21:2949-2960 (2007).
Elliot et al., "Enhancement of therapeutic protein in vivo activities through glycoengineering," Nature Biotechnology, vol. 21: 414-421 (2003).
Fafioffe et al., "Activin and inhibin receptor gene expression in the ewe pituitary throughout the oestrous cycle," Journal of Endocrinology, 182:55-68 (2004).
Fajardo et al., "Treatment with a Soluble Receptor for Activin Improves Bone Mass and Structure in the Axial and Appendicular Skeleton of Female Cynomolgus Macaques (*Macaca fascicularis*)," Bone, 46:64-71 (2010).
Fan et al., "Preclinical evaluation of Hematide, a novel erythropoiesis stimulating agent, for the treatment of anemia," Experimental Hematology 34:1303-1311 (2006).
Farmer, "Brown Fat and Skeletal Muscle: Unlikely Cousins?," Cell, vol. 134(5): 726-727 (2008).
Ferguson et al., "The role of effectors of the activin signalling pathway, activin receptors IIA and IIB, and Smad2, in patterning of tooth development," Development, vol. 128: 4605-4613 (2001).
Foucar, Myelodysplastic/ Myeloproliferative Neoplasms, Am J Clin Pathol, vol. 132: 281-289 (2009).
Fournier et al., "Blockade of the activin receptor IIb activates functional brown adipogenesis and thermogenesis by inducing mitochondrial oxidative metabolism," Mol. Cell. Biol. vol. 32(14): 2871-2879 (2012).
Frankel et al., "Characterization of diphtheria fusion proteins targeted to the human interleukin-3 receptor," Protein Engineering, vol. 13(8): 575-581 (2000).
Frigon, et al, "Regulation of Globin Gene Expression in Human K562 Cells by Recombinant Activin A," Blood, 79(3):765-772 (1992).
Fuller et al., "Activin A Is an Essential Cofactor for Osteoclast Induction," Biochemical and Biophysical Research Communications, 268:2-7 (2000).
Funaba et al., "Expression and Localization of Activin Receptors During Endochondral Bone Development," European Journal of Endocrinology, 144:63-71 (2001).
Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).
Gamer et al., "BMP-3 is a Novel Inhibitor of Both Activin and BMP-4 Signaling in Xenopus Embryos," Developmental Biology, 285:156-168 (2005).
Ge et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).

(56) References Cited

OTHER PUBLICATIONS

GenBank NM_001106, *Homo sapiens* activin A receptor, type IIB (ACVR2B), mRNA, http://www.ncbi.nlm.nih.gov/entrez/viewer.fcgi?db=nucleotide&val=116734707 (Downloaded on Jan. 29, 2007).
Gilbert et al., "Prolonged dystrophin expression and functional correction of mdx mouse muscle following gene transfer with a helper-dependent (gutted) adenovirus-encoding murine dystrophin," Human Molecular Genetics, 12(11)1287-1299 (2003).
Gilchrist et al., "Antagonists of the Receptor-G Protein Interface Block Gi-coupled Signal Transduction," The Journal of Biological Chemistry, 273(24):14912-14919 (1998).
Gonzalez-Cadavid et al., "Organization of the human myostatin gene and expression in healthy men and HIV-infected men with muscle wasting," PNAS, 95:14938-14943 (1998).
Gray et al., "Identification of a binding site on the type II activin receptor for activin and inhibin", The Journal of Biological Chemistry, 275(5):3206-3212(2000).
Greenspan et al., "Defining epitopes: It's not as easy as it seems," Nature Biotechnology, 17:936-937 (1999).
Greenwald et al., "Characterization of the Extracellular Ligand-Binding Domain of the Type II Activin Receptor," Biochemistry, 37(47):16711-16718 (1998).
Greenwald et al., "The BMP7/ActRII Extracellular Domain Complex Provides New Insights into the Cooperative Nature of Receptor Assembly," Molecular Cell, 11:605-617 (2003).
Greenwald et al., "Three-finger toxin fold for the extracellular ligand-binding domain of the type II activin receptor serine kinase," Nature Structural Biology, 6(1):18-22 (1999).
Gregoriadis et al., "Polysialic acids: potential in drug delivery," FEBS, 315(3):271-276 (1993).
Guo et al., Protein Tolerance to Random Amino Acid Change. Proc. Natl. Acad. Sci. USA, 101(25):9205-9210 (Jun. 22, 2004). Epub Jun. 14, 2004.
Gupta et al., "Transforming Growth Factor-beta Superfamily: Evaluation as Breast Cancer Biomarkers and Preventive Agents," Current Cancer Drug Targets, 4:165-182 (2004).
Gura, "Cancer Models: Systems for Identifying New Drugs Are Often Faulty," Science, 278(5340):1041-1042 (1997).
Haidar et al., "Paraspinal extramedullary hematopoiesis in patients with thalassemia intermedia," Eur Spine J., vol. 19: 871-878 (2010).
Hamrick et al., "Bone Mineral Content and Density in the Humerus of Adult Myostatin-Deficient Mice," Calcified Tissue International, 71:63-68 (2002).
Hamrick, "Increased Bone Mineral Density in the Femora of GDF8 Knockout Mice," The Anatomical Record, Part A 272A:388-391 (2003).
Hamrick, et al., "Femoral Morphology and Cross-sectional Geometry of Adult Myostatin-deficient Mice," Bone, 27(3):343-349 (2000).
Harousseau et al., "Multiple Myeloma," American Society of Hematology, pp. 237-256 (2004).
Harrison, et al., "An Activin Mutant with Disrupted ALK4 Binding Blocks Signaling via Type II Receptors," The Journal of Biological Chemistry, 279(27):28036-28044 (2004).
Harrison, et al., "Antagonists of activin signaling: mechanisms and potential biological applications," Trends in Endocrinology and Metabolism, 16(2):73-78 (2005).
Hashimoto et al., "Functional Regulation of Osteoblastic Cells by the Interaction of Activin-A with Follistatin," The Journal of Biological Chemistry, 267(7):4999-5004 (1992).
Hemmati-Brivanlou, et al., "A truncated activin receptor inhibits mesoderm induction and formation of axial structures in Xenopus embryos," Nature, 359:609-614 (1992).
Herbert et al., The Dictionary of Immunology, Academic Press, 3rd Edition, London, pp. 58-59 (1985).
Hilden et al., "Expression of Type II Activin Receptor Genes During Differentiation of Human K562 Cells and cDNA Cloning of the Human Type IIB Activin Receptor," Blood, 83(8):2163-2170 (1994).
Hill et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).
Holm et al., "Functional mapping and single chain construction of the anti-cytokeratin 8 monoclonal antibody TS1," Molecular Immunology, vol. 44(6): 1075-1084 (2007).
"Human Activin RIIA Antibody," R&D Systems, Tools for Cell Biology Research, Catalog No. MAB340 (Mar. 22, 2011).
Hsieh et al., "HIF-prolyl hydroxylase inhibition results in endogenous erythropoietin induction, erythrocytosis, and modest fetal hemoglobin expression in rhesus macaques," Blood, 110(6):2140-2147 (2007).
Ikenoue et al., "Inhibitory Effects of Activin-A on Osteoblast Differentiation During Cultures of Fetal Rat Calvarial Cells," Journal of Cellular Biochemistry, 75:206-214 (1999).
Ito et al., "Presence of activin signal transduction in normal ovarian cells and epithelial ovarian carcinoma," British Journal of Cancer, vol. 82(8): 1415-1420 (2000).
"The Illustrated Guide to Bone Marrow Diagnosis Second Edition," Ed. By G. Kumar. Originally published 2003.
Kaiser, "First Pass at Cancer Genome Reveals Complex Landscape," Science, 313:1370 (2006).
Kanemitsu, "Clinical application of subforms of creatine kinase MM and macro creatine kinases," Journal of Chromatography, vol. 526: 423-438 (1990).
Kaspar, et al., "Retrograde Viral Delivery of IGF-1 Prolongs Survival in a Mouse ALS Model," Science, 301:839-842 (2003).
Kim, et al., "ACE-011, a Soluble Activin Receptor Type IIa IgG-Fc Fusion Protein, Increases Hemoglobin and Hematocrit Levels in Postmenopausal Healthy Women," Blood, 112(11) (2008).
Knight, "Roles of Inhibins, Activins, and Follistatin in the Female Reproductive System," Frontiers in Neuroendocrinology, 17:476-509 (1996).
Koncarevic et al., "A Soluble Activin Receptor Type IIB Prevents the Effects of Androgen Deprivation on Body Composition and Bone Health," Endocrinology, vol. 151(9); 4289-4300 (2010).
Kos et al., "Activin type II receptors in embryonic dorsal root ganglion neurons of the chicken," J. Neurobiol., vol. 47(2): 93-108 (2001).
Kosaki et al., "Left-Right Axis Malformations Associated With Mutations in ACVR2B, the Gene for Human Activin Receptor Type IIB," American Journal of Medical Genetics, 82:70-76 (1999).
Koseki et al., "Role of TGF-beta Family in Osteoclastogenesis Induced by RANKL," Cellular Signaling, 14:31-36 (2002).
Krag et al., "Heregulin ameliorates the dystrophic phenotype in mdx mice," PNAS, 101(38):13856-13860 (2004).
Krneta et al., "Dissociation of Angiogenesis and Tumorigenesis in Follistatin- and Activin-Expressing Tumors," Cancer Research, 66(11):5686-5695 (2006).
Krystal et al., "Transforming Growth Factor ☐1 Is an Inducer of Erythroid Differentiation". J. Exp. Med. vol. 180 pp. 851-860 (1994).
Kubanek, "Introduction: The Role of the Microenvironment and Cytokines on the Modulation of Erythropoiesis," Annals New York Academy of Sciences, pp. 257-258 (1994).
Kumar et al., "Regulation of FSHbeta and GnRH Receptor Gene Expression in Activin Receptor II Knockout Male Mice," Mol. Cell. Endocrinol., 212:19-27 (2003).
Kunihro et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).
Kuntz, "Structure-Based Strategies for Drug Design and Discovery," Science, 257:1078-1082 (1992). (Abstract only).
Lazar, "How Now, Brown Fat?" Science, vol. 321(5892): 1048-1049 (2008).
Kwiatkowski et al., "Iron chelation therapy in sickle-cell disease and other transfusion-dependent anemias," Hematol Oncol Clin N Am., vol. 18: 1355-1377 (2004).
Lazar et al., "Transforming Growth Factor α: Mutation of Aspartic Acid 47 and Leucine 48 Results in Different Biological Activities," Molecular and Cellular Biology, 8(3):1247-1252 (1988).

(56) References Cited

OTHER PUBLICATIONS

Lebrun et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS, 98(16):9306-9311 (2001).
Leto et al., "Activin A Circulating Levels in Patients with Bone Metastasis from Breast or Prostate Cancer," Clin Exp Metastasis, 23:117-122 (2006).
Li et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).
Lifespan Biosciences, Activin Receptor Type 2A (ACVR2A) Mouse anti-Human Monoclonal Antibody—LS-C33835—LifeSpan Biosciences, (2010).
Liu et al., "Characterization of isoforms of activin receptor-interacting protein 2 that augment activin signaling," Journal of Endocrinology, vol. 189: 409-421 (2006).
Lotinun et al., "A Soluble Activin Receptor Type IIA Fusion Protein (ACE-011) Increases Bone Mass via a Dual Anabolic-Antiresorptive Effect in Cynomolgus Monkeys," Bone, 46:1082-1088 (2010).
Lu et al., "Simian Immunodeficiency Virus DNA Vaccine Trial in Macaques," Journal of Virology, 70(6):3978-3991 (1996).
Ludlow et al., "Development of a new antibody to the human inhibin/activin βB subunit and its application to improved inhibin B ELISAs," J. Immunol. Methods, 329:102-111 (2008).
Ma, "Animal Models of Disease," Modern Drug Discovery, 30-36 (2004).
MacCallum et al., "Antibody-antigen Interactions: Contact Analysis and Binding site Topography," J. Mol. Biol, vol. 262: 732-745 (1996).
MacLennan et al., "Multiple Myeloma," BMJ, vol. 308:1033-1036 (1994).
Maguer-Satta et al, "A Novel Role for Fibronectin Type 1 Domain in the Regulation of Human Hematopoietic Cell Adhesiveness Through Binding to Follistatin Domains of FLRG and Follistatin," Experimental Cell Research, 312(4):434-442 (2006).
Maguer-Satta et al, "Regulation of human erythropoiesis by activin A, BMP2, and BMP4, members of the TGFβ family," Experimental Cell Research, 282:110-120 (2003).
Maguer-Satta et al., "FLRG, Member of the Follistatin Family, a New Player in Hematopoiesis," Molecular and Cellular Endocrinology, 225:109-118 (2004).
Marri et al, "Human Biochemistry, Moscow, Mir", vol. 1: 34-35 (1993).
Mathews et al., "Expression Cloning of an Activin Receptor, a Predicted Transmembrane Serine Kinase," Cell, 65(6):973-982 (1991).
Matzuk et al., "Cloning of the human activin receptor cDNA reveals high evolutionary conservation," Biochim Biophys Acta, 1130(1):105-108 (1992).
Matzuk et al., "Different phenotypes for mice deficient in either activins or activin receptor type II," Nature, 374:356-360 (1995).
McCarthy et al., Monoclonal antibodies that recognize the type-2 activin receptor, ACTR2, Hybridoma, vol. 13(3): 199-203 (1994).
McNally, "Powerful Genes—Myostatin Regulation of Human Muscle Mass," N. Engl. J. Med., 350(26):2642-2644 (2004).
McPherron, et al., "GDF-3 and GDF-9: Two New Members of the Transforming Growth Factor-Beta Superfamily Containing a Novel Pattern of Cysteines," Journal of Biological Chemistry, 268(5):3444-3449 (1993).
McPherron, et al., "Regulation of Skeletal Muscle Mass in Mice by a New TGF-beta Superfamily Member," Nature, 387:83-90 (1997).
McPherron and Lee, "Suppression of body fat accumulation in myostatin-deficient mice," The Journal of Clinical Investigation, vol. 109(5): 595-601 (2002).
McPherson et al., "Growth inhibitory response to activin A and B by human prostate tumour cell lines LNCaP and DU145", Journal of Endocrinology, 154:535-545 (1997).
Menstruation: Absent Periods (Amenorrhea), Website downloaded on Jun. 14, 2010, <http://adam.about.com/reports/000101_2.htm?p=1> (11 pages).
Merck Manual. Iron-Utilization Anemias (Sideroblastic Anemias), pp. 1150-1151 (1992).
Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.
Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.
The Merck Manual of Diagnosis and Therapy, 17th Edition. myelodysplastic Syndrome, pp. 865 and 963-955 (1999).
Meriggiola et al., "Follistatin Decreases Activin-Stimulated FSH Secretion with No Effect On GnRH-Stimulated FSH Secretion in Prepubertal Male Monkeys," Endocrinology, 134(4):1967-1970 (1994).
Monoclonal Anti-human Activin RII Antibody, R&D Systems, Catalog No. MAB3391 (Feb. 18, 2009).
The website downloaded Oct. 28, 2014 from the Multiple Myeloma Research Foundation, themmrf.org/multiple-myeloma/symptoms/bone-lesions/, 2 pages total.
Mickle et al., "Genotype-Phenotype Relationships in Cystic Fibrosis," Med. Clin. North Am., 84(3):597-607 (2000).
Miller et al., "Ligand Binding to Proteins: The Binding Landscape Model," Protein Science, 6:2166-2179 (1997).
Miura et al., "Utrophin upregulation for treating Duchenne or Becker muscular dystrophy: how close are we?," Trends in Molecular Medicine, 12(3):122-129 (2006).
Moore et al., "Molecular Basis of Bone Morphogenetic Protein-15 Signaling in Granulosa Cells*," The Journal of Biological Chemistry, vol. 278(1): 304-310 (2003).
Morrison et al., "A soluble activin type IIB receptor improves function in a mouse model of amyotrophic lateral sclerosis," Experimental Neurology vol. 217: 258-268 (2009).
Mosekilde et al., "Emerging Anabolic Treatments in Osteoporosis," Current Drug Safety, 6:62-74 (2011).
Murase et al., "Possible Involvement of Protein Kinases and Smad2 Signaling Pathways on Osteoclast Differentiation Enhanced by Activin A," Journal of Cellular Physiology, 188:236-242 (2001).
Murata et al., "Anti-activin A Antibody (IgY) Specifically Neutralizes Various Activin A Activities," Proceedings of the Society for Experimental Biology & Medicine, 211(1):100-107 (1996).
Nagamine et al., "Immunohistochemical Detection of Activin A, Follistatin, and Activin Receptors during Fracture Healing in the Rat," Journal of Orthopaedic Research, 16:314-321 (1998).
Nakamura et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).
Nemeth, "Hepcidin in Beta-thalassemia," Annals of the New York Academy of Sciences, vol. 1202: 31-35. Published Aug. 2, 2010.
Ngo et al., "Computational Complexity, Protein Structure Prediction, and the Levinthal Paradox," The Protein Folding Problem and Tertiary Structure Prediction, Merz et al., eds., Birkhauser, Boston, 433 and 492-495 (1994).
"NIH website downloaded May 28, 2014 from: web.archive.org/web/20030409091558/http://www.cc.nih.gov/ccc/patient_education/pepubs/subq.pdf; Patient Information Publications: Giving a Subcutaneous Injection ( 6 pages total)".
Ogawa et al., "Bovine Bone Activin Enhances Bone Morphogenetic Protein-Induced Ectopic Bone Formation," The Journal of Biological Chemistry, 267(20):14233-14237 (1992).
Oh et al., "Activin type IIA and IIB receptors mediate Gdf11 signaling in axial vertebral patterning," Genes & Development, 16:2749-2754 (2002).

(56) References Cited

OTHER PUBLICATIONS

Oue et al., "Effect of Local Injection of Activin A on Bone Formation in Newborn Rats," Bone, 15(3):361-366 (1994).
Padlan et al., "Identification of specificity-determining residues in antibodies," The FASEB Journal, vol. 9: 133-139 (1995).
Paulson, "Targeting a new regulator of erythropoiesis to alleviate anemia," Nature Medicine, News and Views, vol. 20(4) (2 pages) (2014).
Pakula and Sauer, "Genetic analysis of protein stability and function," Annu. Rev. Genet., vol. 23: 289-310 (1989).
Patel et al., "The function of Myostatin and strategies of Myostatin blockade—new hope for therapies aimed at promoting growth of skeletal muscle," Neuromuscular Disorders, 15:117-126 (2005).
Paul, Fundamental Immunology, 3rd edition, Raven Press, New York, 1003: 292-295 (1999).
Pearsall et al., An investigative pharmacology study of a GDF-8 (myostatin) inhibitor, ACE-031, in the common Marmoset (*Callithrix jacchus*), Database Biosis, Biosciences Information Service, Accession No. PREV201200750016; Faseb Journal, vol. 22, Experimental Biology Annual Meeting, San Diego, CA Apr. 5-9, 2008 (Abstract).
Pearsall et al., "A Soluble Activin Receptor Type IIA (ACTRIIA) Acts As a Novel Bone Anabolic Agent," The Official Journal of the European Calcified Tissue Society, 34th Europena Symposium on Calcified Tissues, May 2007.
Pearsall et al., "Treatment with a Soluble Activin Type II Receptor Reverses Bone Loss in Ovariectomized Mice," Journal of Bone and Mineral Research 2006 Abstracts, 21(1):s1-s530 (2006).
Pearsall et al., "A soluble activin Type IIA receptor induces bone formation and improves skeletal integrity", PNAS, 105(19):7082-7087 (2008).
Perrien et al., "Inhibin A Is an Endocrine Stimulator of Bone Mass and Strength," Endocrinology, 148(4):1654-1665 (2007).
Phillips, "The challenge of gene therapy and DNA delivery," J. Pharm. Pharmacology, 53:1169-1174 (2001).
Pirollo et al., "Targeted Delivery of Small Interfering RNA: Approaching Effective Cancer Therapies," Cancer Res., 68(5):1247-1250 (2008).
Qi et al., "Blockade of type □ transforming growth factor signaling prevents liver fibrosis and dysfunction in the rat," PNAS, 96:2345-2349 (1999).
Raju, "Glycosylation in the Fc domain of IgG increases resistance to proteolytic cleavage by papain," Biochemical and Biophysical Research Communications, 341:797-803 (2006).
Rebbapragada et al., "Myostatin Signals Through a Transforming Growth Fact beta-Like Signaling Pathway To Block Adipogenesis," Molecular and Cellular Biology, 23(20):7230-7242 (2003).
"Recombinant Human Activin RIIB/Fc Chimera," R&D Systems 339-RB/CF (Aug. 27, 2003).
"Recombinant Human Activin RIIA/Fc Chimera," R&D Systems 340-R2 (Aug. 27, 2003).
Reis et al., "Activin, Inhibin and the Human Breast," Molecular and Cellular Edocrinology, 225:77-82 (2004).
Risbridger et al., "Activins and Inhibins in Endocrine and Other Tumors," Endocrine Reviews, 22(6):836-858 (2001).
Robinson et al., "Inhibins and Activins Regulate Mammary Epithelial Cell Differentiation Through Mesenchymal-epithelial Interactions," Development, 124:2701-2708 (1997).
Rodriquez et al., "Enhanced Osteoclastogenesis Causes Osteopenia in Twisted Gastrulation-Deficient Mice Through Increased BMP Signaling," J. Bone Miner. Res., 24(11):1917-1926 (2009).
Rosenzweig et al., "Cloning and characterization of a human type II receptor for bone morphogenetic proteins," PNAS, 92:7632-7636 (1995).
Ruckle et al., "Single-Dose, Randomized, Double-Blind, Placebo-Controlled Study of ACE-011 (ActRIIA-IgG1) in Postmenopausal Women," Journal of Bone and Mineral Research, vol. 24(4), pp. 744-752 (2009).
Ruzek et al. "Minimal Effects on Immune Parameters Following Chronic Anti-TGF-□ Monoclonal Antibody Administration to Normal Mice", Immunopharmacology and Immunotoxicology, 25(2):235-257 (2003).
Sakai et al., "Activin Enhances Osteoclast-Like Cell Formation in Vitro," Biochemical and Biophysical Research Communications, 195(1):39-46 (1993).
Sakai et al., "Activin Increases Bone Mass and Mechanical Strength of Lumbar Vertebrae in Aged Ovariectomized Rats," Bone, 27(1):91-96 (2000).
Sakai et al., "Activin release from bone coupled to bone resorption in organ culture of neonatal mouse calvaria," Bone, 26(3):235-240 (2000).
Sakai et al., "Involvement of Activin in the Regulation of Bone Metabolism," Molecular and Cellular Endocrinology, 180:183-188 (2001).
Sakai et al., "Local Administration of Activin Promotes Fracture Healing in the Rat Fibula Fracture Model," Bone, 25(2):191-196 (1999).
Sakai et al., "The Measurement of Activin/EDF in Mouse Serum: Evidence for Extragonadal Production", Biochecmical and Biophysical Research Communications, 188(2):921-926 (1992).
Sakai et al., "Osteogenic Activity of Activin in Young Normal Rats and Young Adult and Aged Rats after Ovarlectomy," Bone 23:(Suppl.) 467 (1998).
Sako et al., "Characterization of the Ligand Binding Functionality of the Extracellular Domain of Activin Receptor Type IIB," The Journal of Biological Chemistry, 285(27):21037-21048 (2010).
Satoh et al., "Hemodynamic changes by recombinant erythropoietin therapy in hemodialyzed patients," Hypertension, 15(3):262-266 (1990).
Schmelzer et al., "Purification and Characterization of Recombinant Human Activin B," Biochimica et Biophysica Acta, 1039(2):135-141 (1990).
Schuelke et al., "Myostatin Mutation Associated with Gross Muscle Hypertrophy in a Child," New England Journal of Medicine, 350(26):2682-2688 (2004).
Seale et al., "PRDM16 controls a brown fat/skeletal muscle switch," Nature, vol. 454(7207): 961-967 (2008).
Shao et al., "Effect of Activin A on Globin Gene Expression in Purified Human Erythroid Progenitors," Blood, 79(3):773-781 (1992).
Shao et al., "Efficient synthesis of globoside and isogloboside tetrasaccharides by using beta (1-->3) N-acetylgalactosaminyltransferase/UDP-N-acetyglucosamine C4 epimerase fusion protein," Chem Commun.: 1422-1423 (2003).
Shapiro et al., "Side Effects of Adjuvant Treatment of Breast Cancer," New England Journal of Medicine, vol. 344: 1997-2008 (2001).
Shav-Tal et al., "The Role of Activin A in Regulation of Hemopoiesis," Stem Cells, 20:493-500 (2002).
Shi et al., "Energy Balance, Myostatin, and GILZ: Factors Regulating Adipocyte Differentiation in Belly and Bone," PPAR Research, pp. 1-12 (2007).
Shiozaki et al., "Activin A: A Commitment Factor in Erythroid Differentiation," Biochemical and Biophysical Research Communications, 242:631-635 (1998).
Shiozaki et al, "Evidence for the participation of endogenous activin A/erythroid differentiation factor in the regulation of erythropoiesis," Proc. Natl. Acad. Sci. USA, 89:1553-1556 (1992).
Shiozaki et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).
Shoji et al., "Identification and Characterization of a PDZ Protein That Interacts with Activin Type II Receptors," The Journal of Biological Chemistry, vol. 275(8): 5485-5492 (2000).
Shuto et al., "Osteoblasts Express Types I and II Activin Receptors During Early Intramembranous and Endochondral Bone Formation," Journal of Bone Mineral Research, 12(3):403-411 (1997).
Smith et al., "The analysis of doxorubicin resistance in human breast cancer cells using antibody microarrays," Mol. Cancer Therapy, vol. 5: 2115-2120 (2006).

(56) References Cited

OTHER PUBLICATIONS

Smith et al., The Status, Quality, and Expansion of the NIH Full-Length cDNA Project: The Mammalian Gene Collection (MGC), Genome Res., vol. 14(10b),: 2127-2127 (2004).
Song et al., "The Type II Activin Receptors Are Essential for Egg Cylinder Growth, Gastrulation, and Rostral Head Development in Mice," Development Biology, 213:157-169 (1999).
Pearsall et al., 2007, "The use of a soluble activin receptor type IIa as a novel anabolic agent for treatment of bone loss." Osteoporos Int., 18(Suppl 1):152.
Sun et al., "FSH Directly Regulates Bone Mass," Cell, 125:247-260 (2006).
Suragani et al., "4236 ACE-536, a Modified Type II Activin Receptor Increases Red Blood Cells in Vivo by Promoting Maturation of Late Stage Erythroblasts," 52nd ASH Annual Meeting and Expositions, Orange County Convention Center, Orlando, FL Dec. 4-7, 2010. (abstract).
Suragani et al., "Transforming growth factor-β superfamily ligand trap ACE-536 corrects anemia by promoting late-stage erythropoiesis," Letters, Nature Medicine, Advance Online Publication (44 pages) (2014).
Swanson et al., "Use of Biosensors to Monitor the Immune Response," Biologies, vol. 109: 71-78 (2000).
Swanson, "New Technologies for the Detection of Antibodies to Therapeutic Proteins," Immunogenicity of Therapeutics Biological Products, vol. 112: 127-133 (2003).
Tanno and Miller, "Iron Loading and Overloading due to Ineffective Erythropoiesis," Advances in Hematology, Article ID 358283, Chapter 2 (Abstract) (2010).
Thompson et al., "Structures of an ActRIIB: activin A complex reveal a novel binding mode for TGF-beta ligand: receptor interactions", EMBO 22(7):1555-1566 (2003).
Thompson et al., "Beta A versus beta B: is it merely a matter of express?," Molecular and Cellular Endocrinology, 225:9-17 (2004).
Thorpe and Swanson, "Current methods for Detecting Antibodies against Erythropoietin and Other Recombinant Proteins," Clinical and Diagnostic Laboratory Immunology, vol. 12(1): 28-39 (2005).
Tinsley et al., "Expression of full-length utrophin prevents muscular dystrophy in mdx mice," Nature Medicine, 4(12):1441-1444 (1998).
Tisdale, "Cachexia in Cancer Patients," Nat. Rev. Cancer, 2:862-871 (2002).
Tokuriki et al., "Stability effects of mutations and protein evolvability," Current Opinion in Structural Biology, 19:596-604 (2009).
Trivedi et al., "Investigational Anabolic Therapies for Osteoporosis," Expert Opin. Investig. Drugs, 19(8):995-1005 (2010).
Truksa et al., "Bone morphogenetic proteins 2, 4, and 9 stimulate murine hepcidin 1 expression independently of Hfe, transferrin receptor 2 (Tfr2), and IL-6," PNAS, vol. 103(27): 10289-10293 (2006).
Tseng et al., "New role of bone morphogenetic protein 7 in brown adipogenesis and energy expenditure," Nature: International Weekly Journal of Science (and Supplementary Information), vol. 454(7207): 1000-1004 (2008).
Tsuchida et al., "Activin isoforms signal through type I receptor serine/threonine kinase ALK7," Molecular and Cellular Endocrinology, 220:59-65 (2004).
Tu et al., "Genetic Disruption of Myostatin Reduces the Development of Proatherogenic Dyslipidemia and Atherogenic Lesions in Ldlr Null Mice," Diabetes, 58:1739-1748 (2009).
Type 2 Diabetes, PubMed Health, Diseases and Conditions, U.S. National Library of Medicine, Bethesda, MD (online), Jun. 28, 2011 [retrieved on Jun. 6, 2012). Retrieved from the Internet:<URL:http://www.ncbi.nlm.nih.gov/pubmedhealth/PMH0001356/>.
Ukkola et al., "Adiponectin: A Link Between Excess Adiposity and Associated Comorbidities?", Journal of Molecular Medicine, 80(11):696-702 (2002).
Utzschneider et al., Review: The Role of Insulin Resistance in Nonalcoholic Fatty Liver Disease, J. Clin. Endocrinol. Metab., 91(12):4753-4761 (Dec. 2006), Epub Sep. 12, 2006.

US Biological Technical Data Sheet for A0856-10A, accessed on Feb. 20, 2013.
US Biological, Activin Receptor Type IIA (RIIA) A0856-05E www.usbio.net/technicalsheet.php?item=A0856-05E dated Jun. 8, 2010.
Vajdos et al., "Comprehensive Functional Maps of the Antigen-binding Site of an Anti-ErbB2 Antibody Obtained with Shotgun Scanning mutagenesis," J. Mol. Biol., vol. 320(2): 415-428 (2002).
Vallet et al., "Activin A promotes multiple myeloma-induced osteolysis and is a promising target for myeloma bone disease," PNAS, 107(11):5124-5129 (2010).
Vidal et al., "Making sense of antisense," European Journal of Cancer, 41:2812-2818 (2005).
Wagner et al., "A Phase I/II trial of MYO-029 in Adult Subjects with Muscular Dystrophy," Ann. Neurol., 63:561-571 (2008).
Wagner et al., "Loss of Myostatin Attenuates Severity of Muscular Dystrophy in mdx Mice," Ann. Neurol., 52:832-836 (2002).
Wagner et al., "Muscle regeneration in the prolonged absence of myostatin," PNAS, 102(7):2519-2524 (2005).
Walsh et al., "Myostatin: a modulator of skeletal-muscle stems cells," Biochemical Society Transactions, 33(Pt.6):1513-1517 (2005).
Wang et al., "A Single Amino Acid Determines Lysophospholipid Specificity of the $S1P_1(EDG1)$ and $LPA_1$ (EDG2) Phospholipid Growth Factor Receptors," The Journal of Biological Chemistry, 276(52):49213-49220 (2001).
Wang et al., "GDF-3 is an adipogenic cytokine under high fat dietary condition," Biochemical and Biophysical Research Comm., 321(4):1024-1031 (2004).
Ware, "How I use hydroxyurea to treat young patients with sickle cell anemia," Blood, vol. 115(26): 5300-5311 (2010).
Ward, "An update on disordered iron metabolism and iron overload," Hematology, vol. 15(5): 311-317 (2010).
Weber et al., A slient H-bond can by mutationally activated for high-affinity interaction of BMP-2 and activin type IIB receptor, BMC Structural Biology, 7(6):1-20 (2007).
Wells, "Additivity of Mutational Effects in Proteins," Biochemistry, 29(37):8509-8517 (1990).
Welt et al., "Activin: an endocrine or panacrine agent?," European Journal of Endocrinology 139:469-471 (1998).
Wiater et al., "Inhibin is an Antagonist of Bone Morphogenetic Protein Signaling," The Journal of Biological Chemistry, 278(10):7934-7941 (2003).
Wolfman et al., "Activation of latent myostatin by the BMP-1/tolloid family of metalloproteinases," PNAS, 100(26):15842-15846 (2003).
Wong et al., "Validation parameters for a novel biosensor assay which simultaneously measures serum concentrations of a humanized monoclonal antibody and detects induced antibodies," Journal of Immunological Methods, vol. 209: 1-15 (1997).
Yamato et al., "Induction of apoptosis in Myeloma Cells with Activin A," Japanese Journal of Clinical Hematology; 37th Annual Meeting, Symposium 3, Apoptosis in Blood Disorders, 37:7, pp. 564-567, (2012). (translated).
Yokota et al., "Isolation and characterization of a mouse cDNA clone that expresses mast-cell growth-factor activity in monkey cells," Proc. Natl. Acad. Sci. USA, 81:1070-1074 (1984).
Yu et al., "Specific roles of activin/inhibin in human erythropoiesis in vitro." Annals New York Academy of Sciences, 20(10):1243-1246 (1991).
Yu et al., "Importance of FSH-releasing protein and inhibin in erythrodifferentiation," Nature, 330:765-767 (1987).
Zatz et al., "Serum creatine-kinase (CK) and pyruvate-kinase (PK) activities in Duchenne (DMD) as compared with Becker (BMD) muscular dystrophy," Journal of the Neurological Sciences, vol. 102: 190-196 (1991).
Zhang et al., Effects of Activin A on the Activities of the Mouse Peritoneal Macrophages, Cellular & Molecular Immunology, vol. 2(1): 63-67 (2005).
Zhao et al., "Transgenic expression of myostatin propeptide prevents diet-induced obesity and insulin resistance," Biochemical and Biophysical Research Communications, 337:248-255 (2005).
International Search Report dated Jun. 9, 2016 for International Patent Application No. PCT/US2015/063595.

(56) References Cited

OTHER PUBLICATIONS

Written Opinion of the International Searching Authority dated Jun. 9, 2016 for International Patent Application No. PCT/US2015/063595.
International Search Report dated Jun. 9, 2016 for International Patent Application No. PCT/US2015/063835.
Written Opinion of the International Searching Authority dated Jun. 9, 2016 for International Patent Application No. PCT/US2015/063835.
Akhtari, M., "When to Treat Myelodysplastic Syndromes," Oncology, vol. 25(6): 480-486 (2011).
Anonymous "Ferritin" www.webmd.com/a-to-z-guides/ferritin?page=2 originally published 2008.
Anonymous "Iron and Thalassemia," Accessed on the Internet Apr. 3, 2014 at <sickle.bwh.harvard.edu/thaliron.html>. Published Aug. 25, 1997.
Attie, et al., "A Phase 1 Study of ACE-536, A Regulator of Erythroid Differentiation, in Healthy Volunteers," American Journal of Hematology, vol. 89(7): 766-770 (2014).
Attisano et al., "Novel activin receptors: distinct genes and alternative mRNA splicing generate a repertoire of serine/threonine kinase receptors", Cell 68: 97-108 (1992).
Barzi, et al., "Myelodysplastic Syndromes: A Practical Approach to Diagnosis and Treatment," Cleveland Clinic Journal of Medicine, vol. 77(1): 37-44 (2010).
Bejar et al. Validation of a prognostic model and the impact of SF3B1, DNMT3A, and other mutations in 289 genetically characterized lower risk MOS patient samples. Abstract. Blood, vol. 118, No. 21. Abstract No. 969. (Nov. 18, 2011).
Bejar, et al., "Recent Developments in Myelodysplastic Syndromes," Blood, vol. 124(18): 2793-2803 (2014).
Bennett, et al., "Proposals for the Classification of the Myelodysplastic Syndromes," British Journal of Hematology, vol. 51: 189-199 (1982).
Biankin, et al., "Pancreatic Cancer Genomes Reveal Aberrations in Axon Guidance Pathway Genes," Nature, vol. 491: 399-405 (2012).
Bottomley, et al., "Siderbloastic Anemia: Diagnosis and Management," Hematology Oncology Clinic of North America, vol. 28: 653-670 (2014).
Camaschella, C., "Recent Advances in the Understanding of Inherited Sideroblastic Anemia", British Journal of Haematology, vol. 143:27-38 (2008).
Cao, et al., "Recent Advances in 13-thalassemias," Pediatric Reports, vol. 3(e17): 65-78 (2011).
Casadevall, et al., "Health, Economic, and Quality-of-Life Effects of Erythropoietin and Granulocyte Colony-Stimulating Factor for the Treatment of Myelodysplastic Syndromes: A Randomized, Controlled Trial," Blood, vol. 104(2): 321-327 (2014).
Cazzola, et al., "Quantitative Evaluation of Erythropoietic Activity in Dysmyelopoietic Syndromes," British Journal of Hematology, vol. 50: 55-62 (1982).
Cazzola, et al., "The Genetic Basis of Myelodysplasia and Its Clinical Relevance," Blood, vol. 122(25): 4021-4034 (2013).
Chesnais, et al., "Spliceosome Mutations in Myelodysplastic Syndromes and Chronic Myelomonocytic Leukemia," Impact Journals: Oncotarget, vol. 3(11): 1284-1293 (2012).
Cheson, et al., "Clinical Application and Proposal for Modification of the International Working Group (IWG) Response Criteria in Myelodysplasia," Blood, vol. 108(2): 419-425 (2006).
Cheson, et al., "Report of an International Working Group to Standardize Response Criteria for Myelodysplastic Syndromes," Blood, vol. 96(12): 3671-3674 (2000).
Davidoff, et al., "Patterns of Erythropoiesis-Stimulating Agent Use Among Medicare Beneficiaries with Myelodysplastic Syndromes and Consistency with Clinical Guidelines," Leukemia Research, vol. 37: 675-680 (2013).
Dayyani, et al., "Cause of Death in Patients with Lower-Risk Myelodysplastic Syndrome," Cancer, vol. 116: 2174-2179 (2010).
Demetri, et al., "Quality-of-life Benefit in Chemotherapy Patients Treated With Epoetin Alfa Is Independent of Disease Response or Tumor Type: Results From a Prospective Community Oncology Study," Journal of Clinical Oncology, vol. 16(10): 3412-3425 (1998).
Dolatshad, et al., "Disruption of SF3B1 Results in Deregulated Expression and Splicing of Key Genes and Pathways in Myelodysplastic Syndrome Hematopoietic Stem and Progenitor Cells," Leukemia, vol. 29: 1092-1103 (2015).
Dore et al., "Serum erythropoietin levels in thalassemia intermedia," Annals of Hematology, vol. 67:183-186 (1993).
Esposito, et al., "Labile Plasma Iron in Iron Overload: Redox Activity and Susceptibility to Chelation," Blood, vol. 102(7): 2670-2677 (2003).
Estey, E. H., "Current Challenges in Therapy of Myelodysplastic Syndromes," Current Opinion in Hematology, vol. 1 O: 60-67 (2003).
Fenaux, et al., "Efficacy of Azacitidine Compared with that of Conventional Care Regimens in the Treatment of Higher-Risk Myelodysplastic Syndromes: A Randomised, Open-Label, Phase III Study," The Lancet: Oncoloov, vol. 10: 223-232 (2009).
Furney, et al., "SF3B1 Mutations Are Associated with Alternative Splicing in Uveal Melanoma," Cancer Discovery, vol. 3(10): 1122-1129 (2013).
Galanello, et al., "Combined Iron Chelation Therapy," Annals of the New York Academy of Sciences, vol. 1202: 79-86 (2010).
Garcia-Manero, et al., "Hypomethylating Agents and Other Novel Strategies in Myelodysplastic Syndromes," Journal of Clinical Oncology, vol. 29(5): 516-523 (2011).
Giagounidis, et al., "Outcomes in RBC Transfusion-Dependent Patients with Low-/lntermediate-1-Risk Myelodysplastic Syndromes with Isolated Deletion Sq Treated with Lenalidomide: A Subset Analysis from the MDS-004 Study," European Journal of Hematology, vol. 93: 429-438 (2014).
Glaspy, et al., "Impact of Therapy with Epotin Alfa on Clinical Outcomes in Patients with Nonmyeloid Malignancies During Cancer Chemotherapy in Community Oncology Practice," Journal of Clinical Oncology, vol. 15(3): 1218-1234 (1997).
Glaspy, J. A., "Erythropoietin in Cancer Patients," The Annual Review of Medicine, vol. 60: 181-192 (2009).
Goldberg, et al., "Incidence and Clinical Complications of Myelodysplastic Syndromes Among United States Medicare Beneficiaries," Journal of Clinical Oncology, vol. 28(17): 2847-2852 (2010).
Greenberg, et al., "Myelodysplastic Syndromes: Clinical Practice Guidelines in Oncology," Journal of the National Comprehensive Cancer Network, vol. 9(1): 30-56 (2011).
Greenberg, et al., "Treatment of Myelodysplastic Syndrome Patients with Erythropoietin with or without Granulocyte Colony-Stimulating Factor: Results of a Prospective Randomized Phase 3 Trial by the Eastern Cooperative Oncology Group (E1996)," Blood, vol. 114(12): 2393-2400 (2009).
Hellstrom-Lindberg, et al., "A Validated Decision Model for Treating the Anaemia of Myelodysplastic Syndromes with Erythropoietin + Granulocyte Colony-Stimulating Factor: Significant Effects on Quality of Life," British Journal of Haematology, vol. 120: 1037-1046 (2003).
Hori, et al., "European Best Practice Guidelines 14-16 Inadequate Response to Epoetin," Nephrology Dialysis Transplantation, vol. 15(Supp. 4): 43-50 (2000).
Jacobs et al., "European Best Practice Guidelines 5 Target haemoglobin," Nephrology Dialysis Transplaantation, vol. 15[Suppl4]: 15-19 (2000).
Je, et al., "Mutational Analysis of Splicing Machinery Genes SF3B1, U2AF1 and SRSF2 in Myelodysplasia and Other Common Tumors," International Journal of Cancer, vol. 133: 260-266 (2013).
Jelkmann, et al., "The Erythropoietin Receptor in Normal and Cancer Tissues," Critical Reviews in Oncology/Hematology, vol. 67: 39-61 (2008).
Juneja, et al., "Prevalence and Distribution of Ringed Sideroblasts in Primary Myelodysplastic Syndromes," Journal of Clinical Pathology, vol. 36: 566-569 (1983).
Kalinowski, et al., "The Evolution of Iron Chelators for the Treatment of Iron Overload Disease and Cancer," Pharmacological Reviews, vol. 57(4): 547-583 (2005).

(56) References Cited

OTHER PUBLICATIONS

Kantarjian, et al., "Safety and Efficacy of Romiplostim in Patients With Lower-Risk Myelodysplastic Syndrome and Thrombocytopenia," Journal of Clinical Oncology, vol. 28(3): 437-444 (2010).
Kantarjian, et al., "Survival Advantage with Decitabine Versus Intensive Chemotherapy in Patients with Higher Risk Myelodysplastic Syndrome: Comparison with Historical Experience," Cancer, vol. 109(6): 1133-1137 (2007).
Koury, et al., "Erythropoietin Retards DNA Breakdown and Prevents Programmed Death in Erythroid Progenitor Cells," Science, vol. 248: 378-381 (1990).
Krapf, et al., "Arterial Hypertension Induced by Erythropoietin and Erythropoiesis-Stimulating Agents (ESA)," Clinical Journal of the American Society of Nephrology, vol. 4: 470-480 (2009).
Kumar Mishra and Tiwari, "Iron Overload in Beta Thalassaemia Major and Intermedia Patients," MAEDICA—Journal of Clinical Medicine, vol. 8(4): 328-332 (2013).
Leitch, H. A., "Controversies Surrounding Iron Chelation Therapy For MOS," Blood Reviews, vol. 25: 17-31 (2011).
Liboi, et al., "Erythropoietin Receptor Signals Both Proliferation and Erythroid-Specific Differentiation," Proceedings of the National Academy of Sciences, vol. 90: 11351-11355 (1993).
Lin, et al., "NUP98-HOXD13 Transgenic Mice Develop a Highly Penetrant, Severe Myelodysplastic Syndrome that Progresses to Acute Leukemia," Blood, vol. 106(1): 287-295 (2005).
List, et al., "Lenalidomide in the Myelodysplastic Syndrome with Chromosome Sq Deletion," The New England Journal of Medicine, vol. 355(14): 1456-1465 (2006).
Liu, et al., "Suppression of Fas-FasL Coexpression by Erythropoietin Mediates Erythroblast Expansion During the Erythropoietic Stress Response In Vivo," Blood, vol. 108(1): 123-133 (2006).
Itoh et al. Sideroblastic anemia associated with multiple myeloma in Turner's syndrome. Abstract. Internal medicine Tokyo, Japan, vol. 31, No. 4, pp. 483-485 (Apr. 1992).
Lyons, et al., "Comparison of 24-Month Outcomes in Chelated and Non-Chelated Lower-Risk Patients with Myelodysplastic Syndromes in a Prospective Registry," Leukemia Research, vol. 38: 149-154 (2014).
Lyons, et al., "Hematologic Response to Three Alternative Dosing Schedules of Azacitidine in Patients with Myelodysplastic Syndromes," Journal of Clinical Oncology, vol. 27(11): 1850-1856 (2009).
Malcovati et al. Granulocyte JAK2 (V617F) mutation status in myeloid neoplasms with ringed sideroblasts. Abstract. Blood, vol. 108, No. 11, Part 1, p. 256A (Nov. 16, 2006).
Malcovati, et al., "Clinical Significance of SF3B1 Mutations in Myelodysplastic Syndromes and Myelodysplastic/Myeloproliferative Neoplasms," Blood, vol. 118(24): 6239-6246 (2011).
Malcovati, et al., "Impact of the Degree of Anemia on the Outcome of Patients with Myelodysplastic Syndrome and its Integration into the WHO classification-based Prognostic Scoring System (WPSS)," Haematologica, vol. 96(10): 1433-1440 (2011).
Malcovati, et al., "Prognostic Factors and Life Expectancy in Myelodysplastic Syndromes Classified According to WHO Criteria: A Basis for Clinical Decision Making," Journal of Clinical Oncology, vol. 23(30): 7594-7603 (2005).
Malcovati, et al., "Refractory Anemia with Ring Sideroblasts," Best Practice & Research Clinical Haematology, vol. 26: 377-387 (2013).
Mathews and Vale, "Expression cloning of an activin receptor, a predicted transmembrane serine kinase." Cell 65:973-982 (1991).
Moyo, et al., "Erythropoiesis-Stimulating Agents in the Treatment of Anemia in Myelodysplastic Syndromes: A Meta-Analysis," Annals of Hematolooy, vol. 87: 527-536 (2008).
Mufti, et al, "Diagnosis and Classification of Myelodysplastic Syndrome: International Working Group on Morphology of Myelodysplastic Syndrome (IWGM-MDS) Consensus Proposals for the Definition and Enumeration of Myeloblasts and Ring Sideroblasts," Haematologica, vol. 93(11):1712-1717 (2008).
Murata M, et al. Expression of erythroid differentiation factor in Chinese hamster ovary cells. Biochem Biophys Res Commun 1988; 151: 230-5.
Negrin, et al., "Maintenance Treatment of the Anemia of Myelodysplastic Syndromes with Recombinant Human Granulocyte Colony-Stimulating Factor and Erythropoietin: Evidence for In Vivo Synergy," Blood, vol. 87(10): 4076-4081 (1996).
Oliva, et al., "A Review of Anemia as a Cardiovascular Risk Factor in Patients with Myelodysplastics Syndromes," American Journal of Blood Research, vol. 1 (2): 160-166 (2011).
Ornstein, et al., "Combination Strategies in Myelodysplastic Syndromes," International Journal of Hematology, vol. 95: 26-33 (2012).
Ozcan et al., "Review of therapeutic options and the management of patients with myelodysplastic syndromes," Expert Review Hematol, vol. 6:165-189 (2013).
Papaemmanuil, et al., "Somatic SF3B1 Mutation in Myelodysplasia with Ring Sideroblasts," The New England Journal of Medicine, vol. 365(15): 1384-1395 (2011).
Park, et al., "Predictive Factors of Response and Survival in Myelodysplastic Syndrome Treated with Erythropoietin and G-CSF: The GFM Experience," Blood, vol. 111 (2): 574-582 (2008).
Pereria et al. X-linked sideroblasticanemia (XLSA): Two new mutations identified in males. Abstract. Haematologica, vol. 95, Supp. Suppl. 2, pp. 716-717. Abstract No. 1854 (Jun. 2010).
Rawn, J., "The Silent Risks of Blood Transfusion," Current Opinion in Anaethesiology, vol. 21: 664-668 (2008).
Santini, et al., "Hepcidin Levels and Their Determinants in Different Types of Myelodysplastic Syndromes," PLoS ONE, vol. 6(8): 1-8 (2011).
Santini, V., "Clinical Use of Erythropoietic Stimulating Agents in Myelodysplastic Syndromes," The Oncologist, vol. 16(Supp. 3): 35-42 (2011).
Santini, V., "Treatment of Low-Risk Myelodysplastic Syndrome: Hematopoietic Growth Factors Erythropoietins and Thrombopoietins," Seminars in Hematology, vol. 49(4): 295-303 (2012).
Shen, et al., "DNA Methylation Predicts Survival and Response to Therapy in Patients with Myelodysplastic Syndromes," Journal of Clinical Oncology, vol. 28(4): 605-613 (2010).
Sherman et al., "Multiple-dose, safety, pharmacokinetic, and pharmacodynamic study of sotatercept (ActRIIA-IgG1), a novel erythropoietic agent, in healthy postmenopausal women" J Clin Pharmacol;53:1121-30 (2013).
Siah, et al., "Normal Iron Metabolism and the Pathophysiology of Iron Overload Disorders," The Clinical Biochemist Reviews, vol. 27: 5-16 (2006).
Slichter, S. J., "Evidence-Based Platelet Transfusion Guidelines," American Society of Hematology Education Program: 172-178 (2007).
Sloand, et al., "Alemtuzumab Treatment of Intermediate-1 Myelodysplasia Patients is Associated with Sustained Improvement in Blood Counts and Cytogenetic Remissions," Journal of Clinical Oncology, vol. 28(35): 5166-5173 (2010).
Socolovsky, et al., "Ineffective Erythropoiesis in Stat5a-/-5b-/- Mice Due to Decreased Survival of Early Erythroblasts," Blood, vol. 98(12): 3261-3273 (2001).
Steensma, D. P., "Hematopoietic Growth Factors in Myelodysplastic Syndromes," Seminars in Oncology, vol. 38(5): 635-647 (2011).
Steensma, et al., "The Myelodysplastic Syndromes: Diagnosis and Treatment," Mayo Clinic Proceedings, vol. 81(1): 104-130 (2006).
Steensma, et al., "When is Iron Overload Deleterious, and When and How Should Iron Chelation Therapy Be Administered in Myelodysplastic Syndromes?," Best Practice & Research Clinical Haematology, vol. 26: 431-444 (2013).
Suragani, et al., "Transforming Growth Factor-~ Superfamily Ligand Trap ACE-536 Corrects Anemia By Promoting Late-Stage Erythropoiesis," Nature Medicine, vol. 20(4): 408-417 (2014).
Temraz, et al., "Iron Overload and Chelation Therapy in Myelodysplastic Syndromes," Critical Reviews in Oncology/Hematology, vol. 91: 64-73 (2014).
Terpos et al., "Prolonged Administration of Erythropoietin Increases Response Rate in Myelodysplastic Syndromes: a Phase II Trial in 281 Patients", British Journal of Haematology, vol. 118(1):174-180 (2002).

(56) References Cited

OTHER PUBLICATIONS

The Cancer Genome Atlas Netowrk: Comprehensive Molecular Portraits of Human Breast Tumours.Nature, vol. 490: 61-70 (2012).
Vardiman, et al., "The 2008 Revision of the World Health Organization (WHO) Classification of Myeloid Neoplasms and Acute Leukemia: Rationale and Important Changes," Blood, vol. 114(5): 937-951 (2009).
Vogiatzi et al., "Bone Disease in Thalassemia: A Frequent and Still Unresolved Problem," Journal of Bone and Mineral Research, vol. 24: 543-557 (2008).
Wang, et al., "SF3B1 and Other Novel Cancer Genes in Chronic Lymphocytic Leukemia," The New England Journal of Medicine, vol. 365(26): 2497-2506 (2011 ).
Weatherall, et al., "Red Cells I: Inherited Anaemias," The Lancel, vol. 355: 1169-1175 (2000).
Webb, et al., "The Development and Application of Small Molecule Modulators of SF3b as Therapeutic Agents for Cancer," Drug Discovery Today, vol. 18(1-2): 43-49 (2013).
Whatley, et al., "C-Terminal Deletions in the ALAS2 Gene Lead to Gain of Function and Cause XLinked Dominant Protoporphyria Without Anemia or Iron Overload", American Journal of Human Genetics, vol. 83:408-414 (2008).
Yamashita et al., "Osteogenic protein-1 binds to activin type II receptors and induces certain activin-like effects." J. Cell Biol. 130:217-226 (1995).
Yeo and Whitman, "Nodal signals to SMADs through Cripto-dependent and Cripto-independent mechanisms," Mol. Cell 7: 949-957 (2001).
Zeidan, et al., "There's Risk, and Then There's Risk: The Latest Clinical Prognostic Risk Stratification Models in Myelodysplastic Syndromes," Current Hematologic Malignancy Reports, vol. 8: 351-360 (2013).
Platzbecker et al., "Luspatercept (ACE-536) Increases Hemoglobin and Reduces Transfusion Burden in Patients with Low or Intermediate-1 Risk Myelodysplastic Syndromes (MDS): Preliminary Results from a Phase 2 Study," 56th Annual American Society of Hematology Annual Meeting and Exposition. Dec. 8, 2014.
Platzbecker et al., Oral Presentation: Luspatercept Increases Hemoglobin and Reduces Transfusion Burden in Patients with Low or Intermediate-1 Risk Myelodysplastic Syndromes (MDS): Preliminary Results from a Phase 2 Study. 13th International Symposium on Myelodysplastic Syndromes (MDS). May 2, 2015.
Platzbecker et al., Luspatercept Increases Hemoglobin and Reduces Transfusion Burden in Patients with Low or Intermediate-1 Risk MDS: Preliminary Results from the Phase 2 PACE-MDS Study. 20th Congress of the European Hematology Association. Jun. 13, 2015.
Giagounidis et al., Luspatercept Treatment Leads to Long Term Increases in Hemoglobin and Reductions in Transfusion Burden in Patients with Low or Intermediate-1 Risk Myelodysplastic Syndromes (MDS): Preliminary Results from the Phase 2 PACE-MDS Extension Study. The 57th Annual American Society of Hematology. Dec. 5-8, 2015.
Platzbecker et al., Biomarkers of Ineffective Erythropoiesis Predict Response to Luspatercept in Patients with Low or Intermediate-1 Risk Myelodysplastic Syndromes (MDS): Final Results from the Phase 2 PACE-MDS Study. The 57th Annual American Society of Hematology. Dec. 5-8, 2015.
Platzbecker et al., Luspatercept Increases Hemoglobin and Reduces Transfusion Burden in Patients with Low-Intermediate Risk Myelodysplastic Syndromes (MDS): Long-Term Results from Phase 2 PACE-MDS Study. 21st Congress of the European Hematology Association. Jun. 9-12, 2016.
Chen et al., Pharmacokinetics and Exposure-Response of Luspatercept in Patients With Anemia Due to Low- or Intermediate-1-Risk Myelodysplastic Syndromes (MDS): Preliminary Results From Phase 2 Studies. ASH 2016. Dec. 4, 2016.
Platzbecker et al., Luspatercept Increases Hemoglobin and Reduces Transfusion Burden in Patients with Low-Intermediate Risk Myelodysplastic Syndromes (MDS): Long-Term Results from Phase 2 PACE-MDS Study. ASH 2016. Dec. 6, 2016.
Platzbecker et al., Luspatercept Response in New Subpopulations of Patients With Lower-Risk Myelodysplastic Syndromes (MDS): Update of the PACE Study. MDS Symposium 2017. May 3-6, 2017.
Giagounidis et al., Luspatercept Increases Hemoglobin and Reduces Transfusion Burden in Patients With Lower-Risk Myelodysplastic Syndromes (MDS): Long-Term Results From the Phase 2 PACE-MDS Study. European Hematology Association Congress. Jun. 22-25, 2017.
Platzbecker et al., Luspatercept for the treatment of anaemia in patients with lower-risk myelodysplastic syndromes (PACE-MDS): a multicentre, open-label phase 2 dose-finding study with long-term extension study. The Lancet Oncology 2017. Published online Sep. 1, 2017.
Platzbecker et al., "Mutational Profile and Analysis of Lower-Risk Myelodysplastic Syndromes (MDS) Patients Treated with Luspatercept: Phase 2 PACE-MDS Study." American Society of Hematology . Dec. 9-12, 2017.
Platzbecker et al., "Luspatercept Increases Hemoglobin and Reduces Transfusion Burden in Patients with Low-Intermediate Risk Myelodysplastic Syndromes (MDS): Long-Term Results from Phase 2 PACE-MDS Study", Abstract, Blood, 2016, 128:3168; Published online Dec. 1, 2016.
Platzbecker et al., "ACE-536 Increases Hemoglobin and Reduces Transfusion Burden in Patients with Low or Intermediate-1 Risk Myelodysplastic Syndromes (MDS): Preliminary Results from a Phase 2 Study", Abstract, Blood, 2014, 124:411; Published online Dec. 4, 2014.
Platzbecker et al., "Mutational Profile and Analysis of Lower-Risk Myelodysplastic Syndromes (MDS) Patients Treated with Luspatercept: Phase 2 PACE-MDS Study", Abstract, Blood, 2017, 130:2982; Published online Dec. 7, 2017.
Platzbecker et al., "Luspatercept Response in New Subpopulations of Patients With Lower-Risk Myelodysplastic Syndromes (MDS): Update of the Pace Study", Abstract, 14th International Symposium on Myelodysplastic Syndromes / Leukemia Research 55 S1 (2017) S8-S36.
Platzbecker et al., "Luspatercept Increases Hemoglobin and Reduces Transfusion Burden in Patients With Low or Intermediate-1 Risk Myelodysplastic Syndromes (MDS): Preliminary Results From the Phase 2 PACE-MDS Study", Abstract, European Hematology Association, Abstract, Published May 21, 2015.
Platzbecker et al., "Luspatercept for the treatment of anaemia in patients with lower-risk myelodysplastic syndromes (PACE-MDS): a multicentre, open-label phase 2 dose-finding study with longterm extension study", Abstract, The Lancet: Oncology, 18(10):1338-1347; Published on Sep. 1, 2017.
Platzbecker et al., "Biomarkers of Ineffective Erythropoiesis Predict Response to Luspatercept in Patients with Low or Intermediate-1 Risk Myelodysplastic Syndromes (MDS): Final Results from the Phase 2 PACE-MDS Study", Abstract, Blood, 2015, 126:2862; Published online Dec. 3, 2015.
Platzbecker et al., "Luspatercept Increases Hemoglobin and Reduces Transfusion Burden in Patients With Low-Intermediate Risk Myelodysplastic Syndromes (MDS): Long-Term Results From Phase 2 PACE?MDS Study", Abstract, European Hematology Association, Published May 19, 2016.
Platzbecker et al., "Luspatercept Increases Hemoglobin and Reduces Transfusion Burden in Patients With Low or Intermediate-1 Risk Myelodysplastic Syndromes (MDS): Preliminary Results From a Phase 2 Study", Abstract, 13th International Symposium on Myelodyspastic Syndromes / Leukemia Research 39 S1 (2015) S1-S166.
Giagounidis et al., "Luspatercept Increases Hemoglobin and Reduces Transfusion Burden in Patients With Lower-Risk Myelodysplastic Syndromes (MDS): Long-Term Results From Phase 2 PACE-MDS Study", Abstract, European Hematology Association, Published May 18, 2017.
Chen et al., "Pharmacokinetics and Exposure-Response of Luspatercept in Patients with Anemia Due to Low- or Intermediate-1-Risk

(56) References Cited

OTHER PUBLICATIONS

Myelodysplastic Syndromes (MDS): Preliminary Results from Phase 2 Studies", Abstract, Blood, 2016, 128:1990; Published Dec. 1, 2016.
Giagounidis et al., "Luspatercept Treatment Leads to Long Term Increases in Hemoglobin and Reductions in Transfusion Burden in Patients with Low or Intermediate-1 Risk Myelodysplastic Syndromes (MDS): Preliminary Results from the Phase 2 PACE-MDS Extension Study", Abstract, Blood, 2015, 126:92; Published Dec. 3, 2015.
Balint et al, 1993, "Antibody engineering by parsimonious mutagenesis", Gene 137(1):109-118.
Brown et al, 1992, "The promoter for the procyclic acidic repetitive protein (PARP) genes of Trypanosoma brucei shares features with RNA polymerase I promoters," Mol. Cell Biol. 12(6):2644-2652.
Cunningham et al., 1989, "High-resolution epitope mapping of hGH-receptor interactions by alanine-scanning mutagenesis", Science, 244(4908):1081-1085.
Edge et al., 1981, "Deglycosylation of glycoproteins by trifluoromethanesulfonic acid", Anal Biochem, 118(1):131.
Grodberg et al., 1993, "Alanine scanning mutagenesis of human erythropoietin identifies four amino acids which are critical for biological activity", Eur J Biochem, 218(2):597-601.
Hino et al, 2004, "Bone morphogenetic protein-3 family members and their biological functions", Front Biosci, 9:1520-1529.
Hochuli et al., 1987, "New metal chelate adsorbent selective for proteins and peptides containing neighbouring histidine residues", J. Chromatography, 411:177.
Ike et al., 1983, "Solid phase synthesis of polynucleotides. VIII. Synthesis of mixed oligodeoxyribonucleotides by the phosphotriester solid phase method", Nucleic Acid Res, 11(2):477.
Itakura et al., 1984, "Synthesis and use of synthetic oligonucleotides", Annu Rev Biochem, 53:323.
Itakura et al., 1984, "Expression in *Escherichia coli* of a chemically synthesized gene for the hormone somatostatin", Science, 198:1056.
Jankert et al., 1991, "Rapid and efficient purification of native histidine-tagged protein expressed by recombinant vaccinia virus", PNAS USA, 88(20):8972.
Kozbar et al., 1983, "The production of monoclonal antibodies from human lymphocytes", Immunology Today, 4(3):72.
Kubo et al., 1999, "Osteoporosis influences the late period of fracture healing in a rat model prepared by ovariectomy and low calcium diet", Steroid Biochemistry & Molecular Biology, 68:197-202.
Madura et al., 1993, "N-recognin/Ubc2 interactions in the N-end rule pathway", J. Biol. Chem., 268:12046-12054.
Myers et al., 1986, "Fine structure genetic analysis of a beta-globin promoter", Science, 232:613.
Nagashima et al., 1993, "Alanine-scanning mutagenesis of the epidermal growth factor-like domains of human thrombomodulin identifies critical residues for its cofactor activity", J. Biol. Chem., 268:2888-2892.
Platzbecker et al., 2013, "A phase 2, ascending dose study of ACE-536 to treat anemia in low/intermediate-1 risk MDS patients: The PACE-MDS study", Leukemia Research, 37, S1, S167, p. 322.
Reichel et al., 2017, "Antibody-based strategies for the detection of Luspatercept (ACE-536) in human serum", Drug Testing and Analysis, vol. 9:1721-1730.

Roberts et al., 1992, "Directed evolution of a protein: selection of potent neutrophil elastase inhibitors displayed on M13 fusion phage", PNAS USA, 89(6):2429-2433.
Ruf et al., 1994, "Mutational mapping of functional residues in tissue factor: identification of factor VII recognition determinants in both structural modules of the predicted cytokine receptor homology domain", Biochemistry, 33(6):1565-1572.
Suragani et al., 2014, "Modified Activin Receptor IIB Ligand Trap Mitigates Ineffective Erythropoiesis and Disease Complications in Murine Beta-Thalassemia", Blood, 123(25):3864-3872.
Vidal and Legrain, 1999, "Yeast forward and reverse 'n'-hybrid systems", Nucleic Acids Res., 27(4):919-929.
Wang et al., 1994, "Single amino acid insertions probe the alpha subunit of the *Escherichia coli* F1F0-ATP synthase", J. Biol. Chem., 269(4):3095-3099.
Zhou et al., 2008, "Inhibition of the TGF-beta receptor I kinase promotes hematopoiesis in MDS", Blood, 112(8):3434-3443.
Zheng et al., 2012, "A pilot trial assessing urinary gene expression profiling with an mRNA array for diabetic nephropathy", PLoS One, 7(5): e34824.
Guerra et al., 2018, "Lack of GDF11 does not ameliorate erythropoiesis in beta-thalassemia and does not prevent the activity of the trap-ligand RAP-536", Blood, 132:165, Abstract.
Guerra et al., 2019, "Lack of GDF11 does not improve anemia or prevent the activity of RAP-536 in a mouse model of beta-thalassemia", Blood, 134(6): 568-572.
Rachmilewitz et al., 2011, "How I treat thalassemia", Blood, 118(13):3479-3488.
Cook, 2018, "Bone Marrow Failure Syndromes," Hematopathology (Third Edition) Ch. 5, pp. 187-183. Elsevier Pub. Philadelphia, PA.
Czader and Orazi, 2011, "Myelodysplastic/myeloproliferative neoplasms", Blood and Bone Marrow Pathology 2nd Edition Elsevier Pub. Philadelphia PA Ch. 27, pp. 391-406.
Ginder, 2012, "Microcytic and Hypochromic Anemias," Goldman's Cecil Medicine, ch 162, p. 1039-1052. 24th Edition Elsevier Pub. Philadelphia, PA.
Kanapuru and Ershler, 2010, "Blood Disorders in the Elderly," Brocklehurst's Textbook of Geriatric Medicine and Gerontology :775-790, ch. 93. 7th Edition Elsevier Pub. Philadelphia, PA.
Keightley et al., 2016, "Experimental approaches to studying the nature and impact of splicing variation in zebrafish," Methods in Cell Biology, 135:259-288, 4th Edition Elsevier Cambridge, MA.
List and Komrokji, 2012, "Myelodysplastic Syndronme" Goldman's Cecil Medicine (Twenty Fourth Edition)., Ch. 188, pp. 1200-1203. Elsevier Pub. Philadelphia, PA.
May 2011, "Sideroblastic anemia," Blood and Bone Marrow Pathology (Second Edition), ch.14, pp. 225-235. Elsevier Pub. Waltham, MA.
Naeim et al., 2013, "Myelodysplastic Syndromes/Neoplasms— Classification," Atlas of Hematopathology, Ch. 9, pp. 129-148. Elsevier Pub. Philadelphia, PA.
Singh et al., 2017, "Microcytic Disorders," Hematology Case Studies with Blood Cell Morphology and Pathophysiology Cn 2, P9 9-41. Elsevier Pub. Cambridge, MA.
Thakral, et al., 2018, "Myeloproliferative and "Over-lap" Myelodysplastic/Myeloproliferative Neoplasms," Hematopathology, Ch. 17, pp. 488-538. 3rd Edition Elsevier Pub. Philadelphia, PA.

* cited by examiner

ACTIVIN-ACTRII ANTAGONISTS AND USES FOR TREATING ANEMIA

1. CROSS-REFERENCES TO RELATED APPLICATIONS

This application is a national stage of International Patent Application No. PCT/US2015/063595, filed Dec. 3, 2015, which claims the benefit of priority of U.S. Provisional Patent Application No. 62/086,977, filed Dec. 3, 2014. This application also claims the benefit of priority of U.S. Provisional Patent Application No. 62/088,478, filed Dec. 5, 2014; U.S. Provisional Patent Application No. 62/153,872, filed Apr. 28, 2015; U.S. Provisional Patent Application No. 62/173,782, filed Jun. 10, 2015; and U.S. Provisional Patent Application No. 62/218,728, filed Sep. 15, 2015, the entire contents of each of which are incorporated herein by reference and for all purposes.

2. SEQUENCE LISTING

The present application is being filed with a computer readable form (CRF) copy of the Sequence Listing, submitted as file name "12827_978_999_Substitute_Sequence_Listing.txt", of size 93,786 bytes, which was created on Apr. 20, 2020, which is identical to the paper copy of the Sequence Listing and is incorporated herein by reference in its entirety and for all purposes.

3. FIELD

Provided herein are methods for the long-term treatment in a subject of (i) anemia; (ii) anemia requiring RBC transfusion; (iii) myelodysplastic syndromes (MDS); and/or (iv) non-proliferative chronic myelomonocytic leukemia (CMML), wherein the methods comprise administration of an Activin-ActRII signaling inhibitor to a subject in need of the long-term treatment. Such an Activin-ActRII signaling inhibitor can be signaling inhibitors of ActRIIA and/or ActRIIB signaling. Provided herein are methods of long-term treatment in a subject of (i) anemia; (ii) anemia requiring red blood cell (RBC) transfusion; (iii) MDS; and/or (iv) non-proliferative CMML, wherein the subject has ring sideroblasts.

4. BACKGROUND

Anemia is a decrease in number of red blood cells or less than the normal quantity of hemoglobin in the blood. Anemia can also be caused by decreased oxygen-binding ability of the hemoglobin. Anemia is the most common disorder of the blood. Anemia can be caused by ineffective erythropoiesis. Ineffective erythropoiesis is present if active erythropoiesis takes place but mature red blood cells fail to develop at the proper rate. Progenitor cells undergo apoptosis before the stage of mature red blood cells is reached. MDS comprises hematopoietic stem-cell disorders characterized by ineffective hematopoiesis. Moreover, MDS disorders include disorders characterized by ring sideroblasts. Ring sideroblasts are abnormal erythroblasts. Furthermore, certain somatic mutations associated with MDS cause ring sideroblast formation and ineffective erythropoiesis. Dominant mutations in splicing factor 3B1 (SF3B1) are associated with the formation of ring sideroblasts. Ring sideroblasts are erythroblasts in which there are a minimum of five iron-containing (siderotic) granules covering at least one third of the circumference of the nucleus. See, e.g., Mufti et al., 2008, Haematologica, 93(11):1712-7. Ring sideroblasts contain iron-loaded mitochondria. The presence of ring sideroblasts can be detected by Prussian blue staining and visualization. Ring sideroblasts can be detected in peripheral blood and/or bone marrow smears.

Two related type II receptors, ActRIIA and ActRIIB, have been identified as the type II receptors for activins (Mathews and Vale, 1991, Cell 65:973-982; Attisano et al., 1992, Cell 68: 97-108). Besides activins, ActRIIA and ActRIIB can biochemically interact with several other TGF-beta family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). ALK4 is the primary type I receptor for activins, particularly for activin A, and ALK-7 may serve as a receptor for activins as well, particularly for activin B.

A humanized fusion-protein consisting of the extracellular domain (ECD) of activin-receptor type IIA (ActRIIA) and the human IgG1 Fc domain binds with high-affinity to activin-A blocking signaling through the endogenous ActRIIA-receptor. Activin-A is an erythroid-differentiation-factor affecting late stages of RBC-maturation (Murata M, Onomichi K, Eto Y, Shibai H, and Muramatsu M. Expression of erythroid differentiation factor in Chinese hamster ovary cells. Biochem Biophys Res Commun 1988; 151: 230-5.). ActRII signaling inhibitors have been described for increasing RBC levels (e.g., patent application publication Nos. 20110038831; 20100204092; 20100068215; 20100028332; 20100028331; and 20090163417).

5. SUMMARY

Provided herein is a method of treating a blood-related disorder in a subject, comprising (a) determining a percentage of erythroblasts in the subject that are ring sideroblasts; and (b) administering a pharmaceutically effective dose of an ActRII signaling inhibitor of between 0.1 mg/kg and 2.0 mg/kg to the subject if at least 10%, 11%, 12%, 13%, 14%, 15%, 16%, 17%, 18%, 19%, or 20% of erythroblasts in the subject are ring sideroblasts. In certain embodiments, the blood-related disorder is anemia, myelodysplastic syndromes (MDS), or non-proliferative chronic myelomonocytic leukemia (CMML). In certain embodiments, the percentage of erythroblasts in the subject that are ring sideroblasts is determined at a first time. In certain embodiments, the first time is a within 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months of administering the pharmaceutically effective dose of the ActRII signaling inhibitor to the subject.

Provided herein is a method of treating a blood-related disorder in a subject, comprising administering to the subject an activin receptor type II (ActRII) signaling inhibitor at a pharmaceutically effective dose and for a period of time to achieve (i) a long-term reduction in a percentage of erythroblasts in the subject that are ring sideroblasts as compared to an initial percentage of erythroblasts in the subject that are ring sideroblasts; and/or (ii) a long-term increase in hemoglobin level in the subject as compared to the hemoglobin level in the subject a period of time prior to administering to the subject an initial dose of the ActRII signaling inhibitor; wherein the pharmaceutically effective dose is between 0.1 mg/kg and 2.0 mg/kg, and wherein the initial percentage of erythroblasts in the subject that are ring sideroblasts is at least 10%, 11%, 12%, 13%, 14%, 15%, 16%, 17%, 18%, 19%, or at least 20%. In certain embodiments, the blood-related disorder is anemia, MDS, or non-proliferative CMML. Provided herein is a method of treating anemia in a subject, comprising administering to the subject an activin receptor type II (ActRII) signaling inhibitor at a pharmaceutically effective dose and for a period of time to achieve (i) a long-term reduction in a percentage of erythroblasts in the subject that are ring sideroblasts as compared to an initial percentage of erythroblasts in the subject that are ring sideroblasts; and/or (ii) a long-term increase in hemoglobin level in the subject as compared to the hemoglobin level in the subject a period of time prior to administering to the subject an initial dose of the ActRII signaling inhibitor; wherein the pharmaceutically effective dose is between 0.1 mg/kg and 2.0 mg/kg, and wherein the initial percentage of erythroblasts in the subject that are ring sideroblasts is at least 10%, 11%, 12%, 13%, 14%, 15%, 16%, 17%, 18%, 19%, or at least 20%. In certain embodiments, the subject is a subject requiring RBC transfusion. Provided herein is a method for treating MDS in a subject, comprising administering to the subject an ActRII signaling inhibitor at a pharmaceutically effective dose and for a period of time to achieve (i) a long-term reduction in a percentage of erythroblasts in the subject that are ring sideroblasts as compared to an initial percentage of erythroblasts in the subject that are ring sideroblasts; and/or (ii) a long-term increase in hemoglobin level in the subject as compared to the hemoglobin level in the subject a period of time prior to administering to the subject an initial dose of the ActRII signaling inhibitor; wherein the pharmaceutically effective dose is between 0.1 mg/kg and 2.0 mg/kg, and wherein the initial percentage of erythroblasts in the subject that are ring sideroblasts is at least 10%, 11%, 12%, 13%, 14%, 15%, 16%, 17%, 18%, 19%, or at least 20%. Provided herein is a method for treating non-proliferative CMML in a subject, comprising administering to the subject an ActRII signaling inhibitor at a pharmaceutically effective dose and for a period of time to achieve (i) a long-term reduction in a percentage of erythroblasts in the subject that are ring sideroblasts as compared to an initial percentage of erythroblasts in the subject that are ring sideroblasts; and/or (ii) a long-term increase in hemoglobin level in the subject as compared to the hemoglobin level in the subject a period of time prior to administering to the subject an initial dose of the ActRII signaling inhibitor; wherein the pharmaceutically effective dose is between 0.1 mg/kg and 2.0 mg/kg, and wherein the initial percentage of erythroblasts in the subject that are ring sideroblasts is at least 10%, 11%, 12%, 13%, 14%, 15%, 16%, 17%, 18%, 19%, or at least 20%.

In certain embodiments, the period of time of ActRII signaling inhibitor administration is 1, 2, 3, 4, 5, or 6 months. In certain embodiments, the initial percentage of erythroblasts in the subject that are ring sideroblasts is a percentage of erythroblasts in the subject that are ring sideroblasts a period of time prior to administering to the subject an initial dose of the ActRII signaling inhibitor. In certain embodiments, the long-term reduction in the percentage of erythroblasts in the subject that are ring sideroblasts is maintained for at least 1, 2, 3, 4, 5, 6, 12, 18, or 24 months after the period of time of ActRII signaling inhibitor administration. In certain embodiments, the long-term reduction in the percentage of erythroblasts in the subject that are ring sideroblasts is at least 1.5, 2.5, 5.0, 7.5, or 10.0 fold below the initial percentage of erythroblasts in the subject that are ring sideroblasts for at least 6, 12, 18, or 24 months after the period of time of ActRII signaling inhibitor administration. In certain embodiments, the initial hemoglobin level in the subject is the hemoglobin level in the subject a period of time period of time prior to administering to the subject an initial dose of the ActRII signaling inhibitor. In certain embodiments, the initial hemoglobin level in said subject is less than about 11 g/dL. In certain embodiments, the long-term increase in the hemoglobin level in the subject is maintained for at least 3, 4, 5, 6, 12, 18, or 24 months after the period of time of ActRII signaling inhibitor administration. In certain embodiments, the long-term increase in the hemoglobin level in the subject is a hemoglobin level of between about 11 g/dL and 18 g/dL in the subject for at least 3, 4, 5, 6, 12, 18, or 24 months after the period of time of ActRII signaling inhibitor administration. In certain embodiments, the subject does not require red blood cell transfusion for at least 3, 4, 5, 6, 12, 18, or 24 months after the period of time of ActRII signaling inhibitor administration.

In certain embodiments, the ActRII signaling inhibitor is administered once every three weeks. In certain embodiments, the ActRII signaling inhibitor is administered (i) once every 28 days; or (ii) once every 42 days. In certain embodiments, the ActRII signaling inhibitor is administered via injection. In certain embodiments, the ActRII signaling inhibitor is administered subcutaneously.

In certain embodiments, the method further comprises determining an additional percentage of erythroblasts in the subject that are ring sideroblasts 6, 12, 18, and/or 24 months after the period of time of ActRII signaling inhibitor administration. In certain embodiments, the percentage of erythroblasts in the subject that are ring sideroblasts is determined by Prussian blue staining. In certain embodiments, the method further comprises determining an additional hemoglobin level in the subject 6, 12, 18, and/or 24 months after the period of time of ActRII signaling inhibitor administration.

Also provided herein is a method for treating a blood-related disorder in a subject, wherein the method comprises: (a) determining a first percentage of erythroblasts in the subject that are ring sideroblasts; and (b)(i) administering an ActRII signaling inhibitor to the subject at a pharmaceutically effective dose of between 0.1 mg/kg and 2.0 mg/kg for a short period of time if the first percentage of erythroblasts in the subject that are ring sideroblasts is at least 10%, 11%, 12%, 13%, 14%, 15%, 16%, 17%, 18%, 19%, or at least 20%, or (ii) administering an ActRII signaling inhibitor to the subject at a pharmaceutically effective dose of between 0.1 mg/kg and 2.0 mg/kg for a long period of time if the percentage of erythroblasts in the subject that are ring sideroblasts is less than 10%. In certain embodiments, the blood-related disorder is anemia, anemia requiring transfusion, MDS, or non-proliferative CMML. Also provided herein is a method for treating anemia in a subject, wherein the method comprises: (a) determining a first percentage of erythroblasts in the subject that are ring sideroblasts; and (b)(i) administering an ActRII signaling inhibitor to the subject at a pharmaceutically effective dose of between 0.1 mg/kg and 2.0 mg/kg for a short period of time if the first percentage of erythroblasts in the subject that are ring sideroblasts is at least 10%, 11%, 12%, 13%, 14%, 15%, 16%, 17%, 18%, 19%, or at least 20%, or (ii) administering an ActRII signaling inhibitor to the subject at a pharmaceutically effective dose of between 0.1 mg/kg and 2.0 mg/kg for a long period of time if the percentage of erythroblasts in the subject that are ring sideroblasts is less than 10%. In certain embodiments, the subject is a subject requiring blood transfusions. Also provided herein is a method for treating MDS in a subject, wherein the method comprises: (a) determining a first percentage of erythroblasts in the subject that are ring sideroblasts; and (b)(i) administering an ActRII signaling inhibitor to the subject at a pharmaceutically effective dose of between 0.1 mg/kg and 2.0 mg/kg for a short period of time if the first percentage of erythroblasts in the subject that are ring sideroblasts is at least 10%, 11%, 12%, 13%, 14%, 15%, 16%, 17%, 18%, 19%, or at least 20%, or (ii) administering an ActRII signaling inhibitor to the subject at a pharmaceutically effective dose of between 0.1 mg/kg and 2.0 mg/kg for a long period of time if the percentage of erythroblasts in the subject that are ring sideroblasts is less than 10%. Also provided herein is a method for treating non-proliferative CMML in a subject, wherein the method comprises: (a) determining a first percentage of erythroblasts in the subject that are ring sideroblasts; and (b)(i) administering an ActRII signaling inhibitor to the subject at a pharmaceutically effective dose of between 0.1 mg/kg and 2.0 mg/kg for a short period of time if the first percentage of erythroblasts in the subject that are ring sideroblasts is at least 10%, 11%, 12%, 13%, 14%, 15%, 16%, 17%, 18%, 19%, or at least 20%, or (ii) administering an ActRII signaling inhibitor to the subject at a pharmaceutically effective dose of between 0.1 mg/kg and 2.0 mg/kg for a long period of time if the percentage of erythroblasts in the subject that are ring sideroblasts is less than 10%.

In certain embodiments, the first percentage of erythroblasts in the subject that are ring sideroblasts in the subject administered the ActRII signaling inhibitor for a short period of time is reduced to less than 10%, 9%, 8%, 7%, 6%, 5%, 4%, 3%, 2%, or less than 1% for at least 6, 12, 18, or 24 months after the short period of time of ActRII signaling inhibitor administration. In certain embodiments, the hemoglobin level in the subject is less than about 11 g/dL. In certain embodiments, a hemoglobin level in the subject administered the ActRII signaling inhibitor for a short period of time is between about 11 g/dL and 18 g/dL at least 3, 4, 5, 6, 12, 18, or 24 months after the period of time of ActRII signaling inhibitor administration. In certain embodiments, the short period of time is 1, 2, 3, 4, or 5 months. In certain embodiments, the long period of time is at least 6, 12, 18, or 24 months. In certain embodiments, the subject does not require red blood cell transfusion for at least 3, 4, 5, 6, 12, 18, or 24 months after the period of time of ActRII signaling inhibitor administration.

In certain embodiments, the ActRII signaling inhibitor is administered once every three weeks. In certain embodiments, the ActRII signaling inhibitor is administered (i) once every 28 days; or (ii) once every 42 days. In certain embodiments, the ActRII signaling inhibitor is administered via injection. In certain embodiments, the ActRII signaling inhibitor is administered subcutaneously.

In certain embodiments, the method further comprises determining a second percentage of erythroblasts in the subject that are ring sideroblasts 6, 12, 18, and/or 24 months after the period of time of ActRII signaling inhibitor administration. In certain embodiments, the percentage of erythroblasts in the subject that are ring sideroblasts is determined by Prussian blue staining. In certain embodiments, the method further comprises determining a hemoglobin level in the subject 6, 12, 18, and/or 24 months after the period of time of ActRII signaling inhibitor administration.

Also provided herein is a method of treating a blood-related disorder in a subject, wherein the method comprises: (a) determining that the subject has a percentage of erythroblasts in the subject that are ring sideroblasts of at least 10%, 11%, 12%, 13%, 14%, 15%, 16%, 17%, 18%, 19%, or at least 20%; (b) administering to the subject an initial dose of between 0.1 mg/kg and 2.0 mg/kg of an ActRII signaling inhibitor; (c) determining a second percentage of erythroblasts in the subject that are ring sideroblasts after a period of time; and (d) optionally administering to the subject an adjusted dose of the ActRII signaling inhibitor. In certain embodiments, the blood-related disorder is anemia, anemia requiring transfusion, MDS, or non-proliferative CMML. Also provided herein is a method of treating anemia in a subject, wherein the method comprises: (a) determining that the subject has a percentage of erythroblasts in the subject that are ring sideroblasts of at least 10%, 11%, 12%, 13%, 14%, 15%, 16%, 17%, 18%, 19%, or at least 20%; (b) administering to the subject an initial dose of between 0.1 mg/kg and 2.0 mg/kg of an ActRII signaling inhibitor; (c) determining a second percentage of erythroblasts in the subject that are ring sideroblasts after a period of time; and (d) optionally administering to the subject an adjusted dose of the ActRII signaling inhibitor. In certain embodiments, the subject is a subject requiring blood transfusions. Also provided herein is a method of treating MDS in a subject, wherein the method comprises: (a) determining that the subject has a percentage of erythroblasts in the subject that are ring sideroblasts of at least 10%, 11%, 12%, 13%, 14%, 15%, 16%, 17%, 18%, 19%, or at least 20%; (b) administering to the subject an initial dose of between 0.1 mg/kg and 2.0 mg/kg of an ActRII signaling inhibitor; (c) determining a second percentage of erythroblasts in the subject that are ring sideroblasts after a period of time; and (d) optionally administering to the subject an adjusted dose of the ActRII signaling inhibitor. Also provided herein is a method of treating non-proliferative chronic myelomonocytic leukemia (CMML) in a subject, wherein the method comprises: (a) determining that the subject has a percentage of erythroblasts in the subject that are ring sideroblasts of at least 10%, 11%, 12%, 13%, 14%, 15%, 16%, 17%, 18%, 19%, or at least 20%; (b) administering to the subject an initial dose of between 0.1 mg/kg and 2.0 mg/kg of an ActRII signaling inhibitor; (c) determining a second percentage of erythroblasts in the subject that are ring sideroblasts after a period of time; and (d) optionally administering to the subject an adjusted dose of the ActRII signaling inhibitor.

In certain embodiments, the period of time is 1, 2, 3, 4, 5, or 6 months. In certain embodiments, the initial dose is administered via injection. In certain embodiments, the initial dose is administered subcutaneously. In certain embodiments, the initial dose is administered once every three weeks. In certain embodiments, the initial dose is administered (i) once every 28 days; or (ii) once every 42 days.

In certain embodiments, the initial dose is administered to the subject immediately after the determination of the first percentage of erythroblasts in the subject that are ring sideroblasts or within at most 1 day, 2 days, 3 days, 4 days, 5 days, 6 days, or 1 week, 2 weeks, 1 month, 2 months, 3 months, 4 months, 5 months, 6 months, 7 months, 8 months, 9 months, 10 months, 11 months, or 12 months thereof. In certain embodiments, the adjusted dose is administered to the subject immediately after the determination of the second percentage of erythroblasts in the subject that are ring sideroblasts or within at most 1 day, 2 days, 3 days, 4 days, 5 days, 6 days, or 1 week, 2 weeks, 1 month, 2 months, 3 months, 4 months, 5 months, 6 months, 7 months, 8 months, 9 months, 10 months, 11 months, or 12 months thereof. In certain embodiments, the adjusted dose of the ActRII signaling inhibitor is greater than the initial dose if the second percentage of erythroblasts in the subject that are ring sideroblasts is at least 10%, 11%, 12%, 13%, 14%, 15%, 16%, 17%, 18%, 19%, or at least 20%. In certain embodiments, the adjusted dose is about 0.05 mg/kg, about 0.1 mg/kg, about 0.15 mg/kg, about 0.25 mg/kg, about 0.3 mg/kg, about 0.35 mg/kg, about 0.4 mg/kg, or about 0.5 mg/kg, 0.75 mg/kg, 1.0 mg/kg, 1.33 mg/kg, 1.5 mg/kg, or about 1.75 mg/kg greater than the initial dose. In certain embodiments, the adjusted dose is administered more frequently than the initial dose. In certain embodiments, the adjusted dose is administered every 5, 10, 15, 20, 25, 28, 30, 35, or 40 days. In certain embodiments, the adjusted dose is administered via injection. In certain embodiments, the adjusted dose is administered subcutaneously. In certain embodiments, the adjusted dose is not administered to the subject if the second percentage of erythroblasts in the subject that are ring sideroblasts is less than 10%, 9%, 8%, 7%, 6%, 5%, 4%, 3%, 2%, or less than 1%. In certain embodiments, the adjusted dose is administered for at most 1, 2, 3, 4, 5, or 6 months.

In certain embodiments, the subject does not require red blood cell transfusion for at least 3, 4, 5, 6, 12, 18, or 24 months after the period of time of ActRII signaling inhibitor administration. In certain embodiments, the ActRII signaling inhibitor is administered once every three weeks. In certain embodiments, the ActRII signaling inhibitor is administered (i) once every 28 days; or (ii) once every 42 days. In certain embodiments, the percentage of erythroblasts in the subject that are ring sideroblasts is determined by Prussian blue staining.

Also provided herein is a method for treating a blood-related disorder in a subject, wherein the method comprises: (a) determining the percentage of erythroblasts in the subject that are ring sideroblasts; (b) administering an ActRII signaling inhibitor to the subject at a pharmaceutically effective dose of between 0.1 mg/kg and 2.0 mg/kg if the percentage of erythroblasts in the subject that are ring sideroblasts in the subject is at least 10%, 11%, 12%, 13%, 14%, 15%, 16%, 17%, 18%, 19%, or at least 20%; (c) determining a level of hemoglobin in the subject after ActRII signaling inhibitor is administered to the subject; and (d) discontinuing administration of the ActRII signaling inhibitor to the subject if the level of hemoglobin in the subject is at least 11 g/dL. In certain embodiments, the blood-related disorder is anemia, anemia requiring transfusion, MDS, or non-proliferative CMML. Also provided herein is a method for treating anemia in a subject, wherein the method comprises: (a) determining the percentage of erythroblasts in the subject that are ring sideroblasts; (b) administering an ActRII signaling inhibitor to the subject at a pharmaceutically effective dose of between 0.1 mg/kg and 2.0 mg/kg if the percentage of erythroblasts in the subject that are ring sideroblasts in the subject is at least 10%, 11%, 12%, 13%, 14%, 15%, 16%, 17%, 18%, 19%, or at least 20%; (c) determining a level of hemoglobin in the subject after ActRII signaling inhibitor is administered to the subject; and (d) discontinuing administration of the ActRII signaling inhibitor to the subject if the level of hemoglobin in the subject is at least 11 g/dL. In certain embodiments, the subject requires RBC transfusions. Also provided herein is a method for treating MDS in a subject, wherein the method comprises: (a) determining the percentage of erythroblasts in the subject that are ring sideroblasts; (b) administering an ActRII signaling inhibitor to the subject at a pharmaceutically effective dose of between 0.1 mg/kg and 2.0 mg/kg if the percentage of erythroblasts in the subject that are ring sideroblasts is at least 10%, 11%, 12%, 13%, 14%, 15%, 16%, 17%, 18%, 19%, or at least 20%; (c) determining a level of hemoglobin in the subject after ActRII signaling inhibitor is administered to the subject; and (d) discontinuing administration of the ActRII signaling inhibitor to the subject if the level of hemoglobin in the subject is at least 11 g/dL. Also provided herein is a method for treating non-proliferative CMML in a subject, wherein the method comprises: (a) determining the percentage of erythroblasts in the subject that are ring sideroblasts; (b) administering an ActRII signaling inhibitor to the subject at a pharmaceutically effective dose of between 0.1 mg/kg and 2.0 mg/kg if the percentage of erythroblasts in the subject that are ring sideroblasts is at least 10%, 11%, 12%, 13%, 14%, 15%, 16%, 17%, 18%, 19%, or at least 20%; (c) determining a level of hemoglobin in the subject after ActRII signaling inhibitor is administered to the subject; and (d) discontinuing administration of the ActRII signaling inhibitor to the subject if the level of hemoglobin in the subject is at least 11 g/dL.

In certain embodiments, the ActRII signaling inhibitor is administered to the subject once every three weeks. In certain embodiments, the ActRII signaling inhibitor is administered (i) once every 28 days; or (ii) once every 42 days. In certain embodiments, the ActRII signaling inhibitor is administered via injection. In certain embodiments, the ActRII signaling inhibitor is administered subcutaneously.

In certain embodiments, the level of hemoglobin is determined within 6, 12, 18, and/or 24 months after the ActRII signaling inhibitor is administered.

Also provided herein is a method of promoting erythropoiesis in a subject having a blood-related disorder, the method comprising: (a) determining a percentage of erythroblasts in the subject that are ring sideroblasts; (b) administering a pharmaceutically effective dose of an ActRII signaling inhibitor to the subject for a first period of time; (c) after the first period of time, if the percentage of erythroblasts in the subject that are ring sideroblasts in step (a) had been above 11%, 12%, 13%, 14%, 15%, 16%, 17%, 18%, 19%, or 20%, reducing the dose of the ActRII signaling inhibitor administered to the subject, reducing the frequency of administration of the ActRII signaling inhibitor to the subject, or discontinuing administering of the ActRII signaling inhibitor. In certain embodiments, the blood-related disorder is anemia, anemia requiring transfusion, MDS, or non-proliferative CMML. In certain embodiments, the method further comprises (i) monitoring a hematological parameter in the subject during the first period of time; and (ii) reducing or discontinuing administering of the ActRII signaling inhibitor to the subject if the hematological parameter in the subject is normalized. In certain embodiments, the method further comprises (i) monitoring a hematological parameter in the subject during the first period of time; and (ii) reducing the dose of administering of the ActRII signaling inhibitor to the subject if the hematological parameter in the subject is normalized. In certain embodiments, the method further comprises (i) monitoring a hematological parameter in the subject during the first period of time; and (ii) reducing the frequency of administering of the ActRII signaling inhibitor to the subject if the hematological parameter in the subject is normalized. In certain embodiments, the method further comprises (i) monitoring a hematological parameter in the subject during the first period of time; and (ii) discontinuing administering of the ActRII signaling inhibitor to the subject if the hematological parameter in the subject is normalized. In certain embodiments, the normalized hematological parameter in the subject is a level of the hematological parameter in a reference population. In certain embodiments, the normalized hematological parameter in the subject is an improvement in the hematological parameter in the subject by at least 10%, 20%, 30%, 40%, 50%, 60%, 70%, 80%, 90%, or 100% as compared to the hematological parameter in the subject at a period of time prior to administering to the subject an initial dose of the ActRII signaling inhibitor. In certain embodiments, the period of time prior to administering to the subject an initial dose of the ActRII signaling inhibitor is at least 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the hematological parameter is hemoglobin level, hematocrit, red blood cell count or percentage of erythroblasts in the subject that are ring sideroblasts.

In certain embodiments, the ActRII signaling inhibitor is administered to the subject once every three weeks. In certain embodiments, the ActRII signaling inhibitor is administered (i) once every 28 days; or (ii) once every 42 days. In certain embodiments, the ActRII signaling inhibitor is administered via injection. In certain embodiments, the ActRII signaling inhibitor is administered subcutaneously.

In certain embodiments, the subject has an increased likelihood of achieving normalization of one or more hematological parameters if at least 10%, 11%, 12%, 13%, 14%, 15%, 16%, 17%, 18%, 19%, or 20% of erythroblasts in the subject are ring sideroblasts. In certain embodiments, the hematological parameter is hemoglobin level, hematocrit, red blood cell count, or percentage of erythroblasts in the subject that are ring sideroblasts.

In certain embodiments, the normalized hematological parameter is a level of the hematological parameter in a reference population. In certain embodiments, the normalized hematological parameter is an improvement by at least 10%, 20%, 30%, 40%, 50%, 60%, 70%, 80%, 90%, or 100% as compared to the hematological parameter in the subject at a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months.

Provided herein is a method for long-term treatment of anemia in a subject, comprising administering to the subject an activin receptor type II (ActRII) inhibitor at a pharmaceutically effective dose and for a period of time to achieve (i) a long-term reduction in a ratio of ringed sideroblasts to normal erythroblasts in the subject as compared to an initial ratio of ringed sideroblasts to normal erythroblasts in the subject; and (ii) a long-term increase in hemoglobin level in the subject as compared to the hemoglobin level in the subject prior to administering to the subject the ActRII inhibitor; wherein the pharmaceutically effective dose is between 0.75 mg/kg and 2.0 mg/kg, and wherein the initial ringed sideroblast to normal erythroblast ratio in the subject is at least 1:10, at least 1:7, or at least 1:5. In certain embodiments, the subject is a subject requiring transfusion.

Provided herein is a method for long-term treatment of low or intermediate-1-risk myelodysplastic syndromes (MDS) in a subject, comprising administering to the subject an activin receptor type II (ActRII) inhibitor at a pharmaceutically effective dose and for a period of time to achieve (i) a long-term reduction in a ratio of ringed sideroblasts to normal erythroblasts in the subject as compared to an initial ratio of ringed sideroblasts to normal erythroblasts in the subject; and (ii) a long-term increase in hemoglobin level in the subject as compared to the hemoglobin level in the subject prior to administering to the subject the ActRII inhibitor; wherein the pharmaceutically effective dose is between 0.75 mg/kg and 2.0 mg/kg, and wherein the initial ringed sideroblast to normal erythroblast ratio in the subject is at least 1:10, at least 1:7, or at least 1:5.

Provided herein is a method for long-term treatment of non-proliferative chronic myelomonocytic leukemia (CMML) in a subject, comprising administering to the subject an activin receptor type II (ActRII) inhibitor at a pharmaceutically effective dose and for a period of time to achieve (i) a long-term reduction in a ratio of ringed sideroblasts to normal erythroblasts in the subject as compared to an initial ratio of ringed sideroblasts to normal erythroblasts in the subject; and (ii) a long-term increase in hemoglobin level in the subject as compared to the hemoglobin level in the subject prior to administering to the subject the ActRII inhibitor; wherein the pharmaceutically effective dose is between 0.75 mg/kg and 2.0 mg/kg, and wherein the initial ringed sideroblast to normal erythroblast ratio in the subject is at least 1:10, at least 1:7, or at least 1:5.

Also provided herein is a method for increasing the level of neutrophils in a subject, comprising administering to the subject a pharmaceutically effective dose of an activin receptor type II (ActRII) signaling inhibitor.

Also provided herein is a method for increasing the level of platelets in a subject, comprising administering to the subject a pharmaceutically effective dose of an activin receptor type II (ActRII) signaling inhibitor.

In certain embodiments, the ActRII signaling inhibitor is a polypeptide comprising an amino acid sequence selected from the group consisting of: (a) 90% identical to SEQ ID NO:2; (b) 95% identical to SEQ ID NO:2; (c) 98% identical to SEQ ID NO:2; (d) SEQ ID NO:2; (e) 90% identical to SEQ ID NO:3; (f) 95% identical to SEQ ID NO:3; (g) 98% identical to SEQ ID NO:3; (h) SEQ ID NO:3; (i) 90% identical to SEQ ID NO:6; (j) 95% identical to SEQ ID NO:6; (k) 98% identical to SEQ ID NO:6; (l) SEQ ID NO:6; (m) 90% identical to SEQ ID NO:7; (n) 95% identical to SEQ ID NO:7; (o) 98% identical to SEQ ID NO:7; (p) SEQ ID NO:7; (q) 90% identical to SEQ ID NO:12; (r) 95% identical to SEQ ID NO:12; (s) 98% identical to SEQ ID NO:12; (t) SEQ ID NO:12; (u) 90% identical to SEQ ID NO:17; (v) 95% identical to SEQ ID NO:17; (w) 98% identical to SEQ ID NO:17; (x) SEQ ID NO:17; (y) 90% identical to SEQ ID NO:20; (z) 95% identical to SEQ ID NO:20; (aa) 98% identical to SEQ ID NO:20; (bb) SEQ ID NO:20; (cc) 90% identical to SEQ ID NO:21; (dd) 95% identical to SEQ ID NO:21; (ee) 98% identical to SEQ ID NO:21; (ff) SEQ ID NO:21; (gg) 90% identical to SEQ ID NO:25; (hh) 95% identical to SEQ ID NO:25; (ii) 98% identical to SEQ ID NO:25; and (jj) SEQ ID NO:25.

In certain embodiments, the ActRII signaling inhibitor is an ActRIIA signaling inhibitor. In certain embodiments, the ActRIIA signaling inhibitor is a polypeptide comprising an amino acid sequence selected from the group consisting of: (a) 90% identical to SEQ ID NO:2; (b) 95% identical to SEQ ID NO:2; (c) 98% identical to SEQ ID NO:2; (d) SEQ ID NO:2; (e) 90% identical to SEQ ID NO:3; (f) 95% identical to SEQ ID NO:3; (g) 98% identical to SEQ ID NO:3; (h) SEQ ID NO:3; (i) 90% identical to SEQ ID NO:6; (j) 95% identical to SEQ ID NO:6; (k) 98% identical to SEQ ID NO:6; (l) SEQ ID NO:6; (m) 90% identical to SEQ ID NO:7; (n) 95% identical to SEQ ID NO:7; (o) 98% identical to SEQ ID NO:7; and (p) SEQ ID NO:7.

In certain embodiments, the ActRII signaling inhibitor is a polypeptide comprising the amino acid sequence of SEQ ID NO:7. In certain embodiments, the ActRII signaling inhibitor is a humanized fusion-protein consisting of the extracellular domain of ActRIIA and the human IgG1 Fc domain.

In certain embodiments, the ActRII signaling inhibitor is a signaling inhibitor of ActRIIB. In certain embodiments, the ActRIIB signaling inhibitor is a polypeptide comprising an amino acid sequence selected from the group consisting of: (a) 90% identical to SEQ ID NO:17; (b) 95% identical to SEQ ID NO:17; (c) 98% identical to SEQ ID NO:17; (d) SEQ ID NO:17; (e) 90% identical to SEQ ID NO:20; (f) 95% identical to SEQ ID NO:20; (g) 98% identical to SEQ ID NO:20; (h) SEQ ID NO:20; (i) 90% identical to SEQ ID NO:21; (j) 95% identical to SEQ ID NO:21; (k) 98% identical to SEQ ID NO:21; (l) SEQ ID NO:21; (m) 90% identical to SEQ ID NO:25; (n) 95% identical to SEQ ID NO:25; (o) 98% identical to SEQ ID NO:25; and (p) SEQ ID NO:25.

In certain embodiments, the ActRII signaling inhibitor is a polypeptide comprising the amino acid sequence of SEQ ID NO:25.

In certain embodiments, the ActRII signaling inhibitor is a humanized fusion-protein consisting of the extracellular domain of ActRIIA and the human IgG1 Fc domain.

In certain embodiments, the subject is human.

In certain embodiments, the dose of the ActRII signaling inhibitor is between 0.1 and 2.25 mg/kg. In certain embodiments, the dose of the ActRII signaling inhibitor is between 0.1 and 2.0 mg/kg. In certain embodiments, the dose of the ActRII signaling inhibitor is between 0.7 and 2.0 mg/kg. In certain embodiments, the dose of the ActRII signaling inhibitor is about 0.1 mg/kg, 0.125 mg/kg, 0.3 mg/kg, 0.5 mg/kg, 0.7 mg/kg, 1.0 mg/kg, 1.25 mg/kg, 1.33 mg/kg, 1.5 mg/kg, 1.75 mg/kg, 2.0 mg/kg, or 2.25 mg/kg. In certain embodiments, the dose of the ActRII signaling inhibitor is between 0.1 mg/kg and 0.5 mg/kg, between 0.3 mg/kg and 0.7 mg/kg, between 0.5 mg/kg and 1.0 mg/kg, between 0.7 mg/kg and 1.25 mg/kg, between 1.0 mg/kg and 2.0 mg/kg, or between 1.5 and 2.25 mg/kg.

6. BRIEF DESCRIPTION OF THE FIGURES

FIG. 1 describes the dosing regimen and study design for Example 2. See, Section 8.2. ActRIIA-I refers to ActRIIA signaling inhibitor (SEQ ID NO:7).

FIG. 2 describes the proportion of subjects achieving RBC transfusion independence (RBC-TI) of greater than or equal to 56 days for high transfusion burden (HTB) subjects or RBC-TI for greater than or equal to 56 days with mean hemoglobin (Hb) increase of greater than or equal to 1.5 g/dL over an 8 week transfusion-free period for low transfusion burden (LTB) subjects. ActRIIA-I refers to ActRIIA signaling inhibitor (SEQ ID NO:7).

FIG. 3 depicts the hemoglobin level (Hb, g/dL) and number of RBC transfusion units received by an exemplary HTB subject whom received a 1.0 mg/kg dose of an ActRIIA (SEQ ID NO:7). FIG. 3 demonstrates that the exemplary HTB subject achieves RBC-TI for greater than 56 days.

FIG. 4 demonstrates the maximum duration of transfusion burden response among HTB responders (n=19) after treatment with an ActRIIA signaling inhibitor (SEQ ID NO: 7) at the indicated doses. ActRIIA-I refers to ActRIIA signaling inhibitor (SEQ ID NO:7).

FIG. 5 demonstrates the maximum duration of RBC-TI response among HTB subjects achieving RBC-TI for greater than or equal to 56 days (n=5) after treatment with an ActRIIA signaling inhibitor (SEQ ID NO: 7) at the indicated doses. ActRIIA-I refers to ActRIIA signaling inhibitor (SEQ ID NO:7).

FIG. 6 demonstrates the proportion of LTB subjects achieving RBC-TI for greater than or equal to 56 days and a mean Hb increase of greater than or equal to 1.5 g/dL (n=9) after treatment with an ActRIIA signaling inhibitor (SEQ ID NO:7) at the indicated doses. ActRIIA-I refers to ActRIIA signaling inhibitor (SEQ ID NO:7).

FIG. 7 demonstrates the maximum duration of RBC-TI response among LTB subjects achieving RBC-TI for greater than or equal to 56 days and a mean Hb increase of greater than or equal to 1.5 g/dL (n=5) after treatment with ActRIIA (SEQ ID NO:7) at the indicated doses. ActRIIA-I refers to ActRIIA signaling inhibitor (SEQ ID NO:7).

FIG. 8 describes the dosing regimen and study design for Example 2. See, Section 8.3. BL=baseline. ActRIIB-I refers to ActRIIB signaling inhibitor (SEQ ID NO:25).

FIG. 9 describes the maximum hemoglobin increase in LTB subjects after treatment with an ActRIIB signaling inhibitor (SEQ ID NO:25) at the indicated doses.

FIG. 10 describes the increase in reticulocytes in LTB subjects after treatment with an ActRIIB signaling inhibitor (SEQ ID NO:25) at the indicated doses.

FIG. 11 describes the hemoglobin levels in an exemplary LTB subject administered an ActRIIB signaling inhibitor (SEQ ID NO:25) at the indicated doses and according to the indicated treatment regimen. BL=baseline.

FIG. 12 describes the hemoglobin levels in an exemplary LTB subject administered an ActRIIB signaling inhibitor (SEQ ID NO:25) at the indicated doses and according to the indicated treatment regimen. BL=baseline.

FIG. 13 describes the hemoglobin levels in an exemplary HTB subject administered an ActRIIB signaling inhibitor (SEQ ID NO:25) at the indicated doses and according to the indicated treatment regimen. BL=baseline.

FIG. 14 demonstrates that the exemplary HTB subject achieves RBC-TI for at least 337 days after the initiation of treatment with the ActRIIA-hFc (SEQ ID NO:7).

FIG. 15 demonstrates that the exemplary LTB subject achieves a sustained increase in Hb levels for at least 337 days after the initiation of treatment with the ActRIIA-hFc (SEQ ID NO:7).

Figure 17:
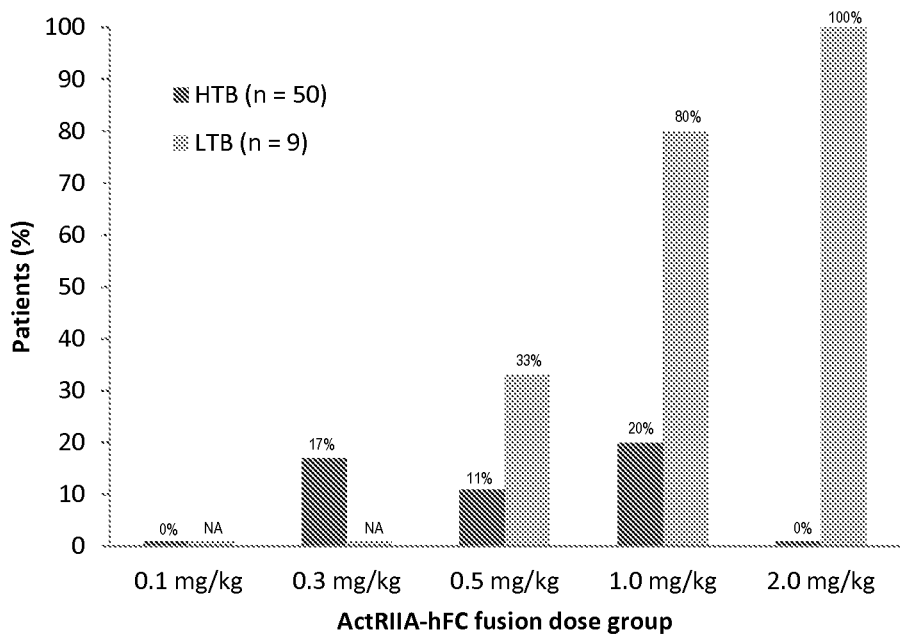

FIG. 17 describes the proportion of subjects achieving RBC transfusion independence (RBC-TI) with a mean hemoglobin increase of equal to or more than 1.5 g/dL for LTB patients over any 8-week period in patients receiving ActRIIA-hFC fusion (SEQ ID NO:7). Dark grey shading indicates HTB and light grey shading indicates LTB patients.

Figure 18:
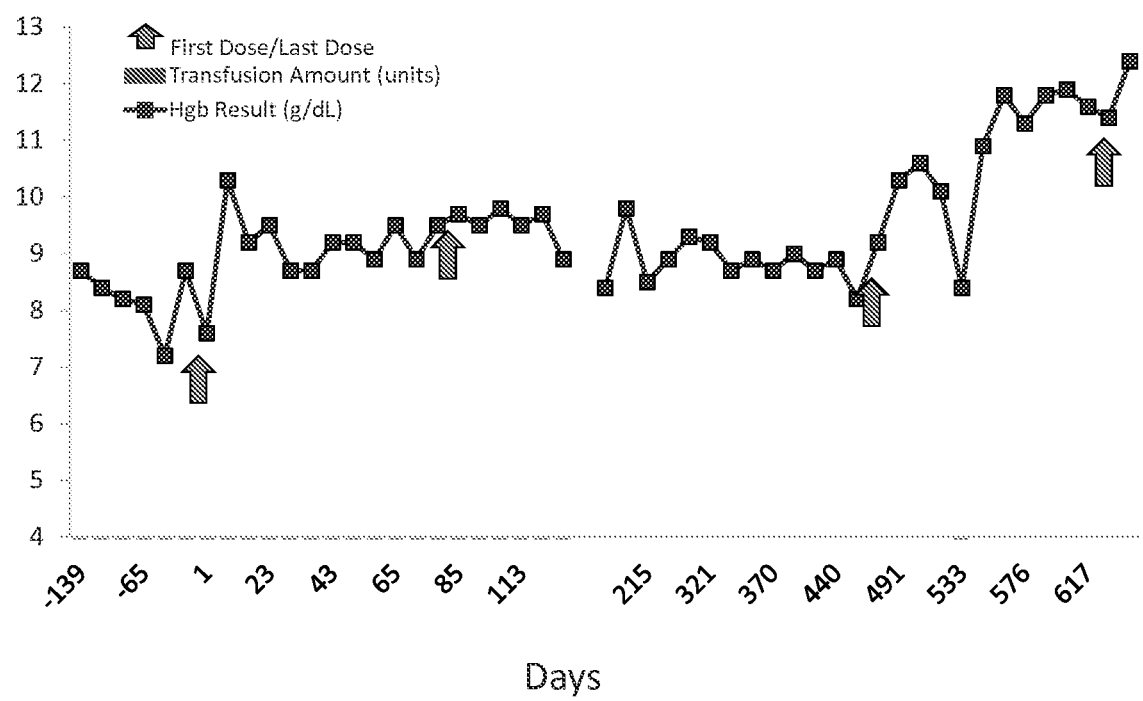

FIG. 18 illustrates the hemoglobin response of an exemplary HTB subject in the course of the 12-month ActRIIA-hFc (SEQ ID NO:7) treatment extension study. First and last treatment doses are indicated by arrows. Blood transfusion events are indicated by bars. Hemoglobin (Hgb) results (in g/dL) are plotted against time (in days).

Figure 19:
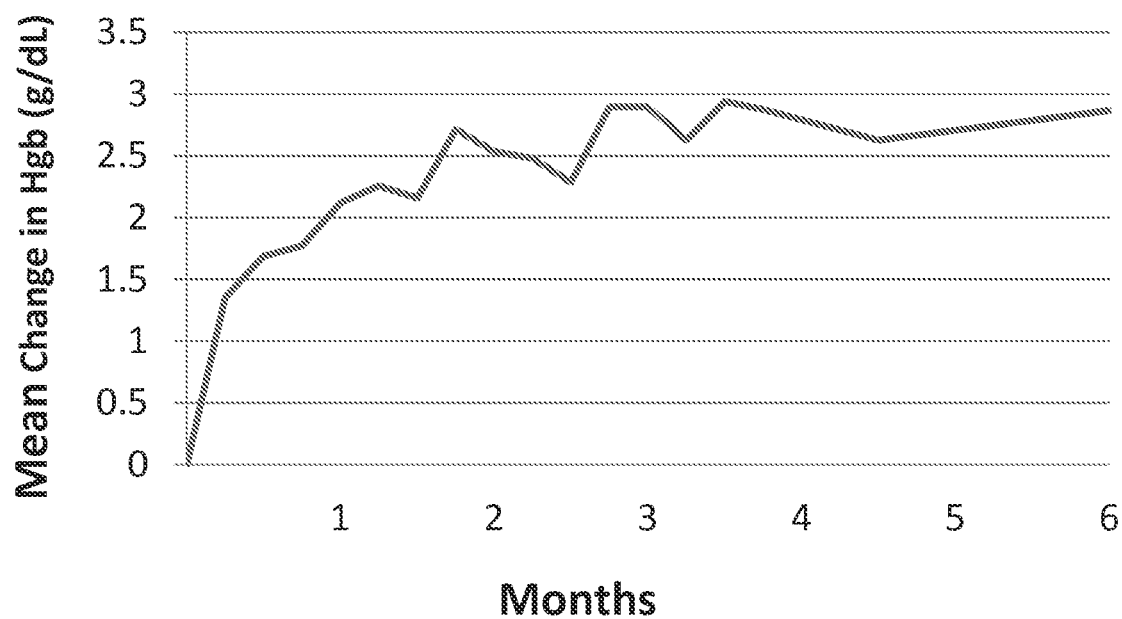

FIG. 19 illustrates the hemoglobin response of an exemplary LTB subject in the course of the 12-month ActRIIA-hFc (SEQ ID NO:7) treatment extension study. The mean change in Hgb (in g/L) is plotted against time (in months).

Figure 20:
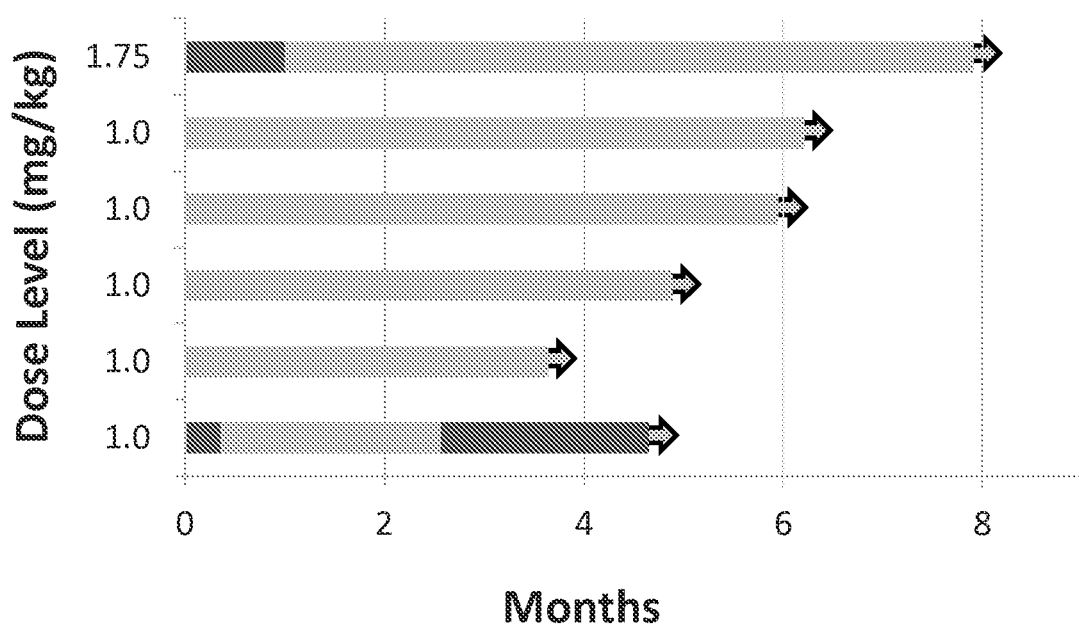

FIG. 20 illustrates transfusion independence responses observed in six subjects in the course of the 12-month ActRIIA-hFc (SEQ ID NO:7) treatment extension study, while receiving ActRIIA-hFc (SEQ ID NO:7) treatments at doses of 1.0 mg/kg (subjects represented by bottom four bars) and 1.75 mg/kg (subject represented by top bar). Four patients experienced continuing transfusion independence throughout the study (middle 4 bars). One patient acquired transfusion independence after about one month of ActRIIA-hFc (SEQ ID NO:7) treatments (top bar). One patient experienced transfusion independence intermittently for about 2 months (bottom bar).

7. DETAILED DESCRIPTION

7.1 Overview

It was unexpectedly found that levels of ring sideroblasts in patients with a blood-related disorder can be used to identify patients responsive to treatment with an inhibitor of Activin-ActRII signaling. Such blood-related disorders can be (i) anemia; (ii) anemia requiring RBC transfusion; (iii) MDS; and/or (iv) non-proliferative CMML. See Section 7.8. Without being bound by theory, about 15% or more ring sideroblasts of erythroblasts in a patient with a blood-related disorder is predictive of an improved clinical response to an inhibitor of Activin-ActRII signaling in the patient, relative to patient with the same blood-related disorder but with less than about 15% ring sideroblasts of erythroblasts. Such an improved clinical response can be increased response of a hematological parameter (such as hemoglobin levels, red blood cell levels, and hematocrit). Such an improved clinical response may manifest itself in a lowered transfusion burden. Further, such an improved clinical response can result in a long term benefit for the patient without continued administration of the inhibitor of Activin-ActRII signaling. In other words, the methods provided herein can result in the improvement of one or more hematological parameters in a patient for a period of time after the administration of the inhibitor of Activin-ActRII signaling has been discontinued.

Accordingly, provided herein are methods for treating a patient with a blood-related disorder, wherein the method comprises (a) determining the percentage of ring sideroblasts among erythroblasts; and (b) administering an inhibitor of Activin-ActRII signaling to the patient if about 15% or more of erythroblasts are ring sideroblasts. More specifically, provided herein are methods for treating a patient with a blood-related disorder, wherein the method comprises (a) determining the percentage of ring sideroblasts among erythroblasts in the patient; (b) administering an inhibitor of Activin-ActRII signaling to the patient; and (c) if at least about 15% of erythroblasts are ring sideroblasts, then (i) reducing the dose of or discontinuing the administration of the inhibitor of Activin-ActRII signaling after a period of time and/or (ii) decreasing the frequency of the administration of the inhibitor of Activin-ActRII signaling after a period of time. A detailed description of these methods can be found in Sections 7.3 and 7.4.

7.2 Terms and Abbreviations

As used herein, "ActRII" refers to activin receptor type II. As used herein, "ActRIIA" refers to activin receptor type IIA. See, for example, Mathews and Vale, 1991, Cell 65:973-982. GenBank™ accession number NM_001278579.1 provides an exemplary human ActRIIA nucleic acid sequence. GenBank™ accession number NP_001265508.1 provides an exemplary human ActRIIA amino acid sequence. As used herein, "ActRIIB" refers to activin receptor type IIB. See, for example, Attisano et al., 1992, Cell 68: 97-108. GenBank™ accession number NM_001106.3 provides an exemplary human ActRIIB nucleic acid sequence. GenBank™ accession number NP_001097.2 provides an exemplary human ActRIIB amino acid sequence.

As used herein, "ActRIIA-mFc" or "mActRIIA-Fc" refers to a mouse activin type IIA receptor-IgG1 fusion protein. See, for example, U.S. Pat. No. 8,173,601. As used herein, "mActRIIB-Fc" or "ActRIIB-mFc" refers to a mouse activin type IIB receptor-IgG1 fusion protein. See, for example, U.S. Pat. No. 8,173,601. As used herein, "hActRIIA-Fc" or "ActRIIA-hFc" refers to a human activin type IIA receptor-IgG1 fusion protein. See, for example, U.S. Pat. No. 8,173,601. In a specific embodiment, hActRIIA-Fc is sotatercept (SEQ ID NO: 7). As used herein, "hActRIIB-Fc" or "ActRIIB-hFc" refers to a human activin type IIB receptor-IgG1 fusion protein. See, for example, U.S. Pat. No. 8,173,601. In a specific embodiment, hActRIIB-Fc is luspatercept (SEQ ID NO: 25).

As used herein, "ALK" refers to anaplastic lymphoma kinase.

As used herein, "BL" refers to baseline.

As used herein, "BMP7" refers to bone morphogenetic protein 7.

As used herein, "CMML" refers to chronic myelomonocytic leukemia.

As used herein, "DEXA" refers to dual-energy X-ray absorptiometry.

As used herein, "DNMT3A" refers to DNA (cytosine-5)-methyltransferase 3A. GenBank™ accession numbers NM_153759.3, NM_022552.4, NM_175629.2, and NM_175630.1 provide exemplary nucleic acid sequences for human DNMT3A. GenBank™ accession numbers NP_715640.2, NP_783329.1, NP_783328.1, and NP_072046.2 provide exemplary amino acid sequences for human DNMT3A.

As used herein, "ECD" refers to extracellular domain.

As used herein, "EPO" refers to erythropoietin.

As used herein, "ESA" refers to erythropoiesis-stimulating agent.

As used herein, "G-CSF" refers to granulocyte colony-stimulating factor.

As used herein, "GM-CSG" refers to granulocyte macrophage colony-stimulating factor.

As used herein, "Hb" refers to hemoglobin.

As used herein, "HBML" refers to honey bee mellitin.

As used herein, "HI-E" refers to erythroid hematological improvement. In certain embodiments, the HI-E is as defined by IWG. In certain embodiments, the HI-E is as defined by the modified 2006 IWG. In certain embodiments, the HI-E for a low transfusion burden patient is an increase in hemoglobin concentration in the patient of at least 1.5 g/dL for at least 8 weeks. In certain embodiments, the HI-E for a high transfusion burden patient is an at least 4 unit reduction in RBC transfusion over 8 weeks.

As used herein, "HTB" refers to high transfusion burden. In certain embodiments, a HTB subject receives greater than or equal to 4 RBC units over the course of 8 weeks.

As used herein, "IgG" refers to immunoglobulin G.

As used herein, "Int-1" refers to the IPSS score of intermediate 1. See Section 7.8.

As used herein, "IPSS" refers to International Prognostic Scoring System. See Section 7.8.

As used herein, "IWG" refers to International Working Group. See, e.g., Cheson et al. Blood. 2000 96:3671-3674. In certain embodiments, IWG refers to the modified 2006 criteria. See, e.g., Cheson et al., 2006, Blood, 108(2).

As used herein, "LTB" refers to low transfusion burden. In certain embodiments, a LTB subject receives less than 4 RBC units over the course of 8 weeks.

As used herein, "MDS" refers to myelodysplastic syndromes.

As used herein, "PD" refers to pharmacodynamic.

As used herein, "PK" refers to pharmacokinetic.

As used herein, "qCT" refers to quantitative computed tomography.

As used herein, "RARS" refers to refractory anemia with ring sideroblasts.

As used herein, "RBC" refers to red blood cells.

As used herein, "RBC-TI" refers to red blood cell transfusion independent.

As used herein, "RCMD-RS" refers to refractory cytopenia with multilineage dysplasia with ring sideroblasts.

As used herein, "RS" refers to ring sideroblast.

As used herein, "SC" refers to subcutaneous.

As used herein, "SETBP1" refers to SET binding protein 1. GenBank™ accession numbers NM_015559.2 and NM_001130110.1 provide exemplary nucleic acid sequences for human SETBP1. GenBank™ accession numbers NP_056374.2 and NP_001123582.1 provide exemplary amino acid sequences for human SETBP1.

As used herein, "SF3B1" refers to splicing factor 3B1. GenBank™ accession numbers NM_012433.3, NM_001005523.2, and NM_001308824.1 provide exemplary nucleic acid sequences for human SF3B1. GenBank™ accession numbers NP_001295753.1, NP_001005526.1, and NP_036565.2 provide exemplary amino acid sequences for human SF3B1.

As used herein, "SPR" refers to surface plasmon resonance.

As used herein, "SRSF2" refers to serine/arginine-rich splicing factor 2. GenBank™ accession numbers NM_003016.4 and NM_001195427.1 provide exemplary nucleic acid sequences for human SRSF2. GenBank™ accession numbers NP_001182356.1 and NP_003007.2 provide exemplary amino acid sequences for human SRSF2.

As used herein, "TET2" refers to tet methylcytosine dioxygenase 2. GenBank™ accession numbers NM_001127208.2 and NM_017628.4 provide exemplary nucleic acid sequences for human TET2. GenBank™ accession numbers NP_001120680.1 and NP_060098.3 provide exemplary amino acid sequences for human TET2.

As used herein, "TGF" refers to transforming growth factor.

As used herein, "TPA" refers to tissue plasminogen activator.

7.3 Methods of Treatment

In certain embodiments, provided herein is a method of treating a subject with a blood-related disorder, wherein the method comprises (a) determining the percentage of erythroblasts in the subject that are ring sideroblasts; and (b) administering a pharmaceutically effective dose of an ActRII signaling inhibitor to the subject if at least 10%, 11%, 12%, 13%, 14%, 15%, 16%, 17%, 18%, 19%, or 20% of erythroblasts in the subject are ring sideroblasts. In certain embodiments, the inhibitor of ActRII signaling is administered to the subject if at least 15% of erythroblasts in the subject are ring sideroblasts. In certain embodiments, the percentage of erythroblasts in the subject that are ring sideroblasts is determined at a first time. In certain embodiments, the first time is a within 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months of administering the pharmaceutically effective dose of the ActRII signaling inhibitor to the subject. In certain embodiments, the blood-related disorder is a blood-related disorder as described in Section 7.8. In certain embodiments, the subject is a subject as described in Section 7.8. In certain embodiments, the subject has hemoglobin levels of less than 11 g/dL. In certain embodiments, the subject has decreased hemoglobin levels as compared to a reference population. In certain embodiments, the reference population is as described in Section 7.10. In certain embodiments, the subject has anemia. In certain embodiments, the subject is a subject requiring RBC transfusion. In certain embodiments, the subject has MDS. In certain embodiments, the subject has non-proliferative CMML. In certain embodiments, the subject has an increased likelihood of achieving normalization of one or more hematological parameters if at least 10%, 11%, 12%, 13%, 14%, 15%, 16%, 17%, 18%, 19%, or 20% of erythroblasts in the subject are ring sideroblasts. In certain embodiments, the subject has an increased likelihood of achieving a normalization of one or more hematological parameters if at least 15% of erythroblasts in the subject are ring sideroblasts. In certain embodiments, the hematological parameter is hemoglobin level. In certain embodiments, the hematological parameter is hematocrit. In certain embodiments, the hematological parameter is red blood cell count. In certain embodiments, the hematological parameter is the percentage of erythroblasts in the subject that are ring sideroblasts. In certain embodiments, the normalized hematological parameter is a level of the hematological parameter in a reference population. In certain embodiments, the reference population is a reference population as described in Section 7.10. In certain embodiments, the normalization of one or more hematological parameters is an improvement by at least 10%, 20%, 30%, 40%, 50%, 60%, 70%, 80%, 90%, or 100% as compared to the hematological parameter in the subject at a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the percentage of erythroblasts in the subject that are ring sideroblasts is determined according to an assay as described in Section 7.10. In certain embodiments, ring sideroblasts are identified according to an assay as described in Section 7.10. In certain embodiments, ring sideroblasts are identified according to Prussian blue staining. In certain embodiments, erythroblasts are identified according to an assay as described in Section 7.10. In certain embodiments the hemoglobin level in the subject is determined according to an assay as described in Section 7.10. In certain embodiments, the pharmaceutically effective dose is a dose as described in Section 7.7. In certain embodiments, the pharmaceutically effectively dose is administered at a frequency as described in Section 7.7. In certain embodiments, the pharmaceutically effective dose is administered as described in Section 7.7. In certain embodiments, the pharmaceutically effective dose is an initial dose as described in Section 7.7. In certain embodiments, the pharmaceutically effective dose is an adjusted dose as described in Section 7.7. In certain embodiments, ActRII signaling inhibitor is administered as a composition as described in Section 7.11. In certain embodiments, the composition is administered at a frequency as described in Section 7.7. In certain embodiments, the composition is administered as described in Section 7.7. In certain embodiments, the ActRII signaling inhibitor is an ActRII signaling inhibitor as described in Section 7.9. In certain embodiments, the ActRII signaling inhibitor is an ActRIIA signaling inhibitor. In certain embodiments, the ActRIIA signaling inhibitor is administered subcutaneously once every 21 days. In certain embodiments, the ActRII signaling inhibitor is an ActRIIA-Fc such as ActRIIA-hFc (e.g., SEQ ID NO:7). In certain embodiments, the ActRII signaling inhibitor is an ActRIIB signaling inhibitor. In certain embodiments, the ActRIIB signaling inhibitor is administered subcutaneously once every 21 days. In certain embodiments, the ActRII signaling inhibitor is an ActRII-Fc such as ActRIIB-hFc (e.g., SEQ ID NO:25).

In certain embodiments, provided herein is a method of treating a blood-related disorder in a subject, comprising administering to the subject an activin receptor type II (ActRII) signaling inhibitor at a pharmaceutically effective dose and for a period of time to achieve (i) a long-term reduction in a percentage of erythroblasts in the subject that are ring sideroblasts as compared to an initial percentage of erythroblasts in the subject that are ring sideroblasts; and (ii) a long-term increase in hemoglobin level in the subject as compared to the hemoglobin level in the subject a period of time prior to administering to the subject an initial dose of the ActRII signaling inhibitor; wherein the pharmaceutically effective dose is between 0.1 mg/kg and 2.0 mg/kg, and wherein at least 10%, 11%, 12%, 13%, 14%, 15%, 16%, 17%, 18%, 19%, or at least 20% of erythroblasts in the subject are ring sideroblasts. In certain embodiments, the pharmaceutically effective dose is between 0.75 mg/kg and 2.0 mg/kg. In certain embodiments, the blood-related disorder is a blood-related disorder as described in Section 7.8. In certain embodiments, the subject is a subject as described in Section 7.8. In certain embodiments, 15% of erythroblasts in the subject are ring sideroblasts. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the subject is a subject requiring RBC transfusion. As used herein, "ring sideroblasts" and "ringed sideroblasts" and "RS" are used interchangeably. In certain embodiments, the ActRII signaling inhibitor is administered for at most 1, 2, 3, 4, 5, or 6 months. In certain embodiments, the initial percentage of erythroblasts in the subject that are ring sideroblasts is a percentage of erythroblasts in the subject that are ring sideroblasts a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the long-term reduction in the percentage of erythroblasts in the subject that are ring sideroblasts is maintained for at least 3, 4, 5, 6, 12, 18, or 24 months after the period of time of ActRII signaling inhibitor administration. In certain embodiments, the long-term reduction in the percentage of erythroblasts in the subject that are ring sideroblasts is maintained for at least 3, 4, 5, 6, 12, 18, or 24 months after the last dose of the ActRII signaling inhibitor is administered and without further administration of the ActRII signaling inhibitor. In certain embodiments, the long-term reduction in the percentage of erythroblasts in the subject that are ring sideroblasts is at least 1.5, 2.5, 5.0, 7.5, or 10.0 fold below the initial percentage of erythroblasts in the subject that are ring sideroblasts for at least 6, 12, 18, or 24 months after the period of time of ActRII signaling inhibitor administration. In certain embodiments, the long-term increase in the hemoglobin level in the subject is maintained for at least 3, 4, 5, 6, 12, 18, or 24 months after the period of time of ActRII signaling inhibitor administration. In certain embodiments, the long-term increase in the hemoglobin level in the subject is a hemoglobin level of between about 11 g/dL and 18 g/dL in the subject for at least 3, 4, 5, 6, 12, 18, or 24 months after the period of time of ActRII signaling inhibitor administration. In certain embodiments, the subject does not require RBC transfusion for at least 3, 4, 5, 6, 12, 18, or 24 months after the period of time of ActRII signaling inhibitor administration. In certain embodiments, the method eliminates requirement for RBC transfusion in the subject for at least 3, 4, 5, 6, 12, 18, or 24 months after ActRII signaling inhibitor administration. In certain embodiments, the long-term reduction in the percentage of erythroblasts in the subject that are ring sideroblasts is at least 1.5, 2.5, 5.0, 7.5, or 10.0 fold below the initial percentage of erythroblasts in the subject that are ring sideroblasts for at least 6, 12, 18, or 24 months after the last dose of the ActRII signaling inhibitor is administered and without further administration of the ActRII signaling inhibitor. In certain embodiments, the long-term increase in the hemoglobin level in the subject is maintained for at least 3, 4, 5, 6, 12, 18, or 24 months after the last dose of the ActRII signaling inhibitor is administered and without further administration of the ActRII signaling inhibitor. In certain embodiments, the long-term increase in the hemoglobin level in the subject is a hemoglobin level of between about 11 g/dL and 18 g/dL in the subject for at least 3, 4, 5, 6, 12, 18, or 24 months after the last dose of the ActRII signaling inhibitor is administered and without further administration of the ActRII signaling inhibitor. In certain embodiments, the subject does not require RBC transfusion for at least 3, 4, 5, 6, 12, 18, or 24 months after the last dose of the ActRII signaling inhibitor is administered and without further administration of the ActRII signaling inhibitor. In certain embodiments, the method eliminates requirement for RBC transfusion in the subject for at least 3, 4, 5, 6, 12, 18, or 24 months after the last dose of the ActRII signaling inhibitor is administered and without further administration of the ActRII signaling inhibitor.

In certain embodiments, the method further comprises determining an additional percentage of erythroblasts in the subject that are ring sideroblasts 6, 12, 18, and/or 24 months after the period of time of ActRII signaling inhibitor administration. In certain embodiments, the method further comprises determining an additional hemoglobin level in the subject 6, 12, 18, and/or 24 months after the period of time of ActRII signaling inhibitor administration.

In certain embodiments, the percentage of erythroblasts in the subject that are ring sideroblasts is determined according to an assay as described in Section 7.10. In certain embodiments, ring sideroblasts are identified according to an assay as described in Section 7.10. In certain embodiments, ring sideroblasts are identified according to Prussian blue staining. In certain embodiments, erythroblasts are identified according to an assay as described in Section 7.10. In certain embodiments the hemoglobin level in the subject is determined according to an assay as described in Section 7.10. In certain embodiments, the subject is a subject as described in Section 7.8. In certain embodiments, at least 10%, 11%, 12%, 13%, 14%, 15%, 16%, 17%, 18%, 19%, or at least 20% of erythroblasts in the subject are ring sideroblasts In certain embodiments, the subject is a subject as described in Section 7.8. In certain embodiments, at least 15% of erythroblasts in the subject are ring sideroblasts. In certain embodiments, the subject has hemoglobin levels of less than 11 g/dL. In certain embodiments, the subject has decreased hemoglobin levels as compared to a reference population. In certain embodiments, the reference population is as described in Section 7.10. In certain embodiments, the subject has anemia. In certain embodiments, the subject is a subject requiring RBC transfusion. In certain embodiments, the subject has MDS. In certain embodiments, the subject has non-proliferative CMML.

In certain embodiments, the pharmaceutically effective dose is a dose as described in Section 7.7. In certain embodiments, the pharmaceutically effectively dose is administered at a frequency as described in Section 7.7. In certain embodiments, the pharmaceutically effective dose is administered as described in Section 7.7. In certain embodiments, the pharmaceutically effective dose is an initial dose. In certain embodiments, the initial dose is administered according a method as described in Section 7.4. In certain embodiments, the pharmaceutically effective dose is an adjusted dose. In certain embodiments, the adjusted dose is administered according to a method as described in Section 7.4.

In certain embodiments, ActRII signaling inhibitor is administered as a composition as described in Section 7.11. In certain embodiments, the composition is administered at a frequency as described in Section 7.7. In certain embodiments, the composition is administered as described in Section 7.7.

In certain embodiments, the ActRII signaling inhibitor is an ActRII signaling inhibitor as described in Section 7.9. In certain embodiments, the ActRII signaling inhibitor is an ActRIIA signaling inhibitor. In certain embodiments, the ActRIIA signaling inhibitor is administered subcutaneously once every 21 days. In certain embodiments, the ActRII signaling inhibitor is an ActRIIA-Fc such as ActRIIA-hFc (e.g., SEQ ID NO:7). In certain embodiments, the ActRII signaling inhibitor is an ActRIIB signaling inhibitor. In certain embodiments, the ActRIIB signaling inhibitor is administered subcutaneously once every 21 days. In certain embodiments, the ActRII signaling inhibitor is an ActRII-Fc such as ActRIIB-hFc (e.g., SEQ ID NO:25).

In certain embodiments, provided herein is a method for treating a blood-related disorder in a subject, wherein the method comprises: (a) determining the percentage of erythroblasts in the subject that are ring sideroblasts; and (b) (i) administering an ActRII signaling inhibitor to the subject at a pharmaceutically effective dose of between 0.1 mg/kg and 2.0 mg/kg for a short period of time if the percentage of erythroblasts in the subject that are ring sideroblasts is least 10%, 11%, 12%, 13%, 14%, 15%, 16%, 17%, 18%, 19%, or at least 20%, or (ii) administering an ActRII signaling inhibitor to the subject at a pharmaceutically effective dose of between 0.1 mg/kg and 2.0 mg/kg for a long period of time if the percentage of erythroblasts in the subject that are ring sideroblasts is less than 10%, 9%, 8%, 7%, 6%, 5%, 4%, 3%, 2%, or 1%. In certain embodiments, the blood-related disorder is a blood-related disorder as described in Section 7.8. In certain embodiments, the subject is a subject as described in Section 7.8. In certain embodiments, the pharmaceutically effective dose is between 0.75 mg/kg and 2.0 mg/kg. In certain embodiments, the subject is a subject requiring RBC transfusion. In certain embodiments, the short period of time of administration of the ActRII signaling inhibitor to the subject is 1, 2, 3, 4, or 5 months. In certain embodiments, the long period of time of administration of the ActRII signaling inhibitor to the subject is at least 6, 12, 18, or 24 months. In a specific embodiment, the short period of time of administration is followed by testing levels of ring sideroblasts at least 0, 3, 4, 5, 6, 12, 28, 24, or 48 months after a last administration of the ActRII signaling inhibitor. In certain embodiments, the ActRII signaling inhibitor is an ActRII signaling inhibitor as described in Section 7.9. In certain embodiments, the ActRII signaling inhibitor is an ActRIIA signaling inhibitor. In certain embodiments, the ActRIIA signaling inhibitor is administered subcutaneously once every 21 days. In certain embodiments, the ActRII signaling inhibitor is an ActRIIA-Fc such as ActRIIA-hFc (e.g., SEQ ID NO:7). In certain embodiments, the ActRII signaling inhibitor is an ActRIIB signaling inhibitor. In certain embodiments, the ActRIIB signaling inhibitor is administered subcutaneously once every 21 days. In certain embodiments, the ActRII signaling inhibitor is an ActRII-Fc such as ActRIIB-hFc (e.g., SEQ ID NO:25).

In certain embodiments, the method further comprises determining an additional percentage of erythroblasts in the subject that are ring sideroblasts 6, 12, 18, and/or 24 months after the period of time of ActRII signaling inhibitor administration. In certain embodiments, the method further comprises determining an additional hemoglobin level in the subject 6, 12, 18, and/or 24 months after the period of time of ActRII signaling inhibitor administration.

In certain embodiments, the method further comprises determining an additional percentage of erythroblasts in the subject that are ring sideroblasts 6, 12, 18, and/or 24 months after the period of time of ActRII signaling inhibitor administration. In certain embodiments, the method further comprises determining the hemoglobin level in the subject 6, 12, 18, and/or 24 months after the period of time of ActRII signaling inhibitor administration. In certain embodiments, the method eliminates requirement for red blood cell transfusion in the subject for at least 3, 4, 5, 6, 12, 18, or 24 months after ActRII signaling inhibitor administration. In certain embodiments, the method eliminates requirement for red blood cell transfusion in the subject for at least 3, 4, 5, 6, 12, 18, or 24 months after the last dose of the ActRII signaling inhibitor is administered and without further administration of the ActRII signaling inhibitor.

In certain embodiments, the percentage of erythroblasts in the subject that are ring sideroblasts is determined according to an assay as described in Section 7.10. In certain embodiments, ring sideroblasts are identified according to an assay as described in Section 7.10. In certain embodiments, ring sideroblasts are identified according to Prussian blue staining. In certain embodiments, erythroblasts are identified according to an assay as described in Section 7.10. In certain embodiments the hemoglobin level in the subject is determined according to an assay as described in Section 7.10. In certain embodiments, the hemoglobin level in the subject is determined according to an assay as described in Section 7.10.

In certain embodiments, the subject is a subject as described in Section 7.8. In certain embodiments, at least 10%, 11%, 12%, 13%, 14%, 15%, 16%, 17%, 18%, 19%, or at least 20% of erythroblasts in the subject are ring sideroblasts. In certain embodiments, at least 15% of erythroblasts in the subject are ring sideroblasts. In certain embodiments, the subject has hemoglobin levels of less than 11 g/dL. In certain embodiments, the subject has decreased hemoglobin levels as compared to a reference population. In certain embodiments, the reference population is as described in Section 7.10. In certain embodiments, the subject has anemia. In certain embodiments, the subject is a subject requiring RBC transfusion. In certain embodiments, the subject has MDS. In certain embodiments, the subject has non-proliferative CMML.

In certain embodiments, the pharmaceutically effective dose is a dose as described in Section 7.7. In certain embodiments, the pharmaceutically effectively dose is administered at a frequency as described in Section 7.7. In certain embodiments, the pharmaceutically effective dose is administered as described in Section 7.7. In certain embodiments, the pharmaceutically effective dose is an initial dose. In certain embodiments, the initial dose is administered according a method as described in Section 7.4. In certain embodiments, the pharmaceutically effective dose is an adjusted dose. In certain embodiments, the adjusted dose is administered according to a method as described in Section 7.4.

In certain embodiments, ActRII signaling inhibitor is administered as a composition as described in Section 7.11. In certain embodiments, the composition is administered at a frequency as described in Section 7.7. In certain embodiments, the composition is administered as described in Section 7.7.

In certain embodiments, the ActRII signaling inhibitor is an ActRII signaling inhibitor as described in Section 7.9. In certain embodiments, the ActRII signaling inhibitor is an ActRIIA signaling inhibitor. In certain embodiments, the ActRIIA signaling inhibitor is administered subcutaneously once every 21 days. In certain embodiments, the ActRII signaling inhibitor is an ActRIIA-Fc such as ActRIIA-hFc (e.g., SEQ ID NO:7). In certain embodiments, the ActRII signaling inhibitor is an ActRIIB signaling inhibitor. In certain embodiments, the ActRIIB signaling inhibitor is administered subcutaneously once every 21 days. In certain embodiments, the ActRII signaling inhibitor is an ActRII-Fc such as ActRIIB-hFc (e.g., SEQ ID NO:25).

In certain embodiments, provided herein are methods for treating a blood-related disorder in a subject comprising administering to the subject a pharmaceutically effective dose of an Activin receptor type II (ActRII) signaling inhibitor, and wherein the subject expresses SF3B1 comprising one or more mutations. In certain embodiments, the one or more mutations is in a non-coding region. In certain embodiments, the one or more mutations is in a coding region. In certain embodiments, SF3B1 is SF3B1 protein. In certain embodiments, SF3B1 is the gene encoding SF3B1. In certain embodiments, the subject is a subject as described in Section 7.8. In certain embodiments, the blood-related disorder is a blood-related disorder as described in Section 7.8. In certain embodiments, the one or more mutations in SF3B1 is as described in Section 7.8. In certain embodiments, at least 10%, 11%, 12%, 13%, 14%, 15%, 16%, 17%, 18%, 19%, or at least 20% of erythroblasts in the subject are ring sideroblasts. In certain embodiments, at least 15% of erythroblasts in the subject are ring sideroblasts. In certain embodiments, the subject has hemoglobin levels of less than 11 g/dL. In certain embodiments, the subject has decreased hemoglobin levels as compared to a reference population. In certain embodiments, the reference population is as described in Section 7.10. In certain embodiments, the subject has anemia. In certain embodiments, the subject is a subject requiring RBC transfusion. In certain embodiments, the subject has MDS. In certain embodiments, the subject has non-proliferative CMML. In certain embodiments, the subject treated in accordance with the methods provided herein has thrombocytopenia. In certain embodiments, the pharmaceutically effective dose is a dose as described in Section 7.7. In certain embodiments, the pharmaceutically effective dose is between 0.1 mg/kg and 2.0 mg/kg of an ActRII signaling inhibitor. In certain embodiments, the pharmaceutically effective dose is between 0.75 mg/kg and 2.0 mg/kg of an ActRII signaling inhibitor. In certain embodiments, the pharmaceutically effectively dose is administered at a frequency as described in Section 7.7. In certain embodiments, the pharmaceutically effective dose is administered as described in Section 7.7. In certain embodiments, the pharmaceutically effective dose is an initial dose. In certain embodiments, the initial dose is administered according a method as described in Section 7.4. In certain embodiments, the pharmaceutically effective dose is an adjusted dose. In certain embodiments, the adjusted dose is administered according to a method as described in Section 7.4. In certain embodiments, ActRII signaling inhibitor is administered as a composition as described in Section 7.11. In certain embodiments, the composition is administered at a frequency as described in Section 7.7. In certain embodiments, the composition is administered as described in Section 7.7. In certain embodiments, the ActRII signaling inhibitor is an ActRII signaling inhibitor as described in Section 7.9. In certain embodiments, the ActRII signaling inhibitor is an ActRIIA signaling inhibitor. In certain embodiments, the ActRIIA signaling inhibitor is administered subcutaneously once every 21 days. In certain embodiments, the ActRII signaling inhibitor is an ActRIIA-Fc such as ActRIIA-hFc (e.g., SEQ ID NO:7). In certain embodiments, the ActRII signaling inhibitor is an ActRIIB signaling inhibitor. In certain embodiments, the ActRIIB signaling inhibitor is administered subcutaneously once every 21 days. In certain embodiments, the ActRII signaling inhibitor is an ActRII-Fc such as ActRIIB-hFc (e.g., SEQ ID NO:25). The subject in need of increasing neutrophil levels can be a subject with ring sideroblasts, anemia, anemia requiring RBC transfusion, non-proliferative CMML, and/or MDS.

7.3.1 Genetic Markers

In certain embodiments, provided herein are methods for treating a blood-related disorder in a subject comprising administering to the subject a pharmaceutically effective dose of an Activin receptor type II (ActRII) signaling inhibitor, and wherein the subject expresses SF3B1 comprising one or more mutations. In certain embodiments, the one or more mutations is in a non-coding region. In certain embodiments, the one or more mutations is in a coding region. In certain embodiments, SF3B1 is SF3B1 protein. In certain embodiments, SF3B1 is the gene encoding SF3B1. In certain embodiments, the subject is a subject as described in Section 7.8. In certain embodiments, the blood-related disorder is a blood-related disorder as described in Section 7.8. In certain embodiments, the one or more mutations in SF3B1 is as described in Section 7.8. In certain embodiments, at least 10%, 11%, 12%, 13%, 14%, 15%, 16%, 17%, 18%, 19%, or at least 20% of erythroblasts in the subject are ring sideroblasts. In certain embodiments, at least 15% of erythroblasts in the subject are ring sideroblasts. In certain embodiments, the subject has hemoglobin levels of less than 11 g/dL. In certain embodiments, the subject has decreased hemoglobin levels as compared to a reference population. In certain embodiments, the reference population is as described in Section 7.10. In certain embodiments, the subject has anemia. In certain embodiments, the subject is a subject requiring RBC transfusion. In certain embodiments, the subject has MDS. In certain embodiments, the subject has non-proliferative CMML. In certain embodiments, the subject treated in accordance with the methods provided herein has thrombocytopenia. In certain embodiments, the pharmaceutically effective dose is a dose as described in Section 7.7. In certain embodiments, the pharmaceutically effective dose is between 0.1 mg/kg and 2.0 mg/kg of an ActRII signaling inhibitor. In certain embodiments, the pharmaceutically effective dose is between 0.75 mg/kg and 2.0 mg/kg of an ActRII signaling inhibitor. In certain embodiments, the pharmaceutically effectively dose is administered at a frequency as described in Section 7.7. In certain embodiments, the pharmaceutically effective dose is administered as described in Section 7.7. In certain embodiments, the pharmaceutically effective dose is an initial dose. In certain embodiments, the initial dose is administered according a method as described in Section 7.4. In certain embodiments, the pharmaceutically effective dose is an adjusted dose. In certain embodiments, the adjusted dose is administered according to a method as described in Section 7.4. In certain embodiments, ActRII signaling inhibitor is administered as a composition as described in Section 7.11. In certain embodiments, the composition is administered at a frequency as described in Section 7.7. In certain embodiments, the composition is administered as described in Section 7.7. In certain embodiments, the ActRII signaling inhibitor is an ActRII signaling inhibitor as described in Section 7.9. In certain embodiments, the ActRII signaling inhibitor is an ActRIIA signaling inhibitor. In certain embodiments, the ActRIIA signaling inhibitor is administered subcutaneously once every 21 days. In certain embodiments, the ActRII signaling inhibitor is an ActRIIA-Fc such as ActRIIA-hFc (e.g., SEQ ID NO:7). In certain embodiments, the ActRII signaling inhibitor is an ActRIIB signaling inhibitor. In certain embodiments, the ActRIIB signaling inhibitor is administered subcutaneously once every 21 days. In certain embodiments, the ActRII signaling inhibitor is an ActRII-Fc such as ActRIIB-hFc (e.g., SEQ ID NO:25). The subject in need of increasing neutrophil levels can be a subject with ring sideroblasts, anemia, anemia requiring RBC transfusion, non-proliferative CMML, and/or MDS.

7.4 Methods of Adjusted Dosing

In certain embodiments, provided herein is a method of treating a blood-related disorder in a subject, wherein the method comprises: (a) determining that at least 10%, 11%, 12%, 13%, 14%, 15%, 16%, 17%, 18%, 19%, or at least 20% of erythroblasts in the subject are ring sideroblasts; (b) administering to the subject an initial dose of between 0.1 mg/kg and 2.0 mg/kg of an ActRII signaling inhibitor; (c) after a period of time, determining a second percentage of erythroblasts in the subject that are ring sideroblasts; and (d) optionally administering to the subject an adjusted dose of the ActRII signaling inhibitor. In certain embodiments, the blood-related disorder is a blood-related disorder as described in Section 7.8. In certain embodiments, the subject is a subject as described in Section 7.8. In certain embodiments, the initial dose is between 0.75 mg/kg and 2.0 mg/kg. In certain embodiments, the subject is a subject requiring RBC transfusion. In certain embodiments, the initial dose is administered to the subject immediately after the determination of the first percentage of erythroblasts in the subject that are ring sideroblasts or within at most 1 day, 2 days, 3 days, 4 days, 5 days, 6 days, or 1 week, 2 weeks, 1 month, 2 months, 3 months, 4 months, 5 months, 6 months, 7 months, 8 months, 9 months, 10 months, 11 months, or 12 months thereof. In certain embodiments, the period of time between administering to the subject the initial dose and determining the second percentage of erythroblasts in the subject that are ring sideroblasts is 1 day, 2 days, 3 days, 4 days, 5 days, 6 days, or 1 week, 2 weeks, 1 month, 2 months, 3 months, 4 months, 5 months, 6 months, 7 months, 8 months, 9 months, 10 months, 11 months, or 12 months. In certain embodiments, the adjusted dose is administered to the subject immediately after the determination of the second percentage of erythroblasts in the subject that are ring sideroblasts or within at most 1 day, 2 days, 3 days, 4 days, 5 days, 6 days, or 1 week, 2 weeks, 1 month, 2 months, 3 months, 4 months, 5 months, 6 months, 7 months, 8 months, 9 months, 10 months, 11 months, or 12 months thereof. In certain embodiments, the adjusted dose of the ActRII signaling inhibitor is less than the initial dose if the second percentage of erythroblasts in the subject that are ring sideroblasts is at least 10%, 11%, 12%, 13%, 14%, 15%, 16%, 17%, 18%, 19%, or at least 20%. In certain embodiments, the second percentage of erythroblasts in the subject that are ring sideroblasts is at least 15%. In certain embodiments, the adjusted dose is not administered to the subject if the second percentage of erythroblasts in the subject that are ring sideroblasts is less than 10%, 9%, 8%, 7%, 6%, 5%, 4%, 3%, 2%, or 1%. In certain embodiments, the method eliminates requirement for red blood cell transfusion in the subject for at least 3, 4, 5, 6, 12, 18, or 24 months after ActRII signaling inhibitor administration.

In certain embodiments, the subject is a subject as described in Section 7.8. In certain embodiments, at least 10%, 11%, 12%, 13%, 14%, 15%, 16%, 17%, 18%, 19%, or at least 20% of erythroblasts in the subject are ring sideroblasts. In certain embodiments, at least 15% of erythroblasts in the subject are ring sideroblasts. In certain embodiments, the subject has hemoglobin levels of less than 11 g/dL. In certain embodiments, the subject has decreased hemoglobin levels as compared to a reference population. In certain embodiments, the reference population is as described in Section 7.10. In certain embodiments, the subject has anemia. In certain embodiments, the subject is a subject requiring RBC transfusion. In certain embodiments, the subject has MDS. In certain embodiments, the subject has non-proliferative CMML. In certain embodiments, the pharmaceutically effective dose is an initial dose as described in Section 7.7. In certain embodiments, the dose is an adjusted dose as described in Section 7.7. In certain embodiments, the pharmaceutically effective dose is an adjusted dose. In certain embodiments, the pharmaceutically effectively dose is administered at a frequency as described in Section 7.7. In certain embodiments, the pharmaceutically effective dose is administered as described in Section 7.7. In certain embodiments, ActRII signaling inhibitor is administered as a composition as described in Section 7.11. In certain embodiments, the composition is administered at a frequency as described in Section 7.7. In certain embodiments, the composition is administered as described in Section 7.7. In certain embodiments, the ActRII signaling inhibitor is an ActRII signaling inhibitor as described in Section 7.9. In certain embodiments, the ActRII signaling inhibitor is an ActRIIA signaling inhibitor. In certain embodiments, the ActRIIA signaling inhibitor is administered subcutaneously once every 21 days. In certain embodiments, the ActRII signaling inhibitor is an ActRIIA-Fc such as ActRIIA-hFc (e.g., SEQ ID NO:7). In certain embodiments, the ActRII signaling inhibitor is an ActRIIB signaling inhibitor. In certain embodiments, the ActRIIB signaling inhibitor is administered subcutaneously once every 21 days. In certain embodiments, the ActRII signaling inhibitor is an ActRII-Fc such as ActRIIB-hFc (e.g., SEQ ID NO:25).

In certain embodiments, provided herein is a method of promoting erythropoiesis in a subject having a blood-related disorder, the method comprising: (a) determining a percentage of erythroblasts in the subject that are ring sideroblasts; (b) administering a pharmaceutically effective dose of an ActRII signaling inhibitor to the subject for a first period of time; and (c) after the first period of time, if the percentage of erythroblasts in the subject that are ring sideroblasts in step (a) had been above 11%, 12%, 13%, 14%, 15%, 16%, 17%, 18%, 19%, or 20%, reducing the dose of the ActRII signaling inhibitor administered to the subject, reducing the frequency of administration of the ActRII signaling inhibitor to the subject, or discontinuing administering of the ActRII signaling inhibitor. In certain embodiments, the method further comprises (i) monitoring a hematological parameter in the subject during the first period of time; and (ii) reducing (e.g., reducing the dose or reducing the frequency) or discontinuing administering of the ActRII signaling inhibitor to the subject if the hematological parameter in the subject is normalized, e.g., if the hematological parameter in the subject is at least at the level of the hematological parameter in a reference population. In certain embodiments, the reference population is the reference population as described in Section 7.10. In certain embodiments, the method further comprises (i) monitoring a hematological parameter in the subject during the first period of time; and (ii) reducing (e.g., reducing the dose or reducing the frequency) or discontinuing administering of the ActRII signaling inhibitor to the subject if the hematological parameter in the subject is normalized, e.g., if the hematological parameter in the subject is improved by at least 10%, 20%, 30%, 40%, 50%, 60%, 70%, 80%, 90%, or 100% as compared to the hematological parameter in the subject a second period of time, wherein the second period of time is a period of time prior to administering to the subject an initial dose of the ActRII signaling inhibitor. In certain embodiments, the first period of time is at least 1 month, 2 months, 3 months, 4 months, 5 months, 6 months, 7 months, 8 months, 9 months, 10 months, 11 months, or 1 year. In certain embodiments, the second period of time is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the hematological parameter is hemoglobin levels. In certain embodiments, the hematological parameter is hematocrit. In certain embodiments, the hematological parameter is red blood cell count. In certain embodiments, the hematological parameter is the percentage of erythroblasts in the subject that are ring sideroblasts. In certain embodiments, the reduced dose of the ActRII signaling inhibitor is a dose as described in Section 7.7. In certain embodiments, the reduced frequency of administering the ActRII signaling inhibitor is a frequency as described in Section 7.7. In certain embodiments, the blood-related disorder is a blood-related disorder as described in Section 7.8. In certain embodiments, the subject is a subject as described in Section 7.8. In certain embodiments, the pharmaceutically effective dose is an initial dose as described in Section 7.7. In certain embodiments, the dose is an adjusted dose as described in Section 7.7. In certain embodiments, the pharmaceutically effective dose is an adjusted dose. In certain embodiments, the pharmaceutically effectively dose is administered at a frequency as described in Section 7.7. In certain embodiments, the pharmaceutically effective dose is administered as described in Section 7.7. In certain embodiments, ActRII signaling inhibitor is administered as a composition as described in Section 7.11. In certain embodiments, the composition is administered at a frequency as described in Section 7.7. In certain embodiments, the composition is administered as described in Section 7.7. In certain embodiments, the ActRII signaling inhibitor is an ActRII signaling inhibitor as described in Section 7.9. In certain embodiments, the ActRII signaling inhibitor is an ActRIIA signaling inhibitor. In certain embodiments, the ActRIIA signaling inhibitor is administered subcutaneously once every 21 days. In certain embodiments, the ActRII signaling inhibitor is an ActRIIA-Fc such as ActRIIA-hFc (e.g., SEQ ID NO:7). In certain embodiments, the ActRII signaling inhibitor is an ActRIIB signaling inhibitor. In certain embodiments, the ActRIIB signaling inhibitor is administered subcutaneously once every 21 days. In certain embodiments, the ActRII signaling inhibitor is an ActRII-Fc such as ActRIIB-hFc (e.g., SEQ ID NO:25).

7.5 Methods of Increasing Neutrophil Levels

In certain embodiments, provided herein are methods for increasing the level of neutrophils in a subject in need of increasing the level of neutrophils, comprising administering to the subject a pharmaceutically effective dose of an Activin receptor type II (ActRII) signaling inhibitor. In certain embodiments, the neutrophil levels are absolute neutrophil counts. In certain embodiments, the level of neutrophils in the subject is increased by at least $0.1 \times 10^9$ per liter, $0.5 \times 10^9$ per liter, $1.0 \times 10^9$ per liter, $5 \times 10^9$ per liter, $1.0 \times 10^{10}$ per liter, $5 \times 10^{10}$ per liter, or $1.0 \times 10^{11}$ as compared to the level of neutrophils in the subject a period of time prior to administering to the subject an initial dose of the ActRII signaling inhibitor. In certain embodiments, the level of neutrophils in the subject is increased by at least 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, or 10 fold as compared to the level of neutrophils in the subject a period of time prior to administering to the subject an initial dose of the ActRII signaling inhibitor. In certain embodiments, the level of neutrophils in the subject is increased by at most 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, or 10 fold as compared to the level of neutrophils in the subject a period of time prior to administering to the subject an initial dose of the ActRII signaling inhibitor. In certain embodiments, the level of neutrophils in the subject is increased for at least 1, 2, 3, 4, 5, or 6 months after administering to the subject the pharmaceutically effective dose of the ActRII signaling inhibitor. In certain embodiments, the level of neutrophils in the subject is increased for at least 1, 2, 3, 4, 5, or 6 months after administration of the pharmaceutically effective dose of the ActRII signaling inhibitor to the subject is terminated. See, also, Section 7.4. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the neutrophil level is measured as described in Section 7.10. In certain embodiments, the absolute neutrophil count is measured as described in Section 7.10. In certain embodiments, the subject is a subject as described in Section 7.8. In certain embodiments, at least 10%, 11%, 12%, 13%, 14%, 15%, 16%, 17%, 18%, 19%, or at least 20% of erythroblasts in the subject are ring sideroblasts. In certain embodiments, at least 15% of erythroblasts in the subject are ring sideroblasts. In certain embodiments, the subject has hemoglobin levels of less than 11 g/dL. In certain embodiments, the subject has decreased hemoglobin levels as compared to a reference population. In certain embodiments, the reference population is as described in Section 7.10. In certain embodiments, the subject has anemia. In certain embodiments, the subject is a subject requiring RBC transfusion. In certain embodiments, the subject has MDS. In certain embodiments, the subject has non-proliferative CMML. In certain embodiments, the subject treated in accordance with the methods provided herein has thrombocytopenia. In certain embodiments, the pharmaceutically effective dose is a dose as described in Section 7.7. In certain embodiments, the pharmaceutically effectively dose is administered at a frequency as described in Section 7.7. In certain embodiments, the pharmaceutically effective dose is administered as described in Section 7.7. In certain embodiments, the pharmaceutically effective dose is an initial dose. In certain embodiments, the initial dose is administered according a method as described in Section 7.4. In certain embodiments, the pharmaceutically effective dose is an adjusted dose. In certain embodiments, the adjusted dose is administered according to a method as described in Section 7.4. In certain embodiments, ActRII signaling inhibitor is administered as a composition as described in Section 7.11. In certain embodiments, the composition is administered at a frequency as described in Section 7.7. In certain embodiments, the composition is administered as described in Section 7.7. In certain embodiments, the ActRII signaling inhibitor is an ActRII signaling inhibitor as described in Section 7.9. In certain embodiments, the ActRII signaling inhibitor is an ActRIIA signaling inhibitor. In certain embodiments, the ActRIIA signaling inhibitor is administered subcutaneously once every 21 days. In certain embodiments, the ActRII signaling inhibitor is an ActRIIA-Fc such as ActRIIA-hFc (e.g., SEQ ID NO:7). In certain embodiments, the ActRII signaling inhibitor is an ActRIIB signaling inhibitor. In certain embodiments, the ActRIIB signaling inhibitor is administered subcutaneously once every 21 days. In certain embodiments, the ActRII signaling inhibitor is an ActRII-Fc such as ActRIIB-hFc (e.g., SEQ ID NO:25). The subject in need of increasing neutrophil levels can be a subject with ring sideroblasts, anemia, anemia requiring RBC transfusion, non-proliferative CMML, and/or MDS.

7.6 Methods of Increasing Platelet Levels

In certain embodiments, provided herein are methods for increasing the level of platelets in a subject in need of increasing the level of platelets, comprising administering to the subject a pharmaceutically effective dose of an Activin receptor type II (ActRII) signaling inhibitor. In certain embodiments, the level of platelets in the subject is increased by at least $1 \times 10^{10}$ per liter, $3 \times 10^{10}$ per liter, $5 \times 10^{10}$ per liter, $1 \times 10^{11}$ per liter, $5 \times 10^{11}$ per liter, or at least $1 \times 10^{12}$ per liter as compared to the level of platelets in the subject a period of time prior to administering to the subject an initial dose of the ActRII signaling inhibitor. In certain embodiments, the level of platelets in the subject is increased by at least 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, or 10 fold as compared to the level of platelets in the subject a period of time prior to administering to the subject an initial dose of the ActRII signaling inhibitor. In certain embodiments, the level of platelets in the subject is increased by at most 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, or 10 fold as compared to the level of platelets in the subject a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the level of platelets in the subject is increased for at least 1, 2, 3, 4, 5, or 6 months after administering to the subject the pharmaceutically effective dose of the ActRII signaling inhibitor. In certain embodiments, the level of neutrophils in the subject is increased for at least 1, 2, 3, 4, 5, or 6 months after administration of the pharmaceutically effective dose of the ActRII signaling inhibitor to the subject is terminated. See, also, Section 7.4. In certain embodiments, the platelet level is measured as described in Section 7.10.

In certain embodiments, the subject is a subject as described in Section 7.8. In certain embodiments, at least 10%, 11%, 12%, 13%, 14%, 15%, 16%, 17%, 18%, 19%, or at least 20% of erythroblasts in the subject are ring sideroblasts. In certain embodiments, at least 15% of erythroblasts in the subject are ring sideroblasts. In certain embodiments, the subject has hemoglobin levels of less than 11 g/dL. In certain embodiments, the subject has decreased hemoglobin levels as compared to a reference population. In certain embodiments, the reference population is as described in Section 7.10. In certain embodiments, the subject has anemia. In certain embodiments, the subject is a subject requiring RBC transfusion. In certain embodiments, the subject has MDS. In certain embodiments, the subject has non-proliferative CMML. In certain embodiments, the subject treated in accordance with the methods provided herein has neutropenia.

In certain embodiments, the pharmaceutically effective dose is a dose as described in Section 7.7. In certain embodiments, the pharmaceutically effectively dose is administered at a frequency as described in Section 7.7. In certain embodiments, the pharmaceutically effective dose is administered as described in Section 7.7. In certain embodiments, the pharmaceutically effective dose is an initial dose. In certain embodiments, the initial dose is administered according a method as described in Section 7.4. In certain embodiments, the pharmaceutically effective dose is an adjusted dose. In certain embodiments, the adjusted dose is administered according to a method as described in Section 7.4.

In certain embodiments, ActRII signaling inhibitor is administered as a composition as described in Section 7.11. In certain embodiments, the composition is administered at a frequency as described in Section 7.7. In certain embodiments, the composition is administered as described in Section 7.7.

In certain embodiments, the ActRII signaling inhibitor is an ActRII signaling inhibitor as described in Section 7.9. In certain embodiments, the ActRII signaling inhibitor is an ActRIIA signaling inhibitor. In certain embodiments, the ActRIIA signaling inhibitor is administered subcutaneously once every 21 days. In certain embodiments, the ActRII signaling inhibitor is an ActRIIA-Fc such as ActRIIA-hFc (e.g., SEQ ID NO:7). In certain embodiments, the ActRII signaling inhibitor is an ActRIIB signaling inhibitor. In certain embodiments, the ActRIIB signaling inhibitor is administered subcutaneously once every 21 days. In certain embodiments, the ActRII signaling inhibitor is an ActRII-Fc such as ActRIIB-hFc (e.g., SEQ ID NO:25).

The subject in need of increasing neutrophil levels can be a subject with ring sideroblasts, anemia, anemia requiring RBC transfusion, non-proliferative CMML, and/or MDS.

7.7 Dose

Provided herein are methods for the treatment in a subject of a blood-related disorder (e.g., anemia, anemia requiring RBC transfusion, MDS and/or non-proliferative CMML), wherein the methods comprise administering to a subject in need of treatment a pharmaceutically effective dose of a signaling inhibitor of ActRII (see, Section 7.9). In certain embodiments, an ActRII signaling inhibitor is a signaling inhibitor of ActRIIA as set forth in Section 7.9.1. In other embodiments, an ActRII signaling inhibitor is a signaling inhibitor of ActRIIB as set forth in Section 7.9.2. In certain embodiments, an ActRII signaling inhibitor is a combination of an ActRIIA signaling inhibitor and an ActRIIB signaling inhibitor. In certain embodiments, the ActRII signaling inhibitor is SEQ ID NO:7. In certain embodiments, the ActRII signaling inhibitor is SEQ ID NO:25.

The dose provided herein can be used in the treatment of blood related diseases, such as, e.g., anemia, anemia requiring RBC transfusion, MDS, and/or non-proliferative CMML. In certain embodiments the dose is a pharmaceutically effective dose.

In certain embodiments, the pharmaceutically effective dose of the ActRII signaling inhibitor is a dose sufficient to ameliorate one or more symptoms of anemia. In certain embodiments, the pharmaceutically effective dose of the ActRII signaling inhibitor is a dose sufficient to prevent at least one symptom of anemia from worsening. Non-limiting examples of anemia include fatigue, loss of energy, rapid heartbeat, shortness of breath, headaches, difficulty concentrating, dizziness, pale skin, leg cramps, and insomnia.

In certain embodiments, the pharmaceutically effective dose of the ActRII signaling inhibitor is a dose sufficient to ameliorate one or more symptoms of non-proliferative CMML. In certain embodiments, the pharmaceutically effective dose of the ActRII signaling inhibitor is a dose sufficient to prevent one or more symptoms of non-proliferative CMML from worsening. Non-limiting examples of symptoms of CMML include splenomegaly, hepatomegaly, anemia, fatigue, shortness of breath, leukopenia, frequent infections, thrombocytopenia, easy bruising or bleeding, fever, weight loss, pale skin and loss of appetite.

In certain embodiments, the pharmaceutically effective dose of the ActRII signaling inhibitor is a dose sufficient to ameliorate one or more symptoms of MDS. In certain embodiments, the pharmaceutically effective dose of the ActRII signaling inhibitor is a dose sufficient to prevent one or more symptoms of MDS from worsening. Non-limiting examples of symptoms of MDS include anemia, shortness of breath, fatigue, pale skin, leukopenia, frequent infections, neutropenia, thrombocytopenia, easy bruising or bleeding, weight loss, fever, loss of appetite, weakness, and bone pain.

In certain embodiments, the ActRII signaling inhibitor is dosed at intervals and amounts sufficient to achieve serum concentrations of 0.2 microgram/kg or greater, for example, serum levels of 1 microgram/kg or 2 microgram/kg or greater. Dosing regimens may be designed to reach serum concentrations of between 0.2 and 15 microgram/kg, and optionally between 1 and 5 microgram/kg. In humans, serum levels of 0.2 microgram/kg may be achieved with a single dose of 0.1 mg/kg or greater and serum levels of 1 microgram/kg may be achieved with a single dose of 0.3 mg/kg or greater. The observed serum half-life of the molecule is between about 20 and 30 days, substantially longer than most Fc fusion proteins, and thus a sustained effective serum level may be achieved, for example, by dosing with 0.2-0.4 mg/kg on a weekly or biweekly basis, or higher doses may be used with longer intervals between dosings. For example, doses of 1-3 mg/kg might be used on a monthly or bimonthly basis, and the effect on bone may be sufficiently durable that dosing is necessary only once every 3, 4, 5, 6, 9, 12 or more months. Serum levels of the ActRII signaling inhibitor can be measured by any means known to the skilled artisan. For example, antibodies against the ActRII signaling inhibitor can be used to determine the serum levels of the ActRII signaling inhibitor using, e.g., an ELISA. In a specific embodiment, the method provided herein also achieves significant effects on bone density and strength.

In certain embodiments, the dose of the ActRII signaling inhibitor is about 0.1 mg/kg, about 0.3 mg/kg, about 0.5 mg/kg, 0.75 mg/kg, about 1.0 mg/kg, about 1.25 mg/kg, about 1.5 mg/kg, about 1.75 mg/kg, about 2.0 mg/kg, or about 2.25 mg/kg. In certain embodiments, the dose of the ActRII signaling inhibitor is between 0.1 mg/kg and 2.25 mg/kg. In certain embodiments, the dose of the ActRII signaling inhibitor is between 0.1 mg/kg and 1 mg/kg. In certain embodiments, the dose of the ActRII signaling inhibitor is between 0.3 mg/kg and 1.25 mg/kg. In certain embodiments, the dose of the ActRII signaling inhibitor is between 0.5 mg/kg and 1.5 mg/kg. In certain embodiments, the dose of the ActRII signaling inhibitor is between 0.1 mg/kg and 2.0 mg/kg. In certain embodiments, the dose of the ActRII signaling inhibitor is between 0.75 mg/kg and 1.0 mg/kg, between 1.0 mg/kg and 1.25 mg/kg, between 1.25 mg/kg and 1.5 mg/kg, between 1.5 mg/kg and 1.75 mg/kg, or between 1.75 mg/kg and 2.0 mg/kg. In certain embodiments, the dose of the ActRII signaling inhibitor is a pharmaceutically effective dose. When used in conjunction with a dose provided herein (e.g., a dose of an ActRII signaling inhibitor or a dose of a second active agent), the word "about" refers to any number within 1, 5 or 10% of the referenced number.

In certain embodiments, the dose of the ActRII signaling inhibitor is a pharmaceutically effective dose. In certain embodiments, the pharmaceutically effective dose of the ActRII signaling inhibitor is about 0.1 mg/kg, about 0.3 mg/kg, about 0.5 mg/kg, 0.75 mg/kg, about 1.0 mg/kg, about 1.25 mg/kg, about 1.5 mg/kg, about 1.75 mg/kg, about 2.0 mg/kg, or about 2.25 mg/kg. In certain embodiments, the pharmaceutically effective dose of the ActRII signaling inhibitor is between 0.1 mg/kg and 2.25 mg/kg. In certain embodiments, the pharmaceutically effective dose of the ActRII signaling inhibitor is between 0.1 mg/kg and 1 mg/kg. In certain embodiments, the pharmaceutically effective dose of the ActRII signaling inhibitor is between 0.3 mg/kg and 1.25 mg/kg. In certain embodiments, the pharmaceutically effective dose of the ActRII signaling inhibitor is between 0.5 mg/kg and 1.5 mg/kg. In certain embodiments, the pharmaceutically effective dose of the ActRII signaling inhibitor is between 0.1 mg/kg and 2.0 mg/kg. In certain embodiments, the pharmaceutically effective dose of the ActRII signaling inhibitor is between 0.75 mg/kg and 1.0 mg/kg, between 1.0 mg/kg and 1.25 mg/kg, between 1.25 mg/kg and 1.5 mg/kg, between 1.5 mg/kg and 1.75 mg/kg, or between 1.75 mg/kg and 2.0 mg/kg.

In certain embodiments, the dose of the ActRII signaling inhibitor is an initial dose. In certain embodiments, the initial dose of the ActRII signaling inhibitor is about 0.1 mg/kg, about 0.3 mg/kg, about 0.5 mg/kg, 0.75 mg/kg, about 1.0 mg/kg, about 1.25 mg/kg, about 1.5 mg/kg, about 1.75 mg/kg, about 2.0 mg/kg, or about 2.25 mg/kg. In certain embodiments, the initial dose of the ActRII signaling inhibitor is between 0.1 mg/kg and 2.25 mg/kg. In certain embodiments, the initial dose of the ActRII signaling inhibitor is between 0.1 mg/kg and 1 mg/kg. In certain embodiments, the initial dose of the ActRII signaling inhibitor is between 0.3 mg/kg and 1.25 mg/kg. In certain embodiments, the initial dose of the ActRII signaling inhibitor is between 0.5 mg/kg and 1.5 mg/kg. In certain embodiments, the initial dose of the ActRII signaling inhibitor is between 0.1 mg/kg and 2.0 mg/kg. In certain embodiments, the initial dose of the ActRII signaling inhibitor is between 0.75 mg/kg and 1.0 mg/kg, between 1.0 mg/kg and 1.25 mg/kg, between 1.25 mg/kg and 1.5 mg/kg, between 1.5 mg/kg and 1.75 mg/kg, or between 1.75 mg/kg and 2.0 mg/kg. In certain embodiments, the initial dose of the ActRII signaling inhibitor is administered (i) once every 28 days; or (ii) once every 42 days. In certain embodiments, the initial dose of the ActRII signaling inhibitor is administered once every three weeks.

In certain embodiments, the dose is an adjusted dose. In certain embodiments, the adjusted dose of the ActRII signaling inhibitor is about 0.1 mg/kg, about 0.3 mg/kg, about 0.5 mg/kg, 0.75 mg/kg, about 1.0 mg/kg, about 1.25 mg/kg, about 1.5 mg/kg, about 1.75 mg/kg, about 2.0 mg/kg, or about 2.25 mg/kg. In certain embodiments, the adjusted dose of the ActRII signaling inhibitor is between 0.1 mg/kg and 2.25 mg/kg. In certain embodiments, the adjusted dose of the ActRII signaling inhibitor is between 0.1 mg/kg and 1 mg/kg. In certain embodiments, the adjusted dose of the ActRII signaling inhibitor is between 0.3 mg/kg and 1.25 mg/kg. In certain embodiments, the adjusted dose of the ActRII signaling inhibitor is between 0.5 mg/kg and 1.5 mg/kg. In certain embodiments, the adjusted dose of the ActRII signaling inhibitor is between 0.1 mg/kg and 2.0 mg/kg. In certain embodiments, the adjusted dose of the ActRII signaling inhibitor is between 0.75 mg/kg and 1.0 mg/kg, between 1.0 mg/kg and 1.25 mg/kg, between 1.25 mg/kg and 1.5 mg/kg, between 1.5 mg/kg and 1.75 mg/kg, or between 1.75 mg/kg and 2.0 mg/kg. In certain embodiments, the adjusted dose of the ActRII signaling inhibitor is administered (i) once every 28 days; or (ii) once every 42 days. In certain embodiments, the adjusted dose of the ActRII signaling inhibitor is administered once every three weeks.

In certain embodiments, the adjusted dose of the ActRII signaling inhibitor is greater than the initial dose. In certain embodiments, the adjusted dose of the ActRII signaling inhibitor is about 2.5 mg, about 5 mg, about 10 mg, about 15 mg, about 20 mg, or about 35 mg greater than the initial dose of the ActRII signaling inhibitor, or about 0.05 mg/kg, about 0.1 mg/kg, about 0.15 mg/kg, about 0.25 mg/kg, about 0.3 mg/kg, about 0.35 mg/kg, about 0.4 mg/kg, or about 0.5 mg/kg greater than the initial dose of the ActRII signaling inhibitor. In certain embodiments, the adjusted dose of the ActRII signaling inhibitor is administered more frequently than the initial dose of the ActRII signaling inhibitor. In certain embodiments, the adjusted dose of the ActRII signaling inhibitor is administered every 5, 10, 15, 20, 25, 28, 30, 35, or 40 days. In certain embodiments, the adjusted dose of the ActRII signaling inhibitor is administered every 1 or 2 weeks.

In certain embodiments, the adjusted dose of the ActRII signaling inhibitor is less than the initial dose. In certain embodiments, the adjusted dose of the ActRII signaling inhibitor is about 2.5 mg, about 5 mg, about 10 mg, about 15 mg, about 20 mg, or about 35 mg less than the initial dose of the ActRII signaling inhibitor, or about 0.05 mg/kg, about 0.1 mg/kg, about 0.15 mg/kg, about 0.25 mg/kg, about 0.3 mg/kg, about 0.35 mg/kg, about 0.4 mg/kg, or about 0.5 mg/kg less than the initial dose of the ActRII signaling inhibitor. In certain embodiments, the adjusted dose of the ActRII signaling inhibitor is administered less frequently than the initial dose of the ActRII signaling inhibitor. In certain embodiments, the adjusted dose of the ActRII signaling inhibitor is administered every 30, 35, 40, 42, 50, 60, 70, 80, or 90 days. In certain embodiments, the adjusted dose of the ActRII signaling inhibitor is administered every 4, 5, 6, 7, or 8 weeks.

In certain embodiments, the dose of the ActRII signaling inhibitor is administered via injection. In certain embodiments, the dose of the ActRII signaling inhibitor is administered once every 28 days or once every 42 days. In certain embodiments, the dose of the ActRII signaling inhibitor is administered once every 21 days. In certain embodiments the ActRII signaling inhibitor is SEQ ID NO:7.

In certain embodiments, the dose of the ActRII signaling inhibitor is administered via injection. In certain embodiments, the dose of the ActRII signaling inhibitor is administered subcutaneously. In certain embodiments, the dose of the ActRII signaling inhibitor is administered once every 3 weeks. In certain embodiments, the ActRII signaling inhibitor is SEQ ID NO:25.

In certain embodiments, the dose of an ActRII signaling inhibitor administered to a subject according to the methods provided herein is sufficient to decrease the percentage of erythroblasts in the subject that are ring sideroblasts by at least 5%, 10%, 15%, 20%, 25%, 30%, 35%, 40%, 45%, 50%, 55%, 60%, 65%, 70%, 75%, 80%, 85%, 90%, 95%, or at least 100% as compared to the percentage of erythroblasts in the subject that are ring sideroblasts a period of time prior to administering to the subject an initial dose of the ActRII signaling inhibitor. In certain embodiments, the dose of an ActRII signaling inhibitor administered to a subject according to the methods provided herein is sufficient to decrease the percentage of erythroblasts in the subject that are ring sideroblasts by at most 5%, 10%, 15%, 20%, 25%, 30%, 35%, 40%, 45%, 50%, 55%, 60%, 65%, 70%, 75%, 80%, 85%, 90%, 95%, or at most 100% as compared to the percentage of erythroblasts in the subject that are ring sideroblasts a period of time prior to administering to the subject an initial dose of the ActRII signaling inhibitor. In certain embodiments, the period of time prior to administering to the subject the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject according to the methods provided herein is sufficient to decrease the percentage of erythroblasts in the subject that are ring sideroblasts for at least 3, 4, 5, 6, 12, 18, 24 or 48 months after administration of the ActRII signaling inhibitor. In certain embodiments, the dose of an ActRII signaling inhibitor administered to a subject according to the methods provided herein is sufficient to decrease the percentage of erythroblasts in the subject that are ring sideroblasts indefinitely after administration of the ActRII signaling inhibitor. In certain embodiments, the dose is between 0.1 mg/kg and 2.0 mg/kg. In certain embodiments, the dose is between 0.75 mg/kg and 2.0 mg/kg. In certain embodiments, the percentage of erythroblasts in the subject that are ring sideroblasts is determined according to an assay as described in Section 7.10. In certain embodiments, the dose of an ActRII signaling inhibitor administered to a subject according to the methods provided herein is sufficient to decrease the levels of ring sideroblasts in the subject by at least 5%, 10%, 15%, 20%, 25%, 30%, 35%, 40%, 45%, 50%, 55%, 60%, 65%, 70%, 75%, 80%, 85%, 90%, 95%, or at least 100% as compared to the levels of ring sideroblasts in the subject a period of time prior to administering to the subject an initial dose of the ActRII signaling inhibitor. In certain embodiments, the dose of an ActRII signaling inhibitor administered to a subject according to the methods provided herein is sufficient to decrease the levels of ring sideroblasts in the subject by at most 5%, 10%, 15%, 20%, 25%, 30%, 35%, 40%, 45%, 50%, 55%, 60%, 65%, 70%, 75%, 80%, 85%, 90%, 95%, or at most 100% as compared to the level of ring sideroblasts in the subject a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject according to the methods provided herein is sufficient to decrease the level of ring sideroblasts in the subject for at least 3, 4, 5, 6, 12, 18, 24 or 48 months after administration of the ActRII signaling inhibitor. In certain embodiments, the dose of an ActRII signaling inhibitor administered to a subject according to the methods provided herein is sufficient to decrease the level of ring sideroblasts in the subject indefinitely after administration of the ActRII signaling inhibitor. In certain embodiments the dose is between 0.1 mg/kg and 2.0 mg/kg. In certain embodiments, the dose is between 0.75 mg/kg and 2.0 mg/kg. In certain embodiments, the level of ring sideroblasts in the subject is determined according to an assay as described in Section 7.10.

In certain embodiments, the dose of an ActRII signaling inhibitor administered to a subject according to the methods provided herein is sufficient to increase the level of hemoglobin in the subject by at least 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, or at least 500% as compared to the level of hemoglobin in the subject a period of time prior to administering to the subject an initial dose of the ActRII signaling inhibitor. In certain embodiments, the dose of an ActRII signaling inhibitor administered to a subject according to the methods provided herein is sufficient to increase the level of hemoglobin in the subject by at most 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, or at most 500% as compared to the level of hemoglobin in the subject a period of time prior to administering to the subject an initial dose of the ActRII signaling inhibitor. In certain embodiments, the dose of an ActRII signaling inhibitor administered to a subject according to the methods provided herein is sufficient to increase the level of hemoglobin in the subject by at least 5%, 10%, 15%, 20%, 25%, 30%, 35%, 40%, 45%, 50%, 55%, or at least 60% as compared to the level of hemoglobin in the subject a period of time prior to administering to the subject an initial dose of the ActRII signaling inhibitor. In certain embodiments, the dose of an ActRII signaling inhibitor administered to a subject according to the methods provided herein is sufficient to increase the level of hemoglobin in the subject by at most 5%, 10%, 15%, 20%, 25%, 30%, 35%, 40%, 45%, 50%, 55%, or at most 60% as compared to the level of hemoglobin in the subject a period of time prior to administering to the subject an initial dose of the ActRII signaling inhibitor. In certain embodiments, the dose of an ActRII signaling inhibitor administered to a subject according to the methods provided herein is sufficient to increase the level of hemoglobin in the subject by at least 0.5 g/dL, 1.0 g/dL, 1.1 g/dL, 1.3 g/dL, 1.5 g/dL, 1.8 g g/dL, 2.0 g/dL, 2.2 g/dL, 2.4 g/dL, 2.6 g/dL, 2.8 g/dL, 3.0 g/dL, 3.2 g/dL, 3.4 g/dL, 3.6 g/dL, 3.8 g/dL, 4.0 g/dL, 4.2 g/dL, 4.4 g/dL, or at least 4.6 g/dL as compared to the level of hemoglobin in the subject a period of time prior to administering to the subject an initial dose of the ActRII signaling inhibitor. In certain embodiments, the dose of an ActRII signaling inhibitor administered to a subject according to the methods provided herein is sufficient to increase the level of hemoglobin by at most 0.5 g/dL, 1.0 g/dL, 1.1 g/dL, 1.3 g/dL, 1.5 g/dL, 1.8 g g/dL, 2.0 g/dL, 2.2 g/dL, 2.4 g/dL, 2.6 g/dL, 2.8 g/dL, 3.0 g/dL, 3.2 g/dL, 3.4 g/dL, 3.6 g/dL, 3.8 g/dL, 4.0 g/dL, 4.2 g/dL, 4.4 g/dL, or at most 4.6 g/dL as compared to the level of hemoglobin in the subject a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject according to the methods provided herein is sufficient to increase the level of hemoglobin in the subject for at least 3, 4, 5, 6, 12, 18, 24 or 48 months after administration of the ActRII signaling inhibitor. In certain embodiments, the dose of an ActRII signaling inhibitor administered to a subject according to the methods provided herein is sufficient to increase the level of hemoglobin in the subject indefinitely after administration of the ActRII signaling inhibitor. In certain embodiments the dose is between 0.1 mg/kg and 2.0 mg/kg. In certain embodiments, the dose is between 0.75 mg/kg and 2.0 mg/kg.

In certain embodiments, the dose of an ActRII signaling inhibitor administered to a subject according to the methods provided herein is sufficient to increase the level of reticulocytes in the subject by at least 5%, 10%, 15%, 20%, 25%, 30%, 35%, 40%, 45%, 50%, 55%, 60%, 65%, 70%, 75%, 80%, 85%, 90%, 95%, or 100% as compared to the level of reticulocytes in the subject a period of time prior to administering to the subject an initial dose of the ActRII signaling inhibitor. In certain embodiments, the dose of an ActRII signaling inhibitor administered to a subject according to the methods provided herein is sufficient to increase the level of reticulocytes in the subject by at most 5%, 10%, 15%, 20%, 25%, 30%, 35%, 40%, 45%, 50%, 55%, 60%, 65%, 70%, 75%, 80%, 85%, 90%, 95%, or at most 100%, 150%, 200%, 300%, 400%, or at most 500% as compared to the level of reticulocytes in the subject a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject according to the methods provided herein is sufficient to increase the level of reticulocytes in the subject for at least 3, 4, 5, 6, 12, 18, 24 or 48 months after administration of the ActRII signaling inhibitor. In certain embodiments, the dose of an ActRII signaling inhibitor administered to a subject according to the methods provided herein is sufficient to increase the level of reticulocytes in the subject indefinitely after administration of the ActRII signaling inhibitor. In certain embodiments the dose is between 0.1 mg/kg and 2.0 mg/kg. In certain embodiments, the dose is between 0.75 mg/kg and 2.0 mg/kg.

In certain embodiments, the dose of an ActRII signaling inhibitor administered to a subject according to the methods provided herein is sufficient to decrease red blood cell transfusion dependence in the subject as compared to the red blood cell transfusion dependence period of time prior to administering to the subject an initial dose of the ActRII signaling inhibitor. In certain embodiments, the dose of an ActRII signaling inhibitor administered to a subject according to the methods provided herein is sufficient to decrease the frequency of red blood cell transfusions in the subject as compared to the frequency of red blood cell transfusions in the subject a period of time prior to administering to the subject an initial dose of the ActRII signaling inhibitor. In certain embodiments, the dose of an ActRII signaling inhibitor administered to a subject treated according to the methods provided herein is sufficient to reduce red blood cell transfusions by at least 30%, 40%, 50%, 60%, 70%, 80%, 90%, or by at least 100%. In certain embodiments, the dose of an ActRII signaling inhibitor administered to a subject treated according to the methods provided herein is sufficient to reduce red blood cell transfusions by at most 30%, 40%, 50%, 60%, 70%, 80%, 90%, or by at most 100%. In certain embodiments, the dose of an ActRII signaling inhibitor administered to a subject treated according to the methods provided herein is sufficient to reduce the units of red blood cells transfused in the subject by at least 4, 5, 6, 7, 8, 9, 11, 12, or 13 units as compared to the units of red blood cells transfused in the subject a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject treated according to the methods provided herein is sufficient to reduce the frequency of red blood cell transfusions by at least 30%, 40%, 50%, 60%, 70%, 80%, 90%, or by 100%. In certain embodiments, the dose of an ActRII signaling inhibitor administered to a subject treated according to the methods provided herein is sufficient to reduce the frequency of red blood cell transfusions by at most 30%, 40%, 50%, 60%, 70%, 80%, 90%, or by 100%. In certain embodiments, the dose of an ActRII signaling inhibitor administered to a subject according to the methods provided herein is sufficient to abrogate the need for red blood cell transfusion in the subject for at least 3, 4, 5, 6, 12, 18, 24 or 48 months after the administration of the ActRII signaling inhibitor. In certain embodiments, the dose of an ActRII signaling inhibitor administered to a subject according to the methods provided herein is sufficient to abrogate the need for red blood cell transfusion in the subject indefinitely after the administration of the ActRII signaling inhibitor. In certain embodiments the dose is between 0.1 mg/kg and 2.0 mg/kg. In certain embodiments, the dose is between 0.75 mg/kg and 2.0 mg/kg. In certain embodiments, one RBC unit refers to about 150 mL, 200 mL, 250 mL, 300 mL, 350 mL, 100-200 mL, 150-250 mL, 200-300 mL, or 250-350 mL of RBCs.

In certain embodiments, the dose of an ActRII signaling inhibitor administered to a subject according to the methods provided herein is sufficient to decrease transfusion burden in the subject by at least 5%, 10%, 15%, 20%, 25%, 30%, 35%, 40%, 45%, 50%, 55%, 60%, 65%, 70%, 75%, 80%, 85%, 90%, 95%, or at least 100% as compared to the transfusion burden in the subject a period of time prior to administering to the subject an initial dose of the ActRII signaling inhibitor. In certain embodiments, the dose of an ActRII signaling inhibitor administered to a subject according to the methods provided herein is sufficient to decrease transfusion burden in the subject by at most 5%, 10%, 15%, 20%, 25%, 30%, 35%, 40%, 45%, 50%, 55%, 60%, 65%, 70%, 75%, 80%, 85%, 90%, 95%, or at most 100% as compared to transfusion burden in the subject a period of time prior to administering to the subject an initial dose of the ActRII signaling inhibitor. In certain embodiments, the dose of an ActRII signaling inhibitor administered to a subject according to the methods provided herein is sufficient to decrease transfusion burden in the subject by at least 33% as compared to the transfusion burden in the subject a period of time prior to administering to the subject an initial dose of the ActRII signaling inhibitor. In certain embodiments, the dose of an ActRII signaling inhibitor administered to a subject according to the methods provided herein is sufficient to decrease transfusion burden in the subject by at least 50% as compared to the transfusion burden in the subject a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject according to the methods provided herein is sufficient to decrease the transfusion burden in the subject for at least 3, 4, 5, 6, 12, 18, 24 or 48 months after administration of the ActRII signaling inhibitor. In certain embodiments, the dose of an ActRII signaling inhibitor administered to a subject according to the methods provided herein is sufficient to decrease the transfusion burden in the subject indefinitely after administration of the ActRII signaling inhibitor. In certain embodiments the dose is between 0.1 mg/kg and 2.0 mg/kg. In certain embodiments, the dose is between 0.75 mg/kg and 2.0 mg/kg.

In certain embodiments, the dose of an ActRII signaling inhibitor administered to a subject according to the methods provided herein is sufficient to decrease iron chelation therapy (e.g., dose or frequency) in the subject by at least 5%, 10%, 15%, 20%, 25%, 30%, 35%, 40%, 45%, 50%, 55%, 60%, 65%, 70%, 75%, 80%, 85%, 90%, 95%, or at least 100% as compared to the iron chelation therapy (e.g., dose or frequency) in the subject a period of time prior to administering to the subject an initial dose of the ActRII signaling inhibitor. In certain embodiments, the dose of an ActRII signaling inhibitor administered to a subject according to the methods provided herein is sufficient to decrease iron chelation therapy (e.g., dose or frequency) in the subject by at most 5%, 10%, 15%, 20%, 25%, 30%, 35%, 40%, 45%, 50%, 55%, 60%, 65%, 70%, 75%, 80%, 85%, 90%, 95%, or at most 100% as compared to iron chelation therapy (e.g., dose or frequency) in the subject a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject according to the methods provided herein is sufficient to decrease the iron chelation therapy (e.g., dose or frequency) in the subject for at least 3, 4, 5, 6, 12, 18, 24 or 48 months after administration of the ActRII signaling inhibitor. In certain embodiments, the dose of an ActRII signaling inhibitor administered to a subject according to the methods provided herein is sufficient to decrease the iron chelation therapy (e.g., dose or frequency) in the subject indefinitely after administration of the ActRII signaling inhibitor. In certain embodiments the dose is between 0.1 mg/kg and 2.0 mg/kg. In certain embodiments, the dose is between 0.75 mg/kg and 2.0 mg/kg.

In certain embodiments, the dose of an ActRII signaling inhibitor administered to a subject according to the methods provided herein is sufficient to decrease serum ferritin levels in the subject by at least 5%, 10%, 15%, 20%, 25%, 30%, 35%, 40%, 45%, or at least 50% as compared to the serum ferritin levels in the subject a period of time prior to administering to the subject an initial dose of the ActRII signaling inhibitor. In certain embodiments, the dose of an ActRII signaling inhibitor administered to a subject according to the methods provided herein is sufficient to decrease serum ferritin levels in the subject by at most 5%, 10%, 15%, 20%, 25%, 30%, 35%, 40%, 45%, 50 as compared to serum ferritin levels in the subject a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject according to the methods provided herein is sufficient to decrease the serum ferritin levels in the subject for at least 3, 4, 5, 6, 12, 18, 24 or 48 months after administration of the ActRII signaling inhibitor. In certain embodiments, the dose of an ActRII signaling inhibitor administered to a subject according to the methods provided herein is sufficient to decrease the serum ferritin levels in the subject indefinitely after administration of the ActRII signaling inhibitor. In certain embodiments the dose is between 0.1 mg/kg and 2.0 mg/kg. In certain embodiments, the dose is between 0.75 mg/kg and 2.0 mg/kg.

In certain embodiments, the dose of an ActRII signaling inhibitor administered to a subject according to the methods provided herein is sufficient to result in erythroid hematological improvement in the subject by at least 1.5 g/dL, 1.8 g/dL, 2.0 g/dL, 2.2 g/dL, 2.4 g/dL, 2.6 g/dL, 2.8 g/dL, 3.0 g/dL, 3.2 g/dL, 3.4 g/dL, 3.6 g/dL, 3.8 g/dL, or at least 4.0 g/dL as compared to the erythroid hematological improvement in the subject a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject according to the methods provided herein is sufficient to result in erythroid hematological improvement in the subject for at least 3, 4, 5, 6, 12, 18, 24 or 48 months after administration of the ActRII signaling inhibitor. In certain embodiments, the dose of an ActRII signaling inhibitor administered to a subject according to the methods provided herein is sufficient to result in erythroid hematological improvement in the subject indefinitely after administration of the ActRII signaling inhibitor. In certain embodiments, the erythroid hematological improvement for a low transfusion burden patient is an increase in hemoglobin concentration in the patient of at least 1.5 g/dL for at least 8 weeks. In certain embodiments, the erythroid hematological improvement for a high transfusion burden patient is an at least 4 unit reduction in RBC transfusion over 8 weeks. In certain embodiments the dose is between 0.1 mg/kg and 2.0 mg/kg. In certain embodiments, the dose is between 0.75 mg/kg and 2.0 mg/kg.

In certain embodiments, the dose of an ActRII signaling inhibitor administered to a subject according to the methods provided herein is sufficient to increase the level of neutrophils in the subject by at least 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, or at least 500% as compared to the level of neutrophils in the subject a period of time prior to administering to the subject an initial dose of the ActRII signaling inhibitor. In certain embodiments, the dose of an ActRII signaling inhibitor administered to a subject according to the methods provided herein is sufficient to increase the level of neutrophils in the subject by at most 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, or at most 500% as compared to the level of neutrophils in the subject a period of time prior to administering to the subject an initial dose of the ActRII signaling inhibitor. In certain embodiments, the dose of an ActRII signaling inhibitor administered to a subject according to the methods provided herein is sufficient to increase the level of neutrophils by at least $0.1 \times 10^9$ per liter, $0.5 \times 10^9$ per liter, $1.0 \times 10^9$ per liter, $5 \times 10^9$ per liter, $1.0 \times 10^{10}$ per liter, $5 \times 10^{10}$ per liter, or $1.0 \times 10^{11}$ per liter as compared to the level of neutrophils in the subject a period of time prior to administration of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject according to the methods provided herein is sufficient to increase the level of neutrophils in the subject for at least 3, 4, 5, 6, 12, 18, 24 or 48 months after administration of the ActRII signaling inhibitor. In certain embodiments, the dose of an ActRII signaling inhibitor administered to a subject according to the methods provided herein is sufficient to increase the level of neutrophils in the subject indefinitely after administration of the ActRII signaling inhibitor. In certain embodiments the dose is between 0.1 mg/kg and 2.0 mg/kg. In certain embodiments, the dose is between 0.75 mg/kg and 2.0 mg/kg.

In certain embodiments, the dose of an ActRII signaling inhibitor administered to a subject according to the methods provided herein is sufficient to increase the level of platelets in the subject by at least 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, or at most 500% as compared to the level of platelets in the subject a period of time prior to administering to the subject an initial dose of the ActRII signaling inhibitor. In certain embodiments, the dose of an ActRII signaling inhibitor administered to a subject according to the methods provided herein is sufficient to increase the level of platelets in the subject by at most 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, or at most 500% as compared to the level of platelets in the subject a period of time prior to administering to the subject an initial dose of the ActRII signaling inhibitor. In certain embodiments, the dose of an ActRII signaling inhibitor administered to a subject according to the methods provided herein is sufficient to increase the level of platelets by at least $1\times10^{10}$ per liter, $3\times10^{10}$ per liter, $5\times10^{10}$ per liter, $1\times10^{11}$ per liter, $5\times10^{11}$ per liter, or at least $1\times10^{12}$ per liter as compared to the level of platelets in the subject a period of time prior to administering to the subject an initial dose of the ActRII signaling inhibitor. In certain embodiments, the period of time prior to administering to the subject an initial dose of the ActRII signaling inhibitor is 1 day, 2 days, 3, days, 4 days, 5 days, 6 days, 1 week, 2 weeks, 3 weeks, 4 weeks, 5 weeks, 6 weeks, 7 weeks, 8 weeks, 3 months, 4 months, 5 months, or 6 months. In certain embodiments, the dose of an ActRII signaling inhibitor administered to a subject according to the methods provided herein is sufficient to increase the level of platelets in the subject for at least 3, 4, 5, 6, 12, 18, 24 or 48 months after administration of the ActRII signaling inhibitor. In certain embodiments, the dose of an ActRII signaling inhibitor administered to a subject according to the methods provided herein is sufficient to increase the level of platelets in the subject indefinitely after administration of the ActRII signaling inhibitor. In certain embodiments the dose is between 0.1 mg/kg and 2.0 mg/kg. In certain embodiments, the dose is between 0.75 mg/kg and 2.0 mg/kg.

When used in conjunction with a dose provided herein (e.g., a dose of an ActRII signaling inhibitor or a dose of a second active agent), the word "about" refers to any number within 1, 5 or 10% of the referenced number.

In certain embodiments, an ActRII signaling inhibitor as described herein is administered subcutaneously or intravenously. In certain embodiments, an ActRII signaling inhibitor as described herein is administered subcutaneously once every three weeks. In certain embodiments, ActRIIA-hFC (SEQ ID NO: 7; also referred to as sotatercept) is administered to a subject treated in accordance with the methods provided herein subcutaneously once every three weeks. In certain embodiments, ActRIIB-hFC (SEQ ID NO: 25; also referred to as luspatercept) is administered to a subject treated in accordance with the methods provided herein subcutaneously once every three weeks.

7.8 Patient Populations

The subjects treated in accordance with the methods described herein can be any mammals such as rodents and primates, and in a preferred embodiment, humans. In certain embodiments, the subject is a human. In certain embodiments, the methods described herein can be used to treat anemia, anemia requiring RBC transfusion, MDS and/or non-proliferative CMML in any mammals, such as rodents and primates, and in a preferred embodiment, in human subjects. In certain embodiments, the methods described herein can be used to increase levels of neutrophils in any mammals, such as rodents and primates, and in a preferred embodiment, in human subjects. In certain embodiments, the methods described herein can be used to increase levels of platelets in any mammals, such as rodents and primates, and in a preferred embodiment, in human subjects.

In certain embodiments, the percentage of erythroblasts in a subject treated in accordance with the methods provided herein that are ring sideroblasts is at least 10%, 11%, 12%, 13%, 14%, 15%, 16%, 17%, 18%, 19%, or at least 20%. In certain embodiments, the percentage of erythroblasts in a subject treated in accordance with the methods provided herein that are ring sideroblasts is at least 15%. In certain embodiments, the percentage of erythroblasts in a subject treated in accordance with the methods provided herein that are ring sideroblasts is about 15%. In certain embodiments, the percentage of erythroblasts in a subject treated in accordance with the methods provided herein that are ring sideroblasts is between about 10% and about 20%. In certain embodiments, the percentage of erythroblasts in a subject treated in accordance with the methods provided herein that are ring sideroblasts is between about 12% and 17%. In certain embodiments, a subject treated in accordance with the methods provided herein has a ringed sideroblast to normal erythroblast ratio of at least 1:10, at least 1:7, or at least 1:5.

In certain embodiments, a subject treated according to the methods provided herein has a blood-related disorder. In certain embodiments, the blood-related disorder is anemia. In certain embodiments, the blood-related disorder is anemia requiring transfusion. In certain embodiments, the blood-related disorder is MDS. In certain embodiments, the blood-related disorder is non-proliferative CMML.

In certain embodiments, a subject treated in accordance with the methods provided herein has been diagnosed with anemia. In some aspects, anemic subjects have a Hb level of less than or equal to 9.0 g/dL. In some aspects, anemic subjects require 2 or more units of RBC transfusions in the 84 days prior to treatment according to the methods provided herein. In certain embodiments, the subject has a high transfusion burden (HTB). HTB subjects require at least 4 units of RBC transfusions per 56 days. In certain embodiments, the subject has a low transfusion burden (LTB). LTB subjects require less than 4 units of RBC transfusions per 56 days. In certain embodiments, the subject is a subject requiring RBC transfusion. In certain embodiments, a subject treated in accordance with the methods provided herein has a sideroblastic anemia, such as, for example, X-linked sideroblastic anemia, autosomal recessive pyridoxine-refractory sideroblastic anemia, X-linked sideroblastic anemia and spinocerebellar ataxia, myopathy, lactic acidosis and sideroblastic anemia, myopathy, lactic acidosis and sideroblastic anemia, thiamine-responsive megaloblastic anemia, pearson marrow-pancreas syndrome, refractory anemia with ring sideroblasts, refractory anemia with ring sideroblasts and marked thrombocytosis, and ethanol-induced and drug-induced sideroblastic anemias. In certain embodiments, a subject treated in accordance with the methods provided herein has been diagnosed with anemia and at least 10%, 11%, 12%, 13%, 14%, 15%, 16%, 17%, 18%, 19%, or at least 20% of erythroblasts in the subject are ring sideroblasts. In certain embodiments, at least 15% of erythroblasts in the subject are ring sideroblasts.

In certain embodiments, a subject treated in accordance with the methods provided herein has been diagnosed with IPSS-defined MDS. In certain embodiments, a subject treated in accordance with the methods provided herein has been diagnosed with IPSS-defined MDS and at least 10%, 11%, 12%, 13%, 14%, 15%, 16%, 17%, 18%, 19%, or at least 20% of erythroblasts in the subject are ring sideroblasts. In certain embodiments, at least 15% of erythroblasts in the subject are ring sideroblasts.

IPSS refers to the International Prognostic Scoring System, which is utilized in the evaluation of prognosis in myelodysplastic syndromes. See, e.g., Greenberg et al., Blood, 1997; 89(6):2079-2088, and Erratum in Blood, 1998; 91:1100. The IPSS utilizes a criteria point system to characterize myelodysplastic syndrome patient outcomes as low risk (0 points; median survival of 5.7 years), intermediate 1 (0.5-1 point; median survival of 3.5 years); intermediate 2 risk (1.5-2.0 points; median survival of 1.2 years); or high risk (2.5-3.5 points; median survival of 0.4 years). The point system evaluates (i) the percentage of bone marrow blasts in the subject; (ii) the karyotype of the subject; and (iii) and cytopenias in the subject (defined as hemoglobin concentration of less than 10 g/dL, absolute neutrophil count of less than 1,800/μL, and platelet count of less than 100,000/μL).

In certain embodiments, a subject treated in accordance with the methods provided herein has been diagnosed with IPSS-R-defined MDS. In certain embodiments, a subject treated in accordance with the methods provided herein has been diagnosed with IPSS-R-defined MDS and at least 10%, 11%, 12%, 13%, 14%, 15%, 16%, 17%, 18%, 19%, or at least 20% of erythroblasts in the subject are ring sideroblasts. In certain embodiments, at least 15% of erythroblasts in the subject are ring sideroblasts.

IPSS-R refers to the International Prognostic Scoring System-Revised, which is utilized in the evaluation of prognosis in myelodysplastic syndromes. See, e.g., Greenberg et al., Blood, 2012; 120(12):2454-2465, and Erratum in Blood, 1998; 91:1100. The IPSS-R utilizes a criteria point system to characterize myelodysplastic syndrome patient outcomes as very low risk (less than or equal to 1.5 points; median survival of 8.8 years), low risk (greater than 1.5 points, less than or equal to 3 points; median survival of 5.3 years); intermediate risk (greater than 3 points, less than or equal to 4.5 points; median survival of 3 years); high risk (greater than 4.5 points, less than or equal to 6 points; median survival of 1.6 years); or very high (greater than 6 points; median survival of 0.8 years). The point system evaluates, inter alia, (i) the percentage of bone marrow blasts in the subject; (ii) the karyotype of the subject; and (iii) and cytopenias in the subject (defined as hemoglobin concentration of less than 10 g/dL, absolute neutrophil count of less than 1,800/μL, and platelet count of less than 100,000/μL).

In certain embodiments, a subject treated in accordance with the methods provided herein has been diagnosed with non-proliferative CMML. In certain embodiments, a subject treated in accordance with the methods provided herein has been diagnosed with non-proliferative CMML and at least 10%, 11%, 12%, 13%, 14%, 15%, 16%, 17%, 18%, 19%, or at least 20% of erythroblasts in the subject are ring sideroblasts.

In certain embodiments, a subject treated in accordance with the methods provided herein has MDS. In certain embodiments, the MDS is IPSS-defined low risk MDS. In certain embodiments, the MDS is IPSS-defined intermediate-1 risk MDS. In certain embodiments, the MDS is IPSS-defined intermediate-2 risk MDS. In certain embodiments, the MDS is IPSS-defined high risk MDS. In certain embodiments, the MDS is IPSS-R-defined very low risk MDS. In certain embodiments, the MDS is IPSS-R-defined low risk MDS. In certain embodiments, the MDS is IPSS-R-defined intermediate risk MDS. In certain embodiments, the MDS is IPSS-R-defined high risk MDS. In certain embodiments, the MDS is IPSS-R-defined very high risk MDS. In certain embodiments, a subject treated in accordance with the methods provided herein (i) has MDS and (ii) has RARS. In certain embodiments, a subject treated in accordance with the methods provided herein (i) has MDS and (ii) has RCMD-RS. In certain embodiments, a subject treated in accordance with the methods provided herein (i) has MDS, (ii) has RARS, and (iii) has RCMD-RS. In certain embodiments, a subject treated in accordance with the methods provided herein (i) has MDS, and (ii) at least 15% of erythroblasts in the subject are ring sideroblasts. In certain embodiments, a subject treated in accordance with the methods provided herein (i) has MDS, (ii) has RARS, and (iii) at least 15% of erythroblasts in the subject are ring sideroblasts. In certain embodiments, a subject treated in accordance with the methods provided herein (i) has MDS, (ii) has RCMD-RS, and (iii) at least 15% of erythroblasts in the subject are ring sideroblasts. In certain embodiments, a subject treated in accordance with the methods provided herein (i) has MDS, (ii) has RARS, (iii) has RCMD-RS, and (iv) at least 15% of erythroblasts in the subject are ring sideroblasts. In certain embodiments, a subject treated in accordance with the methods provided herein (i) has MDS, (ii) has RARS, and (iii) expresses SF3B1 with one or more mutations. In certain embodiments, a subject treated in accordance with the methods provided herein (i) has MDS, (ii) has RCMD-RS, and (iii) expresses SF3B1 with one or more mutations. In certain embodiments, a subject treated in accordance with the methods provided herein (i) has MDS, (ii) has RARS, (iii) has RCMD-RS, and (iv) expresses SF3B1 with one or more mutations. In certain embodiments, a subject treated in accordance with the methods provided herein (i) has MDS, (ii) at least 15% of erythroblasts in the subject are ring sideroblasts, and (iii) expresses SF3B1 with one or more mutations. In certain embodiments, a subject treated in accordance with the methods provided herein (i) has MDS, (ii) has RARS, (iii) at least 15% of erythroblasts in the subject are ring sideroblasts, and (iv) expresses SF3B1 with one or more mutations. In certain embodiments, a subject treated in accordance with the methods provided herein (i) has MDS, (ii) has RCMD-RS, (iii) at least 15% of erythroblasts in the subject are ring sideroblasts, and (iv) expresses SF3B1 with one or more mutations. In certain embodiments, a subject treated in accordance with the methods provided herein (i) has MDS, (ii) has RARS, (iii) has RCMD-RS, (iv) at least 15% of erythroblasts in the subject are ring sideroblasts, and (v) expresses SF3B1 with one or more mutations.

In certain embodiments, a subject treated in accordance with the methods provided herein has non-proliferative CMML. In certain embodiments, a subject treated in accordance with the methods provided herein (i) has non-proliferative CMML and (ii) has RARS. In certain embodiments, a subject treated in accordance with the methods provided herein (i) has non-proliferative CMML and (ii) has RCMD-RS. In certain embodiments, a subject treated in accordance with the methods provided herein (i) has non-proliferative CMML, (ii) has RARS, and (iii) has RCMD-RS. In certain embodiments, a subject treated in accordance with the methods provided herein (i) has non-proliferative CMML, and (ii) at least 15% of erythroblasts in the subject are ring sideroblasts. In certain embodiments, a subject treated in accordance with the methods provided herein (i) has non-proliferative CMML, (ii) has RARS, and (iii) at least 15% of erythroblasts in the subject are ring sideroblasts. In certain embodiments, a subject treated in accordance with the methods provided herein (i) has non-proliferative CMML, (ii) has RCMD-RS, and (iii) at least 15% of erythroblasts in the subject are ring sideroblasts. In certain embodiments, a subject treated in accordance with the methods provided herein (i) has non-proliferative CMML, (ii) has RARS, (iii) has RCMD-RS, and (iv) at least 15% of erythroblasts in the subject are ring sideroblasts. In certain embodiments, a subject treated in accordance with the methods provided herein (i) has non-proliferative CMML, and (ii) expresses SF3B1 with one or more mutations. In certain embodiments, a subject treated in accordance with the methods provided herein (i) has non-proliferative CMML, (ii) has RARS, and (iii) expresses SF3B1 with one or more mutations. In certain embodiments, a subject treated in accordance with the methods provided herein (i) has non-proliferative CMML, (ii) has RCMD-RS, and (iii) expresses SF3B1 with one or more mutations. In certain embodiments, a subject treated in accordance with the methods provided herein (i) has non-proliferative CMML, (ii) has RARS, (iii) has RCMD-RS, and (iv) expresses SF3B1 with one or more mutations. In certain embodiments, a subject treated in accordance with the methods provided herein (i) has non-proliferative CMML, (ii) at least 15% of erythroblasts in the subject are ring sideroblasts, and (iii) expresses SF3B1 with one or more mutations. In certain embodiments, a subject treated in accordance with the methods provided herein (i) has non-proliferative CMML, (ii) has RARS, (iii) at least 15% of erythroblasts in the subject are ring sideroblasts, and (iv) expresses SF3B1 with one or more mutations. In certain embodiments, a subject treated in accordance with the methods provided herein (i) has non-proliferative CMML, (ii) has RCMD-RS, (iii) at least 15% of erythroblasts in the subject are ring sideroblasts, and (iv) expresses SF3B1 with one or more mutations. In certain embodiments, a subject treated in accordance with the methods provided herein has (i) has non-proliferative CMML, (ii) has RARS, (iii) has RCMD-RS, (iv) at least 15% of erythroblasts in the subject are ring sideroblasts, and (v) expresses SF3B1 with one or more mutations.

In certain embodiments, a subject treated in accordance with the methods provided herein expresses a gene with a mutation associated with ineffective erythropoiesis. In certain embodiments, a subject treated in accordance with the methods provided herein expresses one or more splicing factor gene comprising one or more mutation. In a specific embodiment, a subject treated in accordance with the methods provided herein expresses SF3B1 with one or more mutations. In certain embodiments, the one or more mutations is in a non-coding region. In certain embodiments, SF3B1 is the gene encoding SB3B1. In certain embodiments, the one or more mutations is in a coding region. In certain embodiments, SF3B1 is SF3B1 protein. In certain embodiments, the one or more mutations in SF3B1 protein is selected from the group consisting of E622D, R625C, H662Q, H662D, K66N, K666T, K666Q, K666E, A672D, K700E, I704N. In certain embodiments, a subject treated in accordance with the methods provided herein expresses SF3B1 protein with the mutation E622D. In certain embodiments, a subject treated in accordance with the methods provided herein expresses SF3B1 protein with the mutation R625C. In certain embodiments, a subject treated in accordance with the methods provided herein expresses SF3B1 protein with the mutation H662Q. In certain embodiments, a subject treated in accordance with the methods provided herein expresses SF3B1 protein with the mutation H662D. In certain embodiments, a subject treated in accordance with the methods provided herein expresses SF3B1 protein with the mutation K66N. In certain embodiments, a subject treated in accordance with the methods provided herein expresses SF3B1 protein with the mutation K666T. In certain embodiments, a subject treated in accordance with the methods provided herein expresses SF3B1 protein with the mutation K666Q. In certain embodiments, a subject treated in accordance with the methods provided herein expresses SF3B1 protein with the mutation K666E. In certain embodiments, a subject treated in accordance with the methods provided herein expresses SF3B1 protein with the mutation A672D. In certain embodiments, a subject treated in accordance with the methods provided herein expresses SF3B1 with the mutation K700E. In certain embodiments, a subject treated in accordance with the methods provided herein expresses SF3B1 protein with the mutation I704N. In a specific embodiment, a subject treated in accordance with the methods provided herein expresses SRSF2 with one or more mutations. In a specific embodiment, a subject treated in accordance with the methods provided herein expresses DNMT3A with one or more mutations. In a specific embodiment, a subject treated in accordance with the methods provided herein expresses TET2 with one or more mutations. In a specific embodiment, a subject treated in accordance with the methods provided herein expresses SETBP1 with one or more mutations.

In certain embodiments, a subject treated in accordance with the methods provided herein has thrombocytopenia. In certain embodiments, a subject treated in accordance with the methods provided herein has less than $1 \times 10^{11}$ platelets per liter. In certain embodiments, a subject treated in accordance with the methods provided herein has neutropenia. In certain embodiments, a subject treated in accordance with the methods provided herein has an absolute neutrophil count of less than $1 \times 10^9$ per liter.

In certain embodiments, a subject treated in accordance with the methods provided herein has less than 13,000 white blood cells per µL, less than 12,000 white blood cells per µL, less than 11,000 white blood cells per µL, less than 10,000 white blood cells per µL, less than 7,500 white blood cells per µL, or less than 500 white blood cells per µL.

In certain embodiments, hemoglobin levels in a subject treated in accordance with the methods provide herein are less than 10 g/dL, 9 g/dL, 8 g/dL, or 7 g/dL. In certain embodiments, hemoglobin levels in a subject treated in accordance with the methods provided herein are between 7 g/dL and 7.5 g/dL, between 7.5 g/dL and 8 g/dL, between 8 g/dL and 8.5 g/dL, between 8.5 g/dL and 9.0 g/dL, between 9.0 g/dL and 9.5 g/dL, or between 9.5 g/dL and 10.0 g/dL.

In certain embodiments, a subject treated in accordance with the methods provided herein has a low transfusion burden. In certain embodiments, the subject with a low transfusion burden treated in accordance with the methods provided herein requires at most 0, 1, 2, or 3 units of red blood cells per 8 weeks. In certain embodiments, a subject treated in accordance with the methods provided herein has a high transfusion burden. In certain embodiments, the subject with a high transfusion burden treated in accordance with the methods provided herein requires at least 4, 5, 6, 7, 8, 9, 10, 11, 12, or 13 units of red blood cells per 8 weeks.

In certain embodiments, a subject treated in accordance with the methods provided herein has no response, a loss of response, or low chance of response to one or more ESAs.

In certain embodiments, a subject treated in accordance with the methods provided herein has undergone prior treatment with one or more ESAs or is currently undergoing treatment with one or more ESAs. In certain embodiments, a subject treated in accordance with the methods provided herein has undergone prior treatment with hypomethylating agents. In certain embodiments, a subject treated in accordance with the methods provided herein has undergone prior treatment with lenalidomine. In certain embodiments, a subject treated in accordance with the methods provided herein has not undergone treatment with azacitidine, decitabine, ESA, G-CSF, GM-CSG, or lenalidomide. In certain embodiments, a subject treated in accordance with the methods provided herein does not respond to treatment with one or more ESAs. In certain embodiments, a subject treated in accordance with the methods provided herein is refractory to treatment with one or more ESAs. In certain embodiments, a subject treated in accordance with the methods provided herein becomes refractory to treatment with one or more ESAs. In certain embodiments, a subject treated in accordance with the methods provided herein is refractory to prior ESA treatment. In certain embodiments, a subject who is refractory to prior ESA treatment has documented non-response or response that is no longer maintained to prior ESA-containing regimen, either as single agent or combination (e.g., with G-CSF); the ESA regimen must have been either (a) recombinant human erythropoietin of greater than 40,000 IU/week for at least 8 doses or equivalent, or (b) darbepoetin alpha of greater than 500 µg once every three weeks for at least 4 doses or equivalent. In certain embodiments, a subject treated in accordance with the methods provided herein is intolerant to prior ESA-treatment. In certain embodiments, a subject who is intolerant to prior ESA-treatment has documented discontinuation of prior ESA-containing regimen, either as single agent or combination (e.g., with G-CSF), at any time after introduction due to intolerance or an adverse event. In certain embodiments, a subject treated in accordance with the methods provided herein is ESA-ineligible. In certain embodiments, a subject who is ESA-ineligible has a low chance of response to ESA based on an endogenous serum erythropoietin level of greater than 200 U/L for subjects not previously treated with ESAs.

In certain embodiments, the subject treated in accordance with the methods described here can be of any age. In certain embodiments, the subject treated in accordance with the methods described herein is less than 18 years old. In a specific embodiment, the subject treated in accordance with the methods described herein is less than 13 years old. In another specific embodiment, the subject treated in accordance with the methods described herein is less than 12, less than 11, less than 10, less than 9, less than 8, less than 7, less than 6, or less than 5 years old. In another specific embodiment, the subject treated in accordance with the methods described herein is 1-3 years old, 3-5 years old, 5-7 years old, 7-9 years old, 9-11 years old, 11-13 years old, 13-15 years old, 15-20 years old, 20-25 years old, 25-30 years old, or greater than 30 years old. In another specific embodiment, the subject treated in accordance with the methods described herein is 30-35 years old, 35-40 years old, 40-45 years old, 45-50 years old, 50-55 years old, 55-60 years old, or greater than 60 years old. In another specific embodiment, the subject treated in accordance with the methods described herein is 60-65 years old, 65-70 years old, 70-75 years old, 75-80 years old, or greater than 80 years old.

In certain embodiments, the subject treated in accordance with the methods described herein has MDS. In certain embodiments, the subject treated in accordance with the methods described herein has MDS and intact chromosome 5q. In certain embodiments, the subject treated in accordance with the methods provided herein has MDS, intact chromosome 5q, and does not have documented treatment failure with lenalidomide. In certain embodiments, the subject treated in accordance with the methods provided herein has MDS, intact chromosome 5q, and documented treatment failure with lenalidomide. In certain embodiments, the subject treated in accordance with the methods described herein has MDS with chromosome 5q deletion. MDS with chromosome 5q deletion comprises a deletion of the long arm of chromosome 5 and is characterized by, inter alia, macrocytic anemia with oval macrocytes, normal to slightly reduced white blood cell counts, normal to elevated platelet counts, and less than 5% blasts in the bone marrow and blood. In certain embodiments, the subject treated in accordance with the methods provided herein has MDS with chromosome 5q deletion and does not have documented treatment failure with lenalidomide. In certain embodiments, the subject treated in accordance with the methods provided herein has MDS with chromosome 5q deletion and documented treatment failure with lenalidomide. In certain embodiments, treatment failure with lenalidomide comprises loss of response to lenalidomide, no response to lenalidomide after 4 months of treatment with lenalidomide, intolerance to treatment with lenalidomide, or cytopenia precluding treatment with lenalidomide.

In certain embodiments, a subject treated in accordance with the methods provided herein has less than 5% blasts in the bone marrow and blood.

In certain embodiments, a subject treated in accordance with the methods provided herein has an EPO serum concentration of greater than 500 mIU/mL. In certain embodiments, a subject treated in accordance with the methods provided herein has an EPO serum concentration of greater than 200 mIU/mL.

7.9 Signaling Inhibitors of ActRIIA Receptors

Inhibitors of ActRII receptors encompassed herein include ActRIIA signaling inhibitors and ActRIIB signaling inhibitors (see below). In certain embodiments, an ActRII receptor signaling inhibitor is specific to ActRIIA. In other embodiments, an ActRII receptor signaling inhibitor is specific to ActRIIB. In certain embodiments, an ActRII receptor signaling inhibitor preferentially inhibits ActRIIA. In other embodiments, an ActRII receptor signaling inhibitor preferentially inhibits ActRIIB. In certain embodiments, an ActRII receptor signaling inhibitor inhibits both ActRIIA and ActRIIB.

In certain embodiments, signaling inhibitors of ActRII receptors can be polypeptides comprising activin-binding domains of ActRII. Without being bound by theory, such activin-binding domain comprising polypeptides sequester activin and thereby prevent activin signaling. These activin-binding domain comprising polypeptides may comprise all or a portion of the extracellular domain of an ActRII receptor (i.e., all or a portion of the extracellular domain of ActRIIA or all or a portion of the extracellular domain of ActRIIB). In specific embodiments, the extracellular domain of an ActRII receptor is soluble.

In certain embodiments, the activin-binding domain comprising polypeptides are linked to an Fc portion of an antibody (i.e., a conjugate comprising an activin-binding domain comprising polypeptide of an ActRII receptor and an Fc portion of an antibody is generated). Without being bound by theory, the antibody portion confers increased stability on the conjugate. In certain embodiments, the activin-binding domain is linked to an Fc portion of an antibody via a linker, e.g., a peptide linker.

The signaling inhibitors of ActRII receptors used in the compositions and methods described herein comprise molecules that inhibit ActRIIA and/or ActRIIB, directly or indirectly, either extracellularly or intracellularly. In some embodiments, the signaling inhibitors of ActRIIA and/or ActRIIB used in the compositions and methods described herein inhibit ActRIIA and/or ActRIIB via interactions with the receptor(s) itself. In other embodiments, the signaling inhibitors of ActRIIA and/or ActRIIB used in the compositions and methods described herein inhibit ActRIIA and/or ActRIIB via interactions with an ActRIIA and/or ActRIIB ligand, e.g., Activin.

7.9.1 Signaling Inhibitors of ActRIIA

As used herein, the term "ActRIIA" refers to a family of activin receptor type IIa (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain with a cysteine-rich region, a transmembrane domain, and a cytoplasmic domain with predicted serine/threonine kinase activity.

ActRIIA signaling inhibitors to be used in the compositions and methods described herein include, without limitation, activin-binding soluble ActRIIA polypeptides; antibodies that bind to activin (particularly the activin A or B subunits, also referred to as BA or BB) and disrupt ActRIIA binding; antibodies that bind to ActRIIA and disrupt activin binding; non-antibody proteins selected for activin or ActRIIA binding (see e.g., WO/2002/088171, WO/2006/055689, WO/2002/032925, WO/2005/037989, US 2003/0133939, and US 2005/0238646, each of which is incorporated herein by reference in its entirety, for examples of such proteins and methods for design and selection of same); and randomized peptides selected for activin or ActRIIA binding, which can be conjugated to an Fc domain.

In certain embodiments, two or more different proteins (or other moieties) with activin or ActRIIA binding activity, especially activin binders that block the type I (e.g., a soluble type I activin receptor) and type II (e.g., a soluble type II activin receptor) binding sites, respectively, may be linked together to create a bifunctional or multifunctional binding molecule that inhibits ActRIIA and thus can be used in the compositions and methods described herein include. In certain embodiments, Activin-ActRIIA signaling axis antagonists that inhibit ActRIIA include nucleic acid aptamers, small molecules and other agents are used in the compositions and methods described herein include.

(a) ActRIIA Signaling Inhibitors Comprising ActRIIA Polypeptides

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. For example, ActRIIA polypeptides include polypeptides derived from the sequence of any known ActRIIA having a sequence at least about 80% identical to the sequence of an ActRIIA polypeptide, and optionally at least 85%, 90%, 95%, 97%, 98%, 99% or greater identity. For example, an ActRIIA polypeptide may bind to and inhibit the function of an ActRIIA protein and/or activin. An ActRIIB polypeptide may be selected for its ability to promote bone growth and bone mineralization. Examples of ActRIIA polypeptides include human ActRIIA precursor polypeptide (SEQ ID NO: 1) and soluble human ActRIIA polypeptides (e.g., SEQ ID NOs: 2, 3, 7 and 12). With respect to the ActRIIA precursor polypeptide whose amino acid sequence is depicted at SEQ ID NO:1, the signal peptide of the human ActRIIA precursor polypeptide located at amino acid positions 1 to 20; the extracellular domain is located at amino acid positions 21 to 135 and the N-linked glycosylation sites of the human ActRIIA precursor polypeptide (SEQ ID NO: 1) are located at amino acid positions 43 and 56 of SEQ ID NO:1. The nucleic acid sequence encoding the human ActRIIB precursor polypeptide of SEQ ID NO:1 is disclosed as SEQ ID NO:4 (nucleotides 164-1705 of Genbank entry NM_001616). The nucleic acid sequence encoding the soluble human ActRIIA polypeptide of SEQ ID NO:2 is disclosed as SEQ ID NO:5. See Table 21 for a description of the sequences.

In specific embodiments, the ActRIIA polypeptides used in the compositions and methods described herein are soluble ActRIIA polypeptides. An extracellular domain of an ActRIIA protein can bind to activin and is generally soluble, and thus can be termed a soluble, activin-binding ActRIIA polypeptide. Thus, as used herein, the term "soluble ActRIIA polypeptide" generally refers to polypeptides comprising an extracellular domain of an ActRIIA protein, including any naturally occurring extracellular domain of an ActRIIA protein as well as any variants thereof (including mutants, fragments and peptidomimetic forms). Soluble ActRIIA polypeptides can bind to activin; however, the wild type ActRIIA protein does not exhibit significant selectivity in binding to activin versus GDF8/11. Native or altered ActRIIA proteins may be given added specificity for activin by coupling them with a second, activin-selective binding agent. Examples of soluble, activin-binding ActRIIA polypeptides include the soluble polypeptides illustrated in SEQ ID NOs: 2, 3, 7, 12 and 13. Other examples of soluble, activin-binding ActRIIA polypeptides comprise a signal sequence in addition to the extracellular domain of an ActRIIA protein, for example, the honey bee mellitin leader sequence (SEQ ID NO: 8), the tissue plasminogen activator (TPA) leader (SEQ ID NO: 9) or the native ActRIIA leader (SEQ ID NO: 10). The ActRIIA-hFc polypeptide illustrated in SEQ ID NO:13 uses a TPA leader.

In certain embodiments, the signaling inhibitors of ActRIIA used in the compositions and methods described herein comprise a conjugate/fusion protein comprising an activin-binding domain of ActRIIA linked to an Fc portion of an antibody. In certain embodiments, the activin-binding domain is linked to an Fc portion of an antibody via a linker, e.g., a peptide linker. Optionally, the Fc domain has one or more mutations at residues such as Asp-265, lysine 322, and Asn-434. In certain cases, the mutant Fc domain having one or more of these mutations (e.g., an Asp-265 mutation) has a reduced ability to bind to the Fcγ receptor relative to a wild-type Fc domain. In other cases, the mutant Fc domain having one or more of these mutations (e.g., an Asn-434 mutation) has an increased ability to bind to the MHC class I-related Fc-receptor (FcRN) relative to a wild-type Fc domain. Exemplary fusion proteins comprising a soluble extracellular domain of ActRIIA fused to an Fc domain are set forth in SEQ ID NOs:6, 7, 12, and 13.

In a specific embodiment, the ActRIIA signaling inhibitors used in the compositions and methods described herein comprise the extracellular domain of ActRIIA, or a portion thereof, linked to an Fc portion of an antibody, wherein said ActRIIA signaling inhibitor comprises an amino acid sequence that is at least 75% identical to an amino acid sequence selected from SEQ ID NOs:6, 7, 12, and 13. In another specific embodiment, the ActRIIA signaling inhibitors used in the compositions and methods described herein comprise the extracellular domain of ActRIIA, or a portion thereof, linked to an Fc portion of an antibody, wherein said ActRIIA signaling inhibitor comprises an amino acid sequence that is at least 80%, 85%, 90%, 95%, 96%, 97%, 98%, or 99% identical to an amino acid sequence selected from SEQ ID NOs:6, 7, 12, and 13.

In certain embodiments, the signaling inhibitors of ActRIIA used in the compositions and methods described herein comprise a truncated form of an extracellular domain of ActRIIA. The truncation can be at the carboxy terminus and/or the amino terminus of the ActRIIA polypeptide. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 amino acids long relative to the mature ActRIIA polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 N-terminal amino acids of the mature ActRIIA polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 C-terminal amino acids of the mature ActRIIA polypeptide extracellular domain. For example, truncated forms of ActRIIA include polypeptides with amino acids 20-119; 20-128; 20-129; 20-130; 20-131; 20-132; 20-133; 20-134; 20-131; 21-131; 22-131; 23-131; 24-131; and 25-131, wherein the amino acid positions refer to the amino acid positions in SEQ ID NO:1.

In certain embodiments, the signaling inhibitors of ActRIIA used in the compositions and methods described herein comprise an extracellular domain of ActRIIA with one or more amino acid substitutions. In certain embodiments, the signaling inhibitors of ActRIIA used in the compositions and methods described herein comprise a truncated form of an ActRIIA extracellular domain that also carries an amino acid substitution.

In a specific embodiment, the ActRIIA signaling inhibitor to be used in the compositions and methods described herein is a fusion protein between the extracellular domain of the human ActRIIA receptor and the Fc portion of IgG1. In another specific embodiment, the ActRIIA signaling inhibitor to be used in the compositions and methods described herein is a fusion protein between a truncated extracellular domain of the human ActRIIA receptor and the Fc portion of IgG1. In another specific embodiment, the ActRIIA signaling inhibitor to be used in the compositions and methods described herein is a fusion protein between a truncated extracellular domain of the human ActRIIA receptor and the Fc portion of IgG1, wherein the truncated extracellular domain of the human ActRIIA receptor possesses one or more amino acid substitutions.

Functionally active fragments of ActRIIA polypeptides can be obtained, for example, by screening polypeptides recombinantly produced from the corresponding fragment of the nucleic acid encoding an ActRIIA polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIA protein or signaling mediated by activin.

In addition, functionally active variants of ActRIIA polypeptides can be obtained, for example, by screening libraries of modified polypeptides recombinantly produced from the corresponding mutagenized nucleic acids encoding an ActRIIA polypeptide. The variants can be produced and tested to identify those that can function as antagonists (inhibitors) of ActRIIA protein or signaling mediated by activin. In certain embodiments, a functional variant of the ActRIIA polypeptides comprises an amino acid sequence that is at least 75% identical to an amino acid sequence selected from SEQ ID NOs: 2 or 3. In certain cases, the functional variant has an amino acid sequence at least 80%, 85%, 90%, 95%, 97%, 98%, 99% or 100% identical to an amino acid sequence selected from SEQ ID NOs: 2 or 3.

Functional variants may be generated, for example, by modifying the structure of an ActRIIA polypeptide for such purposes as enhancing therapeutic efficacy, or stability (e.g., ex vivo shelf life and resistance to proteolytic degradation in vivo). Such modified ActRIIA polypeptides when selected to retain activin binding, are considered functional equivalents of the naturally-occurring ActRIIA polypeptides. Modified ActRIIA polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIA polypeptide results in a functional homolog can be readily determined by assessing the ability of the variant ActRIIA polypeptide to produce a response in cells in a fashion similar to the wild-type ActRIIA polypeptide.

In certain embodiments, provided herein are specific mutations of the ActRIIA polypeptides that can alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagines-X-serine) (where "X" is any amino acid) which is specifically recognized by appropriate cellular glycosylation enzymes. The alteration may also be made by the addition of, or substitution by, one or more serine or threonine residues to the sequence of the wild-type ActRIIA polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIA polypeptide is by chemical or enzymatic coupling of glycosides to the ActRIIA polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIA polypeptide may be accomplished chemically and/or enzymatically. Chemical deglycosylation may involve, for example, exposure of the ActRIIA polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIA polypeptides can be achieved by the use of a variety of endo- and exo-glycosidases as described by Thotakura et al. (1987) Meth. Enzymol. 138:350. The sequence of an ActRIIA polypeptide may be adjusted, as appropriate, depending on the type of expression system used, as mammalian, yeast, insect and plant cells may all introduce differing glycosylation patterns that can be affected by the amino acid sequence of the peptide. In general, ActRIIA proteins for use in humans will be expressed in a mammalian cell line that provides proper glycosylation, such as HEK293 or CHO cell lines, although other expression systems, such as other mammalian expression cell lines, yeast cell lines with engineered glycosylation enzymes and insect cells, are expected to be useful as well.

Further provided herein are methods of generating mutants, particularly sets of combinatorial mutants of an ActRIIA polypeptide, as well as truncation mutants; pools of combinatorial mutants are especially useful for identifying functional variant sequences. The purpose of screening such combinatorial libraries may be to generate, for example, ActRIIA polypeptide variants which can act as either agonists or antagonist, or alternatively, which possess novel activities all together. A variety of screening assays are provided below, and such assays may be used to evaluate variants. For example, an ActRIIA polypeptide variant may be screened for ability to bind to an ActRIIA ligand, to prevent binding of an ActRIIA ligand to an ActRIIA polypeptide or to interfere with signaling caused by an ActRIIA ligand.

Combinatorially-derived variants can be generated which have a selective or generally increased potency relative to a naturally occurring ActRIIA polypeptide. Likewise, mutagenesis can give rise to variants which have intracellular half-lives dramatically different than the corresponding a wild-type ActRIIA polypeptide. For example, the altered protein can be rendered either more stable or less stable to proteolytic degradation or other cellular processes which result in destruction of, or otherwise inactivation of a native ActRIIA polypeptide. Such variants, and the genes which encode them, can be utilized to alter ActRIIA polypeptide levels by modulating the half-life of the ActRIIA polypeptides. For instance, a short half-life can give rise to more transient biological effects and can allow tighter control of recombinant ActRIIA polypeptide levels within the subject. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIA polypeptide sequences. For instance, a mixture of synthetic oligonucleotides can be enzymatically ligated into gene sequences such that the degenerate set of potential ActRIIA polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see, for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIA polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRIIA polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIA polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, ActRIIA polypeptides may further comprise post-translational modifications in addition to any that are naturally present in the ActRIIA polypeptides. Such modifications include, but are not limited to, acetylation, carboxylation, glycosylation, phosphorylation, lipidation, and acylation. As a result, the modified ActRIIA polypeptides may contain non-amino acid elements, such as polyethylene glycols, lipids, poly- or mono-saccharide, and phosphates. Effects of such non-amino acid elements on the functionality of a ActRIIA polypeptide may be tested by any method known to the skilled artisan. When an ActRIIA polypeptide is produced in cells by cleaving a nascent form of the ActRIIA polypeptide, post-translational processing may also be important for correct folding and/or function of the protein. Different cells (such as CHO, HeLa, MDCK, 293, W138, NIH-3T3 or HEK293) have specific cellular machinery and characteristic mechanisms for such post-translational activities and may be chosen to ensure the correct modification and processing of the ActRIIA polypeptides.

In certain aspects, functional variants or modified forms of the ActRIIA polypeptides include fusion proteins having at least a portion of the ActRIIA polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) fusion partners. As another example, a fusion domain may be selected so as to facilitate detection of the ActRIIA polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus hemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIA polypeptide is fused with a domain that stabilizes the ActRIIA polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth or muscle growth, as desired).

It is understood that different elements of the fusion proteins may be arranged in any manner that is consistent with the desired functionality. For example, an ActRIIA polypeptide may be placed C-terminal to a heterologous domain, or, alternatively, a heterologous domain may be placed C-terminal to an ActRIIA polypeptide. The ActRIIA polypeptide domain and the heterologous domain need not be adjacent in a fusion protein, and additional domains or amino acid sequences may be included C- or N-terminal to either domain or between the domains.

In certain embodiments, the ActRIIA polypeptides described herein contain one or more modifications that are capable of stabilizing the ActRIIA polypeptides. For example, such modifications enhance the in vitro half life of the ActRIIA polypeptides, enhance circulatory half life of the ActRIIA polypeptides or reduce proteolytic degradation of the ActRIIA polypeptides. Such stabilizing modifications include, but are not limited to, fusion proteins (including, for example, fusion proteins comprising an ActRIIA polypeptide and a stabilizer domain), modifications of a glycosylation site (including, for example, addition of a glycosylation site to an ActRIIA polypeptide), and modifications of carbohydrate moiety (including, for example, removal of carbohydrate moieties from an ActRIIA polypeptide). In the case of fusion proteins, an ActRIIA polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, isolated and/or purified forms of the ActRIIA polypeptides, which are isolated from, or otherwise substantially free of, other proteins can be used with the methods and compositions described herein. ActRIIA polypeptides will generally be produced by expression from recombinant nucleic acids.

In certain aspects, provided herein are isolated and/or recombinant nucleic acids encoding any of the ActRIIA polypeptides (e.g., soluble ActRIIA polypeptides), including fragments, functional variants and fusion proteins disclosed herein. For example, SEQ ID NO: 4 encodes the naturally occurring human ActRIIA precursor polypeptide, while SEQ ID NO: 5 encodes the processed extracellular domain of ActRIIA. The subject nucleic acids may be single-stranded or double stranded. Such nucleic acids may be DNA or RNA molecules. These nucleic acids may be used, for example, in methods for making ActRIIA polypeptides or as direct therapeutic agents (e.g., in a gene therapy approach).

In certain aspects, the subject nucleic acids encoding ActRIIA polypeptides are further understood to include nucleic acids that are variants of SEQ ID NO: 4 or 5. Variant nucleotide sequences include sequences that differ by one or more nucleotide substitutions, additions or deletions, such as allelic variants.

In certain embodiments, provided herein are isolated or recombinant nucleic acid sequences that are at least 80%, 85%, 90%, 95%, 97%, 98%, 99% or 100% identical to SEQ ID NO: 4 or 5. One of ordinary skill in the art will appreciate that nucleic acid sequences complementary to SEQ ID NO: 4 or 5, and variants of SEQ ID NO: 4 or 5 are also encompassed herein. In further embodiments, the nucleic acid sequences provided herein can be isolated, recombinant, and/or fused with a heterologous nucleotide sequence, or in a DNA library.

In other embodiments, nucleic acids provided herein also include nucleotide sequences that hybridize under highly stringent conditions to the nucleotide sequence designated in SEQ ID NO: 4 or 5, complement sequence of SEQ ID NO: 4 or 5, or fragments thereof. As discussed above, one of ordinary skill in the art will readily understand that appropriate stringency conditions which promote DNA hybridization can be varied. One of ordinary skill in the art will understand that appropriate stringency conditions which promote DNA hybridization can be varied. For example, one can perform the hybridization at 6.0 times sodium chloride/sodium citrate (SSC) at about 45 degree Celsius, followed by a wash of 2.0 times SSC at 50 degree Celsius. For example, the salt concentration in the wash step can be selected from a low stringency of about 2.0 times SSC at 50 degree Celsius to a high stringency of about 0.2 times SSC at 50 degree Celsius. In addition, the temperature in the wash step can be increased from low stringency conditions at room temperature, about 22 degree Celsius, to high stringency conditions at about 65 degree Celsius. Both temperature and salt may be varied, or temperature or salt concentration may be held constant while the other variable is changed. In one embodiment, nucleic acids which hybridize under low stringency conditions of 6 times SSC at room temperature followed by a wash at 2 times SSC at room temperature can be used with the methods and compositions described herein.

Isolated nucleic acids which differ from the nucleic acids as set forth in SEQ ID NOs: 4 or 5 due to degeneracy in the genetic code are also encompassed herein. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are encompassed herein.

In certain embodiments, the recombinant nucleic acids may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated herein. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the subject nucleic acid is provided in an expression vector comprising a nucleotide sequence encoding an ActRIIA polypeptide and operably linked to at least one regulatory sequence. Regulatory sequences are art-recognized and are selected to direct expression of the ActRIIA polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding an ActRIIA polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast .alpha.-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid provided herein can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIA polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the .beta.-gal containing pBlueBac III).

In a preferred embodiment, a vector will be designed for production of the subject ActRIIA polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIA polypeptides in cells propagated in culture, e.g., to produce proteins, including fusion proteins or variant proteins, for purification.

This disclosure also pertains to a host cell transfected with a recombinant gene including a coding sequence (e.g., SEQ ID NO: 4 or 5) for one or more of the subject ActRIIA polypeptides. The host cell may be any prokaryotic or eukaryotic cell. For example, an ActRIIA polypeptide provided herein may be expressed in bacterial cells such as E. coli, insect cells (e.g., using a baculovirus expression system), yeast, or mammalian cells. Other suitable host cells are known to those skilled in the art.

Accordingly, provided herein are methods of producing the ActRIIA polypeptides. For example, a host cell transfected with an expression vector encoding an ActRIIA polypeptide can be cultured under appropriate conditions to allow expression of the ActRIIA polypeptide to occur. The ActRIIA polypeptide may be secreted and isolated from a mixture of cells and medium containing the ActRIIA polypeptide. Alternatively, the ActRIIA polypeptide may be retained cytoplasmically or in a membrane fraction and the cells harvested, lysed and the protein isolated. A cell culture includes host cells, media and other byproducts. Suitable media for cell culture are well known in the art. The subject ActRIIA polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIA polypeptides and affinity purification with an agent that binds to a domain fused to the ActRIIA polypeptide (e.g., a protein A column may be used to purify an ActRIIA-Fc fusion). In a preferred embodiment, the ActRIIA polypeptide is a fusion protein containing a domain which facilitates its purification. In a preferred embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. As demonstrated herein, ActRIIA-hFc protein was purified to a purity of >98% as determined by size exclusion chromatography and >95% as determined by SDS PAGE. This level of purity was sufficient to achieve desirable effects on bone in mice and an acceptable safety profile in mice, rats and non-human primates.

In another embodiment, a fusion gene coding for a purification leader sequence, such as a poly-(His)/enterokinase cleavage site sequence at the N-terminus of the desired portion of the recombinant ActRIIA polypeptide, can allow purification of the expressed fusion protein by affinity chromatography using a Ni2+ metal resin. The purification leader sequence can then be subsequently removed by treatment with enterokinase to provide the purified ActRIIA polypeptide (e.g., see Hochuli et al., (1987) J. Chromatography 411:177; and Janknecht et al., PNAS USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

ActRIIA-Fc fusion protein can be expressed in stably transfected CHO-DUKX B1 1 cells from a pAID4 vector (SV40 ori/enhancer, CMV promoter), using a tissue plasminogen leader sequence of SEQ ID NO:9. The Fc portion is a human IgG1 Fc sequence, as shown in SEQ ID NO:7. In certain embodiments, upon expression, the protein contained has, on average, between about 1.5 and 2.5 moles of sialic acid per molecule of ActRIIA-Fc fusion protein.

In certain embodiments, the long serum half-life of an ActRIIA-Fc fusion can be 25-32 days in human subjects. Additionally, the CHO cell expressed material can have a higher affinity for activin B ligand than that reported for an ActRIIA-hFc fusion protein expressed in human 293 cells (del Re et al., J Biol Chem. 2004 Dec. 17; 279(51):53126-35). Additionally, without being bound by theory, the use of the TPA leader sequence provided greater production than other leader sequences and, unlike ActRIIA-Fc expressed with a native leader, may provide a highly pure N-terminal sequence. Use of the native leader sequence may result in two major species of ActRIIA-Fc, each having a different N-terminal sequence.

7.9.2 Signaling Inhibitors of ActRIIB

As used herein, the term "ActRIIB" refers to a family of activin receptor type JIB (ActRIIB) proteins from any species and variants derived from such ActRIIB proteins by mutagenesis or other modification. Reference to ActRIIB herein is understood to be a reference to any one of the currently identified forms of the receptor. Members of the ActRIIB family are generally transmembrane proteins, composed of a ligand-binding extracellular domain with a cysteine-rich region, a transmembrane domain, and a cytoplasmic domain with predicted serine/threonine kinase activity.

ActRIIB signaling inhibitors to be used in the compositions and methods described herein include, without limitation, activin-binding soluble ActRIIB polypeptides; antibodies that bind to activin (particularly the activin A or B subunits, also referred to as BA or BB) and disrupt ActRIIB binding; antibodies that bind to ActRIIB and disrupt activin binding; non-antibody proteins selected for activin or ActRIIB binding; and randomized peptides selected for activin or ActRIIB binding, which can be conjugated to an Fc domain.

In certain embodiments, two or more different proteins (or other moieties) with activin or ActRIIB binding activity, especially activin binders that block the type I (e.g., a soluble type I activin receptor) and type II (e.g., a soluble type II activin receptor) binding sites, respectively, may be linked together to create a bifunctional or multifunctional binding molecule that inhibits ActRIIB and thus can be used in the compositions and methods described herein include. In certain embodiments, Activin-ActRIIB signaling axis antagonists that inhibit ActRIIB include nucleic acid aptamers, small molecules and other agents are used in the compositions and methods described herein include.

(a) ActRIIB Signaling Inhibitors Comprising ActRIIB Polypeptides

As used herein, the term "ActRIIB polypeptide" refers to polypeptides comprising any naturally occurring polypeptide of an ActRIIB family member as well as any variants thereof (including mutants, fragments, fusions, and peptidomimetic forms) that retain a useful activity. For example, ActRIIB polypeptides include polypeptides derived from the sequence of any known ActRIIB receptor having a sequence at least about 80% identical to the sequence of an ActRIIB polypeptide, and optionally at least 85%, 90%, 95%, 96%, 97%, 98%, 99% or greater identity. For example, an ActRIIB polypeptide may bind to and inhibit the function of an ActRIIB protein and/or activin. An example of an ActRIIB polypeptide includes the human ActRIIB precursor polypeptide (SEQ ID NO:16 or SEQ ID NO:28). With respect to the ActRIIB precursor polypeptide whose amino acid sequence is depicted as SEQ ID NO:16 or SEQ ID NO:28 (i.e., the human ActRIIB precursor polypeptide), the signal peptide of the ActRIIB precursor polypeptide is located at amino acids 1 to 18; the extracellular domain is located at amino acids 19 to 134 and the potential N-linked glycosylation sites are located at amino acid positions 42 and 65. The nucleic acid sequence encoding the human ActRIIB precursor polypeptide of SEQ ID NO:16 is disclosed as SEQ ID NO:19 (SEQ ID NO:19 provides an alanine at the codon corresponding to amino acid position 64, but could be readily modified by one of skill in the art using methods known in the art to provide an arginine at the codon corresponding to amino acid position 64 instead). See Table 21 for a description of the sequences.

The numbering of amino acids for all of the ActRIIB-related polypeptides described herein is based on the amino acid numbering for SEQ ID NO:16 and SEQ ID NO:28 (which only differ in the amino acid expressed at position 64), unless specifically designated otherwise. For example, if an ActRIIB polypeptide is described as having a substitution/mutation at amino acid position 79, then it is to be understood that position 79 refers to the 79th amino acid in SEQ ID NO:16 or SEQ ID NO:28, from which the ActRIIB polypeptide is derived. Likewise, if an ActRIIB polypeptide is described as having an alanine or an arginine at amino acid position 64, then it is to be understood that position 64 refers to the 64th amino acid in SEQ ID NO:16 or SEQ ID NO:28, from which the ActRIIB polypeptide is derived.

In certain embodiments, the signaling inhibitors of ActRIIB used in the compositions and methods described herein comprise polypeptides comprising an activin-binding domain of ActRIIB. In some embodiments, the activin-binding domains of ActRIIB comprise the extracellular domain of ActRIIB, or a portion thereof. In specific embodiments, the extracellular domain or portion thereof of ActRIIB is soluble. Illustrative modified forms of ActRIIB polypeptides are disclosed in U.S. Patent Application Publication Nos. 20090005308 and 20100068215, the disclosures of which are incorporated herein by reference in their entireties.

In specific embodiments, the ActRIIB polypeptides used in the compositions and methods described herein are soluble ActRIIB polypeptides. The term "soluble ActRIIB polypeptide" generally refers to polypeptides comprising an extracellular domain of an ActRIIB protein, including any naturally occurring extracellular domain of an ActRIIB protein as well as any variants thereof (including mutants, fragments and peptidomimetic forms). Soluble ActRIIB polypeptides can bind to activin; however, the wild type ActRIIB protein does not exhibit significant selectivity in binding to activin versus GDF8/11. In certain embodiments, altered forms of ActRIIB with different binding properties can be used in the methods provided herein. Such altered forms are disclosed, e.g., in international patent application publication Nos. WO 2006/012627 and WO 2010/019261, the disclosures of which are incorporated herein by reference in their entireties. Native or altered ActRIIB proteins may be given added specificity for activin by coupling them with a second, activin-selective binding agent. Exemplary soluble ActRIIB polypeptides include the extracellular domain of a human ActRIIB polypeptide (e.g., SEQ ID NOs: 17, 18, 23, 26, 27, 29, 30, 31, 32, 33, 36, 37, 42, and 43).

An Fc fusion protein having the ActRIIB extracellular sequence disclosed by Hilden et al. (Blood, 1994, 83(8): 2163-70), which has an alanine at the position corresponding to amino acid 64 of the ActRIIB precursor amino acid sequence, i.e., SEQ ID NO: 16 (herein referred to as "A64"), has been demonstrated to possess a relatively low affinity for activin and GDF-11. By contrast, an Fc fusion protein with an arginine at position 64 of the ActRIIB precursor amino acid sequence (herein referred to as "R64") has an affinity for activin and GDF-11 in the low nanomolar to high picomolar range (see, e.g., U.S. Patent Application Publication No. 20100068215, the disclosure of which is herein incorporated in its entirety). An ActRIIB precursor amino acid sequence with an arginine at position 64 is presented in SEQ ID NO: 28. As such, in certain embodiments, the ActRIIB polypeptides used in accordance with the compositions and methods described herein may comprise either (i) an alanine at the position corresponding to amino acid 64 of the ActRIIB precursor amino acid sequence, i.e., SEQ ID NO: 16; or (ii) an arginine at position 64 of the ActRIIB precursor amino acid sequence, i.e., SEQ ID NO: 28. In other embodiments, the ActRIIB polypeptides used in accordance with the compositions and methods described herein may comprise an amino acid that is not alanine or arginine at the position corresponding to amino acid 64 of the ActRIIB precursor amino acid sequence, i.e., SEQ ID NO: 16 or SEQ ID NO:28.

It has been shown that a deletion of the proline knot at the C-terminus of the extracellular domain of ActRIIB reduces the affinity of the receptor for activin (see, e.g., Attisano et al., Cell, 1992, 68(1):97-108). An ActRIIB-Fc fusion protein containing amino acids 20-119 of SEQ ID NO: 28 (i.e., SEQ ID NO:32), "ActRIIB(20-119)-Fc" has reduced binding to GDF-11 and activin relative to an ActRIIB-Fc fusion protein containing amino acids 20-134 of SEQ ID NO: 28 (i.e., SEQ ID NO:31), "ActRIIB(20-134)-Fc", which includes the proline knot region and the complete juxtamembrane domain. However, an ActRIIB-Fc fusion protein containing amino acids 20-129 of SEQ ID NO: 28, "ActRIIB(20-129)-Fc" retains similar but somewhat reduced activity relative to the non-truncated extracellular domain of ActRIIB, even though the proline knot region is disrupted. Thus, ActRIIB polypeptides comprising extracellular domains that stop at amino acid 134, 133, 132, 131, 130 and 129 of SEQ ID NO: 28 (or SEQ ID NO:16) are all expected to be active, but constructs stopping at amino acid 134 or 133 may be most active. Similarly, mutations at any of residues 129-134 are not expected to alter ligand binding affinity by large margins, as indicated by the fact that mutations of P129 and P130 of SEQ ID NO: 28 do not substantially decrease ligand binding. Therefore, the ActRIIB polypeptides used in accordance with the methods and compositions described herein may end as early as amino acid 109 (i.e., the final cysteine) of SEQ ID NO:28 (or SEQ ID NO:16), however, forms ending at or between amino acid positions 109 and 119 of SEQ ID NO:28 (or SEQ ID NO:16) are expected to have reduced ligand binding ability.

Amino acid 29 of SEQ ID NO:16 and SEQ ID NO:28 represents the initial cysteine in the ActRIIB precursor sequence. It is expected that an ActRIIB polypeptide beginning at amino acid 29 of the N-terminus of SEQ ID NO:16 or SEQ ID NO:28, or before these amino acid positions, will retain ligand binding activity. An alanine to asparagine mutation at position 24 of SEQ ID NO:16 or SEQ ID NO:28 introduces an N-linked glycosylation sequence without substantially affecting ligand binding. This confirms that mutations in the region between the signal cleavage peptide and the cysteine cross-linked region, corresponding to amino acids 20-29 of SEQ ID NO:16 or SEQ ID NO:28, are well tolerated. In particular, ActRIIB polypeptides beginning at amino acid position 20, 21, 22, 23 and 24 of SEQ ID NO:16 or SEQ ID NO:28 will retain activity, and ActRIIB polypeptides beginning at amino acid positions 25, 26, 27, 28 and 29 of SEQ ID NO:16 or SEQ ID NO:28 are also expected to retain activity. An ActRIIB polypeptide beginning at amino acid position 22, 23, 24 or 25 of SEQ ID NO:16 or SEQ ID NO:28 will have the most activity.

Taken together, the active portions (i.e., ActRIIB polypeptides) of the ActRIIB precursor protein (i.e., SEQ ID NO:16 or SEQ ID NO:28) to be used in accordance with the methods and compositions described herein will generally comprise amino acids 29-109 of SEQ ID NO:16 or SEQ ID NO:28, and such ActRIIB polypeptides may, for example, begin at a residue corresponding to any one of amino acids 19-29 of SEQ ID NO:16 or SEQ ID NO:28 and end at a position corresponding to any one of amino acids 109-134 of SEQ ID NO:16 or SEQ ID NO:28. Specific examples of ActRIIB polypeptides encompassed herein include those that begin at an amino acid position from 19-29, 20-29 or 21-29 of SEQ ID NO:16 or SEQ ID NO:28 and end at an amino acid position from 119-134, 119-133 or 129-134, 129-133 of SEQ ID NO:16 or SEQ ID NO:28. Other specific examples of ActRIIB polypeptides encompassed herein include those that begin at an amino acid position from 20-24 (or 21-24, or 22-25) of SEQ ID NO:16 or SEQ ID NO:28 and end at an amino acid position from 109-134 (or 109-133), 119-134 (or 119-133) or 129-134 (or 129-133) of SEQ ID NO:16 or SEQ ID NO:28. Variant ActRIIB polypeptides falling within these ranges are also contemplated, particularly those having at least 80%, 85%, 90%, 91%, 92%, 93%, 94%, 95%, 96%, 97%, 98%, or 99% sequence identity or sequence homology to the corresponding portion of SEQ ID NO:16 or SEQ ID NO:28.

In certain embodiments, the signaling inhibitors of ActRIIB used in the compositions and methods described herein comprise a truncated form of an extracellular domain of ActRIIB. The truncation can be at the carboxy terminus and/or the amino terminus of the ActRIIB polypeptide. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 amino acids long relative to the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 N-terminal amino acids of the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 C-terminal amino acids of the mature ActRIIB polypeptide extracellular domain. For example, truncated forms of ActRIIB include polypeptides with amino acids 20-119; 20-128; 20-129; 20-130; 20-131; 20-132; 20-133; 20-134; 20-131; 21-131; 22-131; 23-131; 24-131; and 25-131, wherein the amino acid positions refer to the amino acid positions in SEQ ID NO:16 or SEQ ID NO:28.

Additional exemplary truncated forms of ActRIIB include (i) polypeptides beginning at amino acids at any of amino acids 21-29 of SEQ ID NO:16 or SEQ ID NO:28 (optionally beginning at 22-25 of SEQ ID NO:16 or SEQ ID NO:28) and ending at any of amino acids 109-134 of SEQ ID NO:16 or SEQ ID NO:28; (ii) polypeptides beginning at any of amino acids 20-29 of SEQ ID NO:16 or SEQ ID NO:28 (optionally beginning at 22-25 of SEQ ID NO:16 or SEQ ID NO:28) and ending at any of amino acids 109-133 of SEQ ID NO:16 or SEQ ID NO:28; (iii) polypeptides beginning at any of amino acids 20-24 of SEQ ID NO:16 or SEQ ID NO:28 (optionally beginning at 22-25 of SEQ ID NO:16 or SEQ ID NO:28) and ending at any of amino acids 109-133 of SEQ ID NO:16 or SEQ ID NO:28; (iv) polypeptides beginning at any of amino acids 21-24 of SEQ ID NO:16 or SEQ ID NO:28 and ending at any of amino acids 109-134 of SEQ ID NO:16 or SEQ ID NO:28; (v) polypeptides beginning at any of amino acids 20-24 of SEQ ID NO:16 or SEQ ID NO:28 and ending at any of amino acids 118-133 of SEQ ID NO:16 or SEQ ID NO:28; (vi) polypeptides beginning at any of amino acids 21-24 of SEQ ID NO:16 or SEQ ID NO:28 and ending at any of amino acids 118-134 of SEQ ID NO:16 or SEQ ID NO:28; (vii) polypeptides beginning at any of amino acids 20-24 of SEQ ID NO:16 or SEQ ID NO:28 and ending at any of amino acids 128-133 of SEQ ID NO:16 or SEQ ID NO:28; (viii) polypeptides beginning at any of amino acids 20-24 of SEQ ID NO:16 or SEQ ID NO:28 and ending at any of amino acids 128-133 of SEQ ID NO:16 or SEQ ID NO:28; (ix) polypeptides beginning at any of amino acids 21-29 of SEQ ID NO:16 or SEQ ID NO:28 and ending at any of amino acids 118-134 of SEQ ID NO:16 or SEQ ID NO:28; (x) polypeptides beginning at any of amino acids 20-29 of SEQ ID NO:16 or SEQ ID NO:28 and ending at any of amino acids 118-133 of SEQ ID NO:16 or SEQ ID NO:28; (xi) polypeptides beginning at any of amino acids 21-29 of SEQ ID NO:16 or SEQ ID NO:28 and ending at any of amino acids 128-134 of SEQ ID NO:16 or SEQ ID NO:28; and (xii) polypeptides beginning at any of amino acids 20-29 of SEQ ID NO:16 or SEQ ID NO:28 and ending at any of amino acids 128-133 of SEQ ID NO:16 or SEQ ID NO:28. In a specific embodiment, an ActRIIB polypeptides comprises, consists essentially of, or consists of, an amino acid sequence beginning at amino acid position 25 of SEQ ID NO:16 or SEQ ID NO:28 and ending at amino acid position 131 of SEQ ID NO:16 or SEQ ID NO:28. In another specific embodiment, an ActRIIB polypeptide consists of, or consists essentially of, the amino acid sequence of SEQ ID NO:17, 18, 23, 26, 27, 29, 30, 31, 32, 33, 36, 37, 42, or 43.

Any of the ActRIIB polypeptides disclosed herein may be produced as a homodimer. Any of the ActRIIB polypeptides disclosed herein may be formulated as a fusion protein having a heterologous portion that comprises a constant region from an IgG heavy chain, such as an Fc domain. Any of the ActRIIB polypeptides disclosed herein may comprise an acidic amino acid at the position corresponding to position 79 of SEQ ID NO:16 or SEQ ID NO:28, optionally in combination with one or more additional amino acid substitutions, deletions or insertions relative to SEQ ID NO:16 or SEQ ID NO:28.

In specific embodiments, the signaling inhibitors of ActRIIB used in the compositions and methods described herein comprise an extracellular domain of ActRIIB with one or more amino acid substitutions/mutations. Such an amino acid substitution/mutation can be, for example, an exchange from the leucine at amino acid position 79 of SEQ ID NO:16 or SEQ ID NO:28 to an acidic amino acid, such as aspartic acid or glutamic acid. For example, position L79 of SEQ ID NO:16 or SEQ ID NO:28 may be altered in ActRIIB extracellular domain polypeptides to confer altered activin-myostatin (GDF-11) binding properties. L79A and L79P mutations reduce GDF-11 binding to a greater extent than activin binding. L79E and L79D mutations retain GDF-11 binding, while demonstrating greatly reduced activin binding.

In certain embodiments, the signaling inhibitors of ActRIIB used in the compositions and methods described herein comprise a truncated form of an ActRIIB extracellular domain that also carries an amino acid substitution, e.g., an exchange from the leucine at amino acid position 79 of SEQ ID NO:16 or SEQ ID NO:28 to an acidic amino acid, such as aspartic acid or glutamic acid. In a specific embodiment, the truncated form of an extracellular domain of ActRIIB polypeptide that also carries an amino acid substitution used in the compositions and methods described herein is SEQ ID NO:23. Forms of ActRIIB that are truncated and/or carry one or more amino acid substitutions can be linked to an Fc domain of an antibody as discussed above.

Functionally active fragments of ActRIIB polypeptides can be obtained, for example, by screening polypeptides recombinantly produced from the corresponding fragment of the nucleic acid encoding an ActRIIB polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIB protein or signaling mediated by activin.

In addition, functionally active variants of ActRIIB polypeptides can be obtained, for example, by screening libraries of modified polypeptides recombinantly produced from the corresponding mutagenized nucleic acids encoding an ActRIIB polypeptide. The variants can be produced and tested to identify those that can function as antagonists (inhibitors) of ActRIIB protein or signaling mediated by activin. In certain embodiments, a functional variant of the ActRIIB polypeptides comprises an amino acid sequence that is at least 75% identical to an amino acid sequence selected from SEQ ID NO:17, 18, 23, 26, 27, 29, 30, 31, 32, 33, 36, 37, 42, and 43. In certain embodiments, the functional variant has an amino acid sequence at least 80%, 85%, 90%, 95%, 96%, 97%, 98%, or 99% identical to an amino acid sequence selected from SEQ ID NO:17, 18, 23, 26, 27, 29, 30, 31, 32, 33, 36, 37, 42, and 43.

Functional variants may be generated, for example, by modifying the structure of an ActRIIB polypeptide for such purposes as enhancing therapeutic efficacy, or stability (e.g., ex vivo shelf life and resistance to proteolytic degradation in vivo). Such modified ActRIIB polypeptides when selected to retain activin binding, are considered functional equivalents of the naturally-occurring ActRIIB polypeptides. Modified ActRIIB polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIB polypeptide results in a functional homolog can be readily determined by assessing the ability of the variant ActRIIB polypeptide to produce a response in cells in a fashion similar to the wild-type ActRIIB polypeptide.

Provided herein are methods of generating mutants, particularly sets of combinatorial mutants of an ActRIIB polypeptide, as well as truncation mutants; pools of combinatorial mutants are especially useful for identifying functional variant sequences. The purpose of screening such combinatorial libraries may be to generate, for example, ActRIIB polypeptide variants which can act as either agonists or antagonist, or alternatively, which possess novel activities all together.

It has been demonstrated that the ligand binding pocket of ActRIIB is defined by residues Y31, N33, N35, L38 through T41, E47, E50, Q53 through K55, L57, H58, Y60, S62, K74, W78 through N83, Y85, R87, A92, and E94 through F101 of SEQ ID NO:16 or SEQ ID NO:28. At these positions, it is expected that conservative mutations will be tolerated, although a K74A mutation is well-tolerated, as are R40A, K55A, F82A and mutations at position L79. R40 is a K in Xenopus, indicating that basic amino acids at this position will be tolerated. Q53 is R in bovine ActRIIB and K in Xenopus ActRIIB, and therefore amino acids including R, K, Q, N and H will be tolerated at this position. Thus, a general formula for an ActRIIB polypeptide for use in the methods and compositions described herein is one that comprises amino acids 29-109 of SEQ ID NO:16 or SEQ ID NO:28, but optionally beginning at an amino acid position ranging from 20-24 or 22-25 of SEQ ID NO:16 or SEQ ID NO:28 and ending at an amino acid position ranging from 129-134 of SEQ ID NO:16 or SEQ ID NO:28, and comprising no more than 1, 2, 5, or 15 conservative amino acid changes in the ligand binding pocket, and zero, one or more non-conservative alterations at amino acid positions 40, 53, 55, 74, 79 and/or 82 of SEQ ID NO:16 or SEQ ID NO:28 in the ligand binding pocket. Such an ActRIIB polypeptide may retain greater than 80%, 90%, 95% or 99% sequence identity or sequence homology to the sequence of amino acids 29-109 of SEQ ID NO:16 or SEQ ID NO:28. Sites outside the binding pocket, at which variability may be particularly well tolerated, include the amino and carboxy termini of the extracellular domain of ActRIIB, and positions 42-46 and 65-73. An asparagine to alanine alteration at position 65 of SEQ ID NO:16 or SEQ ID NO:28 (N65A) actually improves ligand binding in the A64 background, and is thus expected to have no detrimental effect on ligand binding in the R64 background. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64.

As a specific example of an ActRIIB polypeptide with a mutation in the ligand binding domain, the positively-charged amino acid residue Asp (D80) of the ligand-binding domain of ActRIIB can be mutated to a different amino acid residue such that the variant ActRIIB polypeptide preferentially binds to GDF8, but not activin. In a specific embodiment, the D80 residue is changed to an amino acid residue selected from the group consisting of: an uncharged amino acid residue, a negative amino acid residue, and a hydrophobic amino acid residue. As a further specific example, the hydrophobic residue L79 can be altered to the acidic amino acids aspartic acid or glutamic acid to greatly reduce activin binding while retaining GDF11 binding. As will be recognized by one of skill in the art, most of the described mutations, variants or modifications may be made at the nucleic acid level or, in some cases, by post translational modification or chemical synthesis. Such techniques are well known in the art.

In specific embodiments, the signaling inhibitors of ActRIIB used in the compositions and methods described herein comprise a conjugate/fusion protein comprising an extracellular domain (e.g., an activin-binding domain) of an ActRIIB receptor linked to an Fc portion of an antibody. Such conjugate/fusion proteins may comprise any of the ActRIIB polypeptides disclosed herein (e.g., any of SEQ ID NOs:17, 18, 23, 26, 27, 29, 30, 31, 32, 33, 36, 37, 42, or 43), any ActRIIB polypeptides known in the art, or any ActRIIB polypeptides generated using methods known in the art and/or provided herein.

In certain embodiments, the extracellular domain is linked to an Fc portion of an antibody via a linker, e.g., a peptide linker. Exemplary linkers include short polypeptide sequences such as 2-10, 2-5, 2-4, 2-3 amino acid residues (e.g., glycine residues), such as, for example, a Gly-Gly-Gly linker. In a specific embodiment, the linker comprises the amino acid sequence Gly-Gly-Gly (GGG). In another specific embodiment, the linker comprises the amino acid sequence Thr-Gly-Gly-Gly (TGGG)(SEQ ID NO. 48). Optionally, the Fc domain has one or more mutations at residues such as Asp-265, lysine 322, and Asn-434. In certain cases, the mutant Fc domain having one or more of these mutations (e.g., an Asp-265 mutation) has a reduced ability to bind to the Fcγ receptor relative to a wild-type Fc domain. In other cases, the mutant Fc domain having one or more of these mutations (e.g., an Asn-434 mutation) has an increased ability to bind to the MHC class I-related Fc-receptor (FcRN) relative to a wild-type Fc domain. Exemplary fusion proteins comprising a soluble extracellular domain of ActRIIB fused to an Fc domain are set forth in SEQ ID NOs: 20, 21, 24, 25, 34, 35, 38, 39, 40, 41, 44, 46, and 47.

In a specific embodiment, the ActRIIB signaling inhibitors used in the compositions and methods described herein comprise the extracellular domain of ActRIIB, or a portion thereof, linked to an Fc portion of an antibody, wherein said ActRIIB signaling inhibitor comprises an amino acid sequence that is at least 75% identical to an amino acid sequence selected from SEQ ID NOs:20, 21, 24, 25, 34, 35, 38, 39, 40, 41, 44, 46, and 47. In another specific embodiment, the ActRIIB signaling inhibitors used in the compositions and methods described herein comprise the extracellular domain of ActRIIB, or a portion thereof, linked to an Fc portion of an antibody, wherein said ActRIIB signaling inhibitor comprises an amino acid sequence that is at least 80%, 85%, 90%, 95%, 96%, 97%, 98%, or 99% identical to an amino acid sequence selected from SEQ ID NOs:20, 21, 24, 25, 34, 35, 38, 39, 40, 41, 44, 46, and 47.

In a specific embodiment, the ActRIIB signaling inhibitor to be used in the compositions and methods described herein is a fusion protein between the extracellular domain of the human ActRIIB receptor and the Fc portion of IgG1. In another specific embodiment, the ActRIIB signaling inhibitor to be used in the compositions and methods described herein is a fusion protein between a truncated extracellular domain of the human ActRIIB receptor and the Fc portion of IgG1. In another specific embodiment, the ActRIIB signaling inhibitor to be used in the compositions and methods described herein is a fusion protein between a truncated extracellular domain of the human ActRIIB receptor and the Fc portion of IgG1, wherein the truncated extracellular domain of the human ActRIIB receptor possesses an amino acid substitution at the amino acid position corresponding to amino acid 79 of SEQ ID NO:16 or SEQ ID NO:28. In one embodiment, the amino acid substitution at the amino acid position corresponding to amino acid 79 of SEQ ID NO:16 or SEQ ID NO:28 is substitution of Leucine for Aspartic Acid (i.e., an L79D mutation).

In a specific embodiment, the ActRIIB signaling inhibitor to be used in the compositions and methods described herein is SEQ ID NO:24 or 25, which represents a fusion protein between the extracellular domain of the human ActRIIB receptor and the Fc portion of IgG1, wherein said ActRIIB extracellular domain comprises amino acids 25-131 of SEQ ID NO:28 with an L79D mutation. The nucleic acid sequence encoding the ActRIIB-Fc fusion protein of SEQ ID NO:24 is presented in SEQ ID NO:45.

In another specific embodiment, the ActRIIB signaling inhibitor to be used in the compositions and methods described herein is SEQ ID NO:34 or 35, which represents a fusion protein between the extracellular domain of the human ActRIIB receptor and the Fc portion of IgG1, wherein said ActRIIB extracellular domain comprises amino acids 25-131 of SEQ ID NO:16 with an L79D mutation.

Asparagine-linked glycosylation recognition sites generally comprise a tripeptide sequence, asparagine-X-threonine (or asparagine-X-serine) (where "X" is any amino acid) which is specifically recognized by appropriate cellular glycosylation enzymes. The alteration may also be made by the addition of, or substitution by, one or more serine or threonine residues to the sequence of the wild-type ActRIIB polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIB polypeptide is by chemical or enzymatic coupling of glycosides to the ActRIIB polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in International Patent Application No. WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIB polypeptide may be accomplished chemically and/or enzymatically. Chemical deglycosylation may involve, for example, exposure of the ActRIIB polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIB polypeptides can be achieved by the use of a variety of endo- and exo-glycosidases as described by Thotakura et al. (1987) Meth. Enzymol. 138:350. The sequence of an ActRIIB polypeptide may be adjusted, as appropriate, depending on the type of expression system used, as mammalian, yeast, insect and plant cells may all introduce differing glycosylation patterns that can be affected by the amino acid sequence of the peptide. In general, ActRIIB proteins for use in humans will be expressed in a mammalian cell line that provides proper glycosylation, such as HEK293 or CHO cell lines, although other expression systems, such as other mammalian expression cell lines, yeast cell lines with engineered glycosylation enzymes and insect cells, are expected to be useful as well.

In specific embodiments, encompassed herein are mutated ActRIIB polypeptides comprising the addition of a further N-linked glycosylation site (N-X-S/T) that increases the serum half-life of an ActRIIB-Fc fusion protein, relative to the ActRIIB(R64)-Fc form. In a specific embodiment, introduction of an asparagine at position 24 of SEQ ID NO:16 or SEQ ID NO:28 (A24N) results in the creation of an NXT sequence that confers a longer half-life. Other NX(T/S) sequences can be found at 42-44 (NQS) and 65-67 (NSS), although the latter may not be efficiently glycosylated with the R at position 64 (i.e., in R64 polypeptides). N-X-S/T sequences may be generally introduced at positions outside the ligand binding pocket of ActRIIB, which is detailed above. Particularly suitable sites for the introduction of non-endogenous N-X-S/T sequences include amino acids 20-29, 20-24, 22-25, 109-134, 120-134 or 129-134 of SEQ ID NO:16 or SEQ ID NO:28. N-X-S/T sequences may also be introduced into the linker between the ActRIIB sequence and the Fc or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E106N, R112N, G120N, E123N, P129N, A132N, R112S and R112T (with all amino acid positions corresponding to the positions they can be found in SEQ ID NO:16 or SEQ ID NO:28). Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T are encompassed herein. Likewise, in an A24N variant, an S26T alteration may be used. Accordingly, an ActRIIB polypeptide may include one or more additional, non-endogenous N-linked glycosylation consensus sequences.

A variety of screening assays are provided herein, and such assays may be used to evaluate ActRIIB polypeptide variants. For example, an ActRIIB polypeptide variant may be screened for ability to bind to an ActRIIB ligand, to prevent binding of an ActRIIB ligand to an ActRIIB polypeptide or to interfere with signaling caused by an ActRIIB ligand. The activity of an ActRIIB polypeptide or its variants may also be tested in a cell-based or in vivo assay.

Combinatorially-derived variants can be generated which have a selective or generally increased potency relative to a naturally occurring ActRIIB polypeptide. Likewise, mutagenesis can give rise to variants which have intracellular half-lives dramatically different than the corresponding wild-type ActRIIB polypeptide. For example, the altered protein can be rendered either more stable or less stable to proteolytic degradation or other cellular processes which result in destruction of, or otherwise inactivation of a native ActRIIB polypeptide. Such variants, and the genes which encode them, can be utilized to alter ActRIIB polypeptide levels by modulating the half-life of the ActRIIB polypeptides. For instance, a short half-life can give rise to more transient biological effects and can allow tighter control of recombinant ActRIIB polypeptide levels within the subject. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIB polypeptide sequences. For instance, a mixture of synthetic oligonucleotides can be enzymatically ligated into gene sequences such that the degenerate set of potential ActRIIB polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIB polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRIIB polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIB polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, ActRIIB polypeptides may further comprise post-translational modifications in addition to any that are naturally present in the ActRIIB polypeptides. Such modifications include, but are not limited to, acetylation, carboxylation, glycosylation, phosphorylation, lipidation, and acylation. As a result, the modified ActRIIB polypeptides may contain non-amino acid elements, such as polyethylene glycols, lipids, poly- or mono-saccharide, and phosphates. Effects of such non-amino acid elements on the functionality of a ActRIIB polypeptide may be tested by any method known to the skilled artisan. When an ActRIIB polypeptide is produced in cells by cleaving a nascent form of the ActRIIB polypeptide, post-translational processing may also be important for correct folding and/or function of the protein. Different cells (such as CHO, HeLa, MDCK, 293, W138, NIH-3T3 or HEK293) have specific cellular machinery and characteristic mechanisms for such post-translational activities and may be chosen to ensure the correct modification and processing of the ActRIIB polypeptides.

In certain aspects, functional variants or modified forms of the ActRIIB polypeptides include fusion proteins having at least a portion of the ActRIIB polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) fusion partners. As another example, a fusion domain may be selected so as to facilitate detection of the ActRIIB polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus hemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIB polypeptide is fused with a domain that stabilizes the ActRIIB polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth or muscle growth, as desired).

It is understood that different elements of the fusion proteins may be arranged in any manner that is consistent with the desired functionality. For example, an ActRIIB polypeptide may be placed C-terminal to a heterologous domain, or, alternatively, a heterologous domain may be placed C-terminal to an ActRIIB polypeptide. The ActRIIB polypeptide domain and the heterologous domain need not be adjacent in a fusion protein, and additional domains or amino acid sequences may be included C- or N-terminal to either domain or between the domains.

In certain embodiments, the ActRIIB polypeptides contain one or more modifications that are capable of stabilizing the ActRIIB polypeptides. For example, such modifications enhance the in vitro half life of the ActRIIB polypeptides, enhance circulatory half life of the ActRIIB polypeptides or reduce proteolytic degradation of the ActRIIB polypeptides. Such stabilizing modifications include, but are not limited to, fusion proteins (including, for example, fusion proteins comprising an ActRIIB polypeptide and a stabilizer domain), modifications of a glycosylation site (including, for example, addition of a glycosylation site to an ActRIIB polypeptide), and modifications of carbohydrate moiety (including, for example, removal of carbohydrate moieties from an ActRIIB polypeptide). In the case of fusion proteins, an ActRIIB polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, isolated and/or purified forms of the ActRIIB polypeptides, which are isolated from, or otherwise substantially free of, other proteins can be used with the methods and compositions described herein. ActRIIB polypeptides will generally be produced by expression from recombinant nucleic acids.

In certain aspects, provided herein are isolated and/or recombinant nucleic acids encoding any of the ActRIIB polypeptides (e.g., soluble ActRIIB polypeptides), including fragments, functional variants and fusion proteins disclosed herein. For example, SEQ ID NO:19 encodes the naturally occurring human ActRIIB precursor polypeptide. The subject nucleic acids may be single-stranded or double stranded. Such nucleic acids may be DNA or RNA molecules. These nucleic acids may be used, for example, in methods for making ActRIIB polypeptides or as direct therapeutic agents (e.g., in a gene therapy approach).

In certain aspects, the nucleic acids encoding ActRIIB polypeptides are further understood to include nucleic acids that are variants of SEQ ID NO: 19 as well as variants of those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43). Variant nucleotide sequences include sequences that differ by one or more nucleotide substitutions, additions or deletions, such as allelic variants.

In certain embodiments, the isolated or recombinant nucleic acid sequences that can be used are at least 80%, 85%, 90%, 95%, 97%, 98%, 99% or 100% identical to SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43). One of ordinary skill in the art will appreciate that nucleic acid sequences complementary to SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43), and variants of SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43) can be used with the methods and compositions described herein. In further embodiments, the nucleic acid sequences can be isolated, recombinant, and/or fused with a heterologous nucleotide sequence, or in a DNA library.

In other embodiments, nucleic acids that can be used also include nucleotide sequences that hybridize under highly stringent conditions to the nucleotide sequence designated in SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43), complement sequence of SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43), or fragments thereof. As discussed above, one of ordinary skill in the art will readily understand that appropriate stringency conditions which promote DNA hybridization can be varied. One of ordinary skill in the art will understand that appropriate stringency conditions which promote DNA hybridization can be varied. For example, one can perform the hybridization at 6.0 times sodium chloride/sodium citrate (SSC) at about 45 degree Celsius, followed by a wash of 2.0 times SSC at 50 degree Celsius. For example, the salt concentration in the wash step can be selected from a low stringency of about 2.0 times SSC at 50 degree Celsius to a high stringency of about 0.2 times SSC at 50 degree Celsius. In addition, the temperature in the wash step can be increased from low stringency conditions at room temperature, about 22 degree Celsius, to high stringency conditions at about 65 degree Celsius. Both temperature and salt may be varied, or temperature or salt concentration may be held constant while the other variable is changed. In one embodiment, nucleic acids which hybridize under low stringency conditions of 6 times SSC at room temperature followed by a wash at 2 times SSC at room temperature can be used with the methods and compositions described herein.

Isolated nucleic acids which differ from the nucleic acids as set forth in SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43) due to degeneracy in the genetic code can also be used. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms can be used with the methods and compositions described herein.

In certain embodiments, the recombinant nucleic acids may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art can be used with the methods and compositions described herein. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the subject nucleic acid is provided in an expression vector comprising a nucleotide sequence encoding an ActRIIB polypeptide and operably linked to at least one regulatory sequence. Regulatory sequences are art-recognized and are selected to direct expression of the ActRIIB polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding an ActRIIB polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast .alpha.-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIB polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the .beta.-gal containing pBlueBac III).

In a preferred embodiment, a vector will be designed for production of the subject ActRIIB polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIB polypeptides in cells propagated in culture, e.g., to produce proteins, including fusion proteins or variant proteins, for purification.

This disclosure also pertains to a host cell transfected with a recombinant gene including a coding sequence (e.g., SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43)) for one or more of the subject ActRIIB polypeptides. The host cell may be any prokaryotic or eukaryotic cell. For example, an ActRIIB polypeptide may be expressed in bacterial cells such as E. coli, insect cells (e.g., using a baculovirus expression system), yeast, or mammalian cells. Other suitable host cells are known to those skilled in the art.

Accordingly, provided herein are methods of producing the ActRIIB polypeptides. For example, a host cell transfected with an expression vector encoding an ActRIIB polypeptide can be cultured under appropriate conditions to allow expression of the ActRIIB polypeptide to occur. The ActRIIB polypeptide may be secreted and isolated from a mixture of cells and medium containing the ActRIIB polypeptide. Alternatively, the ActRIIB polypeptide may be retained cytoplasmically or in a membrane fraction and the cells harvested, lysed and the protein isolated. A cell culture includes host cells, media and other byproducts. Suitable media for cell culture are well known in the art. The subject ActRIIB polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIB polypeptides and affinity purification with an agent that binds to a domain fused to the ActRIIB polypeptide (e.g., a protein A column may be used to purify an ActRIIB-Fc fusion). In a preferred embodiment, the ActRIIB polypeptide is a fusion protein containing a domain which facilitates its purification. In a preferred embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. As demonstrated herein, ActRIIB-hFc protein was purified to a purity of >98% as determined by size exclusion chromatography and >95% as determined by SDS PAGE. This level of purity was sufficient to achieve desirable effects on bone in mice and an acceptable safety profile in mice, rats and non-human primates.

In another embodiment, a fusion gene coding for a purification leader sequence, such as a poly-(His)/enterokinase cleavage site sequence at the N-terminus of the desired portion of the recombinant ActRIIB polypeptide, can allow purification of the expressed fusion protein by affinity chromatography using a Ni2+ metal resin. The purification leader sequence can then be subsequently removed by treatment with enterokinase to provide the purified ActRIIB polypeptide (e.g., see Hochuli et al., (1987) J. Chromatography 411:177; and Janknecht et al., PNAS USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

ActRIIB-Fc fusion protein can be expressed in stably transfected CHO-DUKX B11 cells from a pAID4 vector (SV40 ori/enhancer, CMV promoter), using a tissue plasminogen leader sequence of SEQ ID NO:8. The Fc portion can comprise a human IgG1 Fc sequence, as shown in SEQ ID NO:7. In certain embodiments, upon expression, the protein contained has, on average, between about 1.5 and 2.5 moles of sialic acid per molecule of ActRIIB-Fc fusion protein.

In certain embodiments, the long serum half-life of an ActRIIB-Fc fusion can be 25-32 days in human subjects. Additionally, the CHO cell expressed material can have a higher affinity for activin B ligand than that reported for an ActRIIB-hFc fusion protein expressed in human 293 cells (del Re et al., J Biol Chem. 2004 Dec. 17; 279(51):53126-35). Additionally, without being bound by theory, the use of the TPA leader sequence provided greater production than other leader sequences and, unlike ActRIIB-Fc expressed with a native leader, may provide a highly pure N-terminal sequence. Use of the native leader sequence may result in two major species of ActRIIB-Fc, each having a different N-terminal sequence.

7.9.3 Other ActRII Receptor Signaling Inhibitors

In certain embodiments, the signaling inhibitors of ActRII receptors used in the compositions and methods described herein are nucleic acid compounds.

Examples of categories of nucleic acid compounds that inhibit ActRII receptors include antisense nucleic acids, siRNA or RNAi constructs and catalytic nucleic acid constructs. A nucleic acid compound may be single- or double-stranded. A double-stranded compound may also include regions of overhang or non-complementarity, where one or the other of the strands is single-stranded. A single-stranded compound may include regions of self-complementarity, meaning that the compound may form a so-called "hairpin" or "stem-loop" structure, with a region of double helical structure.

In certain embodiments, the nucleic acid compounds that inhibit ActRII receptors may comprise a nucleotide sequence that is complementary to a region consisting of no more than 1000, no more than 500, no more than 250, no more than 100 or no more than 50, 35, 30, 25, 22, 20 or 18 nucleotides of the full-length ActRII receptor nucleic acid sequence or activin nucleic acid sequence (e.g., the nucleic acid sequence of an activin A or activin B subunit, also referred to as BA or BB). In specific embodiments, the region of complementarity will be at least 8 nucleotides, and optionally at least 10 or at least 15 nucleotides, and optionally between 15 and 25 nucleotides. A region of complementarity may fall within an intron, a coding sequence or a noncoding sequence of the target transcript, such as the coding sequence portion. Generally, a nucleic acid compound that inhibits an ActRII receptor will have a length of about 8 to about 500 nucleotides or base pairs in length, and optionally the length will be about 14 to about 50 nucleotides. A nucleic acid compound that inhibits an ActRII receptor may be a DNA (particularly for use as an antisense), an RNA, or an RNA:DNA hybrid. Any one strand may include a mixture of DNA and RNA, as well as modified forms that cannot readily be classified as either DNA or RNA. Likewise, a double stranded nucleic acid compound may be DNA:DNA, DNA:RNA, or RNA:RNA, and any one strand may also include a mixture of DNA and RNA, as well as modified forms that cannot readily be classified as either DNA or RNA.

The nucleic acid compounds that inhibit an ActRII receptor may include any of a variety of modifications, including one or modifications to the backbone (the sugar-phosphate portion in a natural nucleic acid, including internucleotide linkages) or the base portion (the purine or pyrimidine portion of a natural nucleic acid). In certain embodiments, an antisense nucleic acid compound will have a length of about 15 to about 30 nucleotides and will often contain one or more modifications to improve certain characteristics, such as stability in the serum, stability in a cell, or stability in a place where the compound is likely to be delivered, such as, e.g., the stomach in the case of orally delivered compounds and the lung for inhaled compounds. In the case of an RNAi construct, the strand complementary to the target transcript will generally be RNA or modifications thereof. The other strand may be RNA, DNA, or any other variation. The duplex portion of double stranded or single stranded "hairpin" RNAi construct may, in certain embodiments, have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. In certain embodiments, nucleic acid compounds that inhibit ActRII receptors may inhibit expression of their target by about 50%, 60%, 70%, 75%, 80%, 85%, 90%, 95%, 99%, or more under physiological conditions and at a concentration where a nonsense or sense control has little or no effect. Concentrations for testing the effect of nucleic acid compounds include 1, 5, 10 micromolar, or more.

In other embodiments, the signaling inhibitors of ActRII receptors used in the compositions and methods described herein are antibodies. Such antibodies include antibodies that bind to activin (particularly the activin A or B subunits, also referred to as BA or BB) and disrupt ActRII receptor binding; and antibodies that bind to ActRII receptor polypeptides (e.g., a soluble ActRIIA or soluble ActRIIB polypeptide) and disrupt activin binding.

By using immunogens derived from an ActRII receptor polypeptide or an activin polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ActRII receptor polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ActRII receptor or activin polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ActRII receptor polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an ActRII receptor polypeptide and monoclonal antibodies isolated from a culture comprising such hybridoma cells.

The term "antibody" as used herein is intended to include fragments thereof which are also specifically reactive with a subject polypeptide. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. An antibody is further intended to include bispecific, single-chain, chimeric, humanized and fully human molecules having affinity for an ActRII receptor or activin polypeptide conferred by at least one CDR region of the antibody. An antibody may further comprise a label attached thereto and able to be detected (e.g., the label can be a radioisotope, fluorescent compound, enzyme or enzyme co-factor).

In certain embodiments, the antibody is a recombinant antibody, which term encompasses any antibody generated in part by techniques of molecular biology, including CDR-grafted or chimeric antibodies, human or other antibodies assembled from library-selected antibody domains, single chain antibodies and single domain antibodies (e.g., human VH proteins or camelid VHH proteins). In certain embodiments, an antibody can be a monoclonal antibody, and in certain embodiments. For example, a method for generating a monoclonal antibody that binds specifically to an ActRII receptor polypeptide or activin polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the antigen. Once obtained, a hybridoma can be propagated in a cell culture, optionally in culture conditions where the hybridoma-derived cells produce the monoclonal antibody that binds specifically to the antigen. The monoclonal antibody may be purified from the cell culture.

The adjective "specifically reactive with" as used in reference to an antibody is intended to mean, as is generally understood in the art, that the antibody is sufficiently selective between the antigen of interest (e.g., an ActRII receptor polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody: antigen interaction is the affinity of the antibody for the antigen. Although the desired specificity may be reached with a range of different affinities, generally preferred antibodies will have an affinity (a dissociation constant) of about 10-6, 10-7, 10-8, 10-9 or less. Given the extraordinarily tight binding between activin and an ActRII receptor, it is expected that a neutralizing anti-activin or anti-ActRII receptor antibody would generally have a dissociation constant of 10-10 or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), Western blots, immunoprecipitation assays, and immunohistochemistry.

In certain embodiments, ActRII receptor signaling inhibitors to be used in the compositions and methods described herein include alternative forms of activin, particularly those with alterations in the type I receptor binding domain can bind to type II receptors and fail to form an active ternary complex. In certain embodiments, nucleic acids, such as antisense molecules, siRNAs or ribozymes that inhibit activin A, B, C or E, or, particularly, ActRII receptor expression, can be used in the compositions and methods described herein. In certain embodiments, the ActRII receptor signaling inhibitors to be used in the compositions and methods described herein exhibit selectivity for inhibiting activin-mediated signaling versus other members of the TGF-beta family, particularly with respect to GDF8 and GDF11.

In other embodiments, the signaling inhibitors of ActRII receptors used in the compositions and methods described herein are non-antibody proteins with ActRII receptor antagonist activity, including inhibin (i.e., inhibin alpha subunit), follistatin (e.g., follistatin-288 and follistatin-315), Cerberus, follistatin related protein ("FSRP"), endoglin, activin C, alpha(2)-macroglobulin, and an M108A (methionine to alanine change at position 108) mutant activin A.

In a specific embodiment, the ActRII receptor signaling inhibitor to be used in the compositions and methods described herein is a follistatin polypeptide that antagonizes activin bioactivity and/or binds to activin. The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. Variants of follistatin polypeptides that retain activin binding properties can be identified based on previous studies involving follistatin and activin interactions. For example, WO2008/030367, which is included by reference herein in its entirety, discloses specific follistatin domains ("FSDs") that are shown to be important for activin binding. Follistatin polypeptides include polypeptides derived from the sequence of any known follistatin having a sequence at least about 80% identical to the sequence of a follistatin polypeptide, and optionally at least 85%, 90%, 95%, 96%, 97%, 98%, 99% or greater identity. Examples of follistatin polypeptides include the mature follistatin polypeptide or shorter isoforms or other variants of the human follistatin precursor polypeptide as described, for example, in WO2005/025601, which is included by reference herein in its entirety.

In a specific embodiment, the ActRII receptor signaling inhibitor to be used in the compositions and methods described herein is a follistatin-like related gene (FLRG) that antagonizes activin bioactivity and/or binds to activin. The term "FLRG polypeptide" includes polypeptides comprising any naturally occurring polypeptide of FLRG as well as any variants thereof (including mutants, fragments, fusions, and peptidomimetic forms) that retain a useful activity. Variants of FLRG polypeptides that retain activin binding properties can be identified using routine methods to assay FLRG and activin interactions. See, for example, U.S. Pat. No. 6,537,966, which is included by reference herein in its entirety. FLRG polypeptides include polypeptides derived from the sequence of any known FLRG having a sequence at least about 80% identical to the sequence of an FLRG polypeptide, and optionally at least 85%, 90%, 95%, 96%, 97%, 98%, 99% or greater identity.

In certain embodiments, functional variants or modified forms of the follistatin polypeptides and FLRG polypeptides include fusion proteins having at least a portion of the follistatin polypeptides or FLRG polypeptides and one or more fusion domains, such as, for example, domains that facilitate isolation, detection, stabilization or multimerization of the polypeptide. Suitable fusion domains are discussed in detail above with reference to the ActRIIA and ActRIIB polypeptides. In one embodiment, an ActRII receptor signaling inhibitor is a fusion protein comprising an activin binding portion of a follistatin polypeptide fused to an Fc domain. In another embodiment, an ActRII receptor signaling inhibitor is a fusion protein comprising an activin binding portion of an FLRG polypeptide fused to an Fc domain.

7.10 Assays

Various ActRII polypeptide variants, or soluble ActRII polypeptide variants, may be tested for their ability to inhibit ActRII. In addition, compounds can be tested for their ability to inhibit ActRII. Once signaling inhibitors of ActRII activity are confirmed, these compounds can be used with the methods of the invention. ActRII can be ActRIIA or ActRIIB. The assays below are described for ActRIIA but can be performed analogously for ActRIIB. These assays can be used to (i) identify in a subject anemia, anemia requiring RBC transfusion, MDS, and/or non-proliferative CMML subject subpopulations; (ii) diagnose in a subject anemia, anemia requiring RBC transfusion, MDS, and/or non-proliferative CMML subjects; (iii) monitor in a subject anemia, anemia requiring RBC transfusion, MDS, and/or non-proliferative CMML disease continuation and/or progression; (iv) monitor in a subject the efficacy of the methods provided herein for the treatment in a subject of anemia, anemia requiring RBC transfusion, MDS, and/or non-proliferative CMML; and/or (v) monitor in a subject the efficacy of the ActRII signaling inhibitors described herein.

7.10.1 Reference Population

In certain embodiments, the size of the reference population can be about 1, 5, 10, 25, 50, 75, 100, 200, 250, 300, 400, 500, or 1000 individuals. In certain embodiments, the reference population consists of random volunteers. In certain embodiments, the reference population consists of healthy people. In certain embodiments, the reference population consists of people of the same age, weight, and/or gender as the patient population as described in Section 7.8. In certain embodiments, the reference population consists of people without a blood-related disorder. In certain embodiments, the reference population consists of people with a blood-related disorder, wherein the people in the reference population do not have ring sideroblasts. In certain embodiments, the reference population consists of people with a blood-related disorder, wherein the less than 15%, 14%, 13%, 12%, 11%, 10%, 9%, 8%, 7%, 6%, 5%, 4%, 3%, 2%, or 1% of the erythroblasts in the people are ring sideroblasts. In certain embodiments, the reference population consists of people with a blood-related disorder, wherein the less than 15% of the erythroblasts in the people are ring sideroblasts. In certain embodiments, the blood-related disorder is a blood-related disorder as described in Section 7.8. In certain embodiments, the reference population consists of people without anemia. In certain embodiments, the reference population consists of people without anemia requiring RBC transfusion. In certain embodiments, the reference population consists of people without MDS. In certain embodiments, the reference population consists of people without non-proliferative CMML.

7.10.2 Ring Sideroblasts

Ring sideroblasts are abnormal erythroblasts. Furthermore, certain somatic mutations associated with MDS cause ring sideroblast formation and ineffective erythropoiesis. Dominant mutations in splicing factor 3B1 (SF3B1) are associated with the formation of ring sideroblasts. As used herein, "RS+" refers to a subject in which at least 15% of the erythroblasts in the subject are ring sideroblasts. In certain embodiments, the percentage of ring sideroblasts is the percentage of erythroblasts that are ring sideroblasts. In certain embodiments, the percentage of ring sideroblasts is the percentage of erythroid precursors that are ring sideroblasts. Ring sideroblasts are erythroblasts in which there are a minimum of five iron-containing (siderotic) granules covering at least one third of the circumference of the nucleus. See Mufti et al., 2008, Haematologica, 93(11):1712-7 for a description of the identification of ring sideroblasts in a sample. In ring sideroblasts, iron-loaded mitochondria are visualized as a perinuclear ring of blue granules when stained with Prussian blue. Ring sideroblasts can be detected in peripheral blood and/or bone marrow smears. In particular aspects of the methods provided herein, the ring sideroblasts are in bone marrow aspirates.

7.10.3 Screening Assays

Various ActRII polypeptide variants, or soluble ActRII polypeptide variants, may be tested for their ability to inhibit ActRII. In addition, compounds can be tested for their ability to inhibit ActRII. Once signaling inhibitors of ActRII activity are confirmed, these compounds can be used with the methods provided herein. ActRII can be ActRIIA or ActRIIB. The assays below are described for ActRIIA but can be performed analogously for ActRIIB.

For example, the effect of an ActRIIA polypeptide variant on the expression of genes involved in bone production or bone destruction may be assessed. This may, as needed, be performed in the presence of one or more recombinant ActRIIA ligand proteins (e.g., activin), and cells may be transfected so as to produce an ActRIIA polypeptide and/or variants thereof, and optionally, an ActRIIA ligand. Likewise, an ActRIIA polypeptide may be administered to a mouse or other animal, and one or more bone properties, such as density or volume may be assessed. The healing rate for bone fractures may also be evaluated. Dual-energy x-ray absorptiometry (DEXA) is a well-established, non-invasive, quantitative technique for assessing bone density in an animal. In humans central DEXA systems may be used to evaluate bone density in the spine and pelvis. These are the best predictors of overall bone density. Peripheral DEXA systems may be used to evaluate bone density in peripheral bones, including, for example, the bones of the hand, wrist, ankle and foot. Traditional x-ray imaging systems, including CAT scans, may be used to evaluate bone growth and fracture healing. In addition, bone density can be measured using quantitative computed tomography (qCT). The mechanical strength of bone may also be evaluated.

In certain aspects, provided herein is the use of ActRIIA polypeptides (e.g., soluble ActRIIA polypeptides) and activin polypeptides to identify compounds (agents) which are agonist or antagonists of the activin-ActRIIA signaling pathway. Compounds identified through this screening can be tested to assess their ability to modulate bone growth or mineralization in vitro. Optionally, these compounds can further be tested in animal models to assess their ability to modulate tissue growth in vivo.

There are numerous approaches to screening for therapeutic agents for modulating tissue growth by targeting activin and ActRIIA polypeptides. In certain embodiments, high-throughput screening of compounds can be carried out to identify agents that perturb activin or ActRIIA-mediated effects on bone. In certain embodiments, the assay is carried out to screen and identify compounds that specifically inhibit or reduce binding of an ActRIIA polypeptide to activin. Alternatively, the assay can be used to identify compounds that enhance binding of an ActRIIA polypeptide to activin. In a further embodiment, the compounds can be identified by their ability to interact with an activin or ActRIIA polypeptide.

A variety of assay formats will suffice and, in light of the present disclosure, those not expressly described herein will nevertheless be comprehended by one of ordinary skill in the art. As described herein, the test compounds (agents) used herein may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated herein include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIA polypeptide and activin.

Merely to illustrate, in an exemplary screening assay, the compound of interest is contacted with an isolated and purified ActRIIA polypeptide which is ordinarily capable of binding to activin. To the mixture of the compound and ActRIIA polypeptide is then added a composition containing an ActRIIA ligand. Detection and quantification of ActRIIA/activin complexes provides a means for determining the compound's efficacy at inhibiting (or potentiating) complex formation between the ActRIIA polypeptide and activin. The efficacy of the compound can be assessed by generating dose response curves from data obtained using various concentrations of the test compound. Moreover, a control assay can also be performed to provide a baseline for comparison. For example, in a control assay, isolated and purified activin is added to a composition containing the ActRIIA polypeptide, and the formation of ActRIIA/activin complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIA polypeptide and activin may be detected by a variety of techniques. For instance, modulation of the formation of complexes can be quantitated using, for example, detectably labeled proteins such as radiolabeled (e.g., 32P, 35S, 14C or 3H), fluorescently labeled (e.g., FITC), or enzymatically labeled ActRIIA polypeptide or activin, by immunoassay, or by chromatographic detection.

In certain embodiments, contemplated herein is the use of fluorescence polarization assays and fluorescence resonance energy transfer (FRET) assays in measuring, either directly or indirectly, the degree of interaction between an ActRIIA polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments described herein.

Moreover, an interaction trap assay, also known as the "two hybrid assay," can be used for identifying agents that disrupt or potentiate interaction between an ActRIIA polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, contemplated herein is the use of reverse two hybrid systems to identify compounds (e.g., small molecules or peptides) that dissociate interactions between an ActRIIA polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with an ActRIIA or activin polypeptide. The interaction between the compound and the ActRIIA or activin polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an activin or ActRIIA polypeptide. This may include a solid phase or fluid phase binding event. Alternatively, the gene encoding an activin or ActRIIA polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, provided herein are methods and agents for modulating (stimulating or inhibiting) bone formation and increasing bone mass. Therefore, any compound identified can be tested in whole cells or tissues, in vitro or in vivo, to confirm their ability to modulate bone growth or mineralization. Various methods known in the art can be utilized for this purpose. In particular, the compounds can be tested for their ability to increase bone turnover.

For example, the effect of the ActRIIA or activin polypeptides or test compounds on bone or cartilage growth can be determined by measuring induction of Msx2 or differentiation of osteoprogenitor cells into osteoblasts in cell based assays (see, e.g., Daluiski et al., Nat Genet. 2001, 27(1):84-8; Hino et al., Front Biosci. 2004, 9:1520-9). Another example of cell-based assays includes analyzing the osteogenic activity of the subject ActRIIA or activin polypeptides and test compounds in mesenchymal progenitor and osteoblastic cells. To illustrate, recombinant adenoviruses expressing an activin or ActRIIA polypeptide can be constructed to infect pluripotent mesenchymal progenitor C3H10T1/2 cells, preosteoblastic C2Cl2 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8): 1544-52).

Also provided herein are in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. Andersson et al., J. Endocrinol. 170:529-537 describe a mouse osteoporosis model in which mice are ovariectomized, which causes the mice to lose substantial bone mineral content and bone mineral density, with the trabecular bone losing roughly 50% of bone mineral density. Bone density could be increased in the ovariectomized mice by administration of factors such as parathyroid hormone. In certain aspects, fracture healing assays that are known in the art can be used. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

7.11 Pharmaceutical Compositions

In certain embodiments, activin-ActRII antagonists (e.g., ActRII polypeptides) are formulated with a pharmaceutically acceptable carrier for use with the methods provided herein. For example, an ActRII polypeptide can be administered alone or as a component of a pharmaceutical formulation (therapeutic composition). The subject compounds may be formulated for administration in any convenient way for use in human or veterinary medicine. ActRII can be ActRIIA or ActRIIB.

In certain embodiments, the therapeutic method of the invention includes administering the composition systemically, or locally as an implant or device. When administered, the therapeutic composition for use in this invention is, of course, in a pyrogen-free, physiologically acceptable form. Therapeutically useful agents other than the ActRII antagonists which may also optionally be included in the composition as described above, may be administered simultaneously or sequentially with the subject compounds (e.g., ActRII polypeptides, such as ActRIIA and/or ActRIIB polypeptides (see Section 7.9)).

Typically, ActRII antagonists will be administered parenterally. Pharmaceutical compositions suitable for parenteral administration may comprise one or more ActRII polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., bone). In certain embodiments, compositions provided herein may include a matrix capable of delivering one or more therapeutic compounds (e.g., ActRIIA polypeptides) to a target tissue site (e.g., bone), providing a structure for the developing tissue and optimally capable of being resorbed into the body. For example, the matrix may provide slow release of the ActRIIA polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds provided herein may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., ActRII polypeptides, such as ActRIIA and/or ActRIIB polypeptides (see Section 7.9)). The various factors include, but are not limited to, amount of bone weight desired to be formed, the degree of bone density loss, the site of bone damage, the condition of the damaged bone, the subject's age, sex, and diet, the severity of any disease that may be contributing to bone loss, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

In certain embodiments, provided herein is gene therapy for the in vivo production of ActRII polypeptides. Such therapy would achieve its therapeutic effect by introduction of the ActRII polynucleotide sequences into cells or tissues having the disorders as listed above. Delivery of ActRII polynucleotide sequences can be achieved using a recombinant expression vector such as a chimeric virus or a colloidal dispersion system. Preferred for therapeutic delivery of ActRII polynucleotide sequences is the use of targeted liposomes. The ActRII polypeptides can be ActRIIA and/or ActRIIB polypeptides (see Section 7.9)).

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRII polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRII polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

In certain embodiments, the ActRII signaling inhibitor is substantially pure in a pharmaceutical composition. Specifically, at most 20%, 10%, 5%, 2.5%, 1%, 0.1%, or at most 0.05% of the compounds in the pharmaceutical composition are compounds other than the ActRII signaling inhibitor and the pharmaceutical acceptable carrier.

In a preferred embodiment, the pharmaceutical composition is formulated for subcutaneous administration.

8. EXAMPLES

8.1 Example 1

8.1.1 ActRIIA-Fc Fusion Proteins

A soluble ActRIIA fusion protein that has the extracellular domain of human ActRIIA fused to a human or mouse Fc domain with a minimal linker in between is provided. The constructs are referred to as ActRIIA-hFc and ActRIIA-mFc, respectively. ActRIIA-hFc is provided as SEQ ID NO:7.

The ActRIIA-hFc and ActRIIA-mFc proteins were expressed in CHO cell lines. Three different leader sequences were considered:
  (i) Honey bee mellitin (HBML): SEQ ID NO: 8
  (ii) Tissue Plasminogen Activator (TPA): SEQ ID NO: 9
  (iii) Native ActRIIA: SEQ ID NO: 10

The selected form employs the TPA leader and has the following unprocessed amino acid sequence is set forth in SEQ ID NO: 13. This polypeptide is encoded by SEQ ID NO: 14.

8.1.2 ActRIIB-Fc Fusion Proteins

Crystal structure of an extracellular domain of human ActRIIB fused to a human Fc domain and Activin did not show any role for the final (C-terminal) 15 amino acids (referred to as the "tail" herein) of the extracellular domain in ligand binding. This sequence failed to resolve on the crystal structure, suggesting that these residues are present in a flexible loop that did not pack uniformly in the crystal. Thompson et al. EMBO J. 2003 Apr. 1; 22(7):1555-66. This sequence is also poorly conserved between ActRIIB and ActRIIA. Accordingly, these residues were omitted in the basic, or background, ActRIIB-Fc fusion construct. Additionally, position 64 in the background form is occupied by an alanine, which is generally considered the "wild type" form, although an A64R allele occurs naturally. Thus, the background ActRIIB-Fc fusion has the sequence disclosed as SEQ ID NO:21.

Surprisingly, the C-terminal tail was found to enhance activin and GDF-11 binding, thus a preferred version of ActRIIB-Fc has a sequence SEQ ID NO:20.

A variety of ActRIIB variants that may be used according to the methods described herein are described in the International Patent Application published as WO2006/012627 (see e.g., pp. 59-60), incorporated herein by reference in its entirety.

8.2 Example 2

An Open-Label, Phase 2, Dose-Finding Study of ActRIIA-hFc (SEQ ID NO:7) in Subjects with Low or Intermediate-1 (Int-1)-Risk MDS or Non-Proliferative CMML and Anemia Requiring RBC Transfusion 8.2.1 Introduction Anemia, a hallmark of MDS, is challenging to treat, particularly after failure of erythropoiesis-stimulating agents (ESAs). ActRIIA-hFc (SEQ ID NO:7; "sotatercept") is an activin type HA receptor fusion protein that acts on late-stage erythropoiesis to increase mature erythrocyte release into the circulation (Carrancio et al. Br J Haematol 2014; 165:870-82). Treatment of subjects with ActRIIA-hFc (SEQ ID NO:7) stimulated erythropoiesis and significantly increased hemoglobin (Hb) levels in healthy subjects (Sherman et al. J Clin Pharmacol 2013;53:1121-30), supporting its clinical development for the treatment of anemia in subjects with lower-risk MDS.

8.2.2 Materials and Methods

Figure 1:
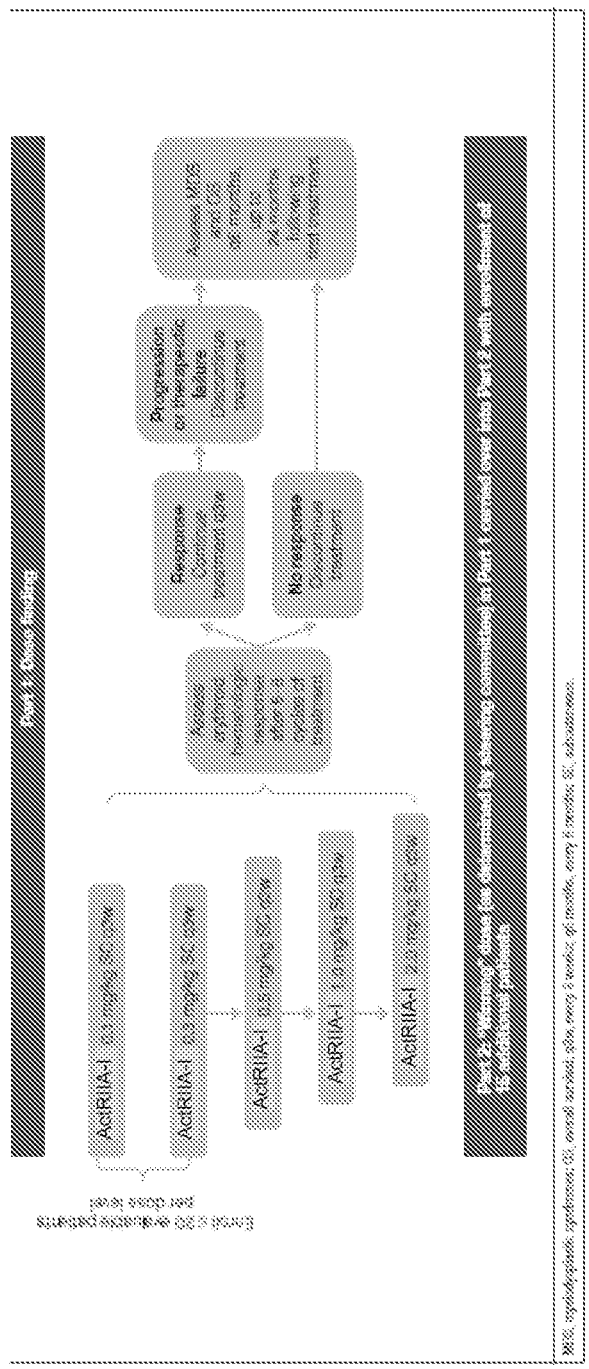
Figure 2:
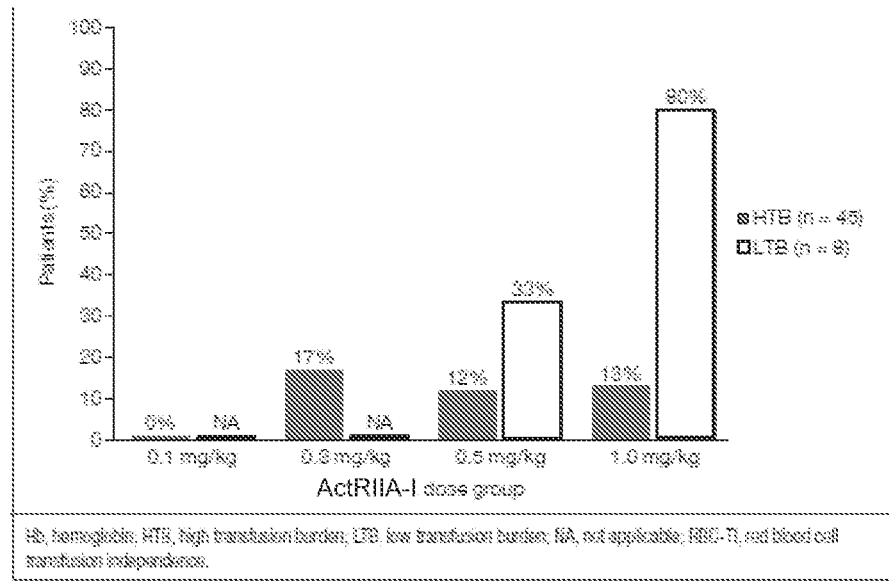

The primary objective of this example is to determine a safe, tolerable, and effective dose of ActRIIA-hFc (SEQ ID NO:7) resulting in erythroid hematological improvement (HI-E; modified IWG 2006 criteria) in subjects with anemia and IPSS-defined Low or Int-1-risk MDS or non-proliferative CMML (white blood cells<13,000/μL). Secondary objectives include rate of RBC-transfusion independence (RBC-TI) greater than or equal to 8 weeks. Eligible subjects had anemia (greater than or equal to 2 RBC units transfusion requirement in the 12 weeks prior to enrollment for Hb less than or equal to 9.0 g/dL) with no response, loss of response, or low chance of response to ESAs (serum erythropoietin [EPO] greater than 500 mIU/mL). See, Table 1 for a description of the subjects studied in this example. Subjects received subcutaneous ActRIIA-hFc (SEQ ID NO:7) at dose levels of 0.1, 0.3, 0.5, or 1.0 mg/kg once every 3 weeks. See, FIG. 1 for an outline of the study design.

8.2.3 Results

A total of 54 MDS subjects were studied: 7, 6, 21, and 20 in the ActRIIA-hFc (SEQ ID NO:7) 0.1, 0.3, 0.5, and 1.0 mg/kg dose groups, respectively. Median age was 71 years (range 56-86) and median time from diagnosis was 4 years (range 0-31); most subjects were male (70%). Subjects received a median of 6 RBC units (range 0-18) in the 8 weeks prior to treatment start. Forty-five subjects (83%) received greater than or equal to 4 RBC units in the 8 weeks prior to treatment start (high transfusion burden; HTB), and 9 subjects (17%) received less than 4 units in the 8 weeks prior to treatment start (low transfusion burden; LTB). Nineteen subjects (35%) had IPSS Low and 34 subjects (63%) had IPSS Int-1-risk MDS; IPSS risk data were missing for 1 patient. Fifty-one subjects (94%) had prior treatment with ESAs, 30 (56%) with hypomethylating agents, 26 (48%) with lenalidomide, and 26 (48%) with other MDS treatments; 15 subjects (28%) had serum EPO >500 mIU/mL.

Figure 3:
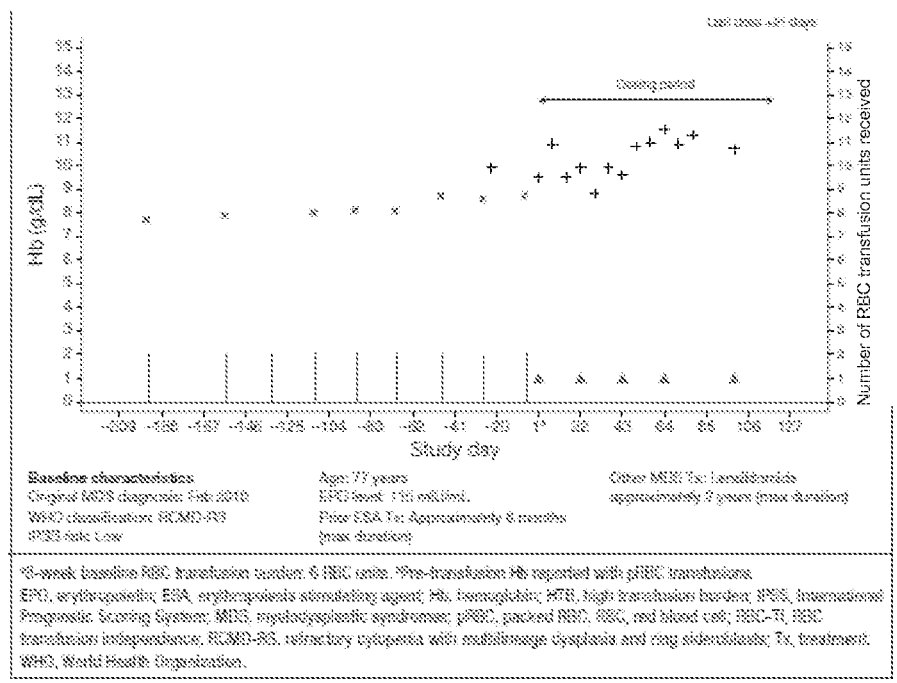
Figure 4:
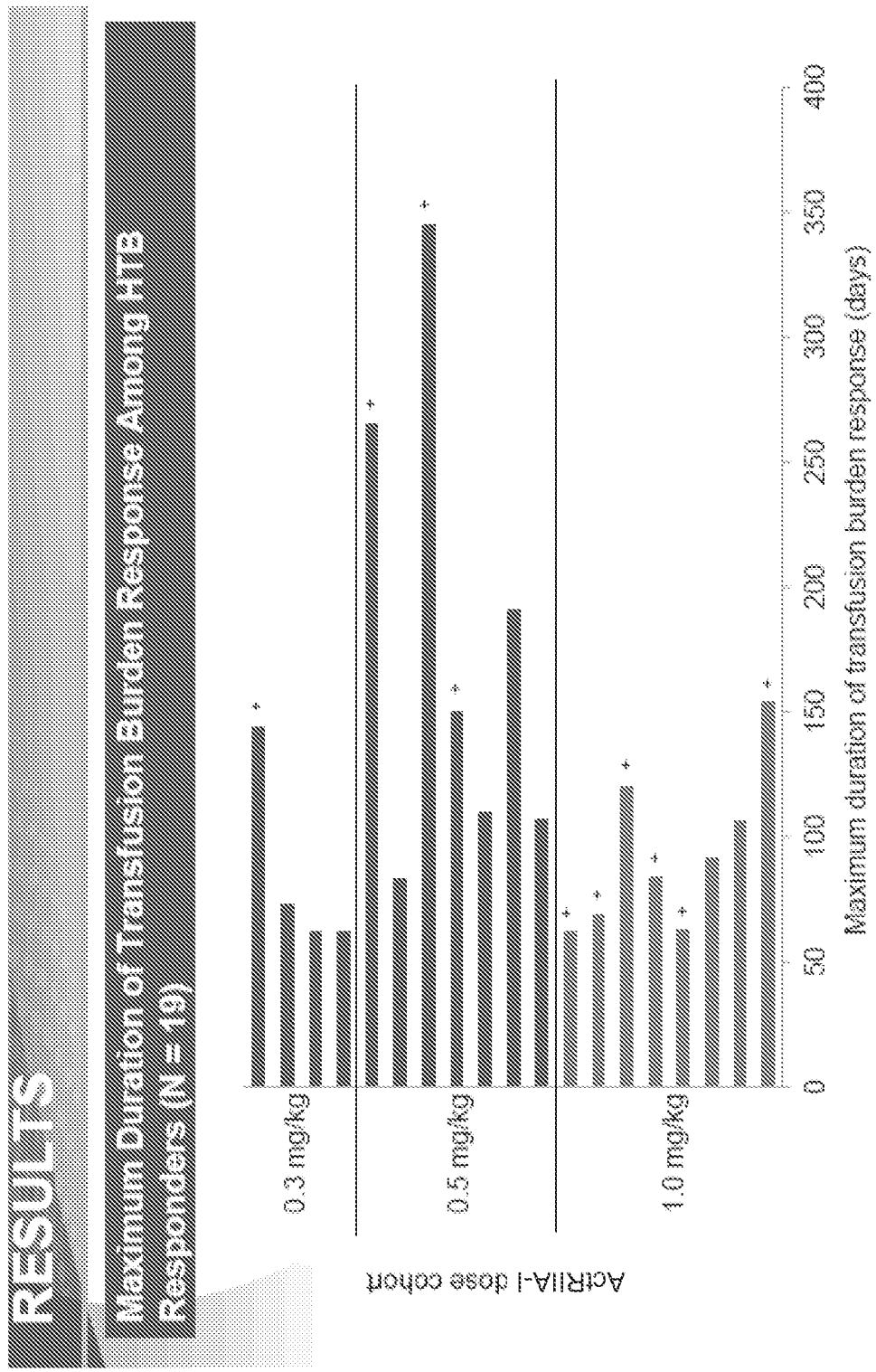
Figure 5:
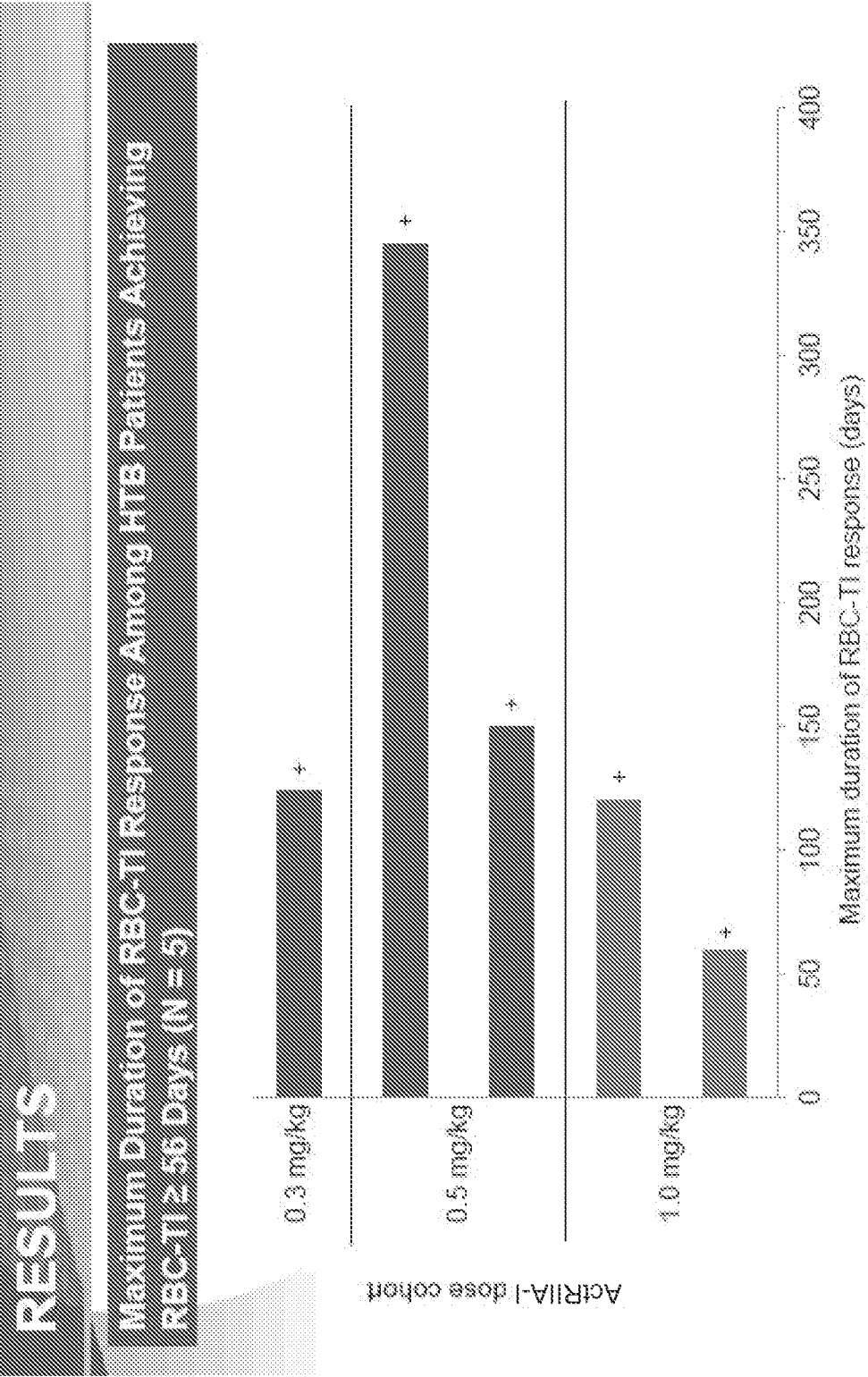

Of the 53 subjects evaluable for efficacy, HI-E was observed in 21 subjects (40%) overall: 0, 4 (67%), 8 (40%), and 9 subjects (45%) in the ActRIIA-hFc (SEQ ID NO:7) 0.1, 0.3, 0.5, and 1.0 mg/kg dose groups, respectively. Nineteen of 44 HTB subjects responded with a greater than or equal to 4 RBC units/8 weeks transfusion burden reduction; duration of transfusion response appeared to be dose-dependent. See, FIG. 3 for an exemplary HTB subject who achieved RBC-TI for greater than 56 days subsequent to treatment with the ActRIIA-hFc. See, FIG. 4, which demonstrates the maximum duration of transfusion burden response among HTB responders after treatment with the ActRIIA-hFc (SEQ ID NO:7). Five HTB subjects achieved RBC-TI greater than or equal to 8 weeks, with RBC-TI duration ranging from 59-345+ days. See, FIG. 5, demonstrating the maximum duration of RBC-TI response among HTB subjects achieving RBC-TI for at least 56 days after treatment with ActRIIA-hFc (SEQ ID NO:7). See, also, Table 2.

A subset of the HTB subjects achieving RBC-TI greater than or equal to 8 weeks had increased percentages of erythroblasts that were ring sideroblasts prior to treatment with the ActRIIA-hFc (SEQ ID NO:7).

Figure 6:
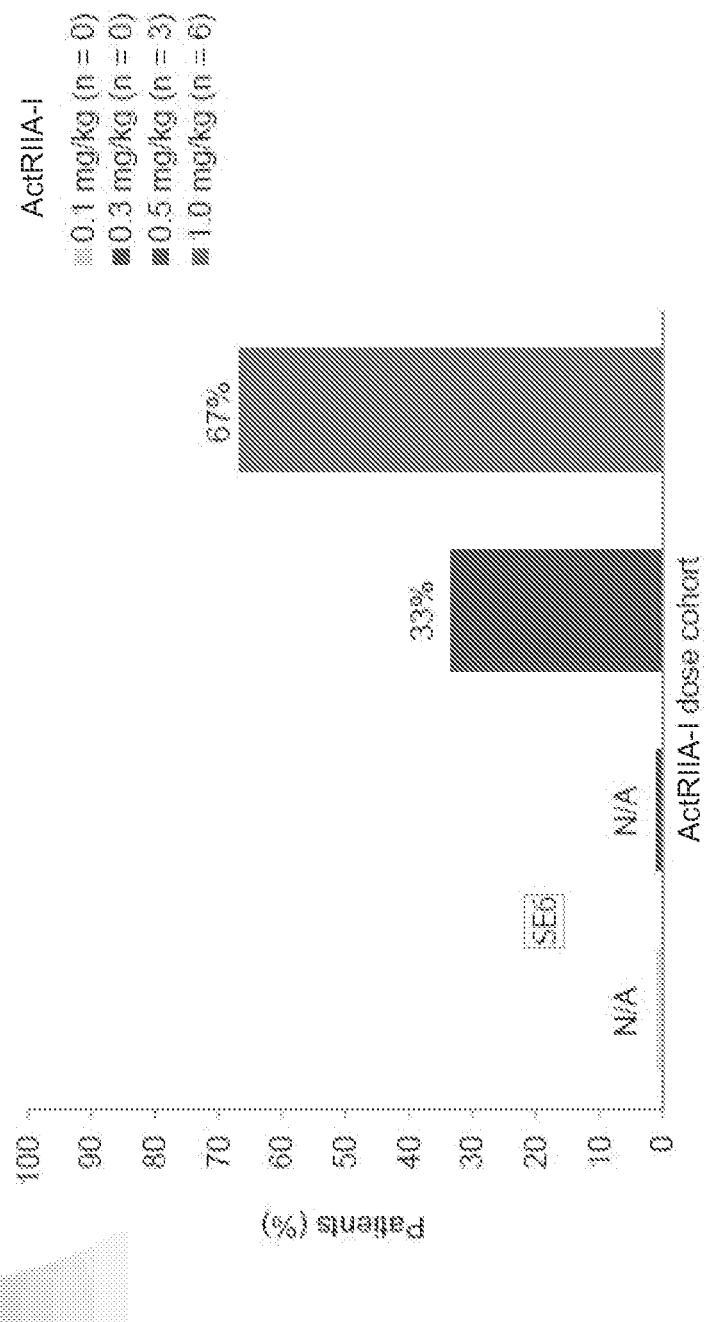
Figure 7:
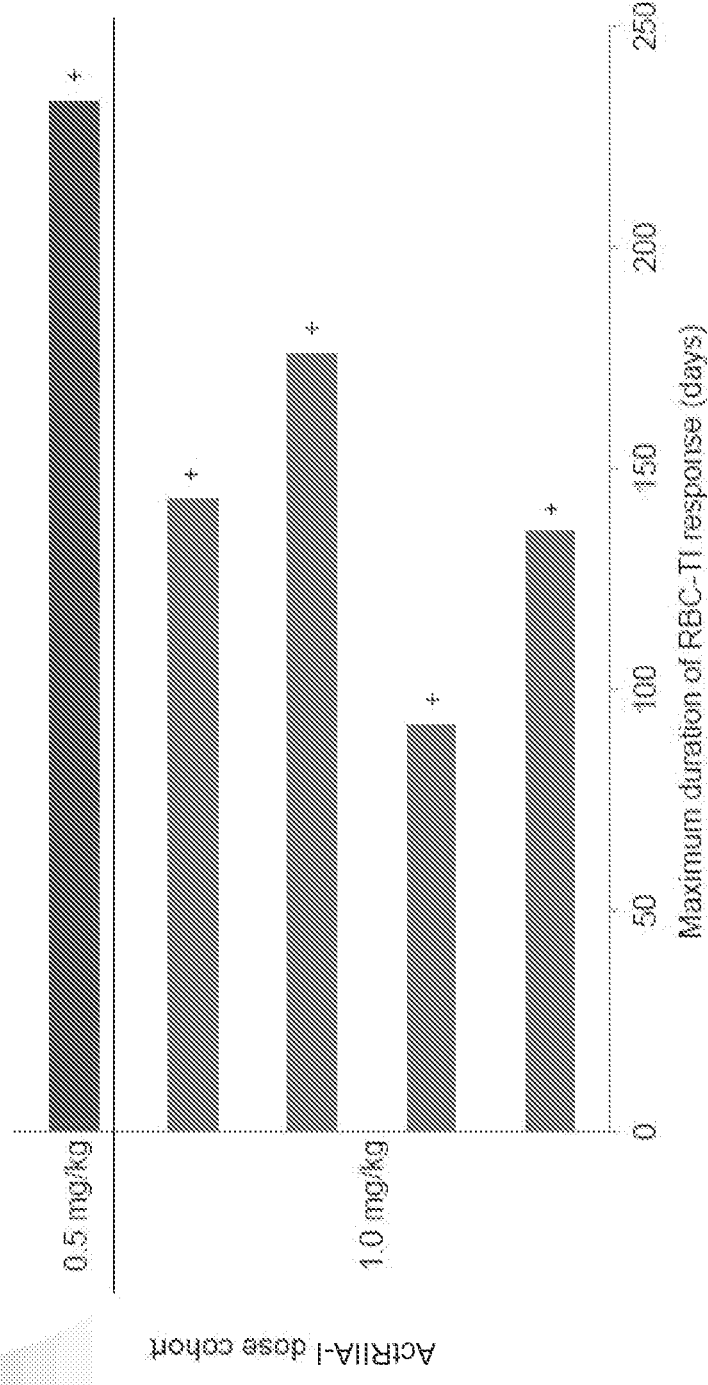

Eight of 9 LTB subjects showed Hb increases, not influenced by transfusion, ranging from 1.3-3.8 g/dL. Of these, 2 subjects had a Hb increase of greater than or equal to 1.5 g/dL sustained for greater than or equal to 8 weeks. Subjects with Hb of greater than 11.0 g/dL were subject to dose delay per protocol, which may have impacted Hb increase sustainability. RBC-TI for greater than or equal to 8 weeks was achieved in 6 LTB subjects. See, FIG. 6, demonstrating the proportion of LTB subjects achieving RBC-TI for at least 56 days and a mean Hb increase of at least 1.5 g/dL after treatment with the ActRIIA-hFc (SEQ ID NO:7). See, FIG. 7, demonstrating the maximum duration of RBC-TI response among LTB achieving RBC-TI for at least 56 days and a mean Hb increase of at least 1.5 g/dL after treatment with the ActRIIA-hFc (SEQ ID NO:7). Increases in platelet and neutrophil levels were seen in subjects with baseline thrombocytopenia and subjects with baseline neutropenia, respectively.

ActRIIA-hFc (SEQ ID NO:7) was generally well tolerated. Twenty subjects (37%) reported greater than or equal to 1 suspected treatment-related adverse event (AE); fatigue (11%), headache (9.3%), decreased appetite (7.4%), and nausea (7.4%) were the most common.

Of 35 subjects (65%) who discontinued treatment, 28 discontinued due to lack of therapeutic effect and 4 due to AEs. Of those AEs leading to discontinuation, 3 were suspected to be treatment-related: 1 patient with grade 2 hemolytic anemia, 1 patient with grade 3 hypertension, and 1 patient with grade 2 muscular weakness in the ActRIIA-hFc (SEQ ID NO:7) 0.3, 0.5, and 1.0 mg/kg dose groups, respectively. Other reasons for discontinuation were withdrawal of consent (n=2; 4%) and patient decision (n=1; 2%).

8.2.4 Conclusions

ActRIIA-hFc (SEQ ID NO:7) is well tolerated in lower-risk MDS subjects at the dose levels tested, with promising evidence of clinical activity in this largely HTB cohort of ESA-refractory, anemic, lower-risk MDS subjects. Further, these data indicate that the presence of ring sideroblasts in subjects prior to treatment with an ActRII inhibitor, e.g., ActRIIA-hFc (SEQ ID NO:7), can be an indicator for long-term treatment, RBC transfusion independence and long-term increases in hemoglobin levels.

TABLE 1

Subject baseline characteristics.

| | ActRIIA inhibitor (SEQ ID NO: 7) dose group | | | | |
|---|---|---|---|---|---|
| Characteristic | 0.1 mg/kg (n = 7) | 0.3 mg/kg (n = 6) | 0.5 mg/kg (n = 21) | 1.0 mg/kg (n = 20) | Overall (N = 54) |
| Age, median (range), years | 65 (58-79) | 73 (66-86) | 69 (56-82) | 74 (60-84) | 71 (56-86) |
| Female, n (%) | 3 (42.9) | 0 | 4 (19.0) | 9 (45.0) | 16 (29.6) |
| Time since original diagnosis, median (range), years | 4 (1-6) | 7 (4-8) | 6 (0-31)[a] | 3 (0-20)[a] | 4 (0-31)[a] |
| RBC transfusion burden, median (range) units/8 weeks | 9 (4-10) | 8 (6-11) | 6 (2-18) | 6 (0-14) | 6 (0-18) |
| RBC transfusion status, n (%) | | | | | |
| HTB[b] | 7 (100) | 6 (100) | 18 (85.7) | 14 (70.0) | 45 (83.3) |
| LTB[c] | 0 | 0 | 3 (14.3) | 6 (30.0) | 9 (16.7) |
| IPSS risk, n (%) | | | | | |
| Low | 3 (42.9) | 4 (66.7) | 5 (23.8) | 8 (40.0) | 20 (37.0) |
| Int-1 | 4 (57.1) | 2 (33.3) | 16 (76.2) | 12 (60.0) | 34 (63.0) |
| Serum EPO level, n (%) | | | | | |
| ≤500 mIU/mL | 4 (57.2) | 5 (83.4) | 7 (33.4) | 13 (65.0) | 29 (53.7) |
| >500 mIU/mL | 3 (42.9) | 1 (16.7) | 6 (28.6) | 5 (25.0) | 15 (27.8) |
| Missing | 0 | 0 | 8 (38.1) | 2 (10.0) | 10 (18.5) |
| Prior use of ESA, n (%) | 6 (85.7) | 6 (100.0) | 20 (95.2) | 19 (95.0) | 51 (94.4) |
| Prior use of hypomethylating agents, n (%) | 6 (85.7) | 6 (100.0) | 13 (61.9) | 5 (25.0) | 30 (55.6) |
| Prior use of lenalidomide, n (%) | 5 (71.4) | 5 (83.3) | 10 (47.6) | 6 (30.0) | 26 (48.1) |
| Prior use of other MDS treatments, n (%)[d] | 6 (85.7) | 5 (83.3) | 9 (42.9) | 6 (30.0) | 26 (48.1) |

[a]0 years indicates <1 year since original diagnosis;
[b]Subjects with RBC transfusion burden ≥ 4 units/8 weeks;
[c]Subjects with RBC transfusion burden < 4 units/8 weeks;
[d]Non-ESA, non-hypomethylating, and non-lenalidomide treatment for MDS; EPO, erythropoietin; ESA, erythropoiesis-stimulating agents; Hb, hemoglobin; HTB, high transfusion burden; Int, Intermediate; IPSS, International Prognostic Scoring System; LTB, low transfusion burden; MDS, myelodysplastic syndromes; RBC, red blood cell.

TABLE 2

Transfusion Response Among HTB Subjects (n = 44)

| | ActRIIA inhibitor (SEQ ID NO: 7) dose group | | | | |
|---|---|---|---|---|---|
| Characteristic | 0.1 mg/kg (n = 7) | 0.3 mg/kg (n = 6) | 0.5 mg/kg (n = 17) | 1.0 mg/kg (n = 14) | Overall (N = 54) |
| Transfusion burden reduction ≥ 4 RBC units/8 weeks, n (%) | 0 | 4 (66.7) | 7 (41.2) | 8 (57.1) | 19 (43.2) |
| Duration of longest response, median (range), days | N/A | 67.5 (62-144) | 150 (83-345) | 87.5 (62-154) | 106.0 (62-345+) |

TABLE 2-continued

Transfusion Response Among HTB Subjects (n = 44)

| | ActRIIA inhibitor (SEQ ID NO: 7) dose group | | | | |
|---|---|---|---|---|---|
| Characteristic | 0.1 mg/kg (n = 7) | 0.3 mg/kg (n = 6) | 0.5 mg/kg (n = 17) | 1.0 mg/kg (n = 14) | Overall (N = 54) |
| RBC-TI ≥ 56 days, n (%) | 0 | 1 (16.7) | 2 (11.8) | 2 (14.3) | 5 (11.1) |

8.3 Example 3

ActRIIB-hFc Increases Hemoglobin and Reduces Transfusion Burden in Subjects with Low or Intermediate-1 Risk MDS: Preliminary Results from a Phase 2 Study

8.3.1 Introduction

ActRIIB-hFc (SEQ ID NO:25; also referred to as luspatercept), a recombinant fusion protein containing modified activin receptor type IIB and IgG Fc, was utilized to treat anemias due to ineffective erythropoiesis, such as MDS. Subjects with MDS often have elevated levels of erythropoietin (EPO) and may be non-responsive or refractory to erythropoiesis-stimulating agents (ESAs). MDS subjects have also been shown to have increased serum GDF11 levels (Suragani R et al., Nature Medicine 2014) and increased Smad 2/3 signaling in the bone marrow (Zhou L et al., Blood 2008). ActRIIB-hFc (SEQ ID NO:25) binds to ligands in the TGF-13 superfamily, including GDF11, inhibits Smad 2/3 signaling, and promotes late-stage erythroid differentiation via a mechanism distinct from ESAs. mActRIIB-Fc (murine version of ActRIIB-hFc (SEQ ID NO:25)) reduced Smad 2 signaling, increased hemoglobin (Hb) levels and decreased bone marrow erythroid hyperplasia in a mouse model of MDS (Suragani R et al., Nature Medicine 2014). In a healthy volunteer study, ActRIIB-hFc (SEQ ID NO:25) was well-tolerated and increased Hb levels (Attie K et al., Am J Hematol 2014).

8.3.2 Materials and Methods

This example presents dose-finding data to evaluate the effects of ActRIIB-hFc (SEQ ID NO:25) on anemia in subjects (see, Table 3 and Table 4) with Low or Int-1 risk MDS who have either high transfusion burden (HTB, defined as greater than or equal to 4 units RBCs/8 weeks prior to baseline) or low transfusion burden (LTB, defined as less than 4 units RBCs/8 weeks prior to baseline). Outcomes include erythroid response (either Hb increase in LTB subjects or reduced transfusion burden in HTB subjects), safety, tolerability, PK, and PD biomarkers.

Figure 8:
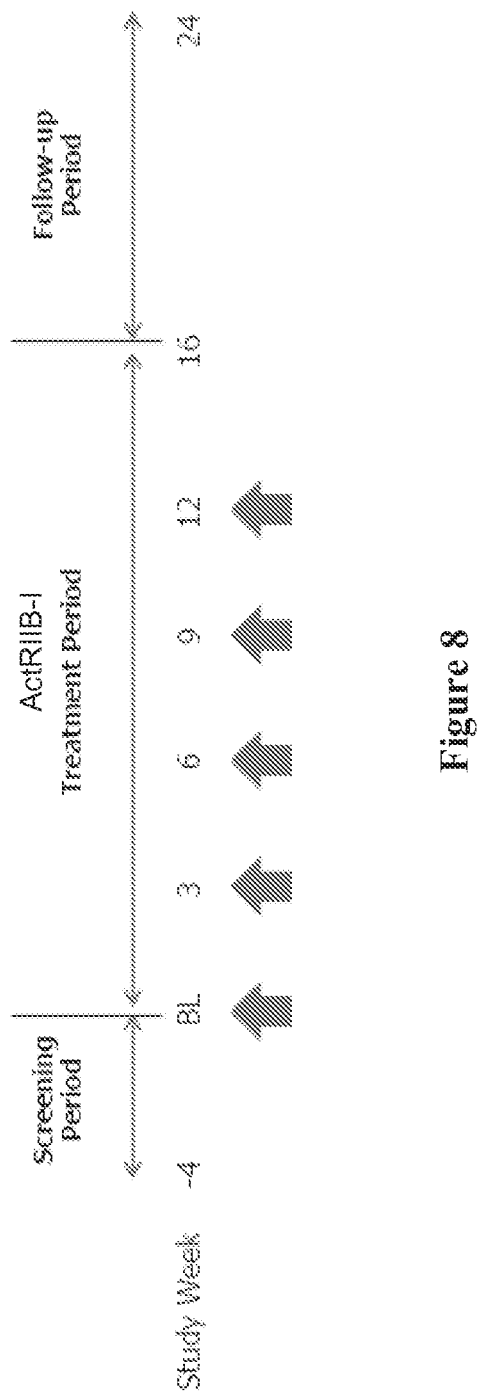

Inclusion criteria included Low or Int-1 risk MDS, at least 18 years in age, anemia (defined as either being HTB subject or having baseline Hb less than 10.0 g/dL in LTB subject), EPO greater than 500 U/L or nonresponsive/refractory to ESAs, no prior azacitidine or decitabine, and no current treatment with ESA, G-CSF, GM-CSF, or lenalidomide. In the dose escalation phase, ActRIIB-hFc (SEQ ID NO:25) was administered by subcutaneous (SC) injection once every 3 weeks in 7 sequential cohorts (n=3-6) at dose levels of 0.125, 0.25, 0.5, 0.75, 1.0, 1.33 and 1.75 mg/kg for up to 5 doses with a 3-month follow-up. An expansion cohort (n=30) is planned, and all subjects completing this study may enroll in a 12-month extension study. See, FIG. 8 for a description of the experimental design and dosing regimen.

8.3.3 Results

Data were available for 26 subjects (7 LTB/19 HTB). Median age was 71 yr (range: 27-88 yr), 50% were female, 54% had prior EPO therapy and 15% had prior lenalidomide. 69% were WHO subtype RCMD, and the remaining subjects were del(5q), RARS, or RAEB-1. Mean (SD) baseline Hb for the LTB subjects (n=7) was 9.1 (0.4) g/dL. Mean (SD) units RBC transfused in the 8 weeks prior to treatment was 0.9 (1.1) units for the LTB subjects and 6.3 (2.4) units for the HTB subjects. See, Tables 3 and 4.

Figure 9:
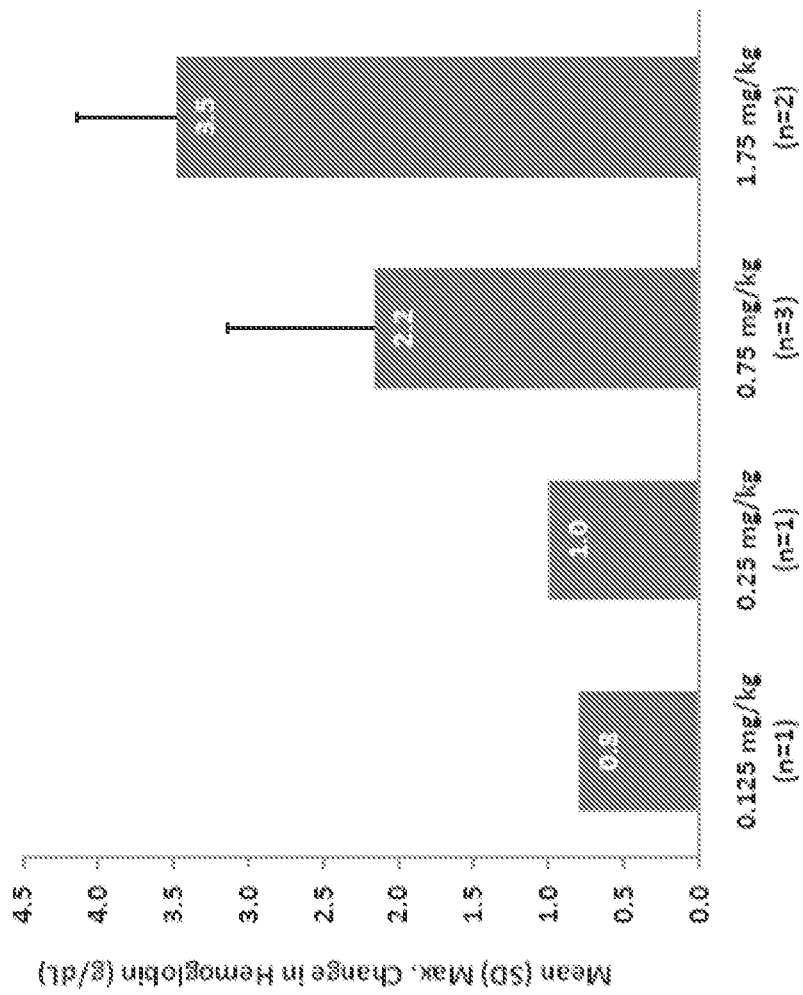
Figure 10:
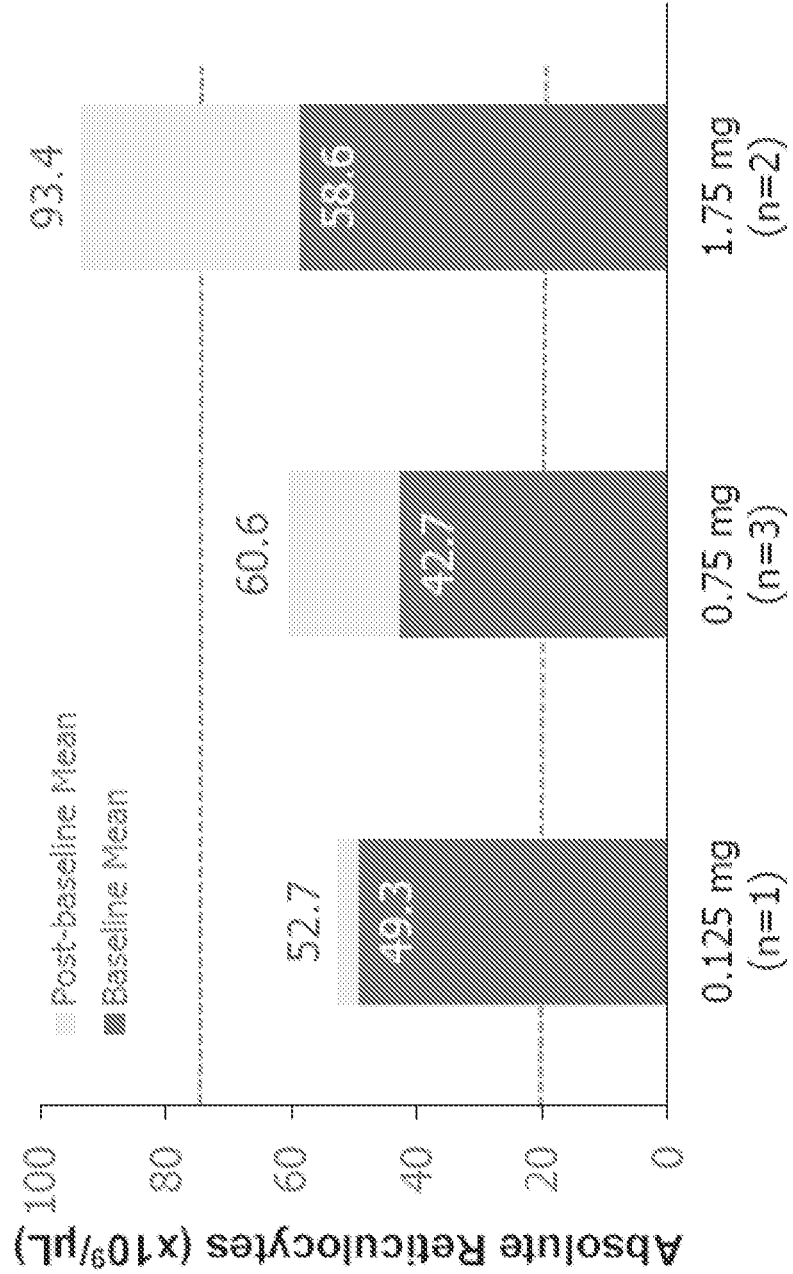
Figure 11:
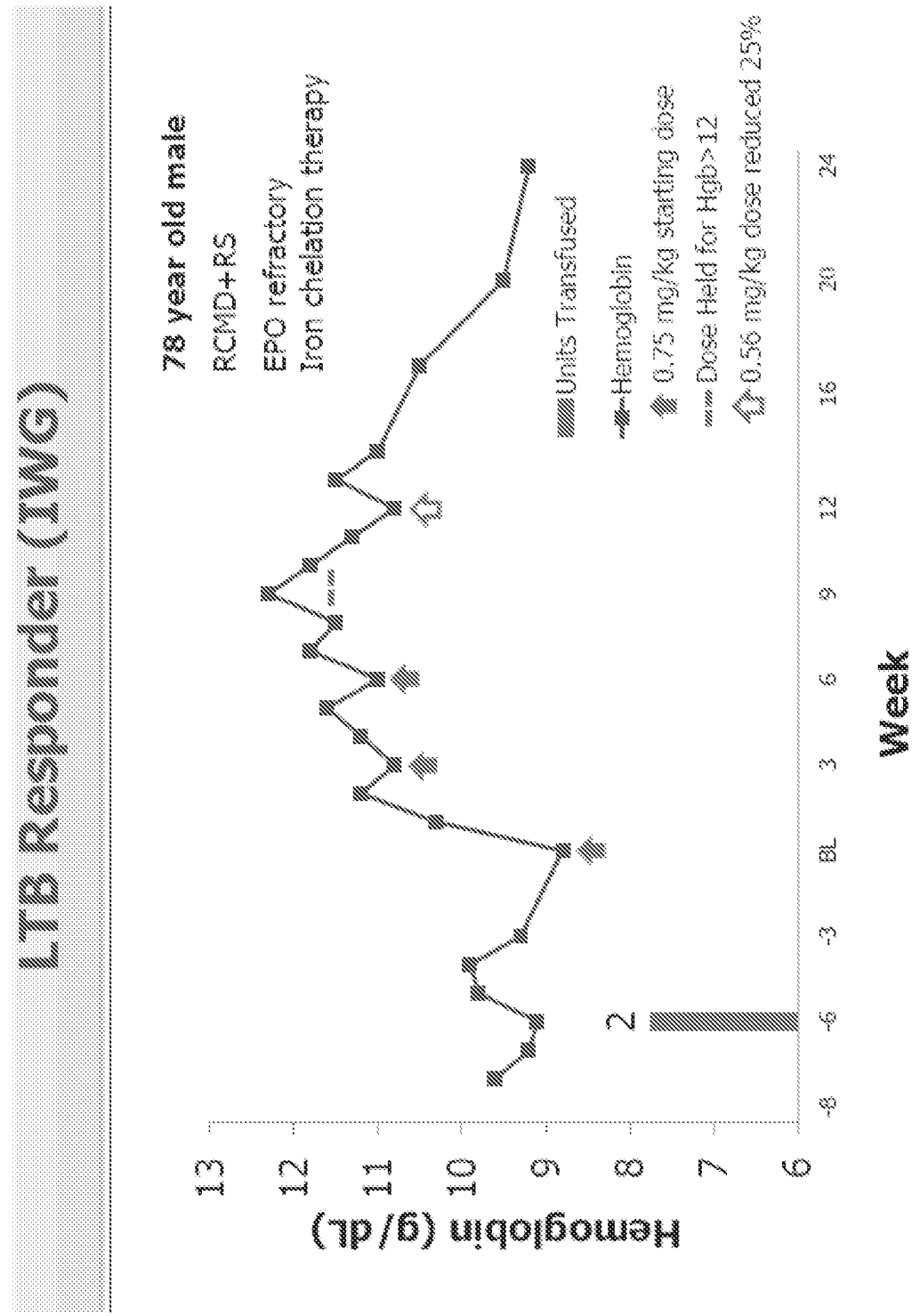
Figure 12:
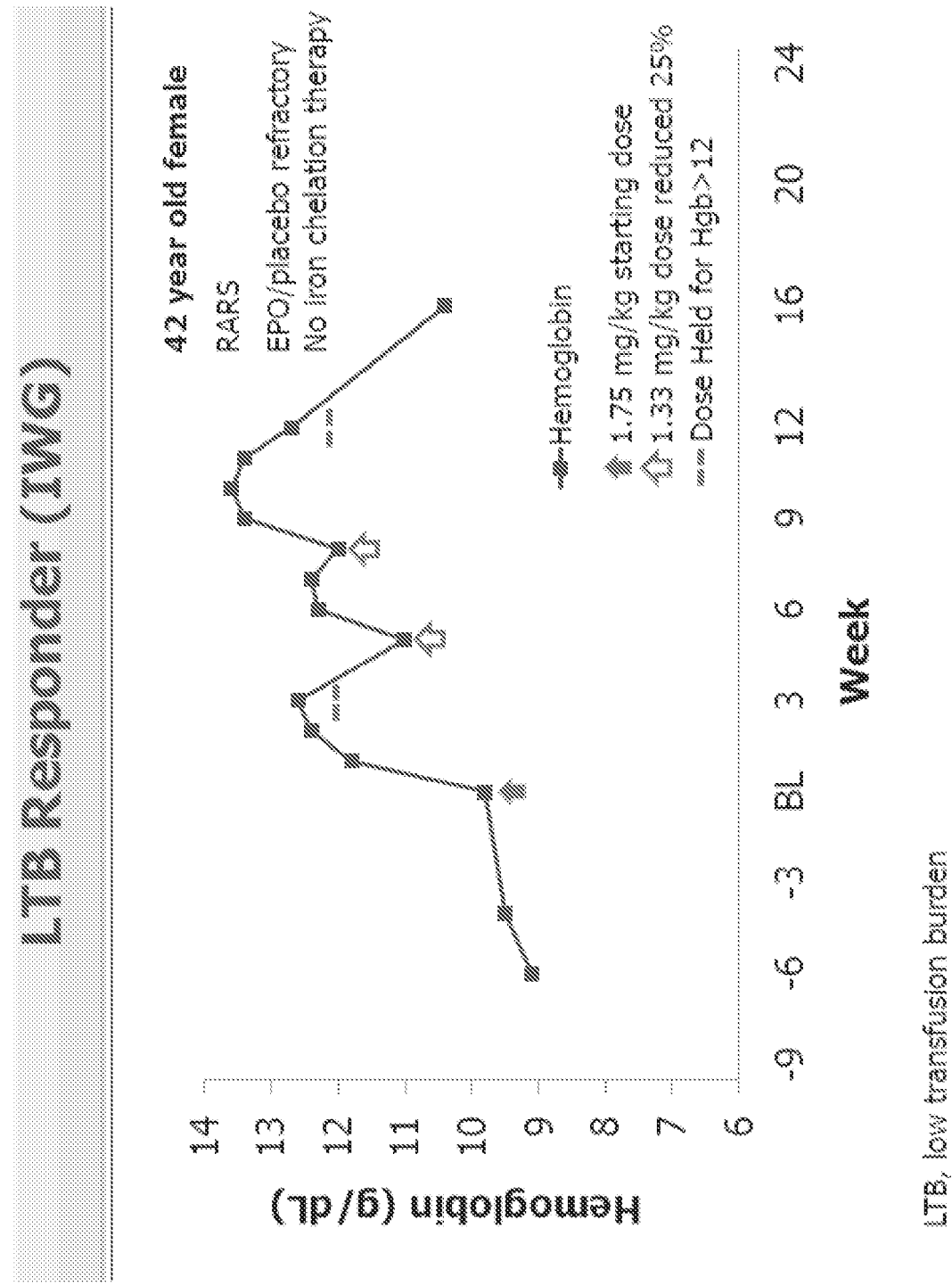

Two of the 7 LTB subjects had an increase in mean Hb 1.5 g/dL over 8 weeks compared to baseline. Mean maximum Hb increase in the LTB subjects was 0.8, 1.0, 2.2, and 2.7 g/dL in the 0.125 (n=1), 0.25 (n=1), 0.75 (n=3), and 1.75 (n=2) mg/kg dose groups, respectively. See, FIG. 9, demonstrating the maximum hemoglobin increase in LTB subjects after treatment with an ActRIIB-hFc (SEQ ID NO:25). LTB subjects administered ActRIIB-hFc (SEQ ID NO:25) exhibited increased reticulocytes and hemoglobin levels. See, FIGS. 10-12 and Table 5. Six of the 7 LTB subjects achieved RBC transfusion independence (RBC-TI) for ≥8 weeks during the study.

Figure 13:
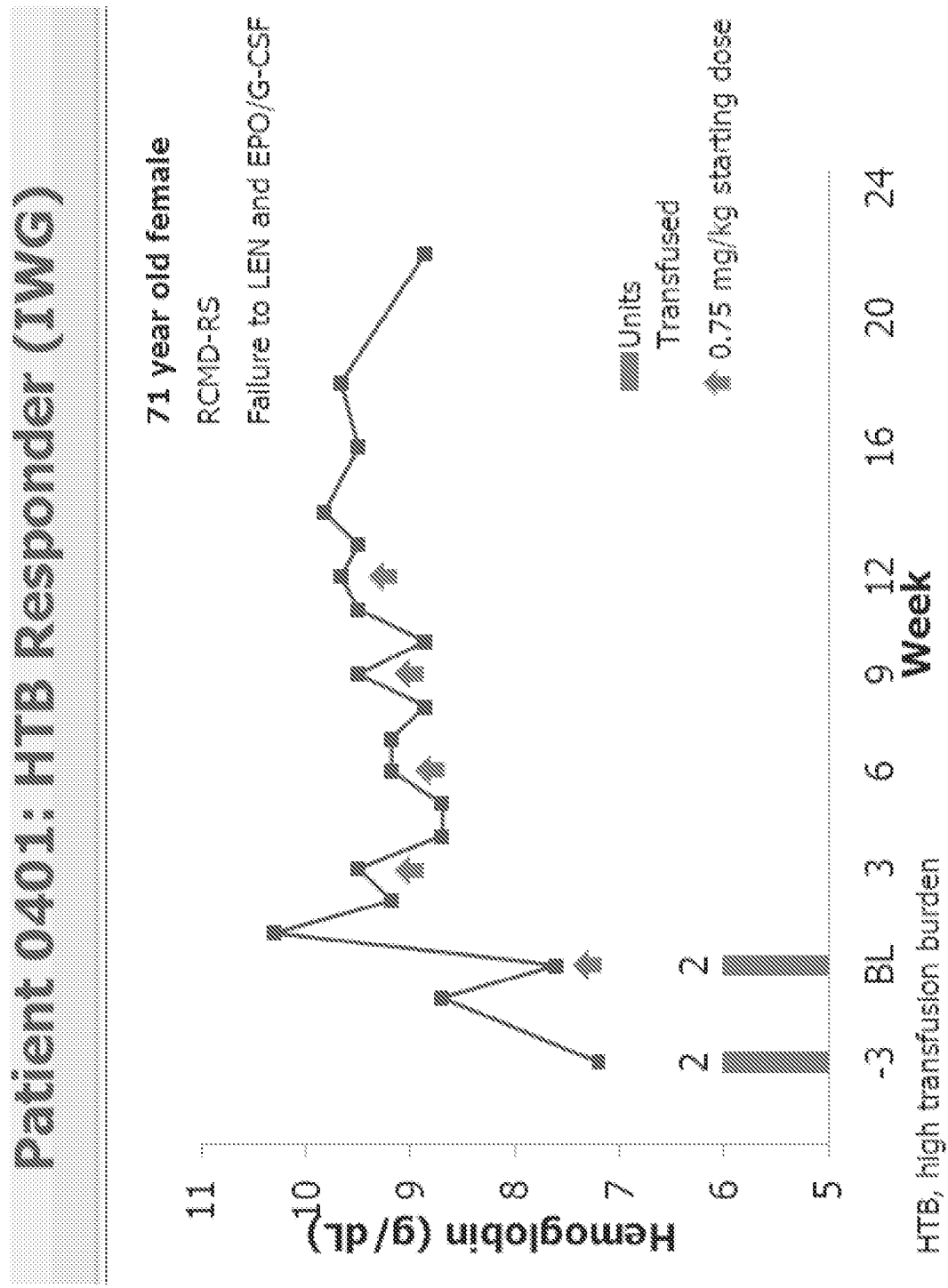

Six of the 19 HTB subjects had a ≥4 unit or ≥50% reduction in RBC units transfused over an 8-week interval during the treatment period compared to the 8 weeks prior to treatment; five of these 6 subjects achieved RBC-TI 8 weeks during the study (range 71-152 days). Increases in hemoglobin levels were observed in HTB subjects administered an ActRIIB-hFc (SEQ ID NO:25). See, e.g., FIG. 13. Increases in neutrophil count following study drug administration were observed in some subjects. A subset of the subjects achieving RBC-TI greater than or equal to 8 weeks, had increased percentages of erythroblasts that were ring sideroblasts prior to treatment of the subjects with the ActRIIB-hFc (SEQ ID NO:25). See, Table 7.

ActRIIB-hFc (SEQ ID NO:25) was generally well tolerated. The most frequent adverse events regardless of causality were: diarrhea (n=4, grade 1/2), bone pain, fatigue, muscle spasms, myalgia, and nasopharyngitis (n=3 each, grade 1/2).

TABLE 3

Baseline Characteristics

| Parameter | N = 26 |
|---|---|
| Age, year, median (range) | 71 (27-88) |
| Sex, males (%) | 13 (50%) |
| Prior ESA treatment, n (%) | 14 (54%) |
| Prior lenalidomide treatment, n (%) | 5 (19%) |
| Low transfusion burden (LTB) | N = 7 (27%) |
| Hemoglobin, g/dL, median (range) | 9.1 (8.3-9.7) |
| Units RBC/8 weeks, median (range) | 0 (0-2) |

TABLE 3-continued

Baseline Characteristics

| Parameter | N = 26 |
|---|---|
| High Transfusion Burden (HTB) | N = 19 (73%) |
| Units RBC/8 weeks, median (range) | 6 (4-13) |

TABLE 4

Efficacy summary of HI-E response rate in subjects treated with ActRIIB (SEQ ID NO: 25) at the indicated doses.

| Subject Subgroup | 0.125-0.5 mg/kg (N = 9) n (%) | 0.75-1.75 mg/kg (N = 17) n (%) |
|---|---|---|
| LTB subjects (N = 7) | 0/2 (0%) | 2/5 (40%) |
| HTB subjects (N = 19) | 2/7 (29%) | 5/12 (42%) |
| All subjects (N = 26) | 2/9 (22%) | 7/17 (41%) |

TABLE 5

Hemoglobin response in LTB subjects

| Response criteria | 0.125-0.5 mg/kg (N = 2) n (%) | 0.75-1.75 mg/kg (N = 5) n (%) |
|---|---|---|
| LTB subjects (N = 7) | 0 | 4 (80%) |
| HTB subjects N = 19) | 0 | 2 (40%) |

TABLE 6

Transfusion response in HTB subjects treated with ActRIIB (SEQ ID NO: 25) at the indicated doses.

| Response criteria (8 weeks), n (%) | 0.125-0.5 mg/kg (N = 7) n (%) | 0.75-1.75 mg/kg (N = 12) n (%) |
|---|---|---|
| LTB subjects (N = 7) | 3 (43%) | 5 (42%) |
| HTB subjects (N = 19) | 2 (29%) | 5 (42%) |
| RBC-TI | 1 (14%) | 3 (25%) |

TABLE 7

IWG Response Rate by ring sideroblast (RS) morphology and mutational analysis

| Response + Rate (IWG) | Cohorts 4-7[a], n = 17; 0.75-1.75 mg/kg; n (%) |
|---|---|
| All subjects | 7/17 (41%) |
| Ring sideroblasts greater than or equal to 15% | |
| Ring sideroblast positive | 7/13 (54%) |
| Ring sideroblast negative | 0/4 (0%) |
| Mutational Analysis | |
| SF3B1+ | 6/9 (67%)[b] |
| SF3B1− | 1/8 (13%) |

[a]Cohort 4: 0.75 mg/kg (n = 3); cohort 5: 1.0 mg/kg (n = 3); cohort 6: 1.33 mg/kg (n = 6); cohort 7: 1.75 mg/kg (n = 2);
[b]Includes 3 subjects who became transfusion independent.

8.3.4 Conclusions

Based on preliminary data in Low or Int-1 MDS subjects, ActRIIB-hFc (SEQ ID NO:25) administered SC every 3 weeks for up to 5 doses increased Hb levels or decreased transfusion requirement, with a favorable safety profile. These data strongly support further evaluation of longer-term treatment of subjects with MDS with ActRIIB-hFc (SEQ ID NO:25).

8.4 Example 4

ActRIIB-hFc (SEQ ID NO:25) Increases Hemoglobin and Reduces Transfusion Burden in Subjects with Low or Intermediate-1 Risk MDS: Preliminary Results from the Phase 2 PACE-MDS Study 8.4.1 Introduction ActRIIB-hFc (SEQ ID NO:25) is a fusion protein (modified activin receptor IIB/IgG Fc) currently being investigated for the treatment of anemias with ineffective erythropoiesis. MDS subjects have increased GDF11 levels (Suragani, Nat Med 2014) and aberrant Smad2,3 signaling in the bone marrow. ActRIIB-hFc (SEQ ID NO:25) binds TGF-β superfamily ligands, including GDF11, Activin B, and BMP6, inhibits Smad2,3 signaling, and promotes late-stage erythroid differentiation, distinct from ESAs. In a healthy volunteer study, ActRIIB-hFc (SEQ ID NO:25) was well-tolerated and increased Hb levels (Attie, Am J Hematol 2014).

8.4.2 Aims

The data presented in this example are from an ongoing, phase 2, multicenter, open-label, dose-finding study to evaluate the effects of ActRIIB-hFc (SEQ ID NO:25) on anemia in subjects with transfusion-dependent (TD) or non-transfusion dependent (NTD) low or int-1 risk MDS. Study outcomes included erythroid response, safety, tolerability, pharmacokinetic biomarkers and pharmacodynamic biomarkers. In low transfusion burden (LTB) subjects, erythroid response was defined as an increase in hemoglobin concentration. In high transfusion burden (HTB) subjects, erythroid response was defined as reduced transfusion burden.

8.4.3 Methods

Inclusion criteria included low or int-1 risk MDS, age ≥18 years, with anemia defined as either Hb <10.0 g/dL (LTB, defined as <4 units RBCs/8 wks prior to baseline) or ≥4 units RBCs/8 weeks prior to baseline (HTB), EPO >500 U/L or nonresponsive/refractory to ESAs, no prior azacitidine or decitabine, and no current treatment with ESA, G-CSF, GM-CSF, or lenalidomide. ActRIIB-hFc (SEQ ID NO:25) was administered by subcutaneous (SC) injection once every 3 weeks in sequential cohorts (n=3-6 each) at dose levels ranging from 0.125 to 1.75 mg/kg for up to 5 doses with a 3-month follow-up. An expansion cohort (n=30) is ongoing, with individual subject dose titrations to response allowed. Subjects completing this study may enroll into a 12-month extension study.

8.4.4 Results

This example provides preliminary safety and efficacy data for 44 subjects (19 females, 25 males; 15 LTB subjects, 29 HTB subjects) out of 58 subjects enrolled in the phase II study. The median age of the subjects was 71 years old. 61% of the subjects had prior EPO therapy. 21% of the subjects had prior lenalidomide therapy. 73% of the subjects had RARS or RCMD-RS. 80% of the subjects had greater than 15% ring sideroblasts in bone marrow.

LTB subjects treated with between 0.75 mg/kg and 1.75 mg/kg (n=13) of ActRIIB-hFc (SEQ ID NO:25) had a 77% response rate for the primary endpoint (Hb increase ≥1.5 g/dL for ≥2 weeks) and a 62% IWG HI-E (International Working Group erythroid hematological improvement)

response rate (Hb increase ≥1.5 g/dL for ≥8 weeks). The mean (standard deviation) maximum change in hemoglobin was 2.7 (standard deviation: 1.1) g/dL in the higher dose groups compared with 0.9 (standard deviation: 0.1) g/dL in the lower dose groups.

HTB subjects treated with between 0.75 mg/kg and 1.75 mg/kg (n=13) of ActRIIB-hFc (SEQ ID NO:25) had a 50% HI-E response rate (≥4 RBC units/8 weeks reduction). The HI-E response rate was 63% for subjects with ≥15% ring sideroblasts (n=30) and 80% for subjects with SF3B1 mutations (n=10). ActRIIB-hFc (SEQ ID NO:25) was generally well-tolerated. The most frequent adverse events regardless of causality were diarrhea, nasopharyngitis, myalgia, bone pain, bronchitis, headache and muscle spasms.

8.4.5 Conclusions

Based on preliminary data in Low/Int-1 MDS subjects, ActRIIB-hFc (SEQ ID NO:25) treatment at therapeutic dose levels for 3 months led to HI-E response for increased Hb levels and/or decreased transfusion requirement in 54% of subjects, with a favorable safety profile. Higher response rates were observed in subjects with ring sideroblast and SF3B1 mutations. These data strongly support utilization of ring sideroblast levels and SF3B1 mutation prevalence as biomarkers for effective treatment with ActRIIB-hFc (SEQ ID NO:25) in subjects with MDS.

8.5 Example 5

An Open-Label, Phase 2, Dose-Finding Study of ActRIIA-hFc (SEQ ID NO:7) in Subjects with Low or Intermediate-1 (Int-1)-Risk MDS or Non-Proliferative CMML and Anemia Requiring RBC Transfusion

8.5.1 Introduction

See the Introduction (Section 8.2.1) and Materials and Methods (Section 8.2.2) for Example 2 (Section 8.2). This example presents additional data from Example 2 (Section 8.2), obtained at a later date in the Phase 2 study.

8.5.2 Results

A total of 59 MDS subjects were treated with either 0.1 mg/kg, 0.3 mg/kg, 0.5 mg/kg, 1.0 mg/kg, or 2.0 mg/kg of ActRIIA-hFc (SEQ ID NO:7). Table 8 provides the baseline characteristics of the subjects for each treatment group.

Of the 53 subjects evaluable for efficacy, HI-E was observed in 23 subjects (43%) overall: 0, 4 (67%), 9 (45%), and 10 subjects (50%) in the ActRIIA-hFc (SEQ ID NO:7) 0.1, 0.3, 0.5, and 1.0 mg/kg dose groups, respectively. Moreover, treatment of HTB subjects with as little as 0.3 mg/kg of ActRIIA-hFc (SEQ ID NO:7) resulted in greater than or equal to 4 RBC units/8 weeks transfusion burden reduction (see Table 9). The duration of the transfusion response appeared to be dose-dependent. Further, of 45 evaluable HTB subjects, 6 (13) achieved RBC-TI for at least 8 weeks (see Table 9). See FIG. 13 for an exemplary HTB subject who achieved RBC-TI for at least 337 days subsequent to the initiation of treatment with the ActRIIA-hFc (SEQ ID NO:7) at a dose of 1.0 mg/kg.

TABLE 8

Subject baseline characteristics.

| Characteristic | ActRIIA signaling inhibitor (SEQ ID NO: 7) dose group | | | | | |
|---|---|---|---|---|---|---|
| | 0.1 mg/kg (n = 7) | 0.3 mg/kg (n = 6) | 0.5 mg/kg (n = 21) | 1.0 mg/kg (n = 20) | 2.0 mg/kg (n = 5) | Overall (N = 59) |
| Age, median (range), years | 65 (58-79) | 73 (66-86) | 69 (56-82) | 74 (60-84) | 73 (47-81) | 71 (47-86) |
| Female, n (%) | 3 (42.9) | 0 | 4 (19.0) | 9 (45.0) | 4 (80) | 20 (34) |
| Time since original diagnosis, median (range), years | 4 (1-6) | 8 (4-10) | 6 (0-31)[a] | 3 (0-20)[a] | 2 (0-5) | 4 (0-31)[a] |
| RBC transfusion burden, median (range) units/8 weeks | 9 (4-10) | 8 (6-11) | 6 (2-16) | 6 (0-10) | 4 (3-8) | 6 (0-16) |
| RBC transfusion status, n (%) | | | | | | |
| HTB[b] | 7 (100) | 6 (100) | 18 (86) | 15 (75) | 4 (80) | 50 (85) |
| LTB[c] | 0 | 0 | 3 (14) | 5 (25) | 1 (2) | 9 (15) |
| IPSS risk, n (%) | | | | | | |
| Low | 4 (57) | 4 (67) | 5 (24) | 7 (35) | 0 | 20 (34) |
| Int-1 | 3 (43) | 2 (33) | 16 (76) | 13 (65) | 5 (100) | 39 *66) |
| Serum EPO level, n (%) | | | | | | |
| ≤500 mIU/mL | 4 (57) | 5 (83) | 11 (52) | 13 (65) | 2 (40) | 35 (59) |
| >500 mIU/mL | 3 (43) | 1 (17) | 8 (38) | 6 (30) | 1 (20) | 19 (32) |
| Missing | 0 | 0 | 2 (10) | 1 (5) | 2 (40) | 5 (9) |
| Prior use of ESA, n (%) | 6 (86) | 6 (100) | 20 (95) | 20 (100) | 4 (80) | 56 (95) |
| Prior use of hypomethylating agents, n (%) | 6 (86) | 6 (100) | 13 (62) | 6 (30) | 0 | 31 (53) |
| Prior use of lenalidomide, n (%) | 5 (71) | 5 (83) | 10 (48) | 6 (30) | 1 (20) | 27 (46) |

TABLE 8-continued

Subject baseline characteristics.

| | ActRIIA signaling inhibitor (SEQ ID NO: 7) dose group | | | | | |
|---|---|---|---|---|---|---|
| Characteristic | 0.1 mg/kg (n = 7) | 0.3 mg/kg (n = 6) | 0.5 mg/kg (n = 21) | 1.0 mg/kg (n = 20) | 2.0 mg/kg (n = 5) | Overall (N = 59) |
| Prior use of other MDS treatments, n (%) | 6 (86) | 5 (83) | 8 (38) | 7 (35) | 0 | 26 (44) |

[a] 0 years indicates <1 year since original diagnosis;
[b] Subjects with RBC transfusion burden ≥ 4 units/8 weeks;
[c] Subjects with RBC transfusion burden < 4 units/8 weeks;
[d] Non-ESA, non-hypomethylating, and non-lenalidomide treatment for MDS; EPO, erythropoietin; ESA, erythropoiesis-stimulating agents; Hb, hemoglobin; HTB, high transfusion burden; Int, Intermediate; IPSS, International Prognostic Scoring System; LTB, low transfusion burden; MDS, myelodysplastic syndromes; RBC, red blood cell.

TABLE 9

Transfusion Response Among HTB Subjects (n = 45)

| | ActRIIA signaling inhibitor (SEQ ID NO: 7) dose group | | | | |
|---|---|---|---|---|---|
| Characteristic | 0.1 mg/kg (n = 7) | 0.3 mg/kg (n = 6) | 0.5 mg/kg (n = 17) | 1.0 mg/kg (n = 15) | Overall (N = 45) |
| Transfusion burden reduction ≥ 4 RBC units/8 weeks, n (%) | 0 | 4 (67) | 8 (47) | 6 (40) | 18 (40) |
| Duration of longest response, median (range), days | NA | 68 (62-173) | 109 (83-345+) | 123 (62-353+) | 99 (62-345+) |
| RBC-TI ≥ 56 days, n (%) | 0 | 1 (17) | 2 (12) | 3 (20) | 6 (13) |
| Duration of RBC-TI ≥ 8 weeks, median (range), days | NA | 124 (124-124) | 347 (154-540) | 78 (59-353) | 139 (59-540) |

Figure 14:
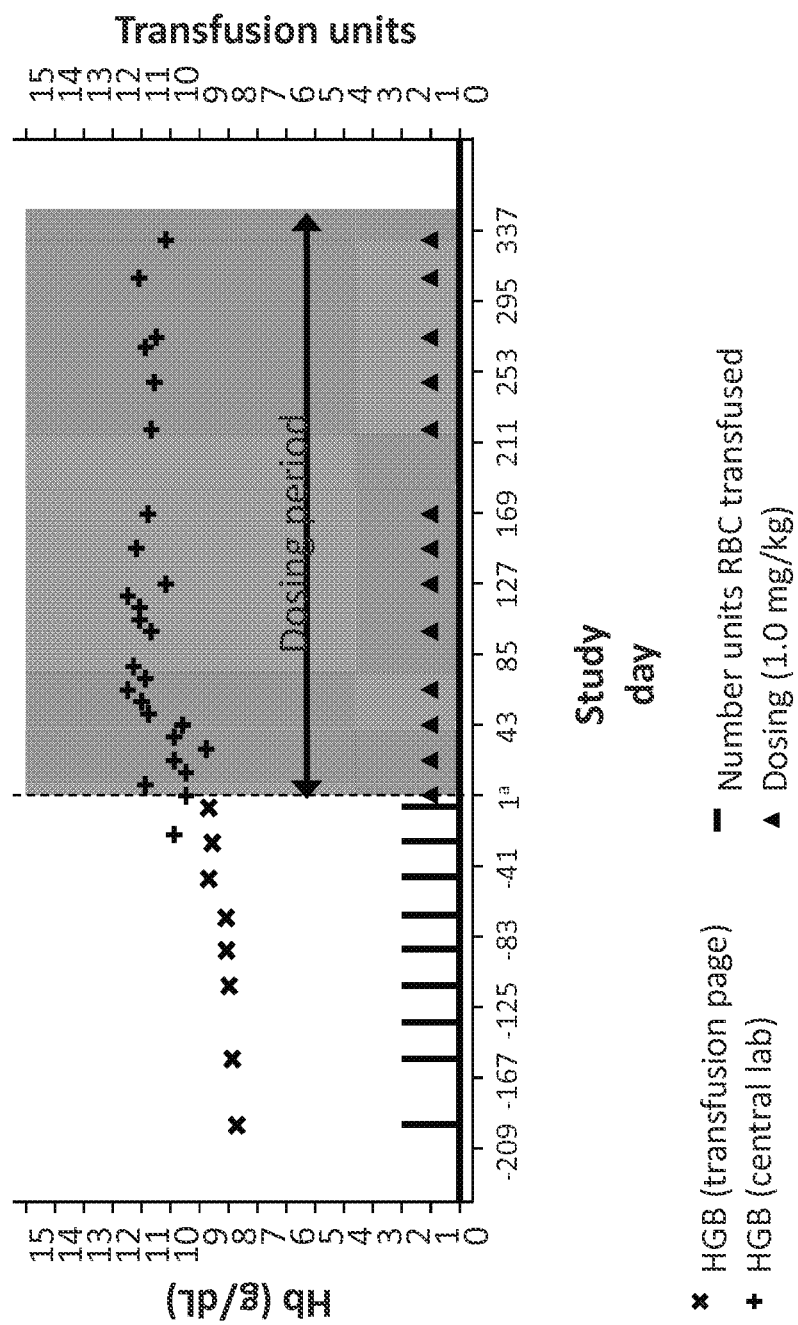
FIG. 14 depicts the hemoglobin level (Hb, g/dL) and number of RBC transfusion units received by an exemplary HTB subject whom received a 1.0 mg/kg dose of an ActRIIA-hFc (SEQ ID NO:7).
Figure 15:
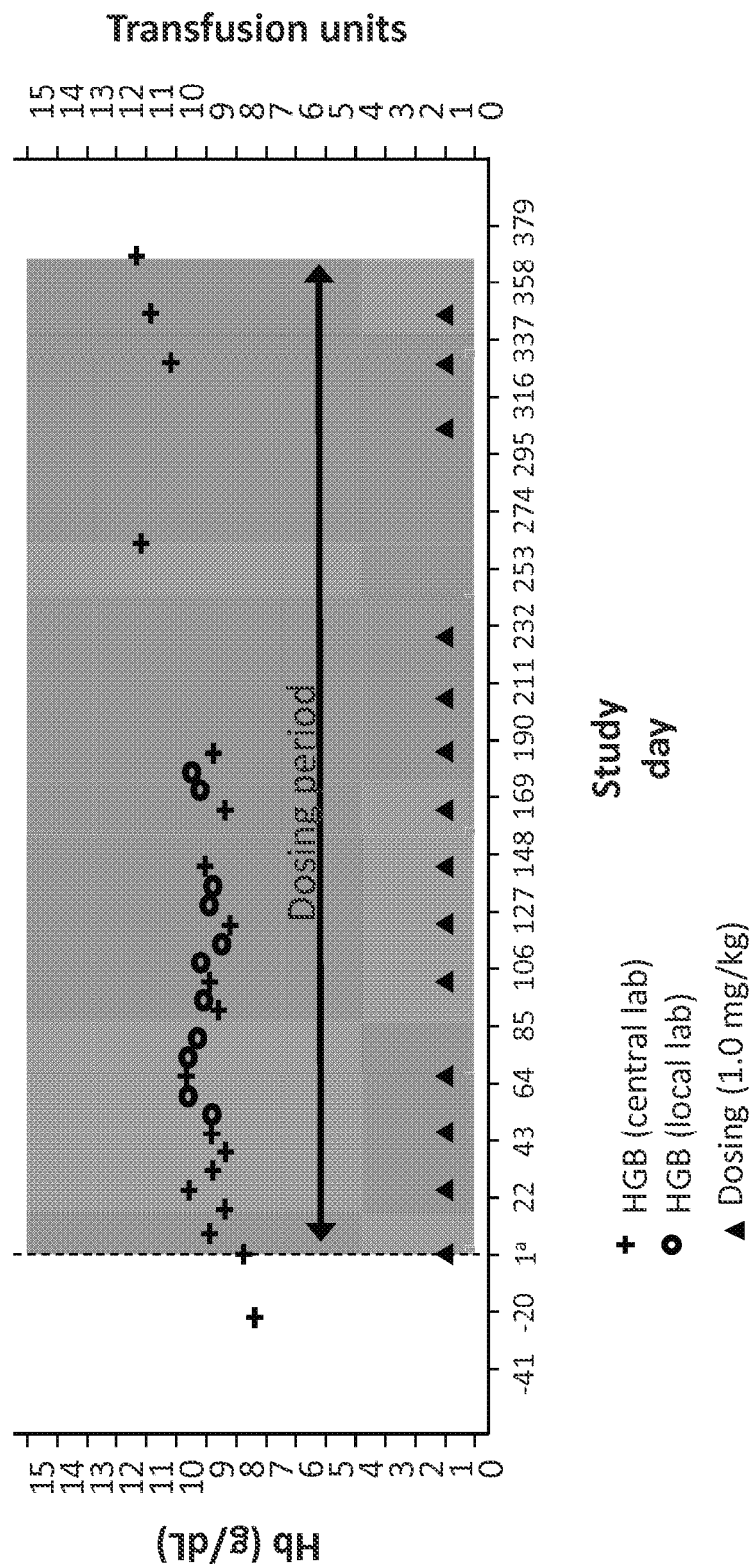
FIG. 15 depicts the hemoglobin level (Hb, g/dL) and number of RBC transfusion units received by an exemplary LTB subject whom received a 1.0 mg/kg dose of an ActRIIA (SEQ ID NO:7).

Additionally, of the 8 LTB subjects treated with ActRIIA-hFc (SEQ ID NO:7), 5 (63%) achieved RBC-TI with a mean Hb increase of at least 1.5 g/dL over any 8-week transfusion-free period. In particular, 33% of LTB subjects treated with 0.5 mg/kg of ActRIIA-hFc (SEQ ID NO:7) and 80% of LTB subjects treated with 1.0 mg/kg of ActRIIA-hFc (SEQ ID NO:7) achieved RBC-TI with a mean Hb increase of at least 1.5 g/dL over any 8-week transfusion-free period. The maximum mean Hb increases in treated LTB subjects treated with ActRIIA-hFc (SEQ ID NO:7) ranged between 1.45 g/dL and 4.44 g/dL. The duration of RBC-TI in the LTB subjects treated with ActRIIA-hFc (SEQ ID NO:7) ranged from 76 to 472 days. LTB subjects with Hb levels of greater than 11.0 g/dL were subject to dose delay, which may have impacted assessment of the duration of the Hb level increase. See FIG. 14 for an exemplary LTB subject who achieved RBC-TI and sustained increase in hemoglobin level for at least 358 days subsequent to the initiation of treatment with the ActRIIA-hFc (SEQ ID NO:7) at a dose of 1.0 mg/kg.

Furthermore, the association between treatment efficacy and the presence of ring sideroblasts (RS) at baseline was evaluated (see, Table 10). HI-E was achieved in 50% of RS-positive subjects. In contrast, HI-E was achieved in only 10% of RS-negative subjects.

TABLE 10

Status of ring sideroblasts in subjects treated with ActRIIA-hFc (SEQ ID NO: 7).

| RS status[a] | Mean EPO level at baseline (mIU/mL) | Mean transfusion burden at baseline (RBC units/8 weeks prior to first dose) | HI-E by ActRIIA-hFc (SEQ ID NO: 7) dose group and RS status n/N (%) | | | | |
|---|---|---|---|---|---|---|---|
| | | | 0.1 mg/kg | 0.3 mg/kg | 0.5 mg/kg | 1.0 mg/kg | Overall |
| RS-positive[b] | 346.53 | 7.04 | 0/6 (0) | 4/4 (100) | 5/9 (56) | 5/9 (56) | 14/28 (50) |

TABLE 10-continued

Status of ring sideroblasts in subjects treated with ActRIIA-hFc (SEQ ID NO: 7).

| RS status[a] | Mean EPO level at baseline (mIU/mL) | Mean transfusion burden at baseline (RBC units/8 weeks prior to first dose) | HI-E by ActRIIA-hFc (SEQ ID NO: 7) dose group and RS status n/N (%) | | | | |
|---|---|---|---|---|---|---|---|
| | | | 0.1 mg/kg | 0.3 mg/kg | 0.5 mg/kg | 1.0 mg/kg | Overall |
| RS-negative[c] | 1447.40 | 6.40 | 0/1 (0) | 0/3 (0) | 0/2 (0) | 1/5 (20) | 1/10 (10) |

[a]RS status is from baseline where available and from post-baseline otherwise; RS status was unknown for 16 subjects;
[b]>15% RS;
[c]≤15% RS ActRIIA-hFc (SEQ ID NO:7) was generally well tolerated. See Table 11. Four subjects discontinued treatment due to suspected treatment-related adverse events: Subject A (0.3 mg/kg dose group), grade 2 hemolytic anemia; Subject B (0.5 mg/kg dose group), grade 3 hypertension; Subject C (1.0 mg/kg dose group), grade 2 muscular weakness; Subject D (2.0 mg/kg dose group), and grade 2 increased blood pressure with grade 2 diarrhea.

8.5.3 Conclusions

ActRIIA-hFc (SEQ ID NO:7) is well tolerated in lower-risk MDS subjects at the dose levels tested, with promising evidence of clinical activity in this largely HTB cohort of ESA-refractory, anemic, lower-risk MDS subjects. Further, these data indicate that the presence of ring sideroblasts in subjects prior to treatment with an ActRII signaling inhibitor, e.g., ActRIIA-hFc (SEQ ID NO:7) can be an indicator for long-term treatment RBC transfusion independence, long-term increases in hemoglobin levels, and enhanced efficacy of the treatment.

8.6 Example 6

ActRIIB-hFc Increases Hemoglobin and Reduces Transfusion Burden in Subjects with Low or Intermediate-1 Risk MDS: Preliminary Results from a Phase 2 Study 8.6.1 Introduction See the Introduction (Section 8.3.1) and Materials and Methods (Section 8.3.2) for Example 3 (Section 8.3). This example presents additional data from Example 3 (Section 8.3), obtained at a later date in the Phase 2 study.

8.6.2 Results

Data were available for 44 subjects (15 LTB/29 HTB). Table 12 provides the baseline characteristics for the subjects studied in this example.

The erythroid response was evaluated in the subjects treated with ActRIIB-hFc (SEQ ID NO:25). For LTB subjects, the primary endpoint was a hemoglobin increase of at least 1.5 g/dL for at least 2 weeks. For HTB subjects, the primary endpoint was an at least 4 unit or at least 50%

TABLE 11

Adverse events in subjects treated with ActRIIA-hFc (SEQ ID NO: 7) at the indicated doses.

| | ActRIIA-hFc (SEQ ID NO: 7) dose group | | | | | |
|---|---|---|---|---|---|---|
| | 0.1 mg/kg (n = 7) | 0.3 mg/kg (n = 6) | 0.5 mg/kg (n = 21) | 1.0 mg/kg (n = 20) | 2.0 mg/kg (n = 5) | Overall (N = 59) |
| Subjects with ≥1 TEAE | 6 (86) | 3 (50) | 20 (95) | 19 (95) | 4 (80) | 52 (88) |
| TEAEs ≥ 10% of subjects | | | | | | |
| Fatigue/asthenia[a] | 0 | 1 (17) | 10 (48) | 12 (60) | 1 (20) | 24 (41) |
| Peripheral edema | 2 (29) | 2 (33) | 4 (19) | 4 (20) | 0 | 12 (20) |
| Diarrhea | 0 | 3 (50) | 11 (52) | 8 (40) | 2 (40) | 12 (20) |
| Nausea | 0 | 1 (17) | 4 (19) | 4 (20) | 1 (20) | 10 (17) |
| Constipation | 0 | 1 (17) | 6 (29) | 2 (10) | 0 | 9 (15) |
| Vomiting | 0 | 1 (17) | 2 (10) | 3 (15) | 1 (20) | 6 (10) |
| Decreased appetite | 0 | 0 | 3 (14) | 3 (15) | 0 | 6 (10) |
| Pain in extremity | 0 | 1 (17) | 2 (10) | 3 (15) | 1 (20) | 6 (10) |
| Headache | 3 (43) | 1 (17) | 2 (10) | 2 (10) | 1 (20) | 9 (15) |
| Dizziness | 1 (14) | 1 (17) | 5 (24) | 6 (30) | 0 | 6 (10) |
| Cough | 1 (14) | 1 (17) | 2 (10) | 5 (25) | 0 | 9 (15) |
| Dyspnea | 0 | 1 (17) | 4 (19) | 2 (10) | 0 | 7 (12) |
| Grade 3-4 TEAEs | 1 (14) | 1 (17) | 9 (43) | 5 (25) | 2 (40) | 18 (31) | reduction in RBC transfusion over 8 weeks. 33% (3/9) of subjects administered lower doses (0.125-0.5 mg/kg of ActRIIB-hFc (SEQ ID NO:25)) achieved the primary endpoint, while 63% (22/35) of subjects administered higher doses (0.75-1.75 mg/kg of ActRIIB-hFc (SEQ ID NO:25)) achieved the primary endpoint.

In addition, the IWG HI-E was evaluated. For LTB subjects, the IWG HI-E is a hemoglobin increase of at least 1.5 g/dL for at least 8 weeks. For HTB subjects, the IWG HI-E is an at least 4 unit reduction in RBC transfusion over 8 weeks. 22% (2/9) of subjects administered lower doses (0.125-0.5 mg/kg of ActRIIB-hFc (SEQ ID NO:25)) achieved the IWG HI-E, while 54% (19/35) of subjects administered higher doses (0.75-1.75 mg/kg of ActRIIB-hFc (SEQ ID NO:25)) achieved the IWG HI-E.

Figure 16:
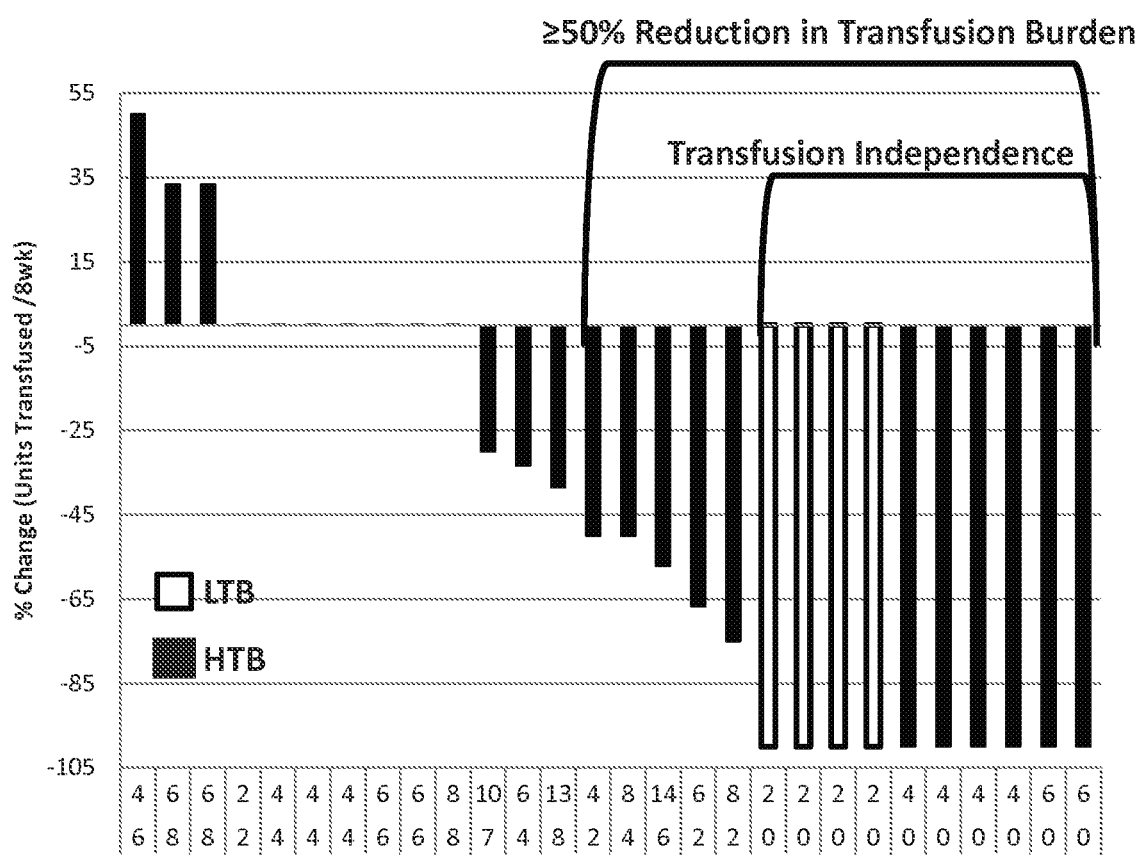
FIG. 16 depicts the transfusion burden in subjects eligible for attaining transfusion independence. Subjects were treated with between 0.75 mg/kg and 1.75 mg/kg of ActRIIB-hFc.

Ring sideroblasts are abnormal erythroblasts. Furthermore, certain somatic mutations associated with MDS cause ring sideroblast formation and ineffective erythropoiesis. Dominant mutations in splicing factor 3B1 (SF3B1) are associated with the formation of ring sideroblasts. As used herein, "RS+" refers to at least 15% ring sideroblasts. Thus, the association between the presence of ring sideroblasts, somatic mutations, and ineffective erythropoiesis and erythroid response and transfusion independence was evaluated in the subjects treated with the higher doses (0.75 mg/kg-1.75 mg/kg) of ActRIIB-hFc (SEQ ID NO:25) (see, Table 13 and Table 14). Subjects treated with ActRIIB-hFc achieved IWG HI-E and transfusion independence (see, Table 13, Table 14, and FIG. 16). These data indicate that there was an increased erythroid response in subjects treated with ActRIIB-hFc (SEQ ID NO:25) when the subjects were RS+ and/or had SF3B1 mutation(s).

TABLE 12

Baseline characteristics for subjects treated with ActRIIB-hFc (SEQ ID NO: 25)

| Parameter | N = 44 |
|---|---|
| Age, year, median (range) | 71 (27-88) |
| Sex, males (%) | 25 (57%) |
| Prior ESA treatment, n (%) | 27 (61%) |
| Prior lenalidomide treatment, n (%) | 9 (21%) |
| Low transfusion burden (LTB) | N = 15 (34%) |
| Hemoglobin, g/dL, median (range) | 9.0 (6.8-10.1) |
| Units RBC/8 weeks, median (range) | 2 (all subjects) |
| High Transfusion Burden (HTB) | N = 19 (73%) |
| Units RBC/8 weeks, median (range) | 6 (4-14) |
| IPSS | N = 44; n (%) |
| Low | 22 (50%) |
| Int-1 | 20 (46%) |
| Int-2 | 2 (4%) |
| IPSS-R | N = 44; n (%) |
| Very low | 2 (4.5%) |
| Low | 25 (57%) |
| Intermediate | 14 (32%) |
| High | 3 (7%) |
| Ring sideroblast (RS) | N = 44; n (%) |
| RS+ | 35 (80%) |
| RS− | 8 (18%) |
| RS non-evaluable | 1 (2%) |

TABLE 12-continued

Baseline characteristics for subjects treated with ActRIIB-hFc (SEQ ID NO: 25)

| Parameter | N = 44 |
|---|---|
| Splicing mutation (SF3B1) | N = 44; n (%) |
| SF3B1+ (mutation present) | 25 (57%) |
| SF3B1− (mutation absent) | 18 (41%) |
| SF3B1 non-evaluable | 1 (2%) |

TABLE 13

Erythroid response in RS+ and SF3B1 mutation positive subjects. For LTB subjects, the IWG HI-E is a hemoglobin increase of at least 1.5 g/dL for at least 8 weeks. For HTB subjects, the IWG HI-E is an at least 4 unit reduction in RBC transfusion over 8 weeks.

| Patient Population | IWG HI-E |
|---|---|
| All Patients (N = 35) | 19/35 (54%) |
| RS+ Patients (N = 30) | 19/30 (63%) |
| RS− Patients (N = 5) | 0/5 (0%) |
| SF3B1+ Patients (N = 22) | 16/22 (73%) |
| SF3B1− Patients (N = 13) | 3/13 (23%) |

TABLE 14

Transfusion independence in RS+ and SF3B1 mutation positive subjects. Transfusion independence refers to RBC transfusion-free for at least 8 weeks on treatment.

| Patient Population | Transfusion independence |
|---|---|
| All Patients (N = 28) | 10/28 36%) |
| RS+ Patients (N = 23) | 9/23 (39%) |
| RS− Patients (N = 4) | 1/4 (25%) |
| SF3B1+ Patients (N = 17) | 7/17 (41%) |
| SF3B1− Patients (N = 11) | 3/11 (27%) |

8.6.3 Conclusions

Administration of ActRIIB-hFc (SEQ ID NO:25) to MDS subjects subcutaneously every three weeks was generally safe and well-tolerated. Erythroid response (IWG HI-E) was achieved in 54% of subjects treated at doses of at least 0.75 mg/kg of ActRIIB-hFc (SEQ ID NO:25). Further, higher rates of erythroid responses were seen in subjects with ring sideroblasts or mutations in SF3B1. In addition, transfusion independence was achieved in 36% of subjects treated with ActRIIB-hFc (SEQ ID NO:25) at doses of at least 0.75 mg/kg.

8.7 Example 7

A Phase 2, Dose-Finding Study of ActRIIA-hFC (SEQ ID NO:7) in Patients with Lower-Risk MDS and Anemia Requiring Transfusion See the Introduction (Section 8.2.1) and Materials and Methods (Section 8.2.2) for Example 2 (Section 8.2). This example presents additional data from Example 2 (Section 8.2), obtained at a later date in the Phase 2 study.

The association between treatment efficacy and the presence of ring sideroblasts (RS) at baseline was further evaluated (see, Table 15).

Achievement of RBC-TI (with a mean Hb increase ≥1.5 g/dL for LTB patients) over any 8-week period is shown in FIG. 17.

TABLE 15

Erythroid Response: Sideroblastic vs Non-Sideroblastic MDS in subjects treated with ActRIIA-hFC fusion (SEQ ID NO: 7). HI-E achieved in 64% sideroblastic and 20% non-sideroblastic patients in the sotatercept 1.0 mg/kg dose group (Chi-square test P = 0.11)

| Ring sideroblasts[a] | HI-E by sotatercept dose group and RS status, n/N (%) | | | | |
|---|---|---|---|---|---|
| | 0.1 mg/kg | 0.3 mg/kg | 0.5 mg/kg | 1.0 mg/kg | 2.0 mg/kg |
| ≥15% | 0/6 | 4/4 (100) | 7/13 (54) | 7/11 (64) | 2/3 (67) |
| <15% | 0/1 | 0/2 | 2/6 (33) | 1/5 (20) | 0/2 |

[a]RS status is from baseline, where available; RS status was unknown for 6 patients.

8.8 Example 8

ActRIIB-hFc Increases Hemoglobin and Reduces Transfusion Burden in Subjects with Low or Intermediate-1 Risk MDS: Preliminary Results from a Phase 2 Study (Continued)

8.8.1 Introduction

See the Introduction (Section 8.3.1) and Materials and Methods (Section 8.3.2) for Example 3 (Section 8.3). This example presents additional data from Example 3 (Section 8.3), obtained at a later date in the Phase 2 study.

8.8.2 Results

A total of 49 MDS subjects were studied. 27 of the 49 MDS subjects were enrolled in a 3-month ActRIIB-hFc (SEQ ID NO:25) dose escalation study (0.125 mg/kg-1.75 mg/kg), and 22 subjects were enrolled in a subsequent extension study, as shown in Table 16. Table 17 provides the baseline characteristics for the subjects studied in this example.

3-Month Dose Escalation Study

The erythroid response was evaluated in the subjects treated with ActRIIB-hFc (SEQ ID NO:25). See Table 18. For LTB subjects, the primary endpoint was a hemoglobin increase of at least 1.5 g/dL for at least 2 weeks. For HTB subjects, the primary endpoint was an at least 4 unit or at least 50% reduction in RBC transfusion over 8 weeks. 33% (3/9) of subjects administered lower doses (0.125-0.5 mg/kg of ActRIIB-hFc (SEQ ID NO:25)) achieved the primary endpoint, while 58% (23/40) of subjects administered higher doses (0.75-1.75 mg/kg of ActRIIB-hFc (SEQ ID NO:25)) achieved the primary endpoint.

In addition, the IWG HI-E was evaluated. See Table 18. For LTB subjects, the IWG HI-E is a hemoglobin increase of at least 1.5 g/dL for at least 8 weeks. For HTB subjects, the IWG HI-E is an at least 4 unit reduction in RBC transfusion over 8 weeks. 22% (2/9) of subjects administered lower doses (0.125-0.5 mg/kg of ActRIIB-hFc (SEQ ID NO:25)) achieved the IWG HI-E, while 48% (19/40) of subjects administered higher doses (0.75-1.75 mg/kg of ActRIIB-hFc (SEQ ID NO:25)) achieved the IWG HI-E.

Furthermore, transfusion independence was evaluated. See Table 18. For subjects receiving at least two RBC units prior to ActRIIB-hFc (SEQ ID NO:25) therapy, transfusion independence was defined as the achievement of at least 8 weeks without transfusion while receiving ActRIIB-hFc (SEQ ID NO:25) treatments. 14% (1/7) of subjects administered lower doses (0.125-0.5 mg/kg of ActRIIB-hFc (SEQ ID NO:25)) achieved transfusion independence, while 37% (11/30) of subjects administered higher doses (0.75-1.75 mg/kg of ActRIIB-hFc (SEQ ID NO:25)) achieved transfusion independence. 4/6 LTB subjects and 7/24 HTB subjects achieved transfusion independence. 10 of the 11 transfusion independent patients had onset within the first 6 weeks of ActRIIB-hFc (SEQ ID NO:25) treatments.

The association between the presence of ring sideroblasts, somatic mutations, and ineffective erythropoiesis and erythroid response and transfusion independence was evaluated in the subjects treated with the higher doses (0.75 mg/kg-1.75 mg/kg) of ActRIIB-hFc (SEQ ID NO:25). See Table 19. 19/40 (48%) of all subjects in higher dose groups achieved the IWG HI-E. 19/35 (54%) of ring sideroblast (RS) positive subjects (defined as having at least 15% erythroid precursors in their bone marrow) achieved the IWG HI-E and 0/4 (0%) of the RS negative subjects achieved IWG HI-E. 14/23 (61%) RS positive subjects with EPO levels below 200 mU/mL achieved the IWG HI-E and 5/12 (42%) RS positive subjects with EPO levels below 200 mU/mL achieved the IWG HI-E. 16/26 (62%) subjects carrying the SF3B1 mutation and 3/13 (23%) subjects not carrying the SF3B1 mutation achieved the IWG HI-E.

In summary, the results presented in this example demonstrated ActRIIB-hFc (SEQ ID NO:25) treatments resulted in a robust erythroid response and transfusion independence, especially in subjects in the higher dose groups. In addition, an enriched erythroid response was found in RS+ positive and SF3B1 mutation positive subjects.

ActRIIA-hFc (SEQ ID NO:7) was generally well tolerated. See Table 20. The majority of adverse events (AEs) were grade 1 or 2. Two possibly related serious adverse events (SAEs) were observed: grade 3 muscle pain (onset day 90) and grade 3 worsening of general condition (onset day 44, recurred day 66, unrelated). One possibly related non-serious grade 3 AE of blast cell count was observed.

TABLE 16

Dosing Schedule of subjects treated with ActRIIB-hFc (SEQ ID NO: 25)

| | Dose Escalation | | | | | | | Expansion |
|---|---|---|---|---|---|---|---|---|
| Dose Level (mg/kg) | 0.125 | 0.25 | 0.5 | 0.75 | 1.0 | 1.33 | 1.75 | 1.0[a] |
| No. of Subjects | 3 | 3 | 3 | 6 | 3 | 6 | 3 | 22 |

[a]Starting dose level; dose level increased to 1.33 mg/kg in 8 subjects and to 1.75 mg/kg in 2 subjects.

TABLE 17

Baseline characteristics for subjects treated with ActRIIB-hFc (SEQ ID NO: 25)

| Parameter | N = 44 |
|---|---|
| Age, year, median (range) | 71 (27-88) |
| Sex, males (%) | 27 (55%) |
| Prior ESA treatment, n (%) | 30 (61%) |
| Prior lenalidomide treatment, n (%) | 9 (18%) |
| Time since diagnosis, yr, median (range) | 2.8 (0.2-13.6) |
| Low transfusion burden (LTB) | N = 17 (35%) |
| Hemoglobin, g/dL, median (range) | 8.7 (6.8-10.1) |
| Units RBC/8 weeks, median (range) | 2 (2-2) (n = 6) |
| High Transfusion Burden (HTB) | N = 32 (65%) |
| Units RBC/8 weeks, median (range) | 6 (4-14) (n = 32) |
| IPSS | N = 49; n (%) |
| Low | 27 (55%) |
| Int-1 | 20 (41%) |
| Int-2 | 2 (4%) |

TABLE 17-continued

Baseline characteristics for subjects treated with ActRIIB-hFc (SEQ ID NO: 25)

| Parameter | N = 44 |
|---|---|
| IPSS-R | N = 44; n (%) |
| Very low | 2 (4.5%) |
| Low | 30 (61%) |
| Intermediate | 14 (29%) |
| High | 3 (6%) |
| Ring sideroblast (RS) | N = 48; n (%) |
| RS+ | 40 (83%) |
| SF3B1+ (mutation present) | 29 (73%) |
| SF3B1− (mutation absent) | 11 (27%) |
| RS− | 8 (17%) |

TABLE 18

Erythroid response and transfusion independence in subjects treated with ActRIIB-hFc (SEQ ID NO: 25)

| Response Criteria | Lower Dose Groups 0.125-0.5 mg/kg N = 9 n % | Higher Dose Groups 0.75-0.175 mg/kg N = 40 n (%) |
|---|---|---|
| Primary Efficacy Endpoint | 3 (33%) | 23 (58%) |
| IWG HI-E | 2 (22%) | 19 (48%) |
| Transfusion Independence | 1/7 (14%) | 11/30 (37%)* |

| | LTB | HTB |
|---|---|---|
| | 4/6 | 7/24 |

*10 of the 11 transfusion independent patients had onset within the first 6 weeks of ActRIIB-hFc (SEQ ID NO: 25) treatments.

TABLE 19

Erythroid response and transfusion independence in subjects treated with ActRIIB-hFc (SEQ ID NO: 25)

| Patient Population | IWG HI-E |
|---|---|
| All Patients | 19/40 (48%) |
| RS positive | 19/35 (54%) |
| EPO < 200 | 14/23 (61%) |
| EPO ≥ 200 | 5/12 (42%) |
| SF3B1 mutation present | 16/26 (62%) |
| SF3B1 mutation present | 3/13 (23%) |

TABLE 20

Adverse events (all grades) reported in ≥4 subjects treated with ActRIIB-hFc (SEQ ID NO: 25), regardless of causality:

| Preferred Term N (%) | Lower Dose Groups 0.125-0.5 mg/kg N = 9 n % | Higher Dose Groups 0.75-0.175 mg/kg N = 40 n (%) | Overall N-49 |
|---|---|---|---|
| Myalgia | 2 (22) | 5 (13) | 7 (14) |
| Diarrhea | 2 (22) | 4 (10) | 6 (12) |
| Nasopharyngitis | 1 (11) | 5 (13) | 6 (12) |
| Headache | 0 | 5 (13) | 5 (10) |
| Abdominal Pain Upper | 1 (11) | 3 (8) | 4 (8) |
| Bone Pain | 1 (11) | 3 (8) | 4 (8) |
| Bronchitis | 0 | 4 (10) | 4 (8) |
| Fatigue | 0 | 4 (10) | 4 (8) |
| Hypertension | 0 | 4 (10) | 4 (8) |
| Muscle Spasms | 2 (22) | 2 (5) | 4 (8) |

Extension Study

Subjects who completed the 3-month dose escalation study were eligible to enroll in a subsequent 12-month extension study. Starting dose levels of ActRIIB-hFc (SEQ ID NO:25) were 1.0 mg/kg for subjects whose treatment was interrupted for more than 3 months. Subjects whose ActRIIB-hFc (SEQ ID NO:25) treatment was uninterrupted continued their treatments at the same dose level as their last dose in the 3-month treatment protocol.

A total of 58 subjects were enrolled in the 3-month treatment study. Of these, 22 subjects were enrolled in a 12-month extension study, 9 low transfusion burden patients and 13 high transfusion burden patients. In the extension study, 17/22 subjects continued their ActRIIB-hFc (SEQ ID NO:25) treatments uninterrupted and 5/22 subjects entered after an interruption of >3 months.

For the 9 low transfusion burden patients, the mean hemoglobin increase at one month was approximately 2 g/dL, increased to between 2.5 and 3.0 g/dL and was maintained for the 6-month period for which data are available.

For the 13 high transfusion burden patients, 43% achieved transfusion independence with several patients maintaining this transfusion independence for more than 6 months with the longest ongoing transfusion independent patient at nearly 8 months. All of these patients remained on study.

FIG. 18 shows the results for an exemplary subject. An RS-positive HTB subject was treated at a dose of 0.75 mg/kg ActRIIB-hFc (SEQ ID NO:25) in the initial 3-month treatment study and was enrolled in the 12-month extension study after an 11-month ActRIIB-hFc (SEQ ID NO:25) treatment interruption, during which the subject received EPO.

A durable hemoglobin response was observed in LTB subjects. 8/9 subjects achieved the IWG HI-E. FIG. 19 shows the hemoglobin response of an exemplary subject.

Subjects in the 12-month extension study showed durable transfusion independence response. FIG. 20 illustrates the results of 6 subjects. 5 subjects show a continuing transfusion independence response after 2-7 month while receiving ActRIIB-hFc (SEQ ID NO:25) treatments at doses of 1.0 mg/kg (4 subjects) and 1.75 mg/kg (1 subject). One subjects (last row in FIG. 20), received two dose titrations from 1.0 mg/kg to 1.33 mg/kg and 1.75 mg/kg. This latter subject experienced transfusion independence intermittently for about 2 months and continues to achieve the IWG HI-E response.

In conclusion, the results presented in this example demonstrated that lower risk RS-positive MDS subjects treated with ActRIIB-hFc (SEQ ID NO:25) demonstrated a robust hematologic improvement, especially if treated at doses of ≥0.75 mg/kg. ActRIIB-hFc (SEQ ID NO:25) treatments were generally well tolerated. Longer-term treatment with ActRIIB-hFc (SEQ ID NO:25) demonstrated sustained increases in hemoglobin level and maintained transfusion independence.

8.9 Example 9

A Phase III Study of ActRIIB-hFc (SEQ ID NO:25) to Treat Anemia Due to IPSS-R Very Low-, Low-, or Intermediate-Risk MDS This example provides an overview of a phase 3, double blind, placebo-controlled, multicenter, randomized study to determine the efficacy and safety of ActRIIB-hFc (SEQ ID NO:25) for the treatment of anemia due to IPSS-R very low-, low-, or intermediate-risk MDS in subjects with ring sideroblasts (at least 15% of erythroblasts are ring sideroblasts) who require RBC transfusions.

Anemia is considered to be one of the most prevalent cytopenias in patients who have myelodysplastic syndrome, an umbrella term used to describe disorders relating to the ineffective production of red blood cells, white blood cells, and/or platelets. Ranging in severity from mild (asymptomatic) to severe, anemia can result in patients requiring RBC transfusions, which can lead to further complications from iron overload. The goal of this study is to assess the safety and efficacy of ActRIIB-hFc (SEQ ID NO: 25) versus placebo in anemic patients who are categorized as IPSS-R very low-, low-, or intermediate-risk MDS, have ring sideroblasts present, and require RBC transfusions. The design of the study will allow a period of initial randomization of patients into either the ActRIIB-hFc (SEQ ID NO:25) or placebo arm, followed by a double-blind treatment period, and then an MDS disease assessment visit. For those patients that are determined to be experiencing clinical benefit as judged from the study Investigator by this disease assessment visit, they will be permitted to enter the double-blind Extension Phase of the study. Once patients are discontinued from study treatment, they will enter a post-treatment follow-up period.

8.9.1 Study Design

Subjects be administered an initial dose of 1.0 mg/kg of ActRIIB-hFc (SEQ ID NO: 25), subcutaneously, once every three weeks. Control subjects will be administered placebo, subcutaneously, once every three weeks.

(a) Inclusion Criteria

Inclusion criteria for subject participation in this study includes: (1) subject is ≥18 years of age the time of signing the informed consent form; (2) subject has a diagnosis of MDS that meets International Prognostic Scoring System-Revised (IPSS-R) classification of very low-, low-, or intermediate risk-disease and has: (a) greater than 15% of erythroid precursors in the bone marrow are ring sideroblasts, and (b) fewer than 5% blasts in the bone marrow; (3) subjects requiring red blood cell transfusions >2 units in an 8-week period; (4) Eastern Cooperative Oncology Group (ECOG) score of 0, 1, or 2; (5) subjects who are refractory/intolerant/ineligible to prior ESA treatment; refractory to prior ESA-treatment requires documentation of non-response or response that is no longer maintained to prior ESA-containing regimen, either as single agent or combination (e.g., with G-CSF); the ESA regimen must have been either (a) recombinant human erythropoietin of greater than 40,000 IU/week for at least 8 doses or equivalent, or (b) darbepoetin alpha of greater than 500 µg once every three weeks for at least 4 doses or equivalent; intolerant to prior ESA-treatment requires documentation of discontinuation of prior ESA-containing regimen, either as single agent or combination (e.g., with G-CSF), at any time after introduction due to intolerance or an adverse event; ESA-ineligible requires a low chance of response to ESA based on an endogenous serum erythropoietin level of greater than 200 U/L for subjects not previously treated with ESAs.

(b) Exclusion Criteria

The presence of any of the following will exclude a subject from enrollment in the study: (1) prior therapy with disease modifying agents (e.g., immune-modulatory drug, hypomethylating agents, or immunosuppressive therapy) or experimental agents for underlying MDS disease; (2) MDS associated with del 5q cytogenetic abnormality; (3) secondary MDS, i.e., MDS that is known to have arisen as the result of chemical injury or treatment with chemotherapy and/or radiation for other diseases; (4) known clinically significant anemia due to iron, vitamin B12, or folate deficiencies, or autoimmune or hereditary hemolytic anemia, or gastrointestinal bleeding; iron deficiency will be determined by a bone marrow aspirate stain for iron, calculated transferrin saturation (iron/total iron binding capacity) ≤20%, or serum ferritin ≤15 µg/L; (6) prior allogeneic or autologous stem cell transplant; (7) known history of diagnosis of Acute myeloid leukemia (AML); (8) use of any of the following within 5 weeks prior to randomization: anticancer cytotoxic chemotherapeutic agent or treatment, corticosteroid, except for subjects on a stable or decreasing dose for ≥1 week prior to randomization for medical conditions other than MDS, iron-chelating agents, except for subjects on a stable or decreasing dose for at least 8 weeks prior to randomization, other RBC hematopoietic growth factors (e.g., Interleukin-3); (9) prior history of malignancies, other than MDS, unless the subject has been free of the disease for ≥5 years; subjects with the following history/concurrent conditions are allowed: basal or squamous cell carcinoma of the skin, carcinoma in situ of the cervix, carcinoma in situ of the breast, incidental histologic finding of prostate cancer (T1a or T1b using the tumor, nodes, metastasis clinical staging system); or (10) major surgery within 8 weeks prior to randomization; subjects must have completely recovered from any previous surgery prior to randomization.

(c) Outcome Measurements

The primary outcome measurement for this study is the determination of the proportion of subjects administered ActRIIB-hFc (SEQ ID NO: 25) whom are RBC transfusion independent (i.e., do not require RBC transfusion) for any consecutive 56-day period.

Secondary outcome measurements include the determination of the proportion of subjects administered ActRIIB-hFc (SEQ ID NO: 25) having RBC transfusion independent (i.e., do not require RBC transfusion) for any consecutive 84-day period after administration of ActRIIB-hFc (SEQ ID NO:25). The proportion of subjects administered ActRIIB-hFc (SEQ ID NO:25) having a decrease in the number of RBC units transfused over a 16-week period after administration of ActRIIB-hFc (SEQ ID NO:25) will also be determined. Further, the maximum duration of RBC transfusion independence in subjects administered ActRIIB-hFc (SEQ ID NO:25) will also be determined. Finally, the time required for subjects administered ActRIIB-hFc (SEQ ID NO:25) to reach RBC transfusion independence will also be determined; the time to RBC transfusion independence is defined as the time between randomization and the date on which transfusion independence is first observed (e.g., day 1 of 56 days without any RBC transfusions).

The proportion of subjects administered ActRIIB-hFc (SEQ ID NO:25) achieving a modified erythroid hematological improvement over any consecutive 56-day period after administration of ActRIIB-hFc (SEQ ID NO:25) will also be determined. In certain aspects, the erythroid hematological improvement is as defined by IWG. In certain aspects, the erythroid hematological improvement is as defined by the modified 2006 IWG. In certain aspects, the erythroid hematological improvement for a low transfusion burden patient is an increase in hemoglobin concentration in the patient of at least 1.5 g/dL for at least 8 weeks. In certain aspects, the erythroid hematological improvement for a high transfusion burden patient is an at least 4 unit reduction in RBC transfusion over 8 weeks.

The proportion of subjects administered ActRIIB-hFc (SEQ ID NO:25) and achieving an increase in at least 1.0 g/dL of hemoglobin (as compared to hemoglobin concentration in the subject prior to administration of ActRIIB-hFc (SEQ ID NO:25) to the subject) over any consecutive 56-day period in the absence of RBC transfusion will be determined.

The mean decrease in serum ferritin levels in subjects administered ActRIIB-hFc (SEQ ID NO:25) as compared to serum ferritin levels prior to ActRIIB-hFc (SEQ ID NO:25 administration will be determined. Analysis of covariance (ANCOVA) will be used to compare the treatment difference between groups, with the stratification factors and baseline (pre-ActRIIB-hFC (SEQ ID NO:25) administration) serum ferritin value as covariates.

The mean decrease in iron chelation therapy use in subjects administered ActRIIB-hFc (SEQ ID NO:25) as compared to iron chelation therapy use prior to ActRIIB-hFc (SEQ ID NO:25 administration will be determined. The change in daily iron chelation therapy dose for each subject is calculated as the difference of post-baseline mean daily dose and baseline mean daily dose. Analysis of covariance (ANCOVA) will be used to compare the treatment difference between groups, with the stratification factors and baseline iron chelation therapy values and covariates.

The proportion of subjects administered ActRIIB-hFc (SEQ ID NO:25) achieving a neutrophil hematologic improvement over any consecutive 56-day period after administration of ActRIIB-hFc (SEQ ID NO:25) will also be determined. In certain aspects, the neutrophil hematological improvement is as defined by IWG. In certain aspects, the neutrophil hematological improvement is an increase in neutrophils by at least 100% and greater than 500/uL over a period of 56 consecutive days in the subject after administration of ActRIIB-hFc (SEQ ID NO:25) to the subject.

The proportion of subjects progressing to acute myeloid leukemia will also be determined.

The European Organization for Research and Treatment of Cancer Quality of Life Questionnaire will also be utilized and evaluated.

Adverse events, overall survival, population pharmacokinetics, and adverse events will also be evaluated.

9. DESCRIPTION OF THE SEQUENCES

TABLE 21

Sequence Information

| SEQ ID NO | DESCRIPTION | SEQUENCE |
|---|---|---|
| 1 | human ActRIIA precursor polypeptide | MGAAAKLAFAVFLISCSSGAILGRSETQECLFFNANWEKD RTNQTGVEPCYGDKDKRRHCFATWKNISGSIEIVKQGCWL DDINCYDRTDCVEKKDSPEVYFCCCEGNMCNEKFSYFPE MEVTQPTSNPVTPKPPYYNILLYSLVPLMLIAGIVICAFWV YRHHKMAYPPVLVPTQDPGPPPPSPLLGLKPLQLLEVKAR GRFGCVWKAQLLNEYVAVKIFPIQDKQSWQNEYEVYSLP GMKHENILQFIGAEKRGTSVDVDLWLITAFHEKGSLSDFL KANVVSWNELCHIAETMARGLAYLHEDIPGLKDGHKPAIS HRDIKSKNVLLKNNLTACIADFGLALKFEAGKSAGDTHGQ VGTRRYMAPEVLEGAINFQRDAFLRIDMYAMGLVLWELA SRCTAADGPVDEYMLPFEEEIGQHPSLEDMQEVVVHKKK RPVLRDYWQKHAGMAMLCETIEECWDHDAEARLSAGCV GERITQMQRLTNIITTEDIVTVVTMVTNVDFPPKESSL |
| 2 | human ActRIIA soluble (extracellular), processed polypeptide sequence | ILGRSETQECLFFNANWEKDRTNQTGVEPCYGDKDKRRH CFATWKNISGSIEIVKQGCWLDDINCYDRTDCVEKKDSPE VYFCCCEGNMCNEKFSYFPEMEVTQPTSNPVTPKPP |
| 3 | human ActRIIA soluble (extracellular), processed polypeptide sequence with the C-terminal 15 amino acids deleted | ILGRSETQECLFFNANWEKDRTNQTGVEPCYGDKDKRRH CFATWKNISGSIEIVKQGCWLDDINCYDRTDCVEKKDSPE VYFCCCEGNMCNEKFSYFPEM |
| 4 | nucleic acid sequence encoding human ActRIIA precursor protein | ATGGGAGCTGCTGCAAAGTTGGCGTTTGCCGTCTTTCTT ATCTCCTGTTCTTCAGGTGCTATACTTGGTAGATCAGAA ACTCAGGAGTGTCTTTTCTTTAATGCTAATTGGGAAAAA GACAGAACCAATCAAACTGGTGTTGAACCGTGTTATGG TGACAAAGATAAACGGCGGCATTGTTTTGCTACCTGGA AGAATATTTCTGGTTCCATTGAAATAGTGAAACAAGGTT GTTGGCTGGATGATATCAACTGCTATGACAGGACTGATT GTGTAGAAAAAAAAGACAGCCCTGAAGTATATTTTTGT TGCTGTGAGGGCAATATGTGTAATGAAAAGTTTTCTTAT TTTCCAGAGATGGAAGTCACACAGCCCACTTCAAATCC |

TABLE 21-continued

Sequence Information

| SEQ ID NO | DESCRIPTION | SEQUENCE |
|---|---|---|
| | | AGTTACACCTAAGCCACCCTATTACAACATCCTGCTCTA<br>TTCCTTGGTGCCACTTATGTTAATTGCGGGGATTGTCAT<br>TTGTGCATTTTGGGTGTACAGGCATCACAAGATGGCCTA<br>CCCTCCTGTACTTGTTCCAACTCAAGACCCAGGACCACC<br>CCCACCTTCTCCATTACTAGGGTTGAAACCACTGCAGTT<br>ATTAGAAGTGAAAGCAAGGGGAAGATTTGGTTGTGTCT<br>GGAAAGCCCAGTTGCTTAACGAATATGTGGCTGTCAAA<br>ATATTTCCAATACAGGACAAACAGTCATGGCAAAATGA<br>ATACGAAGTCTACAGTTTGCCTGGAATGAAGCATGAGA<br>ACATATTACAGTTCATTGGTGCAGAAAAACGAGGCACC<br>AGTGTTGATGTGGATCTTTGGCTGATCACAGCATTTCAT<br>GAAAAGGGTTCACTATCAGACTTTCTTAAGGCTAATGTG<br>GTCTCTTGGAATGAACTGTGTCATATTGCAGAAACCATG<br>GCTAGAGGATTGGCATATTTACATGAGGATATACCTGG<br>CCTAAAAGATGGCCACAAACCTGCCATATCTCACAGGG<br>ACATCAAAAGTAAAAATGTGCTGTTGAAAAACAACCTG<br>ACAGCTTGCATTGCTGACTTTGGGTTGGCCTTAAAATTT<br>GAGGCTGGCAAGTCTGCAGGCGATACCCATGGACAGGT<br>TGGTACCCGGAGGTACATGGCTCCAGAGGTATTAGAGG<br>GTGCTATAAACTTCGAAAGGGATGCATTTTTGAGGATA<br>GATATGTATGCCATGGGATTAGTCCTATGGGAACTGGCT<br>TCTCGCTGTACTGCTGCAGATGGACCTGTAGATGAATAC<br>ATGTTGCCATTTGAGGAGGAAATTGGCCAGCATCCATCT<br>CTTGAAGACATGCAGGAAGTTGTTGTGCATAAAAAAAA<br>GAGGCCTGTTTTAAGAGATTATTGGCAGAAACATGCTG<br>GAATGGCAATGCTCTGTGAAACCATTGAAGAATGTTGG<br>GATCACGACGCAGAAGCCAGGTTATCAGCTGGATGTGT<br>AGGTGAAAGAATTACCCAGATGCAGAGACTAACAAATA<br>TTATTACCACAGAGGACATTGTAACAGTGGTCACAATG<br>GTGACAAATGTTGACTTTCCTCCCAAAGAATCTAGTCTA<br>TGA |
| 5 | nucleic acid sequence encoding a human ActRIIA soluble (extracellular) polypeptide | ATACTTGGTAGATCAGAAACTCAGGAGTGTCTTTTCTTT<br>AATGCTAATTGGGAAAAAGACAGAACCAATCAAACTGG<br>TGTTGAACCGTGTTATGGTGACAAAGATAAACGGCGGC<br>ATTGTTTTGCTACCTGGAAGAATATTTCTGGTTCCATTG<br>AAATAGTGAAACAAGGTTGTTGGCTGGATGATATCAAC<br>TGCTATGACAGGACTGATTGTGTAGAAAAAAAAGACAG<br>CCCTGAAGTATATTTTTGTTGCTGTGAGGGCAATATGTG<br>TAATGAAAAGTTTTCTTATTTTCCAGAGATGGAAGTCAC<br>ACAGCCCACTTCAAATCCAGTTACACCTAAGCCACCC |
| 6 | fusion protein comprising a soluble extracellular domain of ActRIIA fused to an Fc domain | THTCPPCPAPELLGGPSVFLFPPKPKDTLMISRTPEVTCVVV<br>D(A)VSHEDPEVKFNWYVDGVEVHNAKTKPREEQYNSTY<br>RVVSVLTVLHQDWLNGKEYKCK(A)VSNKALPVPIEKTISK<br>AKGQPREPQVYTLPPSREEMTKNQVSLTCLVKGFYPSDIA<br>VEWESNGQPENNYKTTPPVLDSDGPFFLYSKLTVDKSRW<br>QQGNVFSCSVMHEALHN(A)HYTQKSLSLSPGK* |
| 7 | Extracellular domain of human ActRIIA fused to a human Fc domain | ILGRSETQECLFFNANWEKDRTNQTGVEPCYGDKDKRRH<br>CFATWKNISGSIEIVKQGCWLDDINCYDRTDCVEKKDSPE<br>VYFCCCEGNMCNEKFSYFPEMEVTQPTSNPVTPKPPTGGG<br>THTCPPCPAPELLGGPSVFLFPPKPKDTLMISRTPEVTCVVV<br>DVSHEDPEVKFNWYVDGVEVHNAKTKPREEQYNSTYRV<br>VSVLTVLHQDWLNGKEYKCKVSNKALPVPIEKTISKAKG<br>QPREPQVYTLPPSREEMTKNQVSLTCLVKGFYPSDIAVEW<br>ESNGQPENNYKTTPPVLDSDGSFFLYSKLTVDKSRWQQGN<br>VFSCSVMHEALHNHYTQKSLSLSPGK |
| 8 | Leader sequence of Honey bee mellitin (HBML) | MKFLVNVALVFMVVYISYIYA |
| 9 | Leader sequence of Tissue Plasminogen Activator (TPA) | MDAMKRGLCCVLLLCGAVFVSP |
| 10 | Native ActRIIA | MGAAAKLAFAVFLISCSSGA |
| 11 | ActRIIA-hFc and ActRIIA-mFc N-terminal sequence | ILGRSETQE |

TABLE 21-continued

Sequence Information

| SEQ ID NO | DESCRIPTION | SEQUENCE |
|---|---|---|
| 12 | ActRIIA-Fc Protein with deletion of the C-terminal 15 amino acids of the extracellular domain of ActRIIA | ILGRSETQECLFFNANWEKDRTNQTGVEPCYGDKDKRRH CFATWKNISGSIEIVKQGCWLDDINCYDRTDCVEKKDSPE VYFCCCEGNMCNEKFSYFPEMTGGGTHTCPPCPAPELLGG PSVFLFPPKPKDTLMISRTPEVTCVVVDVSHEDPEVKFNW YVDGVEVHNAKTKPREEQYNSTYRVVSVLTVLHQDWLN GKEYKCKVSNKALPVPIEKTISKAKGQPREPQVYTLPPSRE EMTKNQVSLTCLVKGFYPSDIAVEWESNGQPENNYKTTPP VLDSDGSFFLYSKLTVDKSRWQQGNVFSCSVMHEALHNH YTQKSLSLSPGK |
| 13 | Unprocessed ActRIIA-hFc with TPA leader sequence | MDAMKRGLCCVLLLCGAVFVSPGAAILGRSETQECLFFNA NWEKDRTNQTGVEPCYGDKDKRRHCFATWKNISGSIEIV KQGCWLDDINCYDRTDCVEKKDSPEVYFCCCEGNMCNE KFSYFPEMEVTQPTSNPVTPKPPTGGGTHTCPPCPAPELLG GPSVFLFPPKPKDTLMISRTPEVTCVVVDVSHEDPEVKFN WYVDGVEVHNAKTKPREEQYNSTYRVVSVLTVLHQDWL NGKEYKCKVSNKALPVPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 14 | Nucleic acid sequence encoding Unprocessed ActRIIA-hFc with TPA leader sequence | ATGGATGCAATGAAGAGAGGGCTCTGCTGTGTGCTGCT GCTGTGTGGAGCAGTCTTCGTTTCGCCCGGCGCGCTAT ACTTGGTAGATCAGAAACTCAGGAGTGTCTTTTTTTAAT GCTAATTGGGAAAAAGACAGAACCAATCAAACTGGTGT TGAACCGTGTTATGGTGACAAAGATAAACGGCGGCATT GTTTTGCTACCTGGAAGAATATTTCTGGTTCCATTGAAT AGTGAAACAAGGTTGTTGGCTGGATGATATCAACTGCT ATGACAGGACTGATTGTGTAGAAAAAAAAGACAGCCCT GAAGTATATTTCTGTTGCTGTGAGGGCAATATGTGTAAT GAAAAGTTTTCTTATTTTCCGGAGATGGAAGTCACACAG CCCACTTCAAATCCAGTTACACCTAAGCCACCCACCGGT GGTGGAACTCACACATGCCCACCGTGCCCAGCACCTGA ACTCCTGGGGGGACCGTCAGTCTTCCTCTTCCCCCCAAA ACCCAAGGACACCCTCATGATCTCCCGGACCCCTGAGG TCACATGCGTGGTGGTGGACGTGAGCCACGAAGACCCT GAGGTCAAGTTCAACTGGTACGTGGACGGCGTGGAGGT GCATAATGCCAAGACAAAGCCGCGGGAGGAGCAGTAC AACAGCACGTACCGTGTGGTCAGCGTCCTCACCGTCCTG CACCAGGACTGGCTGAATGGCAAGGAGTACAAGTGCAA GGTCTCCAACAAAGCCCTCCCAGTCCCCATCGAGAAAA CCATCTCCAAAGCCAAAGGGCAGCCCCGAGAACCACAG GTGTACACCCTGCCCCCATCCCGGGAGGAGATGACCAA GAACCAGGTCAGCCTGACCTGCCTGGTCAAAGGCTTCT ATCCCAGCGACATCGCCGTGGAGTGGGAGAGCAATGGG CAGCCGGAGAACAACTACAAGACCACGCCTCCCGTGCT GGACTCCGACGGCTCCTTCTTCCTCTATAGCAAGCTCAC CGTGGACAAGAGCAGGTGGCAGCAGGGGAACGTCTTCT CATGCTCCGTGATGCATGAGGCTCTGCACAACCACTAC ACGCAGAAGAGCCTCTCCCTGTCTCCGGGTAAATGAGA ATTC |
| 15 | human ActRIIB soluble (extracellular), processed polypeptide sequence with the N-terminal 6 amino acids of the EC domain deleted and the C-terminal 4 amino acids of the EC domain deleted (amino acids 25-130 of SEQ ID NO: 28) and with an L79D mutation | ETRECIYYNANWELERTNQSGLERCEGEQDKRLHCYASW RNSSGTIELVKKGCWDDDFNCYDRQECVATEENPQVYFC CCEGNFCNERFTHLPEAGGPEVTYEPPP |
| 16 | human ActRIIB precursor protein sequence (A64) | MTAPWVALALLWGSLWPGSGRGEAETRECIYYNANWEL ERTNQSGLERCEGEQDKRLHCYASWANSSGTIELVKKGC WLDDFNCYDRQECVATEENPQVYFCCCEGNFCNERFTHL PEAGGPEVTYEPPPTAPTLLTVLAYSLLPIGGLSLIVLLAFW MYRHRKPPYGHVDIHEDPGPPPPSPLVGLKPLQLLEIKARG |

TABLE 21-continued

Sequence Information

| SEQ ID NO | DESCRIPTION | SEQUENCE |
|---|---|---|
| | | RFGCVWKAQLMNDFVAVKIFPLQDKQSWQSEREIFSTPG<br>MKHENLLQFIAAEKRGSNLEVELWLITAFHDKGSLTDYLK<br>GNIITWNELCHVAETMSRGLSYLHEDVPWCRGEGHKPSIA<br>HRDFKSKNVLLKSDLTAVLADFGLAVRFEPGKPPGDTHG<br>QVGTRRYMAPEVLEGAINFQRDAFLRIDMYAMGLVLWEL<br>VSRCKAADGPVDEYMLPFEEEIGQHPSLEELQEVVVHKK<br>MRPTIKDHWLKHPGLAQLCVTIEECWDHDAEARLSAGCV<br>EERVSLIRRSVNGTTSDCLVSLVTSVTNVDLPPKESSI |
| 17 | human ActRIIB soluble (extracellular), processed polypeptide sequence (amino acids 19-134 of SEQ ID NO: 16) | SGRGEAETRECIYYNANWELERTNQSGLERCEGEQDKRL<br>HCYASWANSSGTIELVKKGCWLDDFNCYDRQECVATEEN<br>PQVYFCCCEGNFCNERFTHLPEAGGPEVTYEPPPTAPT |
| 18 | human ActRIIB soluble (extracellular), processed polypeptide sequence with the C-terminal 15 amino acids deleted (amino acids 19-119 of SEQ ID NO: 16) | SGRGEAETRECIYYNANWELERTNQSGLERCEGEQDKRL<br>HCYASWANSSGTIELVKKGCWLDDFNCYDRQECVATEEN<br>PQVYFCCCEGNFCNERFTHLPEA |
| 19 | nucleic acid sequence encoding a human ActRIIB (A64) precursor protein | ATGACGGCGCCCTGGGTGGCCCTCGCCCTCCTCTGGGG<br>ATCGCTGTGGCCCGGCTCTGGGCGTGGGGAGGCTGAGA<br>CACGGGAGTGCATCTACTACAACGCCAACTGGGAGCTG<br>GAGCGCACCAACCAGAGCGGCCTGGAGCGCTGCGAAG<br>GCGAGCAGGACAAGCGGCTGCACTGCTACGCCTCCTGG<br>GCCAACAGCTCTGGCACCATCGAGCTCGTGAAGAAGGG<br>CTGCTGGCTAGATGACTTCAACTGCTACGATAGGCAGG<br>AGTGTGTGGCCACTGAGGAGAACCCCCAGGTGTACTTC<br>TGCTGCTGTGAAGGCAACTTCTGCAACGAGCGCTTCACT<br>CATTTGCCAGAGGCTGGGGGCCCGGAAGTCACGTACGA<br>GCCACCCCCGACAGCCCCCACCCTGCTCACGGTGCTGG<br>CCTACTCACTGCTGCCCATCGGGGGCCTTTCCCTCATCG<br>TCCTGCTGGCCTTTTGGATGTACCGGCATCGCAAGCCCC<br>CCTACGGTCATGTGGACATCCATGAGGACCCTGGGCCT<br>CCACCACCATCCCCTCTGGTGGGCCTGAAGCCACTGCA<br>GCTGCTGGAGATCAAGGCTCGGGGCGCTTTGGCTGTG<br>TCTGGAAGGCCCAGCTCATGAATGACTTTGTAGCTGTCA<br>AGATCTTCCCACTCCAGGACAAGCAGTCGTGGCAGAGT<br>GAACGGGAGATCTTCAGCACACCTGGCATGAAGCACGA<br>GAACCTGCTACAGTTCATTGCTGCCGAGAAGCGAGGCT<br>CCAACCTCGAAGTAGAGCTGTGGCTCATCACGGCCTTCC<br>ATGACAAGGGCTCCCTCACGGATTACCTCAAGGGGAAC<br>ATCATCACATGGAACGAACTGTGTCATGTAGCAGAGAC<br>GATGTCACGAGGCCTCTCATACCTGCATGAGGATGTGC<br>CCTGGTGCCGTGGCGAGGGCCACAAGCCGTCTATTGCC<br>CACAGGGACTTTAAAAGTAAGAATGTATTGCTGAAGAG<br>CGACCTCACAGCCGTGCTGGCTGACTTTGGCTTGGCTGT<br>TCGATTTGAGCCAGGGAAACCTCCAGGGGACACCCACG<br>GACAGGTAGGCACGAGACGGTACATGGCTCCTGAGGTG<br>CTCGAGGGAGCCATCAACTTCCAGAGAGATGCCTTCCT<br>GCGCATTGACATGTATGCCATGGGGTTGGTGCTGTGGG<br>AGCTTGTGTCTCGCTGCAAGGCTGCAGACGGACCCGTG<br>GATGAGTACATGCTGCCCTTTGAGGAAGAGATTGGCCA<br>GCACCCTTCGTTGGAGGAGCTGCAGGAGGTGGTGGTGC<br>ACAAGAAGATGAGGCCCACCATTAAAGATCACTGGTTG<br>AAACACCCGGGCCTGGCCCAGCTTTGTGTGACCATCGA<br>GGAGTGCTGGGACCATGATGCAGAGGCTCGCTTGTCCG<br>CGGGCTGTGTGGAGGAGCGGGTGTCCCTGATTCGGAGG<br>TCGGTCAACGGCACTACCTCGGACTGTCTCGTTTCCCTG<br>GTGACCTCTGTCACCAATGTGGACCTGCCCCCTAAAGA<br>GTCAAGCATCTAA |

TABLE 21-continued

Sequence Information

| SEQ ID NO | DESCRIPTION | SEQUENCE |
|---|---|---|
| 20 | fusion protein comprising a soluble extracellular domain of ActRIIB (A64; SEQ ID NO: 17) fused to an Fc domain | SGRGEAETRECIYYNANWELERTNQSGLERCEGEQDKRL HCYASWANSSGTIELVKKGCWLDDFNCYDRQECVATEEN PQVYFCCCEGNFCNERFTHLPEAGGPEVTYEPPPTAPTGG GTHTCPPCPAPELLGGPSVFLFPPKPKDTLMISRTPEVTCVV VDVSHEDPEVKFNWYVDGVEVHNAKTKPREEQYNSTYR VVSVLTVLHQDWLNGKEYKCKVSNKALPVPIEKTISKAK GQPREPQVYTLPPSREEMTKNQVSLTCLVKGFYPSDIAVE WESNGQPENNYKTTPPVLDSDGSFFLYSKLTVDKSRWQQ GNVFSCSVMHEALHNHYTQKSLSLSPGK |
| 21 | fusion protein comprising a soluble extracellular domain of ActRIIB (A64) with the C-terminal 15 amino acids deleted (SEQ ID NO: 18) fused to an Fc domain | SGRGEAETRECIYYNANWELERTNQSGLERCEGEQDKRL HCYASWANSSGTIELVKKGCWLDDFNCYDRQECVATEEN PQVYFCCCEGNFCNERFTHLPEAGGGTHTCPPCPAPELLG GPSVFLFPPKPKDTLMISRTPEVTCVVVDVSHEDPEVKFN WYVDGVEVHNAKTKPREEQYNSTYRVVSVLTVLHQDWL NGKEYKCKVSNKALPVPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 22 | human ActRIIB soluble (extracellular), processed polypeptide sequence with the N-terminal 6 amino acids of the EC domain deleted and the C-terminal 5 amino acids of the EC domain deleted (amino acids 25-129 of SEQ ID NO: 28) and with an L79D mutation | ETRECIYYNANWELERTNQSGLERCEGEQDKRLHCYASW RNSSGTIELVKKGCWDDDFNCYDRQECVATEENPQVYFC CCEGNFCNERFTHLPEAGGPEVTYEPP |
| 23 | human ActRIIB soluble (extracellular), processed polypeptide sequence with the N-terminal 6 amino acids of the EC domain deleted and the C-terminal 3 amino acids of the EC domain deleted (amino acids 25-131 of SEQ ID NO: 28) and with an L79D mutation | ETRECIYYNANWELERTNQSGLERCEGEQDKRLHCYASW RNSSGTIELVKKGCWDDDFNCYDRQECVATEENPQVYFC CCEGNFCNERFTHLPEAGGPEVTYEPPPT |
| 24 | Unprocessed ActRIIB-Fc fusion protein with the N-terminal 6 amino acids of the EC domain deleted and the C-terminal 3 amino acids of the EC domain deleted (amino acids 25-131 of SEQ ID NO: 28) and with an L79D mutation and with TPA leader sequence | MDAMKRGLCCVLLLCGAVFVSPGAAETRECIYYNANWEL ERTNQSGLERCEGEQDKRLHCYASWRNSSGTIELVKKGC WDDDFNCYDRQECVATEENPQVYFCCCEGNFCNERFTHL PEAGGPEVTYEPPPTGGGTHTCPPCPAPELLGGPSVFLFPPK PKDTLMISRTPEVTCVVVDVSHEDPEVKFNWYVDGVEVH NAKTKPREEQYNSTYRVVSVLTVLHQDWLNGKEYKCKV SNKALPAPIEKTISKAKGQPREPQVYTLPPSREEMTKNQVS LTCLVKGFYPSDIAVEWESNGQPENNYKTTPPVLDSDGSF FLYSKLTVDKSRWQQGNVFSCSVMHEALHNHYTQKSLSL SPGK |

TABLE 21-continued

Sequence Information

| SEQ ID NO | DESCRIPTION | SEQUENCE |
|---|---|---|
| 25 | Processed ActRIIB-Fc fusion protein with the N-terminal 6 amino acids of the EC domain deleted and the C-terminal 3 amino acids of the EC domain deleted (amino acids 25-131 of SEQ ID NO: 28) and with an L79D mutation | ETRECIYYNANWELERTNQSGLERCEGEQDKRLHCYASW RNSSGTIELVKKGCWDDDFNCYDRQECVATEENPQVYFC CCEGNFCNERFTHLPEAGGPEVTYEPPPTGGGTHTCPPCPA PELLGGPSVFLFPPKPKDTLMISRTPEVTCVVVDVSHEDPE VKFNWYVDGVEVHNAKTKPREEQYNSTYRVVSVLTVLH QDWLNGKEYKCKVSNKALPAPIEKTISKAKGQPREPQVYT LPPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGK |
| 26 | human ActRIIB soluble (extracellular), processed polypeptide sequence (amino acids 20-134 of SEQ ID NO: 16) | GRGEAETRECIYYNANWELERTNQSGLERCEGEQDKRLH CYASWANSSGTIELVKKGCWLDDFNCYDRQECVATEENP QVYFCCCEGNFCNERFTHLPEAGGPEVTYEPPPTAPT |
| 27 | human ActRIIB soluble (extracellular), processed polypeptide sequence with the C-terminal 15 amino acids deleted (amino acids 20-119 of SEQ ID NO: 16) | GRGEAETRECIYYNANWELERTNQSGLERCEGEQDKRLH CYASWANSSGTIELVKKGCWLDDFNCYDRQECVATEENP QVYFCCCEGNFCNERFTHLPEA |
| 28 | human ActRIIB precursor protein sequence (R64) | MTAPWVALALLWGSLWPGSGRGEAETRECIYYNANWEL ERTNQSGLERCEGEQDKRLHCYASWRNSSGTIELVKKGC WLDDFNCYDRQECVATEENPQVYFCCCEGNFCNERFTHL PEAGGPEVTYEPPPTAPTLLTVLAYSLLPIGGLSLIVLLAFW MYRHRKPPYGHVDIHEDPGPPPPSPLVGLKPLQLLEIKARG RFGCVWKAQLMNDFVAVKIFPLQDKQSWQSEREIFSTPG MKHENLLQFIAAEKRGSNLEVELWLITAFHDKGSLTDYLK GNIITWNELCHVAETMSRGLSYLHEDVPWCRGEGHKPSIA HRDFKSKNVLLKSDLTAVLADFGLAVRFEPGKPPGDTHG QVGTRRYMAPEVLEGAINFQRDAFLRIDMYAMGLVLWEL VSRCKAADGPVDEYMLPFEEEIGQHPSLEELQEVVVHKK MRPTIKDHWLKHPGLAQLCVTIEECWDHDAEARLSAGCV EERVSLIRRSVNGTTSDCLVSLVTSVTNVDLPPKESSI |
| 29 | human ActRIIB soluble (extracellular), processed polypeptide sequence (amino acids 19-134 of SEQ ID NO: 28) | SGRGEAETRECIYYNANWELERTNQSGLERCEGEQDKRL HCYASWRNSSGTIELVKKGCWLDDFNCYDRQECVATEEN PQVYFCCCEGNFCNERFTHLPEAGGPEVTYEPPPTAPT |
| 30 | human ActRIIB soluble (extracellular), processed polypeptide sequence with the C-terminal 15 amino acids deleted (amino acids 19-119 of SEQ ID NO: 28) | SGRGEAETRECIYYNANWELERTNQSGLERCEGEQDKRL HCYASWRNSSGTIELVKKGCWLDDFNCYDRQECVATEEN PQVYFCCCEGNFCNERFTHLPEA |

TABLE 21-continued

Sequence Information

| SEQ ID NO | DESCRIPTION | SEQUENCE |
|---|---|---|
| 31 | human ActRIIB soluble (extracellular), processed polypeptide sequence (amino acids 20-134 of SEQ ID NO: 28) | GRGEAETRECIYYNANWELERTNQSGLERCEGEQDKRLH CYASWRNSSGTIELVKKGCWLDDFNCYDRQECVATEENP QVYFCCCEGNFCNERFTHLPEAGGPEVTYEPPPTAPT |
| 32 | human ActRIIB soluble (extracellular), processed polypeptide sequence with the C-terminal 15 amino acids deleted (amino acids 20-119 of SEQ ID NO: 28) | GRGEAETRECIYYNANWELERTNQSGLERCEGEQDKRLH CYASWRNSSGTIELVKKGCWLDDFNCYDRQECVATEENP QVYFCCCEGNFCNERFTHLPEA |
| 33 | human ActRIIB soluble (extracellular), processed polypeptide sequence with the N-terminal 6 amino acids of the EC domain deleted and the C-terminal 3 amino acids of the EC domain deleted (amino acids 25-131 of SEQ ID NO: 16) and with an L79D mutation | ETRECIYYNANWELERTNQSGLERCEGEQDKRLHCYASW ANSSGTIELVKKGCWDDDFNCYDRQECVATEENPQVYFC CCEGNFCNERFTHLPEAGGPEVTYEPPPT |
| 34 | Unprocessed ActRIIB-Fc fusion protein with the N-terminal 6 amino acids of the EC domain deleted and the C-terminal 3 amino acids of the EC domain deleted (amino acids 25-131 of SEQ ID NO: 16) and with an L79D mutation and with TPA leader sequence | MDAMKRGLCCVLLLCGAVFVSPGAAETRECIYYNANWEL ERTNQSGLERCEGEQDKRLHCYASWANSSGTIELVKKGC WDDDFNCYDRQECVATEENPQVYFCCCEGNFCNERFTHL PEAGGPEVTYEPPPTGGGTHTCPPCPAPELLGGPSVFLFPPPK PKDTLMISRTPEVTCVVVDVSHEDPEVKFNWYVDGVEVH NAKTKPREEQYNSTYRVVSVLTVLHQDWLNGKEYKCKV SNKALPAPIEKTISKAKGQPREPQVYTLPPSREEMTKNQVS LTCLVKGFYPSDIAVEWESNGQPENNYKTTPPVLDSDGSF FLYSKLTVDKSRWQQGNVFSCSVMHEALHNHYTQKSLSL SPGK |
| 35 | Processed ActRIIB-Fc fusion protein with the N-terminal 6 amino acids of the EC domain deleted and the C-terminal 3 amino acids of the EC domain deleted (amino acids 25-131 of SEQ ID NO: 16) and with an L79D mutation | ETRECIYYNANWELERTNQSGLERCEGEQDKRLHCYASW ANSSGTIELVKKGCWDDDFNCYDRQECVATEENPQVYFC CCEGNFCNERFTHLPEAGGPEVTYEPPPTGGGTHTCPPCPA PELLGGPSVFLFPPPKPKDTLMISRTPEVTCVVVDVSHEDPE VKFNWYVDGVEVHNAKTKPREEQYNSTYRVVSVLTVLH QDWLNGKEYKCKVSNKALPAPIEKTISKAKGQPREPQVYT LPPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGK |

TABLE 21-continued

Sequence Information

| SEQ ID NO | DESCRIPTION | SEQUENCE |
|---|---|---|
| 36 | human ActRIIB soluble (extracellular), processed polypeptide sequence (amino acids 20-134 of SEQ ID NO: 28) with L79D mutation | GRGEAETRECIYYNANWELERTNQSGLERCEGEQDKRLH CYASWRNSSGTIELVKKGCWDDDFNCYDRQECVATEENP QVYFCCCEGNFCNERFTHLPEAGGPEVTYEPPPTAPT |
| 37 | human ActRIIB soluble (extracellular), processed polypeptide sequence (amino acids 20-134 of SEQ ID NO: 16) with L79D mutation | GRGEAETRECIYYNANWELERTNQSGLERCEGEQDKRLH CYASWANSSGTIELVKKGCWDDDFNCYDRQECVATEENP QVYFCCCEGNFCNERFTHLPEAGGPEVTYEPPPTAPT |
| 38 | human ActRIIB soluble (extracellular), processed polypeptide sequence (amino acids 20-134 of SEQ ID NO: 28) with L79D mutation fused to an Fc domain with a GGG linker | GRGEAETRECIYYNANWELERTNQSGLERCEGEQDKRLH CYASWRNSSGTIELVKKGCWDDDFNCYDRQECVATEENP QVYFCCCEGNFCNERFTHLPEAGGPEVTYEPPPTAPTGGG THTCPPCPAPELLGGPSVFLFPPKPKDTLMISRTPEVTCVVV DVSHEDPEVKFNWYVDGVEVHNAKTKPREEQYNSTYRV VSVLTVLHQDWLNGKEYKCKVSNKALPAPIEKTISKAKG QPREPQVYTLPPSREEMTKNQVSLTCLVKGFYPSDIAVEW ESNGQPENNYKTTPPVLDSDGSFFLYSKLTVDKSRWQQGN VFSCSVMHEALHNHYTQKSLSLSPGK |
| 39 | human ActRIIB soluble (extracellular), processed polypeptide sequence (amino acids 20-134 of SEQ ID NO: 16) with L79D mutation fused to an Fc domain | GRGEAETRECIYYNANWELERTNQSGLERCEGEQDKRLH CYASWANSSGTIELVKKGCWDDDFNCYDRQECVATEENP QVYFCCCEGNFCNERFTHLPEAGGPEVTYEPPPTAPTGGG THTCPPCPAPELLGGPSVFLFPPKPKDTLMISRTPEVTCVVV DVSHEDPEVKFNWYVDGVEVHNAKTKPREEQYNSTYRV VSVLTVLHQDWLNGKEYKCKVSNKALPAPIEKTISKAKG QPREPQVYTLPPSREEMTKNQVSLTCLVKGFYPSDIAVEW ESNGQPENNYKTTPPVLDSDGSFFLYSKLTVDKSRWQQGN VFSCSVMHEALHNHYTQKSLSLSPGK |
| 40 | human ActRIIB soluble (extracellular), processed polypeptide sequence (amino acids 20-134 of SEQ ID NO: 28) with L79D mutation fused to an Fc domain and with TPA leader sequence | MDAMKRGLCCVLLLCGAVFVSPGASGRGEAETRECIYYN ANWELERTNQSGLERCEGEQDKRLHCYASWRNSSGTIEL VKKGCWDDDFNCYDRQECVATEENPQVYFCCCEGNFCN ERFTHLPEAGGPEVTYEPPPTAPTGGGTHTCPPCPAPELLG GPSVFLFPPKPKDTLMISRTPEVTCVVVDVSHEDPEVKFN WYVDGVEVHNAKTKPREEQYNSTYRVVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPGK |

TABLE 21-continued

Sequence Information

| SEQ ID NO | DESCRIPTION | SEQUENCE |
|---|---|---|
| 41 | human ActRIIB soluble (extracellular), processed polypeptide sequence (amino acids 20-134 of SEQ ID NO: 16) with L79D mutation fused to an Fc domain and with TPA leader sequence | MDAMKRGLCCVLLLCGAVFVSPGASGRGEAETRECIYYN ANWELERTNQSGLERCEGEQDKRLHCYASWANSSGTIEL VKKGCWDDDFNCYDRQECVATEENPQVYFCCCEGNFCN ERFTHLPEAGGPEVTYEPPPTAPTGGGTHTCPPCPAPELLG GPSVFLFPPKPKDTLMISRTPEVTCVVVDVSHEDPEVKFN WYVDGVEVHNAKTKPREEQYNSTYRVVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 42 | human ActRIIB soluble (extracellular), processed polypeptide sequence having a variant C-terminal sequence (disclosed in WO2007/053775) | GRGEAETRECIYYNANWELERTNQSGLERCEGEQDKRLH CYASWRNSSGTIELVKKGCWLDDFNCYDRQECVATEENP QVYFCCCEGNFCNERFTHLPEAGGPEGPWASTTIPSGGPEA TAAAGDQGSGALWLCLEGPAHE |
| 43 | human ActRIIB soluble (extracellular), processed polypeptide sequence having a variant C-terminal sequence (disclosed in WO2007/053775) having an L79D mutation | GRGEAETRECIYYNANWELERTNQSGLERCEGEQDKRLH CYASWRNSSGTIELVKKGCWDDDFNCYDRQECVATEENP QVYFCCCEGNFCNERFTHLPEAGGPEGPWASTTIPSGGPEA TAAAGDQGSGALWLCLEGPAHE |
| 44 | human ActRIIB soluble (extracellular), processed polypeptide sequence having a variant C-terminal sequence (disclosed in WO2007/053775) having an L79D mutation fused to an Fc domain with a TGGG linker | GRGEAETRECIYYNANWELERTNQSGLERCEGEQDKRLH CYASWRNSSGTIELVKKGCWDDDFNCYDRQECVATEENP QVYFCCCEGNFCNERFTHLPEAGGPEGPWASTTIPSGGPEA TAAAGDQGSGALWLCLEGPAHETGGGTHTCPPCPAPELL GGPSVFLFPPKPKDTLMISRTPEVTCVVVDVSHEDPEVKFN WYVDGVEVHNAKTKPREEQYNSTYRVVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 45 | Nucleic Acid Sequence Encoding SEQ ID NO: 24 | ATGGATGCAATGAAGAGAGGGCTCTGCTGTGTGCTGCT GCTGTGTGGAGCAGTCTTCGTTTCGCCCGGCGCCGCCGA AACCCGCGAATGTATTTATTACAATGCTAATTGGGAACT CGAACGGACGAACCAATCCGGGCTCGAACGGTGTGAGG GGGAACAGGATAAACGCCTCCATTGCTATGCGTCGTGG AGGAACTCCTCCGGGACGATTGAACTGGTCAAGAAAGG GTGCTGGGACGACGATTTCAATTGTTATGACCGCCAGG AATGTGTCGCGACCGAAGAGAATCCGCAGGTCTATTTC TGTTGTTGCGAGGGGAATTTCTGTAATGAACGGTTTACC CACCTCCCCGAAGCCGGCGGGCCCGAGGTGACCTATGA ACCCCCGCCCACCGGTGGTGGAACTCACACATGCCCAC CGTGCCCAGCACCTGAACTCCTGGGGGGACCGTCAGTC TTCCTCTTCCCCCCAAAACCCAAGGACACCCTCATGATC TCCCGGACCCCTGAGGTCACATGCGTGGTGGTGGACGT GAGCCACGAAGACCCTGAGGTCAAGTTCAACTGGTACG TGGACGGCGTGGAGGTGCATAATGCCAAGACAAAGCCG CGGGAGGAGCAGTACAACAGCACGTACCGTGTGGTCAG CGTCCTCACCGTCCTGCACCAGGACTGGCTGAATGGCA AGGAGTACAAGTGCAAGGTCTCCAACAAAGCCCTCCCA GCCCCCATCGAGAAAACCATCTCCAAAGCCAAAGGGCA GCCCCGAGAACCACAGGTGTACACCCTGCCCCCATCCC GGGAGGAGATGACCAAGAACCAGGTCAGCCTGACCTGC CTGGTCAAAGGCTTCTATCCCAGCGACATCGCCGTGGA |

TABLE 21-continued

Sequence Information

| SEQ ID NO | DESCRIPTION | SEQUENCE |
|---|---|---|
| | | GTGGGAGAGCAATGGGCAGCCGGAGAACAACTACAAG ACCACGCCTCCCGTGCTGGACTCCGACGGCTCCTTCTTC CTCTATAGCAAGCTCACCGTGGACAAGAGCAGGTGGCA GCAGGGGAACGTCTTCTCATGCTCCGTGATGCATGAGG CTCTGCACAACCACTACACGCAGAAGAGCCTCTCCCTGT CCCCGGGTAAATGA |
| 46 | fusion protein comprising a soluble extracellular domain of ActRIIB (R64; SEQ ID NO: 29) fused to an Fc domain | SGRGEAETRECIYYNANWELERTNQSGLERCEGEQDKRL HCYASWRNSSGTIELVKKGCWLDDFNCYDRQECVATEEN PQVYFCCCEGNFCNERFTHLPEAGGPEVTYEPPPTAPTGG GTHTCPPCPAPELLGGPSVFLFPPKPKDTLMISRTPEVTCVV VDVSHEDPEVKFNWYVDGVEVHNAKTKPREEQYNSTYR VVSVLTVLHQDWLNGKEYKCKVSNKALPVPIEKTISKAK GQPREPQVYTLPPSREEMTKNQVSLTCLVKGFYPSDIAVE WESNGQPENNYKTTPPVLDSDGSFFLYSKLTVDKSRWQQ GNVFSCSVMHEALHNHYTQKSLSLSPGK |
| 47 | fusion protein comprising a soluble extracellular domain of ActRIIB (R64) with the C-terminal 15 amino acids deleted (SEQ ID NO: 30) fused to an Fc domain | SGRGEAETRECIYYNANWELERTNQSGLERCEGEQDKRL HCYASWRNSSGTIELVKKGCWLDDFNCYDRQECVATEEN PQVYFCCCEGNFCNERFTHLPEAGGGTHTCPPCPAPELLG GPSVFLFPPKPKDTLMISRTPEVTCVVVDVSHEDPEVKFN WYVDGVEVHNAKTKPREEQYNSTYRVVSVLTVLHQDWL NGKEYKCKVSNKALPVPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPGK |

10. EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

What is claimed:

1. A method of treating low or intermediate-1 risk myelodysplastic syndrome in a subject with transfusion burden, comprising administering an activin receptor type II (ActRII) signaling inhibitor at between 0.1 mg/kg and 2.0 mg/kg to the subject, wherein, prior to said administering, at least 15% of erythroblasts in the subject are ring sideroblasts, and wherein the ActRII signaling inhibitor is a polypeptide comprising: (i) a fragment of the extracellular domain of ActRIIB, wherein the fragment consists of the amino acid sequence of SEQ ID NO:23; (ii) a linker; and (iii) an Fc of an IgG.

2. The method of claim 1, wherein the method further comprises:
   a. monitoring a hematological parameter in the subject after administering said dose; and
   a. reducing the dose and/or frequency of administering of the ActRII signaling inhibitor to the subject if the hematological parameter in the subject is normalized; or discontinuing administering of the ActRII signaling inhibitor to the subject if the hematological parameter in the subject is normalized.

3. The method of 2, wherein the hematological parameter is hemoglobin level, hematocrit, red blood cell count or percentage of erythroblasts in the subject that are ring sideroblasts.

4. The method of claim 1, wherein the percentage of erythroblasts in the subject that are ring sideroblasts is determined by Prussian blue staining.

5. The method of claim 1, wherein the ActRII signaling inhibitor is administered
   a. once every three weeks, once every 28 days, or once every 42 days; and/or
   b. subcutaneously.

6. The method of claim 1, wherein the ActRII signaling inhibitor is an ActRIIB signaling inhibitor.

7. The method of claim 1, wherein the ActRII signaling inhibitor is a polypeptide comprising the amino acid sequence of SEQ ID NO:25.

8. The method of claim 1, wherein the subject is a human.

9. The method of claim 1, wherein the subject has at least 20% of erythroblasts are ring sideroblasts prior to said administering.

10. The method of claim 1, the ActRII signaling inhibitor is a polypeptide comprising an amino acid sequence at least 98% identical to the amino acid sequence of SEQ ID NO:25.

11. A method of treating low or intermediate-1 risk myelodysplastic syndrome in a subject with transfusion burden, comprising:
    a. administering to the subject an initial dose of between 0.1 mg/kg and 2.0 mg/kg of an ActRII signaling inhibitor, wherein, prior to said administering, at least 15% of erythroblasts in the subject are ring sideroblasts;
    b. after administering said initial dose, determining the percentage of erythroblasts in the subject that are ring sideroblasts; and
    c. optionally administering to the subject an adjusted dose of the ActRII signaling inhibitor;
    wherein, the adjusted dose of the ActRII signaling inhibitor is (i) greater than the initial dose if the percentage of erythroblasts in the subject that are ring sideroblasts determined in step (b) is at least 15% or (ii) not administered to the subject if the percentage of erythroblasts in the subject that are ring sideroblasts determined in step (b) is less than 10%, 9%, 8%, 7%, 6%, 5%, 4%, 3%, 2%, or less than 1%, and wherein the ActRII signaling inhibitor is a polypeptide comprising: (i) a fragment of the extracellular domain of ActRIIB, wherein the fragment consists of the amino acid sequence of SEQ ID NO:23; (ii) a linker; and (iii) an Fc of an IgG.

12. The method of claim 11, wherein the method further comprises:
    a. monitoring a hematological parameter in the subject after administering said initial dose; and
    b. reducing the dose and/or frequency of administering of the ActRII signaling inhibitor to the subject if the hematological parameter in the subject is normalized; or
    discontinuing administering of the ActRII signaling inhibitor to the subject if the hematological parameter in the subject is normalized.

13. The method of 12, wherein the hematological parameter is hemoglobin level, hematocrit, red blood cell count or percentage of erythroblasts in the subject that are ring sideroblasts.

14. The method of claim 11, wherein the percentage of erythroblasts in the subject that are ring sideroblasts is determined by Prussian blue staining.

15. The method of claim 11, wherein the ActRII signaling inhibitor is administered
    a. once every three weeks, once every 28 days, or once every 42 days; and/or
    b. subcutaneously.

16. The method of claim 11, wherein the ActRII signaling inhibitor is an ActRIIB signaling inhibitor.

17. The method of claim 11, wherein the ActRII signaling inhibitor is a polypeptide comprising the amino acid sequence of SEQ ID NO:25.

18. The method of claim 11, wherein the subject is a human.

19. The method of claim 11, wherein the subject has at least 20% of erythroblasts are ring sideroblasts prior to said administering.

20. The method of claim 11, the ActRII signaling inhibitor is a polypeptide comprising an amino acid sequence at least 98% identical to the amino acid sequence of SEQ ID NO:25.

* * * * *

UNITED STATES PATENT AND TRADEMARK OFFICE
CERTIFICATE OF CORRECTION

PATENT NO. : 11,471,510 B2
APPLICATION NO. : 15/532329
DATED : October 18, 2022
INVENTOR(S) : Kenneth M. Attie et al.

It is certified that error appears in the above-identified patent and that said Letters Patent is hereby corrected as shown below:

In the Claims

In Column 193, Line 33, Claim 2, replace "a" with --b--;

In Column 193, Line 39, Claim 3, replace "of 2" with --of claim 2--.

In Column 194, Line 49, Claim 13, replace "of 12" with --of claim 12--.

Signed and Sealed this
Sixteenth Day of May, 2023

Katherine Kelly Vidal
*Director of the United States Patent and Trademark Office*

SEQUENCE LISTING

```
<160> NUMBER OF SEQ ID NOS: 48

<210> SEQ ID NO 1
<211> LENGTH: 513
<212> TYPE: PRT
<213> ORGANISM: Homo sapiens
<220> FEATURE:
<223> OTHER INFORMATION: human ActRIIA precursor polypeptide

<400> SEQUENCE: 1

Met Gly Ala Ala Ala Lys Leu Ala Phe Ala Val Phe Leu Ile Ser Cys
1               5                  10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80
```

```
Asp Asp Ile Asn Cys Tyr Asp Arg Thr Asp Cys Val Glu Lys Lys Asp
                85                  90                  95

Ser Pro Glu Val Tyr Phe Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
    450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495
```

```
Val Val Thr Met Val Thr Asn Val Asp Phe Pro Pro Lys Glu Ser Ser
        500                 505                 510

Leu

<210> SEQ ID NO 2
<211> LENGTH: 115
<212> TYPE: PRT
<213> ORGANISM: Homo sapiens
<220> FEATURE:
<223> OTHER INFORMATION: human ActRIIA soluble (extracellular),
      processed polypeptide sequence

<400> SEQUENCE: 2

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 3
<211> LENGTH: 100
<212> TYPE: PRT
<213> ORGANISM: Artificial Sequence
<220> FEATURE:
<223> OTHER INFORMATION: human ActRIIA soluble (extracellular),
      processed polypeptide sequence with the C-terminal 15 amino acids
      deleted

<400> SEQUENCE: 3

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met
            100

<210> SEQ ID NO 4
<211> LENGTH: 1542
<212> TYPE: DNA
<213> ORGANISM: Homo sapiens
<220> FEATURE:
```

<223> OTHER INFORMATION: nucleic acid sequence encoding human ActRIIA
      precursor protein

<400> SEQUENCE: 4

```
atgggagctg ctgcaaagtt ggcgtttgcc gtctttctta tctcctgttc ttcaggtgct    60
atacttggta gatcagaaac tcaggagtgt cttttcttta atgctaattg ggaaaaagac   120
agaaccaatc aaactggtgt tgaaccgtgt tatggtgaca agataaacg gcggcattgt   180
tttgctacct ggaagaatat ttctggttcc attgaaatag tgaaacaagg ttgttggctg   240
gatgatatca actgctatga caggactgat tgtgtagaaa aaaagacag ccctgaagta   300
tattttgtt gctgtgaggg caatatgtgt aatgaaaagt tttcttattt tccagagatg   360
gaagtcacac agcccacttc aaatccagtt acacctaagc caccctatta caacatcctg   420
ctctattcct tggtgccact tatgttaatt gcggggattg tcatttgtgc attttgggtg   480
tacaggcatc acaagatggc ctaccctcct gtacttgttc aactcaaga cccaggacca   540
ccccacctt ctccattact agggttgaaa ccactgcagt tattagaagt gaaagcaagg   600
ggaagatttg gttgtgtctg gaaagcccag ttgcttaacg aatatgtggc tgtcaaaata   660
tttccaatac aggacaaaca gtcatggcaa aatgaatacg aagtctacag tttgcctgga   720
atgaagcatg agaacatatt acagttcatt ggtgcagaaa acgaggcac cagtgttgat   780
gtggatcttt ggctgatcac agcatttcat gaaaagggtt cactatcaga cttttcttaag   840
gctaatgtgg tctcttggaa tgaactgtgt catattgcag aaaccatggc tagaggattg   900
gcatatttac atgaggatat acctggccta aaagatggcc acaaacctgc catatctcac   960
agggacatca aaagtaaaaa tgtgctgttg aaaaacaacc tgacagcttg cattgctgac  1020
tttgggttgg ccttaaaatt tgaggctggc aagtctgcag gcgatacccca tggacaggtt  1080
ggtacccgga ggtacatggc tccagaggta ttagagggtg ctataaactt cgaaagggat  1140
gcattttga ggatagatat gtatgccatg ggattagtcc tatgggaact ggcttctcgc  1200
tgtactgctg cagatggacc tgtagatgaa tacatgttgc catttgagga ggaaattggc  1260
cagcatccat ctcttgaaga catgcaggaa gttgttgtgc ataaaaaaaa gaggcctgtt  1320
ttaagagatt attggcagaa acatgctgga atggcaatgc tctgtgaaac cattgaagaa  1380
tgttgggatc acgacgcaga agccaggtta tcagctggat gtgtaggtga aagaattacc  1440
cagatgcaga gactaacaaa tattattacc acagaggaca ttgtaacagt ggtcacaatg  1500
gtgacaaatg ttgactttcc tcccaaagaa tctagtctat ga                    1542
```

<210> SEQ ID NO 5  
<211> LENGTH: 345  
<212> TYPE: DNA  
<213> ORGANISM: Homo sapiens  
<220> FEATURE:  
<223> OTHER INFORMATION: nucleic acid sequence encoding a human ActRIIA
      soluble (extracellular) polypeptide

<400> SEQUENCE: 5

```
atacttggta gatcagaaac tcaggagtgt cttttcttta atgctaattg ggaaaaagac    60
agaaccaatc aaactggtgt tgaaccgtgt tatggtgaca agataaacg gcggcattgt   120
tttgctacct ggaagaatat ttctggttcc attgaaatag tgaaacaagg ttgttggctg   180
gatgatatca actgctatga caggactgat tgtgtagaaa aaaagacag ccctgaagta   240
tattttgtt gctgtgaggg caatatgtgt aatgaaaagt tttcttattt tccagagatg   300
gaagtcacac agcccacttc aaatccagtt acacctaagc caccc                  345
```

<210> SEQ ID NO 6
<211> LENGTH: 228
<212> TYPE: PRT
<213> ORGANISM: Artificial Sequence
<220> FEATURE:
<223> OTHER INFORMATION: fusion protein comprising a soluble
      extracellular domain of ActRIIA fused to an Fc domain

<400> SEQUENCE: 6

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Ala Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Ala Val Ser Asn Lys Ala Leu Pro Val Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Pro Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Ala His Tyr Thr Gln Lys Ser Leu Ser Leu
    210                 215                 220

Ser Pro Gly Lys
225

<210> SEQ ID NO 7
<211> LENGTH: 344
<212> TYPE: PRT
<213> ORGANISM: Artificial Sequence
<220> FEATURE:
<223> OTHER INFORMATION: Extracellular domain of human ActRIIA fused to
      a human Fc domain

<400> SEQUENCE: 7

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

```
Cys Tyr Asp Arg Thr Asp Cys Val Glu Lys Lys Asp Ser Pro Glu Val
 65                  70                  75                  80

Tyr Phe Cys Cys Cys Glu Gly Asn Met Cys Asn Glu Lys Phe Ser Tyr
                 85                  90                  95

Phe Pro Glu Met Glu Val Thr Gln Pro Thr Ser Asn Pro Val Thr Pro
            100                 105                 110

Lys Pro Pro Thr Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 8
<211> LENGTH: 21
<212> TYPE: PRT
<213> ORGANISM: Honey bee
<220> FEATURE:
<223> OTHER INFORMATION: Leader sequence of Honey bee mellitin (HBML)

<400> SEQUENCE: 8

Met Lys Phe Leu Val Asn Val Ala Leu Val Phe Met Val Val Tyr Ile
 1               5                  10                  15

Ser Tyr Ile Tyr Ala
            20

<210> SEQ ID NO 9
<211> LENGTH: 22
<212> TYPE: PRT
<213> ORGANISM: Artificial Sequence
<220> FEATURE:
<223> OTHER INFORMATION: Leader sequence of Tissue Plasminogen Activator
      (TPA)
```

<400> SEQUENCE: 9

Met Asp Ala Met Lys Arg Gly Leu Cys Cys Val Leu Leu Leu Cys Gly
1               5                   10                  15

Ala Val Phe Val Ser Pro
            20

<210> SEQ ID NO 10
<211> LENGTH: 20
<212> TYPE: PRT
<213> ORGANISM: Artificial Sequence
<220> FEATURE:
<223> OTHER INFORMATION: Native ActRIIA

<400> SEQUENCE: 10

Met Gly Ala Ala Ala Lys Leu Ala Phe Ala Val Phe Leu Ile Ser Cys
1               5                   10                  15

Ser Ser Gly Ala
            20

<210> SEQ ID NO 11
<211> LENGTH: 9
<212> TYPE: PRT
<213> ORGANISM: Artificial Sequence
<220> FEATURE:
<223> OTHER INFORMATION: ActRIIA-hFc and ActRIIA-mFc N-terminal sequence

<400> SEQUENCE: 11

Ile Leu Gly Arg Ser Glu Thr Gln Glu
1               5

<210> SEQ ID NO 12
<211> LENGTH: 329
<212> TYPE: PRT
<213> ORGANISM: Artificial Sequence
<220> FEATURE:
<223> OTHER INFORMATION: ActRIIA-Fc Protein with deletion of the
      C-terminal 15 amino acids of the extracellular domain of ActRIIA

<400> SEQUENCE: 12

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Thr Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

```
Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
        180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
        260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
        290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 13
<211> LENGTH: 369
<212> TYPE: PRT
<213> ORGANISM: Artificial Sequence
<220> FEATURE:
<223> OTHER INFORMATION: Unprocessed ActRIIA-hFc with TPA leader
      sequence

<400> SEQUENCE: 13

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190
```

```
            Pro Val Lys Phe Asn Trp Tyr Val Asp Gly Val Glu Val His Asn
                195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Val Pro Ile Glu Lys
                245                 250                 255

Thr Ile Ser Lys Ala Lys Gly Gln Pro Arg Glu Pro Gln Val Tyr Thr
                260                 265                 270

Leu Pro Pro Ser Arg Glu Glu Met Thr Lys Asn Gln Val Ser Leu Thr
                275                 280                 285

Cys Leu Val Lys Gly Phe Tyr Pro Ser Asp Ile Ala Val Glu Trp Glu
                290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
                340                 345                 350

Ala Leu His Asn His Tyr Thr Gln Lys Ser Leu Ser Leu Ser Pro Gly
                355                 360                 365

Lys
```

<210> SEQ ID NO 14
<211> LENGTH: 1114
<212> TYPE: DNA
<213> ORGANISM: Artificial Sequence
<220> FEATURE:
<223> OTHER INFORMATION: Nucleic acid sequence encoding Unprocessed
    ActRIIA-hFc with TPA leader sequence

<400> SEQUENCE: 14

```
atggatgcaa tgaagagagg gctctgctgt gtgctgctgc tgtgtggagc agtcttcgtt    60
tcgcccggcg ccgctatact tggtagatca gaaactcagg agtgtctttt tttaatgcta   120
attgggaaaa agacagaacc aatcaaactg gtgttgaacc gtgttatggt gacaaagata   180
aacggcggca ttgttttgct acctggaaga atatttctgg ttccattgaa tagtgaaaca   240
aggttgttgg ctggatgata tcaactgcta tgacaggact gattgtgtag aaaaaaaaga   300
cagccctgaa gtatatttct gttgctgtga gggcaatatg tgtaatgaaa gttttcttat   360
ttttccggag atggaagtca cacagcccac ttcaaatcca gttacaccta agccacccac   420
cggtggtgga actcacacat gcccaccgtg cccagcacct gaactcctgg ggggaccgtc   480
agtcttcctc ttccccccaa aacccaagga caccctcatg atctcccgga cccctgaggt   540
cacatgcgtg gtggtggacg tgagccacga agaccctgag gtcaagttca actggtacgt   600
ggacggcgtg gaggtgcata atgccaagac aaagccgcgg gaggagcagt acaacagcac   660
gtaccgtgtg gtcagcgtcc tcaccgtcct gcaccaggac tggctgaatg gcaaggagta   720
caagtgcaag gtctccaaca aagccctccc agtcccatc gagaaaacca tctccaaagc   780
caaagggcag ccccgagaac cacaggtgta caccctgccc ccatcccggg aggagatgac   840
caagaaccag gtcagcctga cctgcctggt caaaggcttc tatccagcg acatcgccgt   900 ggagtgggag agcaatgggc agccggagaa caactacaag accacgcctc ccgtgctgga   960
```

```
ctccgacggc tccttcttcc tctatagcaa gctcaccgtg acaagagcag gtggcagca    1020 ggggaacgtc ttctcatgct ccgtgatgca tgaggctctg cacaaccact acacgcagaa    1080
gagcctctcc ctgtctccgg gtaaatgaga attc                                 1114
```

<210> SEQ ID NO 15
<211> LENGTH: 106
<212> TYPE: PRT
<213> ORGANISM: Artificial Sequence
<220> FEATURE:
<223> OTHER INFORMATION: modified human ActRIIB soluble (extracellular)

<400> SEQUENCE: 15

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro
            100                 105
```

<210> SEQ ID NO 16
<211> LENGTH: 512
<212> TYPE: PRT
<213> ORGANISM: Homo sapiens
<220> FEATURE:
<223> OTHER INFORMATION: human ActRIIB precursor protein sequence (A64)

<400> SEQUENCE: 16

```
Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175
```

```
Gly Pro Pro Pro Pro Ser Pro Leu Val Gly Leu Lys Pro Leu Gln Leu
                180                 185                 190

Leu Glu Ile Lys Ala Arg Gly Arg Phe Gly Cys Val Trp Lys Ala Gln
195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
                260                 265                 270

Leu Thr Asp Tyr Leu Lys Gly Asn Ile Ile Thr Trp Asn Glu Leu Cys
                275                 280                 285

His Val Ala Glu Thr Met Ser Arg Gly Leu Ser Tyr Leu His Glu Asp
                290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
                340                 345                 350

Gly Asp Thr His Gly Gln Val Gly Thr Arg Arg Tyr Met Ala Pro Glu
                355                 360                 365

Val Leu Glu Gly Ala Ile Asn Phe Gln Arg Asp Ala Phe Leu Arg Ile
                370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
                420                 425                 430

His Lys Lys Met Arg Pro Thr Ile Lys Asp His Trp Leu Lys His Pro
                435                 440                 445

Gly Leu Ala Gln Leu Cys Val Thr Ile Glu Glu Cys Trp Asp His Asp
450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
                500                 505                 510
```

<210> SEQ ID NO 17
<211> LENGTH: 116
<212> TYPE: PRT
<213> ORGANISM: Homo sapiens
<220> FEATURE:
<223> OTHER INFORMATION: human ActRIIB soluble (extracellular),
      processed polypeptide sequence (amino acids 19-134 of SEQ ID
      NO:16)

<400> SEQUENCE: 17

```
Ser Gly Arg Gly Glu Ala Glu Thr Arg Glu Cys Ile Tyr Tyr Asn Ala
1               5                   10                  15
```

```
Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr
        115

<210> SEQ ID NO 18
<211> LENGTH: 101
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 amino acids
      deleted (amino acids 19-119 of SEQ ID NO:16)

<400> SEQUENCE: 18

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala
            100

<210> SEQ ID NO 19
<211> LENGTH: 1539
<212> TYPE: DNA
<213> ORGANISM: Homo sapiens
<220> FEATURE:
<223> OTHER INFORMATION: nucleic acid sequence encoding a human ActRIIB
      (A64) precursor

<400> SEQUENCE: 19
atgacggcgc cctgggtggc cctcgccctc ctctggggat cgctgtggcc cggctctggg      60
cgtggggagg ctgagacacg ggagtgcatc tactacaacg ccaactggga gctggagcgc     120
accaaccaga gcggcctgga gcgctgcgaa ggcgagcagg acaagcggct gcactgctac     180
gcctcctggg ccaacagctc tggcaccatc gagctcgtga agaagggctg ctggctagat     240
gacttcaact gctacgatag gcaggagtgt gtggccactg aggagaaccc ccaggtgtac     300
ttctgctgct gtgaaggcaa cttctgcaac gagcgcttca ctcatttgcc agaggctggg     360
ggcccggaag tcacgtacga gccaccccca acagccccca cctgctcac ggtgctggcc      420
```

```
tactcactgc tgcccatcgg gggcctttcc ctcatcgtcc tgctggcctt ttggatgtac    480
cggcatcgca agccccccta cggtcatgtg acatccatg aggaccctgg gcctccacca    540
ccatcccctc tggtgggcct gaagccactg cagctgctgg agatcaaggc tcggggcgc    600
tttggctgtg tctggaaggc ccagctcatg aatgactttg tagctgtcaa gatcttccca    660
ctccaggaca agcagtcgtg gcagagtgaa cgggagatct tcagcacacc tggcatgaag    720
cacgagaacc tgctacagtt cattgctgcc gagaagcgag gctccaacct cgaagtagag    780
ctgtggctca tcacggcctt ccatgacaag ggctcccctca cggattacct caaggggaac    840
atcatcacat ggaacgaact gtgtcatgta gcagagacga tgtcacgagg cctctcatac    900
ctgcatgagg atgtgccctg gtgccgtggc gagggccaca agccgtctat tgcccacagg    960
gactttaaaa gtaagaatgt attgctgaag agcgacctca cagccgtgct ggctgacttt   1020
ggcttggctg ttcgatttga gccagggaaa cctccagggg acacccacgg acaggtaggc   1080
acgagacggt acatggctcc tgaggtgctc gagggagcca tcaacttcca gagagatgcc   1140
ttcctgcgca ttgacatgta tgccatgggg ttggtgctgt gggagcttgt gtctcgctgc   1200
aaggctgcag acggacccgt ggatgagtac atgctgccct ttgaggaaga gattggccag   1260
caccccttcgt tggaggagct gcaggaggtg gtggtgcaca gaagatgag gcccaccatt   1320
aaagatcact ggttgaaaca cccgggcctg gcccagcttt gtgtgaccat cgaggagtgc   1380
tgggaccatg atgcagaggc tcgcttgtcc gcgggctgtg tggaggagcg ggtgtccctg   1440
attcggaggt cggtcaacgg cactacctcg gactgtctcg tttccctggt gacctctgtc   1500
accaatgtgg acctgccccc taaagagtca agcatctaa                          1539
```

<210> SEQ ID NO 20
<211> LENGTH: 344
<212> TYPE: PRT
<213> ORGANISM: Artificial Sequence
<220> FEATURE:
<223> OTHER INFORMATION: fusion protein comprising a soluble
      extracellular domain of ActRIIB (A64; SEQ ID NO:17) fused to an Fc
      domain

<400> SEQUENCE: 20

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

```
Val Asp Val Ser His Glu Asp Pro Glu Val Lys Phe Asn Trp Tyr Val
            165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
            195                 200                 205

Asp Trp Leu Asn Gly Lys Glu Tyr Lys Cys Lys Val Ser Asn Lys Ala
            210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
            245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
            275                 280                 285

Lys Thr Thr Pro Pro Val Leu Asp Ser Asp Gly Ser Phe Phe Leu Tyr
            290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
            325                 330                 335

Ser Leu Ser Leu Ser Pro Gly Lys
            340

<210> SEQ ID NO 21
<211> LENGTH: 329
<212> TYPE: PRT
<213> ORGANISM: Artificial Sequence
<220> FEATURE:
<223> OTHER INFORMATION: fusion protein comprising a soluble
      extracellular domain of ActRIIB (A64) with the C-terminal 15 amino
      acids deleted (SEQ ID NO:18) fused to an Fc domain

<400> SEQUENCE: 21

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
            35                  40                  45

Ser Gly Thr Ile Glu Leu Val Lys Lys Gly Cys Trp Leu Asp Asp Phe
50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
            85                  90                  95

His Leu Pro Glu Ala Gly Gly Thr His Thr Cys Pro Pro Cys Pro
            100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
            130                 135                 140

Val Val Asp Val Ser His Glu Asp Pro Glu Val Lys Phe Asn Trp Tyr
145                 150                 155                 160
```

Val Asp Gly Val Glu Val His Asn Ala Lys Thr Lys Pro Arg Glu Glu
            165                 170                 175

Gln Tyr Asn Ser Thr Tyr Arg Val Ser Val Leu Thr Val Leu His
        180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
        290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 22
<211> LENGTH: 105
<212> TYPE: PRT
<213> ORGANISM: Artificial Sequence
<220> FEATURE:
<223> OTHER INFORMATION: modified human ActRIIB soluble (extracellular)

<400> SEQUENCE: 22

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro
            100                 105

<210> SEQ ID NO 23
<211> LENGTH: 107
<212> TYPE: PRT
<213> ORGANISM: Artificial Sequence
<220> FEATURE:
<223> OTHER INFORMATION: modified human ActRIIB soluble (extracellular)

<400> SEQUENCE: 23

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

```
Leu His Cys Tyr Ala Ser Trp Arg Asn Ser Ser Gly Thr Ile Glu Leu
        35                  40                  45

Val Lys Lys Gly Cys Trp Asp Asp Phe Asn Cys Tyr Asp Arg Gln
 50                  55                  60

Glu Cys Val Ala Thr Glu Glu Asn Pro Gln Val Tyr Phe Cys Cys
 65                  70                  75                  80

Glu Gly Asn Phe Cys Asn Glu Arg Phe Thr His Leu Pro Glu Ala Gly
                    85                  90                  95

Gly Pro Glu Val Thr Tyr Glu Pro Pro Thr
                100                 105
```

<210> SEQ ID NO 24
<211> LENGTH: 360
<212> TYPE: PRT
<213> ORGANISM: Artificial Sequence
<220> FEATURE:
<223> OTHER INFORMATION: Unprocessed ActRIIB-Fc fusion protein with
      modifications

<400> SEQUENCE: 24

```
Met Asp Ala Met Lys Arg Gly Leu Cys Cys Val Leu Leu Leu Cys Gly
 1               5                  10                  15

Ala Val Phe Val Ser Pro Gly Ala Ala Glu Thr Arg Glu Cys Ile Tyr
                20                  25                  30

Tyr Asn Ala Asn Trp Glu Leu Glu Arg Thr Asn Gln Ser Gly Leu Glu
            35                  40                  45

Arg Cys Glu Gly Glu Gln Asp Lys Arg Leu His Cys Tyr Ala Ser Trp
 50                  55                  60

Arg Asn Ser Ser Gly Thr Ile Glu Leu Val Lys Lys Gly Cys Trp Asp
 65                  70                  75                  80

Asp Phe Asn Cys Tyr Asp Arg Gln Glu Cys Val Ala Thr Glu Glu
                    85                  90                  95

Asn Pro Gln Val Tyr Phe Cys Cys Cys Glu Gly Asn Phe Cys Asn Glu
                100                 105                 110

Arg Phe Thr His Leu Pro Glu Ala Gly Gly Pro Glu Val Thr Tyr Glu
            115                 120                 125

Pro Pro Thr Gly Gly Gly Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
                260                 265                 270

Lys Asn Gln Val Ser Leu Thr Cys Leu Val Lys Gly Phe Tyr Pro Ser
```

```
            275                 280                 285
Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 25
<211> LENGTH: 335
<212> TYPE: PRT
<213> ORGANISM: Artificial Sequence
<220> FEATURE:
<223> OTHER INFORMATION: Processed ActRIIB-Fc fusion protein with
      modifications

<400> SEQUENCE: 25

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270
```

```
Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
        290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 26
<211> LENGTH: 115
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID
      NO:16)

<400> SEQUENCE: 26

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 27
<211> LENGTH: 100
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 amino acids
      deleted (amino acids 20-119 of SEQ ID NO:16)

<400> SEQUENCE: 27

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
```

<210> SEQ ID NO 28
<211> LENGTH: 512
<212> TYPE: PRT
<213> ORGANISM: Homo sapiens
<220> FEATURE:
<223> OTHER INFORMATION: human ActRIIB precursor protein sequence (R64)

<400> SEQUENCE: 28

| | | | | | | | | | | | | | | | |
|---|---|---|---|---|---|---|---|---|---|---|---|---|---|---|---|
| Met | Thr | Ala | Pro | Trp | Val | Ala | Leu | Ala | Leu | Leu | Trp | Gly | Ser | Leu | Trp |
| 1 | | | | 5 | | | | | 10 | | | | | 15 | |
| Pro | Gly | Ser | Gly | Arg | Gly | Glu | Ala | Glu | Thr | Arg | Glu | Cys | Ile | Tyr | Tyr |
| | | | 20 | | | | | 25 | | | | | 30 | | |
| Asn | Ala | Asn | Trp | Glu | Leu | Glu | Arg | Thr | Asn | Gln | Ser | Gly | Leu | Glu | Arg |
| | | 35 | | | | | 40 | | | | | 45 | | | |
| Cys | Glu | Gly | Glu | Gln | Asp | Lys | Arg | Leu | His | Cys | Tyr | Ala | Ser | Trp | Arg |
| 50 | | | | | 55 | | | | | 60 | | | | | |
| Asn | Ser | Ser | Gly | Thr | Ile | Glu | Leu | Val | Lys | Lys | Gly | Cys | Trp | Leu | Asp |
| 65 | | | | 70 | | | | | 75 | | | | | 80 | |
| Asp | Phe | Asn | Cys | Tyr | Asp | Arg | Gln | Glu | Cys | Val | Ala | Thr | Glu | Glu | Asn |
| | | | | 85 | | | | | 90 | | | | | 95 | |
| Pro | Gln | Val | Tyr | Phe | Cys | Cys | Cys | Glu | Gly | Asn | Phe | Cys | Asn | Glu | Arg |
| | | | | 100 | | | | | 105 | | | | | 110 | |
| Phe | Thr | His | Leu | Pro | Glu | Ala | Gly | Gly | Pro | Glu | Val | Thr | Tyr | Glu | Pro |
| | | | 115 | | | | | 120 | | | | | 125 | | |
| Pro | Pro | Thr | Ala | Pro | Thr | Leu | Leu | Thr | Val | Leu | Ala | Tyr | Ser | Leu | Leu |
| 130 | | | | | 135 | | | | | 140 | | | | | |
| Pro | Ile | Gly | Gly | Leu | Ser | Leu | Ile | Val | Leu | Leu | Ala | Phe | Trp | Met | Tyr |
| 145 | | | | | 150 | | | | | 155 | | | | | 160 |
| Arg | His | Arg | Lys | Pro | Pro | Tyr | Gly | His | Val | Asp | Ile | His | Glu | Asp | Pro |
| | | | | 165 | | | | | 170 | | | | | 175 | |
| Gly | Pro | Pro | Pro | Pro | Ser | Pro | Leu | Val | Gly | Leu | Lys | Pro | Leu | Gln | Leu |
| | | | 180 | | | | | 185 | | | | | 190 | | |
| Leu | Glu | Ile | Lys | Ala | Arg | Gly | Arg | Phe | Gly | Cys | Val | Trp | Lys | Ala | Gln |
| | | 195 | | | | | 200 | | | | | 205 | | | |
| Leu | Met | Asn | Asp | Phe | Val | Ala | Val | Lys | Ile | Phe | Pro | Leu | Gln | Asp | Lys |
| 210 | | | | | 215 | | | | | 220 | | | | | |
| Gln | Ser | Trp | Gln | Ser | Glu | Arg | Glu | Ile | Phe | Ser | Thr | Pro | Gly | Met | Lys |
| 225 | | | | | 230 | | | | | 235 | | | | | 240 |
| His | Glu | Asn | Leu | Leu | Gln | Phe | Ile | Ala | Ala | Glu | Lys | Arg | Gly | Ser | Asn |
| | | | | 245 | | | | | 250 | | | | | 255 | |
| Leu | Glu | Val | Glu | Leu | Trp | Leu | Ile | Thr | Ala | Phe | His | Asp | Lys | Gly | Ser |
| | | | 260 | | | | | 265 | | | | | 270 | | |
| Leu | Thr | Asp | Tyr | Leu | Lys | Gly | Asn | Ile | Ile | Thr | Trp | Asn | Glu | Leu | Cys |
| | | 275 | | | | | 280 | | | | | 285 | | | |
| His | Val | Ala | Glu | Thr | Met | Ser | Arg | Gly | Leu | Ser | Tyr | Leu | His | Glu | Asp |
| | 290 | | | | | 295 | | | | | 300 | | | | |
| Val | Pro | Trp | Cys | Arg | Gly | Glu | Gly | His | Lys | Pro | Ser | Ile | Ala | His | Arg |
| 305 | | | | | 310 | | | | | 315 | | | | | 320 |
| Asp | Phe | Lys | Ser | Lys | Asn | Val | Leu | Leu | Lys | Ser | Asp | Leu | Thr | Ala | Val |
| | | | | 325 | | | | | 330 | | | | | 335 | |
| Leu | Ala | Asp | Phe | Gly | Leu | Ala | Val | Arg | Phe | Glu | Pro | Gly | Lys | Pro | Pro |
| | | | 340 | | | | | 345 | | | | | 350 | | |
| Gly | Asp | Thr | His | Gly | Gln | Val | Gly | Thr | Arg | Arg | Tyr | Met | Ala | Pro | Glu |

-continued

```
                355                 360                 365
Val Leu Glu Gly Ala Ile Asn Phe Gln Arg Asp Ala Phe Leu Arg Ile
        370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
        420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
                500                 505                 510
```

<210> SEQ ID NO 29
<211> LENGTH: 116
<212> TYPE: PRT
<213> ORGANISM: Homo sapiens
<220> FEATURE:
<223> OTHER INFORMATION: human ActRIIB soluble (extracellular),
      processed polypeptide sequence (amino acids 19-134 of SEQ ID
      NO:28)

<400> SEQUENCE: 29

```
Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
                20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
                100                 105                 110

Thr Ala Pro Thr
        115
```

<210> SEQ ID NO 30
<211> LENGTH: 101
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 amino acids
      deleted (amino acids 19-119 of SEQ ID NO:28)

<400> SEQUENCE: 30

```
Ser Gly Arg Gly Glu Ala Glu Thr Arg Glu Cys Ile Tyr Tyr Asn Ala
1               5                   10                  15
```

-continued

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala
            100

<210> SEQ ID NO 31
<211> LENGTH: 115
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID
      NO:28)

<400> SEQUENCE: 31

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 32
<211> LENGTH: 100
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 amino acids
      deleted (amino acids 20-119 of SEQ ID NO:28)

<400> SEQUENCE: 32

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

```
Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                 85                  90                  95

Leu Pro Glu Ala
            100

<210> SEQ ID NO 33
<211> LENGTH: 107
<212> TYPE: PRT
<213> ORGANISM: Artificial Sequence
<220> FEATURE:
<223> OTHER INFORMATION: human ActRIIB soluble (extracellular),
      processed polypeptide with modifications

<400> SEQUENCE: 33

Glu Thr Arg Glu Cys Ile Tyr Tyr Asn Ala Asn Trp Glu Leu Glu Arg
 1               5                  10                  15

Thr Asn Gln Ser Gly Leu Glu Arg Cys Glu Gly Glu Gln Asp Lys Arg
                20                  25                  30

Leu His Cys Tyr Ala Ser Trp Ala Asn Ser Ser Gly Thr Ile Glu Leu
            35                  40                  45

Val Lys Lys Gly Cys Trp Asp Asp Phe Asn Cys Tyr Asp Arg Gln
 50                  55                  60

Glu Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Thr
            100                 105

<210> SEQ ID NO 34
<211> LENGTH: 360
<212> TYPE: PRT
<213> ORGANISM: Artificial Sequence
<220> FEATURE:
<223> OTHER INFORMATION: Unprocessed ActRIIB-Fc fusion protein with
      modifications

<400> SEQUENCE: 34

Met Asp Ala Met Lys Arg Gly Leu Cys Cys Val Leu Leu Leu Cys Gly
 1               5                  10                  15

Ala Val Phe Val Ser Pro Gly Ala Ala Glu Thr Arg Glu Cys Ile Tyr
                20                  25                  30

Tyr Asn Ala Asn Trp Glu Leu Glu Arg Thr Asn Gln Ser Gly Leu Glu
            35                  40                  45

Arg Cys Glu Gly Glu Gln Asp Lys Arg Leu His Cys Tyr Ala Ser Trp
 50                  55                  60

Ala Asn Ser Ser Gly Thr Ile Glu Leu Val Lys Lys Gly Cys Trp Asp
 65                  70                  75                  80

Asp Asp Phe Asn Cys Tyr Asp Arg Gln Glu Cys Val Ala Thr Glu Glu
                 85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
    130                 135                 140
```

-continued

```
Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 35
<211> LENGTH: 335
<212> TYPE: PRT
<213> ORGANISM: Artificial Sequence
<220> FEATURE:
<223> OTHER INFORMATION: Processed ActRIIB-Fc fusion protein with
      modifications

<400> SEQUENCE: 35

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Ala Asn Ser Ser Gly Thr Ile Glu Leu
            35                  40                  45

Val Lys Lys Gly Cys Trp Asp Asp Asp Phe Asn Cys Tyr Asp Arg Gln
        50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140
```

-continued

```
Pro Glu Val Thr Cys Val Val Asp Val Ser His Glu Asp Pro Glu
145                 150                 155                 160

Val Lys Phe Asn Trp Tyr Val Asp Gly Val Glu Val His Asn Ala Lys
            165                 170                 175

Thr Lys Pro Arg Glu Glu Gln Tyr Asn Ser Thr Tyr Arg Val Val Ser
        180                 185                 190

Val Leu Thr Val Leu His Gln Asp Trp Leu Asn Gly Lys Glu Tyr Lys
    195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 36
<211> LENGTH: 115
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID
      NO:28) with L79D mutation

<400> SEQUENCE: 36

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 37
<211> LENGTH: 115
<212> TYPE: PRT
<213> ORGANISM: Artificial Sequence
<220> FEATURE:
```

<223> OTHER INFORMATION: human ActRIIB soluble (extracellular),
processed polypeptide sequence (amino acids 20-134 of SEQ ID
NO:16) with L79D mutation

<400> SEQUENCE: 37

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Thr
            100                 105                 110

Ala Pro Thr
        115

<210> SEQ ID NO 38
<211> LENGTH: 343
<212> TYPE: PRT
<213> ORGANISM: Artificial Sequence
<220> FEATURE:
<223> OTHER INFORMATION: human ActRIIB soluble (extracellular),
processed polypeptide sequence (amino acids 20-134 of SEQ ID
NO:28) with L79D mutation fused to an Fc domain with a GGG linker

<400> SEQUENCE: 38

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp

```
              195                 200                 205
Trp Leu Asn Gly Lys Glu Tyr Lys Cys Lys Val Ser Asn Lys Ala Leu
        210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
                260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
        290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 39
<211> LENGTH: 343
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID
      NO:16) with L79D mutation fused to an Fc domain

<400> SEQUENCE: 39

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205
```

```
Trp Leu Asn Gly Lys Glu Tyr Lys Cys Lys Val Ser Asn Lys Ala Leu
        210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
                260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
        290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 40
<211> LENGTH: 368
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID
      NO:28) with L79D mutation fused to an Fc domain and with TPA
      leader sequence

<400> SEQUENCE: 40

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
                100                 105                 110

Asn Phe Cys Asn Glu Arg Phe Thr His Leu Pro Glu Ala Gly Gly Pro
            115                 120                 125

Glu Val Thr Tyr Glu Pro Pro Pro Thr Ala Pro Thr Gly Gly Gly Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
                180                 185                 190

Glu Val Lys Phe Asn Trp Tyr Val Asp Gly Val Glu Val His Asn Ala
            195                 200                 205
```

```
Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
                260                 265                 270

Pro Pro Ser Arg Glu Glu Met Thr Lys Asn Gln Val Ser Leu Thr Cys
            275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
                340                 345                 350

Leu His Asn His Tyr Thr Gln Lys Ser Leu Ser Leu Ser Pro Gly Lys
            355                 360                 365

<210> SEQ ID NO 41
<211> LENGTH: 368
<212> TYPE: PRT
<213> ORGANISM: Artificial Sequence
<220> FEATURE:
<223> OTHER INFORMATION: human ActRIIB soluble (extracellular),
      processed polypeptide sequence (amino acids 20-134 of SEQ ID
      NO:16) with L79D mutation fused to an Fc domain and with TPA
      leader sequence

<400> SEQUENCE: 41

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
                20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
    50                  55                  60

Cys Tyr Ala Ser Trp Ala Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190
```

```
Glu Val Lys Phe Asn Trp Tyr Val Asp Gly Val Glu His Asn Ala
            195                 200                 205

Lys Thr Lys Pro Arg Glu Glu Gln Tyr Asn Ser Thr Tyr Arg Val Val
        210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
        290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 42
<211> LENGTH: 141
<212> TYPE: PRT
<213> ORGANISM: Artificial Sequence
<220> FEATURE:
<223> OTHER INFORMATION: human ActRIIB soluble (extracellular),
      processed polypeptide sequence having a variant C-terminal
      sequence (disclosed in WO2007/053775)

<400> SEQUENCE: 42

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Ala Gly Asp Gln Gly Ser
        115                 120                 125

Gly Ala Leu Trp Leu Cys Leu Glu Gly Pro Ala His Glu
    130                 135                 140

<210> SEQ ID NO 43
<211> LENGTH: 141
<212> TYPE: PRT
<213> ORGANISM: Artificial Sequence
<220> FEATURE:
```

<223> OTHER INFORMATION: human ActRIIB soluble (extracellular),
processed polypeptide sequence having a variant C-terminal
sequence (disclosed in WO2007/053775)

<400> SEQUENCE: 43

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu
    130                 135                 140

<210> SEQ ID NO 44
<211> LENGTH: 370
<212> TYPE: PRT
<213> ORGANISM: Artificial Sequence
<220> FEATURE:
<223> OTHER INFORMATION: human ActRIIB soluble (extracellular),
processed polypeptide sequence having a variant C-terminal
sequence (disclosed in WO2007/053775)

<400> SEQUENCE: 44

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu Thr Gly Gly
    130                 135                 140

Gly Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu 180                 185                 190
Asp Pro Glu Val Lys Phe Asn Trp Tyr Val Asp Gly Val Glu Val His
                195                 200                 205
Asn Ala Lys Thr Lys Pro Arg Glu Glu Gln Tyr Asn Ser Thr Tyr Arg
            210                 215                 220
Val Val Ser Val Leu Thr Val Leu His Gln Asp Trp Leu Asn Gly Lys
225                 230                 235                 240
Glu Tyr Lys Cys Lys Val Ser Asn Lys Ala Leu Pro Ala Pro Ile Glu
                245                 250                 255
Lys Thr Ile Ser Lys Ala Lys Gly Gln Pro Arg Glu Pro Gln Val Tyr
            260                 265                 270
Thr Leu Pro Pro Ser Arg Glu Glu Met Thr Lys Asn Gln Val Ser Leu
        275                 280                 285
Thr Cys Leu Val Lys Gly Phe Tyr Pro Ser Asp Ile Ala Val Glu Trp
        290                 295                 300
Glu Ser Asn Gly Gln Pro Glu Asn Asn Tyr Lys Thr Thr Pro Pro Val
305                 310                 315                 320
Leu Asp Ser Asp Gly Ser Phe Phe Leu Tyr Ser Lys Leu Thr Val Asp
                325                 330                 335
Lys Ser Arg Trp Gln Gln Gly Asn Val Phe Ser Cys Ser Val Met His
            340                 345                 350
Glu Ala Leu His Asn His Tyr Thr Gln Lys Ser Leu Ser Leu Ser Pro
        355                 360                 365
Gly Lys
    370

<210> SEQ ID NO 45
<211> LENGTH: 1083
<212> TYPE: DNA
<213> ORGANISM: Artificial Sequence
<220> FEATURE:
<223> OTHER INFORMATION: Nucleic Acid Sequence Encoding SEQ ID NO:24

<400> SEQUENCE: 45
atggatgcaa tgaagagagg gctctgctgt gtgctgctgc tgtgtggagc agtcttcgtt      60
tcgcccggcg ccgccgaaac ccgcgaatgt atttattaca atgctaattg ggaactcgaa     120
cggacgaacc aatccgggct cgaacggtgt gaggggaaca aggataaacg cctccattgc     180
tatgcgtcgt ggaggaactc ctccgggacg attgaactgg tcaagaaagg gtgctgggac     240
gacgatttca attgttatga ccgccaggaa tgtgtcgcga ccgaagagaa tccgcaggtc     300
tatttctgtt gttgcgaggg gaatttctgt aatgaacggt ttacccacct ccccgaagcc     360
ggcgggcccg aggtgaccta tgaaccccg cccaccggtg gtggaactca cacatgccca     420
ccgtgcccag cacctgaact cctgggggga ccgtcagtct tcctcttccc cccaaaaccc     480
aaggacaccc tcatgatctc ccggacccct gaggtcacat gcgtggtggt ggacgtgagc     540
cacgaagacc ctgaggtcaa gttcaactgg tacgtggacg gcgtggaggt gcataatgcc     600
aagacaaagc cgcgggagga gcagtacaac agcacgtacc gtgtggtcag cgtcctcacc     660
gtcctgcacc aggactggct gaatggcaag gagtacaagt gcaaggtctc caacaaagcc     720
ctcccagccc ccatcgagaa aaccatctcc aaagccaaag ggcagccccg agaaccacag     780
gtgtacaccc tgcccccatc ccgggaggag atgaccaaga accaggtcag cctgacctgc     840
ctggtcaaag gcttctatcc cagcgacatc gccgtggagt gggagagcaa tgggcagccg     900
gagaacaact acaagaccac gcctcccgtg ctggactccg acggctcctt cttcctctat     960

```
agcaagctca ccgtggacaa gagcaggtgg cagcagggga acgtcttctc atgctccgtg    1020
atgcatgagg ctctgcacaa ccactacacg cagaagagcc tctccctgtc cccgggtaaa    1080
tga                                                                  1083
```

<210> SEQ ID NO 46
<211> LENGTH: 344
<212> TYPE: PRT
<213> ORGANISM: Artificial Sequence
<220> FEATURE:
<223> OTHER INFORMATION: fusion protein comprising a soluble
      extracellular domain of ActRIIB (R64; SEQ ID NO:29) fused to an Fc
      domain

<400> SEQUENCE: 46

```
Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320
```

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 47
<211> LENGTH: 329
<212> TYPE: PRT
<213> ORGANISM: Artificial Sequence
<220> FEATURE:
<223> OTHER INFORMATION: fusion protein comprising a soluble
      extracellular domain of ActRIIB (R64) with the C-terminal 15 amino
      acids deleted (SEQ ID NO:30) fused to an Fc domain

<400> SEQUENCE: 47

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

```
<210> SEQ ID NO 48
<211> LENGTH: 4
<212> TYPE: PRT
<213> ORGANISM: Artificial Sequence
<220> FEATURE:
<223> OTHER INFORMATION: Linker sequence

<400> SEQUENCE: 48

Thr Gly Gly Gly
1
```